US009005616B2

(12) United States Patent
Langermann et al.

(10) Patent No.: US 9,005,616 B2
(45) Date of Patent: Apr. 14, 2015

(54) METHODS AND COMPOSITIONS FOR THE INHIBITION OF TRANSPLANT REJECTION

(75) Inventors: Solomon Langermann, Baltimore, MD (US); Linda Liu, Clarksville, MD (US)

(73) Assignee: Amplimmune, Inc., Gaithersburg, MD (US)

( * ) Notice: Subject to any disclaimer, the term of this patent is extended or adjusted under 35 U.S.C. 154(b) by 0 days.

(21) Appl. No.: 13/392,399

(22) PCT Filed: Aug. 31, 2010

(86) PCT No.: PCT/US2010/047384
§ 371 (c)(1),
(2), (4) Date: Feb. 24, 2012

(87) PCT Pub. No.: WO2011/026132
PCT Pub. Date: Mar. 3, 2011

(65) Prior Publication Data
US 2012/0177645 A1    Jul. 12, 2012

Related U.S. Application Data

(60) Provisional application No. 61/378,361, filed on Aug. 30, 2010, provisional application No. 61/286,537, filed on Dec. 15, 2009, provisional application No. 61/266,854, filed on Dec. 4, 2009, provisional application No. 61/254,930, filed on Oct. 26, 2009, provisional application No. 61/238,605, filed on Aug. 31, 2009.

(51) Int. Cl.
*A61K 38/16*     (2006.01)
*C07K 14/705*    (2006.01)
*C07K 16/46*     (2006.01)
*G01N 33/68*     (2006.01)
*A61K 38/17*     (2006.01)
*C07K 16/28*     (2006.01)

(52) U.S. Cl.
CPC ........ *G01N 33/6863* (2013.01); *A61K 38/1709* (2013.01); *C07K 14/70532* (2013.01); *C07K 16/2827* (2013.01); *C07K 2317/50* (2013.01); *C07K 2317/56* (2013.01); *C07K 2317/72* (2013.01); *C07K 2319/32* (2013.01); *G01N 33/6866* (2013.01); *G01N 33/6869* (2013.01); *G01N 2800/52* (2013.01)

(58) Field of Classification Search
CPC ..................... C07K 14/70532; C07K 2319/30; C07K 2319/32
See application file for complete search history.

(56) References Cited

U.S. PATENT DOCUMENTS

| | | |
|---|---|---|
| 3,840,513 A | 10/1974 | Umezawa |
| 4,272,398 A | 6/1981 | Jaffe |
| 4,376,110 A | 3/1983 | David |
| 4,634,664 A | 1/1987 | Oestberg |
| 4,634,666 A | 1/1987 | Engleman |
| 4,650,764 A | 3/1987 | Temin |
| 4,704,692 A | 11/1987 | Ladner |
| 4,769,330 A | 9/1988 | Paoletti |
| 4,853,871 A | 8/1989 | Pantoliano |
| 4,861,627 A | 8/1989 | Mathiowitz |
| 4,861,719 A | 8/1989 | Miller |
| 4,925,673 A | 5/1990 | Steiner |
| 4,946,778 A | 8/1990 | Ladner |
| 4,980,289 A | 12/1990 | Temin |
| 5,013,556 A | 5/1991 | Woodle |
| 5,120,727 A | 6/1992 | Kao |
| 5,124,263 A | 6/1992 | Temin |
| 5,155,020 A | 10/1992 | Paoletti |
| 5,162,333 A | 11/1992 | Failli |
| 5,175,099 A | 12/1992 | Wills |
| 5,202,332 A | 4/1993 | Hughes |
| 5,204,243 A | 4/1993 | Paoletti |
| 5,225,336 A | 7/1993 | Paoletti |
| 5,225,539 A | 7/1993 | Winter |
| 5,240,846 A | 8/1993 | Collins |
| 5,260,203 A | 11/1993 | Ladner |
| 5,278,056 A | 1/1994 | Bank |
| 5,283,173 A | 2/1994 | Fields |
| 5,284,656 A | 2/1994 | Platz |
| 5,304,489 A | 4/1994 | Rosen |
| 5,385,908 A | 1/1995 | Nelson |

(Continued)

FOREIGN PATENT DOCUMENTS

| | | |
|---|---|---|
| WO | 9007861 | 7/1990 |
| WO | 9110741 | 7/1991 |

(Continued)

OTHER PUBLICATIONS

Yuan et al. (Transplant. Immunology, 2009, 21: 143-149).*
Wang et al. (Transplantation, 2009, 87:482-490).*
Tandon et al. (Eye, 2009, 23: 635-639).*
Naef et al. (Respiration, 2007, 74: 418-422).*
Gandhi et al. (Current Opinion in Organ Transplantation, 2008, 13: 622-626).*
Singh et al. (Cochrane Database Syst. Rev. Oct. 7, 2009; (4):CD007848; p. 1-55).*
Miller, et al., Curr. Prot. Immunol., Unit-15.1 : 1-26 (2010) (provided by Applicant).*
Benson, et al., Current Opin. Rheumatol., 26(2)197-203 (2014) (provided by Applicant).*
Rieckmann, et al., J. Neurological Science, 277:S42-S45 (2009) (provided by Applicant).*

(Continued)

*Primary Examiner* — Ilia Ouspenski
(74) *Attorney, Agent, or Firm* — Pabst Patent Group LLP

(57) ABSTRACT

Methods for modulating immune responses in a subject are provided. A preferred embodiment provides methods and compositions for reducing or inhibiting transplant rejection in a subject, preferably a human subject. Transplant rejection can be inhibited or reduced in a subject by administering an effective amount of B7-H4 polypeptide, fragments or fusions thereof to inhibit or reduce the biological activity of an immune cell or to reduce the amounts of proinflammatory molecules at a site of transplant. Th1, Th17 and Th22 cells are exemplary T cells that can be targeted for inhibition by B7-H4 polypeptides, fusion proteins or fragments thereof to inhibit or reduce inflammation.

40 Claims, 7 Drawing Sheets

(56) References Cited

U.S. PATENT DOCUMENTS

| | | |
|---|---|---|
| 5,451,569 A | 9/1995 | Wong |
| 5,484,790 A | 1/1996 | Failli |
| 5,530,006 A | 6/1996 | Waranis |
| 5,530,101 A | 6/1996 | Queen |
| 5,545,806 A | 8/1996 | Lonberg |
| 5,559,112 A | 9/1996 | Skotnicki |
| 5,565,332 A | 10/1996 | Hoogenboom |
| 5,567,709 A | 10/1996 | Skotnicki |
| 5,569,825 A | 10/1996 | Lonberg |
| 5,585,089 A | 12/1996 | Queen |
| 5,625,126 A | 4/1997 | Lonberg |
| 5,633,425 A | 5/1997 | Lonberg |
| 5,661,016 A | 8/1997 | Lonberg |
| 5,693,761 A | 12/1997 | Queen |
| 5,693,762 A | 12/1997 | Queen |
| 5,733,743 A | 3/1998 | Johnson |
| 5,736,142 A | 4/1998 | Sette |
| 5,741,957 A | 4/1998 | Deboer |
| 5,770,429 A | 6/1998 | Lonberg |
| 5,780,462 A | 7/1998 | Lee |
| 5,789,650 A | 8/1998 | Lonberg |
| 5,814,318 A | 9/1998 | Lonberg |
| 5,821,333 A | 10/1998 | Carter |
| 5,837,242 A | 11/1998 | Holliger |
| 5,849,992 A | 12/1998 | Meade |
| 5,858,657 A | 1/1999 | Winter |
| 5,871,907 A | 2/1999 | Winter |
| 5,874,299 A | 2/1999 | Lonberg |
| 5,877,218 A | 3/1999 | Herzig |
| 5,877,397 A | 3/1999 | Lonberg |
| 5,932,448 A | 8/1999 | Tso |
| 5,989,591 A | 11/1999 | Nagi |
| 6,015,809 A | 1/2000 | Zhu |
| 6,468,546 B1 | 10/2002 | Mitcham |
| 6,537,968 B1 | 3/2003 | Lezdey |
| 6,562,576 B2 | 5/2003 | Manfredi |
| 6,790,624 B2 | 9/2004 | Mayer |
| 6,891,030 B2 * | 5/2005 | Chen .......................... 536/23.5 |
| 6,962,980 B2 | 11/2005 | Mitcham |
| 6,982,323 B1 | 1/2006 | Wang |
| 7,132,511 B2 | 11/2006 | Carr |
| 7,189,563 B2 | 3/2007 | Eaton |
| 7,202,334 B1 | 4/2007 | Mitcham |
| 7,304,149 B2 | 12/2007 | Murphy |
| 7,449,300 B2 | 11/2008 | Chen |
| 7,622,565 B2 | 11/2009 | Chen |
| 7,847,081 B2 | 12/2010 | Chen |
| 7,875,702 B2 | 1/2011 | Chen |
| 7,931,896 B2 | 4/2011 | Chen |
| 7,989,173 B2 | 8/2011 | Chen |
| 1,339,281 A1 | 2/2012 | Langerman |
| 8,129,347 B2 | 3/2012 | Chen |
| 8,236,767 B2 | 8/2012 | Chen |
| 2002/0165347 A1 | 11/2002 | Fox |
| 2002/0168762 A1 | 11/2002 | Chen |
| 2004/0152105 A1 | 8/2004 | Vogt |
| 2004/0175380 A1 | 9/2004 | Allison |
| 2004/0180047 A1 | 9/2004 | Chen |
| 2004/0229795 A1 | 11/2004 | Roemisch |
| 2005/0163772 A1 | 7/2005 | Dong |
| 2005/0202536 A1 | 9/2005 | Chen |
| 2008/0159998 A1 | 7/2008 | Ichim |
| 2008/0160036 A1 | 7/2008 | Chen |
| 2008/0177039 A1 | 7/2008 | Chen |
| 2008/0206235 A1 | 8/2008 | Chen |
| 2009/0011444 A1 | 1/2009 | Chen |
| 2009/0018315 A1 | 1/2009 | Chen |
| 2009/0022747 A1 | 1/2009 | Chen |
| 2009/0087416 A1 | 4/2009 | Chen |
| 2009/0124573 A1 | 5/2009 | Mazmanian |
| 2009/0142342 A1 | 6/2009 | Chen |
| 2011/0171207 A1 | 7/2011 | Chen |
| 2011/0195073 A1 | 8/2011 | Chen |
| 2012/0039883 A1 | 2/2012 | Chen |
| 2012/0141504 A1 | 6/2012 | Chen |

FOREIGN PATENT DOCUMENTS

| | | |
|---|---|---|
| WO | 9117271 | 11/1991 |
| WO | 9201047 | 1/1992 |
| WO | 9220791 | 11/1992 |
| WO | 9301222 | 1/1993 |
| WO | 9504738 | 2/1995 |
| WO | 9507707 | 3/1995 |
| WO | 9516691 | 6/1995 |
| WO | 9522972 | 8/1995 |
| WO | 9717613 | 5/1997 |
| WO | 9717614 | 5/1997 |
| WO | 9823635 | 6/1998 |
| WO | 9963088 | 12/1999 |
| WO | 0001385 | 1/2000 |
| WO | 0012758 | 3/2000 |
| WO | 0036107 | 6/2000 |
| WO | 0100814 | 1/2001 |
| WO | 0202587 | 1/2002 |
| WO | 0202624 | 1/2002 |
| WO | 0210187 | 2/2002 |
| WO | 2004022594 | 3/2004 |
| WO | 2004000221 | 12/2004 |
| WO | 2004113500 | 12/2004 |
| WO | 2006101487 | 9/2006 |
| WO | 2006124667 | 11/2006 |
| WO | 2006133396 | 12/2006 |
| WO | 2007039150 | 4/2007 |
| WO | 2007067681 | 6/2007 |
| WO | 2008083228 | 7/2008 |
| WO | 2008083239 | 7/2008 |
| WO | 2008138017 | 11/2008 |
| WO | 2009089036 | 7/2009 |

OTHER PUBLICATIONS

Sandborn, Curr Gastroenterol Rep., 5 (6):501-5 (2003) (provided by Applicant).*

Nepom, et al., Immunol. Rev., 241(1):49-62 (2011) (provided by Applicant).*

Adachi, "Tumoricidal effect of human macrophage-colony-stimulating factor against human-ovarian-carcinoma-bearing athymic mice and its therapeutic effect when combined with cisplatin", Cancer Immunol. Immunother. 37(1): 1-6, (1993).

Afzali, et al., "The role of T helper 17 (Th17) and regulatory T cells (Treg) in human organ transplantation and autoimmune disease", Clin Exp Immunol, 148 (1):32-46 (2007).

Aldovini, "Humoral and cell-mediated immune responses to live recombinant BCG-HIV vaccines", Nature, 351:479-482 (1991).

Alegre, et al., "Mechanisms of CTLA-4-Ig in tolerance induction", Curr Pharm Des, 12:149-60 (2006).

Alexander, et al., "Development of high potency universal DR-restricted helper epitopes by modification of high affinity DR-blocking peptides", Immunity, 1 (9):751-761 (1994).

Amoura, et al., "Nucleosome-restricted antibodies are detected before anti-dsDNA and/or antihistone antibodies in serum of MRL-Mp lpr/lpr and +/+ mice, and are present in kidney eluates of lupus mice with proteinuria", Arthritis Rheum., 37(11):1684-8 (1994).

Angal, et al., "A single amino acid substitution abolishes the heterogeneity of chimeric mouse/human (IgG4) antibody", Mol. Immunol, 30(1):105-8 (1993).

Arakawa, et al., "Formation of heterodimers from three neurotrophins, nerve growth factor, neurotrophin-3, and brain-derived neurotrophic factor", J. Biol. Chem., 269(45): 27833-39 (1994).

Attwood, "The Babel of Bioinformatics", Science Compass, 290:471-73 (2000).

Bird, "Single-chain antigen-binding proteins", Science, 242:423-426 (1988).

Blazar, et al., Infusion of anti B7.1 (CD80) and anti-B7.2 (CD86) monoclonal antibodies inhibits murine graft-versus-host disease lethality in part via direct effects on CD4+ and CD8+ T cells, J. Immunology, 157: 3250-3259 (1996).

Bona, et al.,"Immune Response : idiotype anti-idiotype network", CRC Crit. Rev. Immunol., 1:33-81 (1981)

(56) References Cited

OTHER PUBLICATIONS

Bonder, et al., "Essential role for neutrophil recruitment to the liver in concanavalin A-induced hepatitis", J. Immunol., 172(1):45-53 (2004).
Bordignon, et al., "Gene therapy in peripheral blood lymphocytes and bone marrow for ADA-immunodeficient patients", Science, 270:470-475 (1995).
Brown, et al., "Treatment of mice with the neutrophil-depleting antibody RB6-8C5 results in early development of experimental lyme arthritis via the recruitment of Fr-I-polymorphonuclear leukocyte-like cells", Infect. Immun., 72(9):4956-65 (2004).
Cassatella, "The production of cytokines by polymorphonuclear neutrophils", Immunol. Today, 16(1):21-6 (1995).
Chambers and Allison, "Co-stimulation in T cell responses", Curr. Opin. Immunol., 9:396-404 (1997).
Chapman, "A phase I trial of intraperitoneal recombinant interleukin 2 in patients with ovarian carcinoma", Investigational New Drugs, 6(3)179-188. (1988).
Chapoval, et al., "B7-H3: a costimulatory molecule for T cell activation and IFN-gamma production, Nat. Immunol., 2(3):269-74 (2001).
Chapoval, et al., "Immunoglobulin fusion proteins as a tool for evaluation of t-cell costimulatory molecules", Methods Mol. Med., 45:247-255(2000).
Chen, et al., "Impaired glucose homeostasis, neutrophil trafficking and function in mice lacking the glucose-6-phosphate transporter", Hum. Mol. Genet., 12:2547-2558 (2003).
Chen, "Co-inhibitory molecules of the B7-CD28 family in the control of T-cell Immunity", Nat. Rev. Immunol., 4(5):33647 (2004).
Chen, "Soluble TNF-alpha receptors are constitutively shed and downregulate adhesion molecule expression in malignant gliomas", J. Neuropathol. Exp. Neurol., 56(5), 541-550 (1997).
Chicz, et al., "Specificity and promiscuity among naturally processed peptides bound to HLA-DR alleles", J. Exp. Med.., 178(1):27-47 (1993).
Choi, et al., "Genomic organization and expression analysis of B7-H4, an immune inhibitory molecule of the B7 family", J. Immunol, 171:4650-4 (2003).
Co, et al., "Chimeric and humanized antibodies with specificity for the CD33 antigen", J. Immunol. 148(4):1149-1154 (1992).
Coyle, et al., "The CD28-related molecule ICOS is required for effective T cell-dependent immune responses", Immunity, 13(1):95-105 (2000).
Coyle, et al., "The expanding B7 superfamily: increasing complexity in costimulatory signals regulating T cell function", Nat. Immunol., 2(3):203-9 (2001).
Crystal, "Gene therapy strategies for pulmonary disease", Am. J. Med., 92 (6A):44S-52S (1992).
Dau, et al., The fundamental basis for therapeutic plasmapheresis in autoimmune diseases, Transfusion Sci., 17(2):235-44 (1996).
De Oca, et al., "Polymorphonuclear neutrophils are necessary for the recruitment of CD8(+) T cells in the liver in a pregnant mouse model of *Chlamydophila abortus* (*Chlamydia psittaci* serotype I) infection", Infect. Immun., 68(3):1746-51 (2000).
Dong, et al., "B7-H1, a third member of the B7 family, co-stimulates T-cell proliferation and interleukin-10 secretion", Nat. Med., 5:1365-69 (1999).
Dong, et al., "B74-H1 determines accumulation and deletion of intrahepatic CD8 (+) T lymphocytes", Immunity, 20:327-336 (2004).
Dong, et al., "Costimulating aberrant T cell responses by B7-H1 autoantibodies in rheumatoid arthritis", J. Clin. Invest., 111(3):363-70 (2003).
Dong, et al., "Immune regulation by novel costimulatory molecules", Immunol. Res., 28:39-48 (2003).
Dong, et al., "Tumor-associated B7-H1 promotes T-cell apoptosis: a potential mechanism of immune evasion", Nature Med., 8:793-800 (2002).
Edwards, et al., "Comparison of toxicity and survival following intraperitoneal recombinant interleukin-2 for persistent ovarian cancer after platinum: twenty-four-hour versus 7-day infusion", J. Clin. Oncol., 15(11):3399-3407 (1997).
Edwards, "The formation of a structure with the features of synovial lining by subcutaneous injection of air: an in vivo tissue culture system", J. Pathol., 134:147-156 (1981).
Emamaullee, et al., "Costimulatory blockade with belatacept in clinical and experimental transplantation—a review", Expert Opin. Biol. Ther. 9(6):789-96 (2009).
Eyles, et al., "Granulocyte colony-stimulating factor and neutrophils—forgotten mediators of inflammatory disease", Nat. Clin. Pract. Rheumatol., 2(9):500-1 0 (2006).
Faas, et al., "Primary structure and functional characterization of a soluble, alternatively spliced form of B7-1", J. Immunol., 164(12):6340-8 (2000).vbTab.
Falk, et al., "Pool sequencing of natural HLA-DR, DQ, and DP ligands reveals detailed peptide motifs, constraints of processing, and general rules", Immunogenetics, 39(4):230-242 (1994).
Fava, et al., "Critical role of peripheral blood phagocytes and the involvement of complement in tumour necrosis factor enhancement of passive collagen-arthritis", Clin. Exp. Immuno., 94(2): 261-8 (1993).
Feldmann, "Rheumatoid arthritis", Cell, 85(3):307-10 (1996).
Fink, "Monoclonal antibodies as diagnostic reagents for the identification and characterization of human tumor antigens", Prog. Clin. Pathol., 9:121-133 (1984).
Flies, et al., "Cutting edge: A monoclonal antibody specific for the programmed death-1 homolog prevents graft-versus-host disease in mouse models", J Immunol., 187:1537-41 (2011).
Freedman, et al., "Intraperitoneal adoptive immunotherapy of ovarian carcinoma with tumor-infiltrating lymphocytes and low-dose recombinant interleukin-2: a pilot trial", J. of Immunotherapy Emphasis Tumor Immunol., 16(3):198-210 (1994).
Freeman, et al., "Engagement of the PD-1 immunoinhibitory receptor by a novel B7 family member leads to negative regulation of lymphocyte activation", J. Exp. Med., 192(7):1027-34 (2000).
Gandhi, et al., "Costimulation targeting therapies in organ transplantation", Curr Opin Organ Transplant, 13:622-26 (2008).
Genbank Accession No. AY280972.1 "*Homo sapiens* immune costimulatory protein B7-H4 mRNA, complete cds", 2 pages, submitted Apr. 22, 2003, first published Jun. 1, 2003, accessed Feb. 18, 2009.
Genbank Accession No. NM_178594, "*Mus musculus* V-set domain containing T cell activation inhibitor 1 (Vtcn1), mRNA" , 4 pages, submitted Oct. 1, 2009 , updated Mar. 26, 2012, accessed May 15, 2012.
Guatelli, "Isothermal, in vitro amplification of nucleic acids by a multienzyme reaction modeled after retroviral replication", Proc. Natl. Acad. Sci. USA, 87 (5):1874-1878 (1990).
Guo, et al., "All-trans retinol, vitamin D and other hydrophobic compounds bind in the axial pore of the five-stranded coiled-coil domain of cartilage oligomeric matrix protein", EMBO J., 17: 5265-72 (1998).
Halloran, et al., "The role of an epithelial neutrophil-activating peptide-78-like protein in rat adjuvant-induced arthritis", J. Immunol., 162(12):7492-500 (1999).
Hammer, et al., "Promiscuous and allele-specific anchors in HLA-DR-binding peptides", Cell, 74(1):197-203 (1993).
Healy, et al., "Neutrophil transendothelial migration potential predicts rejection severity in human cardiac transplantation", Eur J Cardiothorac Surg, 29:760-6 (2006).
Henikoff, "Amino acid substitution matrices from protein blocks", Proc. Natl. Acad. Sci. U.S.A., 89:10915-10919 (1992).
Hickman, "Gene expression following direct injection of DNA into liver", Hum. Gene Ther., 5:1477-1483 (1994).
Hill, et al., "A field guide to foldamers", Chem Rev., 101(12):3893-4012 (2001).
Hochman, "An active antibody fragment (Fv) composed of the variable portions of heavy and light chains", Biochemistry, 12:1130-1135 (1973).
Hoiseth and Stocker, "Aromatic-dependent *Salmonella typhimurium* are non-virulent and effective as live vaccines", Nature, 291, 238-239 (1981).

(56) References Cited

OTHER PUBLICATIONS

Hu, et al., "WD-40 repeat region regulates Apaf-1 self-association and procaspase-9 activation", J Biol Chem., 273:33489-94 (1998).
Huang, "Structural chemistry and therapeutic intervention of protein-protein interactions in immune response, human immunodeficiency virus entry, and apoptosis," Pharmacology and Therapeutics, 86: 201-15 (2000).
Hubbard, et al., "Anti-neutrophil-elastase defenses of the lower respiratory tract in alpha 1-antitrypsin deficiency directly augmented with an aerosol of alpha 1-antitrypsin", Ann. Intern. Med., 111(3):206-12 (1989).
Huse, "Generation of a large combinatorial library of the immunoglobulin repertoire in phage lambda", Science, 246(4935):1275-1281 (1989).
Huston, "Protein engineering of antibody binding sites: recovery of specific activity in an anti-digoxin single-chain Fv analogue produced in *Escherichia coli*", Proc. Natl. Acad. Sci. USA, 85:5879-5883 (1988).
Hyrup, et al., "Peptide nucleic acids (PNA): synthesis, properties and potential applications", Bioorgan. Med. Chem. 4:5-23 (1996).
Ikonomidis, "Delivery of a viral antigen to the class I processing and presentation pathway by *Listeria monocytogenes*", J. Exp. Med., 180:2209-2218 (1994).
Jablonska and Peitruska, "Release of soluble tumor necrosis factor receptors from polymorphonuclear cells of breast cancer patients", Arch. Immunol. Ther. Exp. (Warsz), 45 (5-6), 449-453 (1997).
Jeannin, et al., "Soluble CD86 is a costimulatory molecule for human T lymphocytes", Immunity, 13(3):303-12 (2000).
Jerne, "Towards a network theory of the immune system" Ann. Immunol., 125C:373-389 (1974).
Jost, "Mammalian expression and secretion of functional single-chain Fv molecules", J Biol Chem., 269:26267-26273 (1994).
Kakimoto, et al., "Suppressive effect of a neutrophil elastase inhibitor on the development of collagen-induced arthritis", Cell Immunol, 165(1):26-32 (1995).
Kamata, et al., "src homology 2 domain-containing tyrosine phosphatase SHP-1 controls the development of allergic airway inflammation", J. Clin. Invest., 111:109-119 (2003).
Katahira, et al., "Complex formation between Tap and p15 affects binding to FG-repeat nucleoporins and nucleocytoplasmic shuttling", J. Biol. Chem., 277:9242-6 (2002).
Keir and Sharpe, "The B7/CD28 costimulatory family in autoimmunity", Immunol. Rev., 204:128-43 (2005).
Keliey and Roths, "Interaction of mutant lpr gene with background strain influences renal disease", Clin. Immuno. Immunopathol., 37(2):220-9 (1985).
Kikuchi, "Effects of granulocyte-colony-stimulating factor and interleukin-2 on ascites formation and the survival time of nude mice bearing human ovarian cancer cells", Cancer Immunol. Immunother., 43(5): 257-261 (1996).
Kim, et al., "Clustering of Shaker-type K+ channels by interaction with a family of membrane-associated guanylate kinases", Nature, 378: 85-8 (1995).
Kinoshita, et al., "Costimulation by B7-1 and B7-2 is required for autoimmune disease in MRL-Faslpr mice", J. Immunol., 164(11):6046-56 (2000).
Knapp and Liu, "Hydrodynamic delivery of DNA", Methods Mol. Bio., 245:245-50 (2004).
Kohler and Milstein, "Continuous cultures of fused cells secreting antibody of predefined specificity", Nature, 256:495-497 (1975).
Komau, et al., "Domain interaction between NMDA receptor subunits and the postsynaptic density protein PSD-95", Sci., 269:1737-40 (1995).
Kotzin, "Systemic lupus erythematosus", Cell, 85(3), 303-6 (1996).
Krambeck, et al., "B7-H4 expression in renal cell carcinoma and tumor vasculature: associations with cancer progression and survival", Proc. Natl. Acad. Sci. USA, 103 (27):10391-10396 (2006).
Krummel and Allison, "CTLA-4 engagement inhibits IL-2 accumulation and cell cycle progression upon activation of resting T cells", J. Exp. Med., 183:2533-40 (1996).

Kryczek, et al., "B7-H4 expression identifies a novel suppressive macrophage population in human ovarian carcinoma", J Exp. Med., 203:871-881 (2006).
Kryczek, et al., "Cutting edge: Induction of B7-H4 on APCs through IL-10: Novel suppressive mode for regulatory T cells", J. Immunol., 177(1):40-44 (2006).
Latchman, et al., "PD-L2 is a second ligand for PD-1 and inhibits T cell activation", Nature Immunol., 2:261-8 (2001).
Lenshow, et al., "CD28/B7 system of T cell costimulation", Annu. Rev, Immunol., 14:233-58 (1996).
Lewis, "PCRs Competitors Are Alive and Well and Moving Rapidly Towards Commercialization", Genetic Engineering News 12:1-3 (1992).
Li, et al., "Biochemical analysis of the regulatory T cell protein lymphocyte activation gene-3 (LAG-3 CD223)", J. Immunol., 173(11):6806-1 2 (2004).
Liang, et al. "Autoantibody responses and pathology regulated by B7-1 and B7-2 costimulation in MRL/lpr lupus", J. Immunol., 165(6):3436-43 (2000).
Lissoni, "Intracavitary administration of interleukin-2 as palliative therapy for neoplastic effusions", Tumori, 78(2)118-120 (1992).
Liu, "Cationic transfection lipids", Curr. Med. Chem., 10:1307-1315 (2003).
Lowenstein, "Simultaneous detection of amplicon and HSV-1 helper encoded proteins reveals that neurons and astrocytoma cells do express amplicon-borne transgenes in the absence of synthesis of virus Immediate early proteins", Brain Res. Molec. Brain Res, 30:169-175 (1995).
Malashkevich, et al., "The crystal structure of a five-stranded coiled coil in COMP: a prototype ion channel", Science, 274: 761-5 (1996).
Malchesky, et al., "Are selective macromolecule removal plamapheresis systems useful for autoimmune diseases or hyperlipidemia?", ASAIO J., 39 (4):868-72 (1993).
Mathiowitz, "Novel microcapsules for delivery systems", Reactive Polymers, 6:275-283 (1987).
Mathiowitz, "Polyanhydride microspheres as drug carriers. II. microencapsulation by solvent removal", J. Appl. Polymer Sol., 35:755-774 (1988).
Mathiowitz and Langer, "Polyanhydride microspheres as drug carriers. I. Hot-melt microencapsulation", J. Controlled Release, 5:13-22 (1987).
Matta, et al., "IL-27 production and STAT3-dependent upregulation of B7-H1 mediate immune regulatory functions of liver plasmacytoid dendritic cells", J Immunol., 188:5227-37 (2012).
McColl, et al., "Treatment with anti-granulocyte antibodies inhibits the effector phase of experimental autoimmune encephalomyelitis", J. Immunol., 161(11), 6421-6 (1998).
McGrath and Nader, "The role of coinhibitory signaling pathways in transplantation and tolerance", Frontiers in Immunol., 3(47):1-17 (2012).
Medina, et al. "Therapeutic effect of phenantroline in two rat models of inflammatory bowel disease", Scand J Gastroenterol., 36(12):1314-9 (2001).
Metzler, et al., "Solution structure of human CTLA-4 and delineation of a CD80/CD86 binding site conserved in CD28", Nat. Struct. Biol., 4(7):527-31 (1997).
Michael, et al., "The hematologic aspects of disseminated (systemic) lupus erythematosus", Blood, 6(11):1059-72 (1951).
Moreland, et al., "Treatment of rheumatoid arthritis with a recombinant human tumor necrosis factor receptor (p75)-Fc fusion protein", N. Engl. J. Med., 337:141-7 (1997).
Moss, "Poxvirus expression vectors", Curr. Top. Microbial. Immunol, 158:25-38 (1992).
Moss, "Poxvirus vectors: cytoplasmic expression of transferred genes", Curr. Opin. Genet. Dev., 3:86-90 (1993).
Moss, "Use of vaccinia virus as an infectious molecular cloning and expression vector", Gene Amplif Anal 3:201-213 (1983).
Moss, "Vaccinia virus: a tool for research and vaccine development", Science, 252:1662-1667 (1991).
Moss, "Vaccinia virus vectors", Biotechnology, 20: 345-362 (1992).

(56) References Cited

OTHER PUBLICATIONS

Mueller, et al., "Humanized porcine VCAM-specific monoclonal antibodies with chimeric IgG2/G4 constant regions block human leukocyte binding to porcine endothelial cells", Molecular Immonology, 34(6): 441-52 (1997).
Murphy, "Long-term correction of obesity and diabetes in genetically obese mice by a single intramuscular injection of recombinant adeno-associated virus encoding mouse leptin", Proc Natl Acad Sci., 94:13921-13926 (1997).
Nandakumar, et al., "Collagen type II-specific monoclonal antibody-induced arthritis in mice: description of the disease and the influence of age, sex, and genes", Am. J. Pathol., 163(5), 1827-37 (2003).
Nathan, "Neutrophils and immunity: challenges and opportunities", Nature Rev. Immunol., 6:173-182 (2006).
Needleman and Wunsch, "A general method applicable to the search for similarities in the amino acid sequence of two proteins", J. Mol. Biol., 48:443-453 (1970).
Newmark, et al., "Preparation and properties of adducts of streptokinase and streptokinase-plasmin complex with polyethylene glycol and pluronic Polyol F38", J. Appl. Biochem., 4:185-189 (1982).
Ostberg et al., "Human X (mouse X human) hybridomas stably producing human antibodies", Hybridoma, 2:361-367 (1983).
Ottow, et al., "Immunotherapy of intraperitoneal cancer with interleukin 2 and lymphokine-activated killer cells reduces tumor load and prolongs survival in murine models" Cellular Immunology, 104:366-376 (1987).
Ou, et al., "B7-H4.Ig inhibits human beta-cell destruction mediated by beta cell-specific cytotoxic T cells derived from patients with type 1 diabetes", 54(Suppl. 1): A311 (2005).
O\Brien, "An improved method of preparing microcarriers for biolistic transfection", Brain Res, Brain Res. Protco., 10:12-15 (2002).
Parra and Bond, "Inverse agonism: from curiosity to accepted dogma, but is it clinically relevant?", Curr. Opin. Pharmacol., 7(2):146-50 (2007).
Paterson, et al., "The programmed deth-1 ligand 1:B7-1 pathway restrains diabetogenic effector T cells in vivo", J Immunol., 187(3):1097-1105 (2011).
Peplinski, "Vaccinia virus for human gene therapy", Surgical Oncology Clinics of North America, 7: 575-588 (1998).
Piccini and Paoletti, "Vaccinia: virus, vector, vaccine", Adv. Virus Res., 34:43-64 (1988).vbTab.
Pillai, et al. "Overview of immunosuppression in liver transplantation", World J Gastroenterol, 15(34): 4225-33 (2009).
Pillinger and Abramson, "The neutrophil in rheumatoid arthritis", Rheum. Dis. Clin. North. Am., 21(3):691-714 (1995).
Pluckthun, "Expression of functional antibody Fv and Fab fragments in *Escherichia coli*", Methods Enzymol., 178: 497-515 (1989)
Poirier, "Protective immunity evoked by oral administration of attenuated aroA *Salmonella typhimurium* expressing cloned streptococcal M protein", J. Exp. Med., 168:25-32 (1988).
Prasad, et al., "B7S1, a novel B7 family member that negatively regulates T cell activation", Immunity, 18(6):863-873 (2003).
Queen, et al., "A humanized antibody that binds to the interleukin 2 receptor", Proc. Natl. Acad. Sci. USA, 86(24)10029-10033 (1989).
Queen, et al., "Cell-type specific regulation of a kappa immunoglobulin gene by promoter and enhancer elements", Immunol. Rev., 89:49 (1986).
Quismorio, "Hemotalogica and lymphoid abnormalities in systemic lupus etythematosus" in Dubio\s Lupus Erythematosus, (eds. Wallace and Han), Lippincott & Williams:Phillidephia, PA, pp. 793-819 (2002).
Radsak, et al., "The heat shock protein Gp96 binds to human neutrophils and monocytes and stimulates effector functions", Blood, 101:2810-2815 (2003).
Radsak, et al., "Triggering receptor expressed on myeloid cells-1 in neutrophil inflammatory responses: differential regulation of activation and survival", J. Immunol., 172:4956-4963 (2004).

Radziejewski, et al., "Heterodimers of the neurotrophic factors: formation, isolation, and differential stability", Biochem., 32(48): 13350-6 (1993).
Rajewsky, "Genetics, expression, and function of idiotypes", Ann. Rev. Immunol., 1:569-607 (1983).
Rathmell and Thompson, "The central effectors of cell death in the immune system", Annu. Rev. Immunol., 17:781-828 (1999).
Reynolds, "Chimeric viral vectors—the best of both worlds", Molecular Medicine Today, 5:25-31 (1999).
Rousseaux, "Optimal conditions for the preparation of proteolytic fragments from monoclonal IgG of different rat IgG subclasses", Meth. Enzymol., 121:663-69 (1986).
Sadoff, "Oral *Salmonella typhimurium* vaccine expressing circumsporozoite protein protects against malaria", Science, 240:336-338 (1988).
Salceda, et al. "The immunomodulatory protein B7-H4 is overexpressed in breast and ovarian cancers and promotes epithelial cell transformation", Exp. Cell Res., 306(1)128-41 (2005).
Samulski, "Targeted integration of adeno-associated virus (AAV) into human chromosome 19", EMBO J., 10:3941-3950 (1991).
Santos, et al., "Anti-neutrophil monoclonal antibody therapy inhibits the development of adjuvant arthritis", Clin. Exp. Immunol., 107(2):24-53 (1997).
Scapini, et al., "The neutrophil as a cellular source of chemokines", Immunol. Rev., 177: 195-203 (2000).
Schafer, et al., "Induction of a cellular immune response to a foreign antigen by a recombinant *Listeria monocytogenes* vaccine", J. Immunol., 149:53-59 (1992).
Schimmer, et al., "Streptococcal cell wall-induced arthritis. Requirements for neutrophils, P-selectin, intercellular adhesion molecule-I, and macrophage-inflammatory protein-2", J. Immunol., 159(8):4103-8 (1997).
Sharon, et al., "Preparation of Fv fragment from the mouse myeloma XRPC-25 immunoglobulin possessing anti-dinitrophenyl activity", Biochemistry, 15:1591-1594 (1976).
Sica, et al., "B7-H4, a molecule of the B7 family, negatively regulates T cell immunity", Immunity, 18:849-861 (2003).
Simon, et al., "B7-H4 is a novel membrane-bound protein and a candidate serum and tissue biomarker for ovarian cancer", Cancer Res., 66(3):1570-1575 (2006).
Sinigaglia, et al., "A malaria T-cell epitope recognized in association with most mouse and human MHC class II molecules", Nature, 336(6201):778-780 (1988).
Skerra, "Assembly of a functional immunoglobulin Fv fragment in *Escherichia coli*", Science, 240: 1038-1041 (1988).
Skolnick, et al., "From genes to protein structure and function: novel applications of computational approaches in the genomic era", Trends Biotechnol., 18(1):34-9 (2000).
Son, "Cisplatin-based interferon gamma gene therapy of murine ovarian carcinoma", Cancer Gene Therapy, 4(6):391-396 (1997).
Soriano, "Targeted and nontargeted liposomes for in vivo transfer to rat liver cells of a plasmid containing the preproinsulin I gene", Proc. Natl. Acad. Sci. USA, 80:7128-7131 (1983).
Southwood, et al., "Several common HLA-DR types share largely overlapping peptide binding repertoires", J. Immunology, 160(7):3363-3373 (1998).
Sparano, et al., "Phase II trials of high-dose interleukln-2 and lymphokine-activated killer cells in advanced breast carcinoma and carcinoma of the lung, ovary, and pancreas and other tumors", J. of Immunotherapy Emphasis Tumor Immunol., 16(3):216.223 (1994).
Stavenhagen, et al., "Fc optimization of therapeutic antibodies enhances their ability to kill tumor cells in vitro and controls tumor expansion in vivo via low-affinity activating Fcgamma receptors", Cancer Res., 57(18):8882-90 (2007).
Stone, "Viral vectors for gene delivery and gene therapy within the endocrine system", J. Endocrinology, 164:103-118 (2000).
Stover, "New use of BCG for recombinant vaccines", Nature, 351:456-460 (1991).
Sudol, "Structure and function of the WW domain", Prog. Biophys. Mol. Bio., 65:113-32 (1996).
Sugaya, "Inhibition of tumor growth by direct intratumoral gene transfer of herpes simplex virus thymidine kinase gene with DNA-liposome complexes", Hum. Gene Ther., 7(2):223-230 (1996).

(56) References Cited

OTHER PUBLICATIONS

Suh, et al., "Generation and characterization of B7-H4/B7S1/B7x-deficient mice", Mol. Cell. Biol., 26:6403-6411 (2006).
Summerton and Weller, "Morpholino antisense oligomers: design, preparation, and properties", Antisense Nucleic Acid Drug Dev. 7:187-95 (1997).
Sun, et al., "B7-H3 and B7-H4 expression in non-small-cell lung cancer", Lung Cancer, 53 (2):143-151 (2006).
Sun, et al., "Costimulatory molecule-targeted antibody therapy of a spontaneous autoimmune disease", Nat. Med. 8(12):1405-13 (2002).
Swallow, et al., "B7h, a novel costimulatory homolog of B7.1 and B7.2, is induced by TNFalpha", Immunity, 11:423-432 (1999).
Szala, "The use of cationic liposomes DC-CHOL/DOPE and DDAB/DOPE for direct transfer of *Escherichia coli* cytosine deaminase gene into growing melanoma tumors", Gene Therapy, 3(11): 1026-1031 (1996).
Tada, et al., "CD28-deficient mice are highly resistant to collagen-induced arthritis", J. Immunol., 162(1):203-8 (1999).
Tamada, et al., "Cutting edge: selective impairment of CD8+ T cell function in mice lacking the TNF superfamily member LIGHT", J Immunol., 168:4832-4835 (2002).
Tamada, et al., "Modulation of T-cell-mediated immunity in tumor and graft-versus-host disease models through the LIGHT co-stimulatory pathway", Nature Med., 6:283-289 (2000).
Tamura, et al., "B7-H1 costimulation preferentially enhances CD28-independent T-helper cell function", Blood, 97:1809-1816 (2001).
Titomirov, "In vivo electroporation and stable transformation of skin cells of newborn mice by plasmid DNA", Biochim. Biophys. Acta., 1088:131-134 (1991).
Tringler, et al., "B7-H4 is highly expressed in ductal and lobular breast cancer", Clin. Cancer Res., 11(5):1842-1848 (2005).
Tringler, et al., "B7-H4 overexpression in ovarian tumors", Gynecol, Oncol., 100(1):44-52 (2006).
Tseng, et al., " B7-DC, a new dendritic cell molecule with potent costimulatory properties for T cells", J. Exp. Med., 193:839-846 (2001).
Tsushima, et al., "Preferential contribution of B7-H1 to programmed death-1-mediated regulation of hapten-specific allergic inflammatory responses", Eur. J. Immunol., 33:2773-2782 (2003).
Urbain, "Idiotypes, recurrent idiotypes and internal images", Ann. Immunol. 133D(2):179-189 (1982).
Vidal, et al., "Design of peptoid analogue dimers and measure of their affinity for Grb2 SH3 domains", Biochemistry, 43, 7336-44 ((2004).
Vincennti, et al., "Costimulation blockade in autoimmunity and transplantation", Allergy Clin Immunol, 121(2):299-306 (2008).
Wahl, "Improved radioimaging and tumor localization with monoclonal F(ab')2", J. Nuc. Med. 24:316-325 (1983).
Walunas, et al., "CTLA-4 ligation blocks CD28-dependent T cell activation", J. Exp. Med., 183:2541-50 (1996).
Wan, et al., "Aberrant regulation of synovial T cell activation by soluble costimulatory molecules in rheumatoid arthritis", J.Immunol., 177(12):8844-50 (2006).

Wang, et al., "B7-H4 pathway in islet transplantation and $2$-cell replacement therapies", J Transplant., Article ID 418902:1-8 (2011).
Wang, et al., "Costimulation of T cells by B7-H2, a B7-like molecule that binds ICOS", Blood, 96:2808-13 (2000).
Wang and Huang, "pH-sensitive immunoliposomes mediate target-cell-specific delivery and controlled expression of a foreign gene in mouse", Proc. Natl. Acad. Sci. USA, 84:7851 (1987).
Watanabe, et al., "BTLA is a lymphocyte inhibitory receptor with similarities to CTLA-4 and PD-1", Nature Immunol., 4(7):670-679 (2006).
Weiss, "Hot prospect for new gene amplifier", Science 254:1292-1293 (1991).
Weiss and Taylor, "Retrovirus receptors", Cell, 82:531-533 (1995).
Wilcox, et al., "Ligation of CD137 receptor prevents and reverses established anergy of CD8+ cytolytic T lymphocytes in vivo", Blood, 103:177-184 (2004).
Williams, et al., "Synergy between anti-CD4 and anti-tumor necrosis factor in the amelioration of established collagen-induced arthritis", Proc. Natl. Acad. Sci. U. S. A., 91:2762-6 (1994).
Wilson, "Hepatocyte-directed gene transfer in vivo leads to transient improvement of hypercholesterolemia in low density lipoprotein receptor-deficient rabbits", J. Biol. Chem., 267:963-967 (1992).
Winter, "Man-made antibodies", Nature, 349:293-299 (1991).
Wipke and Allen, "Essential role of neutrophils in the initiation and progression of a murine model of rheumatoid arthritis", J. Immunol., 167(3)1601-8 (2001).
Wolff, "Direct gene transfer into mouse muscle in vivo", Science, 247:1465-1468 (1990).
Wong, "Human GM-CSF: molecular cloning of the complementary DNA and purification of the natural and recombinant proteins", Science, 228(4701):810-815 (1985).
Wu, "Receptor-mediated gene delivery and expression in vivo", J. Biol. Chem., 263:14621-14624 (1988).
Wu, "Targeting genes: delivery and persistent expression of a foreign gene driven by mammalian regulatory elements in vivo", J. Biol. Chem., 264:16985-16987 (1989).
Yang, et al., "The novel costimulatory programmed death ligand 1/B7.1 pathway is functional in inhibiting alloimmune responses in vivo", J Immunol., 187:1113-19 (2011).
Yoshinaga, et al., "T-cell co-stimulation through B7RP-1 and ICOS", Nature, 402:827-32 (1999).
Yu, "Liposome-mediated in vivo E1A gene transfer suppressed dissemination of ovarian cancer cells that overexpress HER-2/neu", Oncogene, 11(7):1383-1388 (1995).
Yuan, et al., "B7-H4 transfection prolongs beta-cell graft survival", Transplant Immun., 21(3):143-9 (2009).
Zakaria, et al., "Plasmapheresis in severe autoimmune hepatitis", Hepatology, 34(4):A529 (2001).
Zang, et al., "B7x: A widely expressed 87 family member that inhibits T cell activation", Proc. Natl. Acad. Sci. USA, 100(18):10388-10392 (2003).
Zhou, et al., "Structure and ligand recognition of the phosphotyrosine binding domain of Shc", Nature, 378:584-92 (1995).

\* cited by examiner

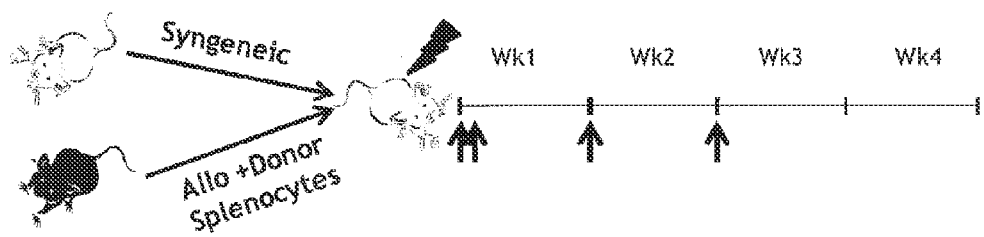
4 groups:
- Syngeneic BM transplants
- Allo BM transplants, control IgG, 0.5 mg, Day 0, 1, 7 and 14
- Allo BM transplants, B7-H4-Ig, 0.5 mg, Day 0, 1, 7 and 14
- Allo BM transplants, PBS, Day 0, 1, 7 and 14
*FIG. 3*
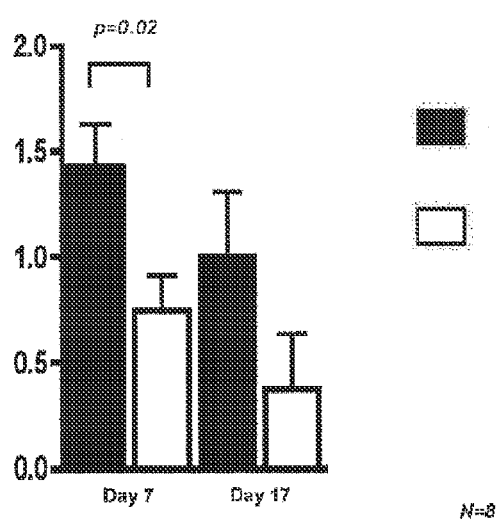
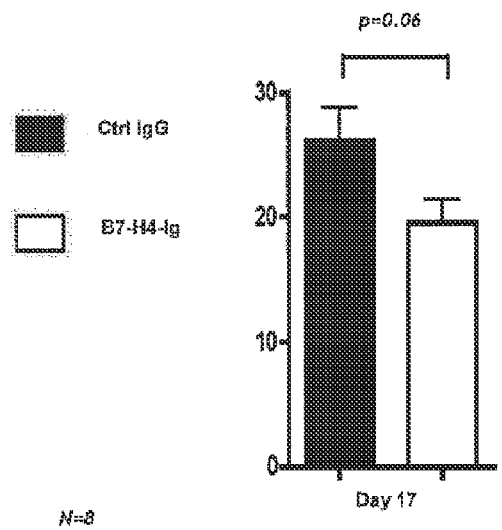
*FIG. 4A*  *FIG. 4B*

SEQUENCE LISTING

```
<160> NUMBER OF SEQ ID NOS: 141

<210> SEQ ID NO 1
<211> LENGTH: 852
<212> TYPE: DNA
<213> ORGANISM: Mus musculus

<400> SEQUENCE: 1
atggcttcct tggggcagat catcttttgg agtattatta acatcatcat catcctggct      60
ggggccatcg cactcatcat tggctttggc atttcaggca agcacttcat cacggtcacg     120
accttcacct cagctggaaa cattggagag gacgggaccc tgagctgcac ttttgaacct     180
gacatcaaac tcaacggcat cgtcatccag tggctgaaag aaggcatcaa aggtttggtc     240
cacgagttca agaaggcaa agacgacctc tcacagcagc atgagatgtt cagaggccgc      300
acagcagtgt ttgctgatca ggtggtagtt ggcaatgctt ccctgagact gaaaaacgtg     360
cagctcacgg atgctggcac ctacacatgt tacatccgca cctcaaaagg caagggaat      420 gcaaaccttg agtataagac cggagccttc agtatgccag agataaatgt ggactataat     480
gccagttcag agagtttacg ctgcgaggct cctcggtggt tcccccagcc cacagtggcc     540
tgggcatctc aagtcgacca aggagccaat ttctcagaag tctccaacac cagctttgag    600
ttgaactctg agaatgtgac catgaaggtc gtatctgtgc tctacaatgt cacaatcaac     660
aacacatact cctgtatgat tgaaaacgac attgccaaag ccaccgggga catcaaagtg     720
acagattcag aggtcaaaag gcgaagtcag ctgcagttgc tgaactctgg gccttccccg     780 tgtgttttt cttctgcctt tgtggctggc tgggcactcc tatctctctc ctgttgcctg      840
```

```
atgctaagat ga                                                      852
```

```
<210> SEQ ID NO 2
<211> LENGTH: 283
<212> TYPE: PRT
<213> ORGANISM: Mus musculus

<400> SEQUENCE: 2
```

| | | | | | | | | | | | | | | | |
|---|---|---|---|---|---|---|---|---|---|---|---|---|---|---|---|
| Met | Ala | Ser | Leu | Gly | Gln | Ile | Ile | Phe | Trp | Ser | Ile | Ile | Asn | Ile | Ile |
| 1 | | | | 5 | | | | | 10 | | | | | 15 | |
| Ile | Ile | Leu | Ala | Gly | Ala | Ile | Ala | Leu | Ile | Ile | Gly | Phe | Gly | Ile | Ser |
| | | | 20 | | | | 25 | | | | 30 | | | | |
| Gly | Lys | His | Phe | Ile | Thr | Val | Thr | Phe | Thr | Ser | Ala | Gly | Asn | Ile | |
| | | 35 | | | | 40 | | | | 45 | | | | | |
| Gly | Glu | Asp | Gly | Thr | Leu | Ser | Cys | Thr | Phe | Glu | Pro | Asp | Ile | Lys | Leu |
| | 50 | | | | 55 | | | | 60 | | | | | | |
| Asn | Gly | Ile | Val | Ile | Gln | Trp | Leu | Lys | Glu | Gly | Ile | Lys | Gly | Leu | Val |
| 65 | | | | 70 | | | | 75 | | | | | | 80 | |
| His | Glu | Phe | Lys | Glu | Gly | Lys | Asp | Asp | Leu | Ser | Gln | Gln | His | Glu | Met |
| | | | 85 | | | | 90 | | | | | 95 | | | |
| Phe | Arg | Gly | Arg | Thr | Ala | Val | Phe | Ala | Asp | Gln | Val | Val | Val | Gly | Asn |
| | | 100 | | | | 105 | | | | 110 | | | | | |
| Ala | Ser | Leu | Arg | Leu | Lys | Asn | Val | Gln | Leu | Thr | Asp | Ala | Gly | Thr | Tyr |
| | 115 | | | | 120 | | | | 125 | | | | | | |
| Thr | Cys | Tyr | Ile | Arg | Ser | Ser | Lys | Gly | Lys | Gly | Asn | Ala | Asn | Leu | Glu |
| 130 | | | | 135 | | | | 140 | | | | | | | |
| Tyr | Lys | Thr | Gly | Ala | Phe | Ser | Met | Pro | Glu | Ile | Asn | Val | Asp | Tyr | Asn |
| 145 | | | | 150 | | | | 155 | | | | | | 160 | |
| Ala | Ser | Ser | Glu | Ser | Leu | Arg | Cys | Glu | Ala | Pro | Arg | Trp | Phe | Pro | Gln |
| | | | 165 | | | | 170 | | | | 175 | | | | |
| Pro | Thr | Val | Ala | Trp | Ala | Ser | Gln | Val | Asp | Gln | Gly | Ala | Asn | Phe | Ser |
| | | 180 | | | | 185 | | | | 190 | | | | | |
| Glu | Val | Ser | Asn | Thr | Ser | Phe | Glu | Leu | Asn | Ser | Glu | Asn | Val | Thr | Met |
| | 195 | | | | 200 | | | | 205 | | | | | | |
| Lys | Val | Val | Ser | Val | Leu | Tyr | Asn | Val | Thr | Ile | Asn | Asn | Thr | Tyr | Ser |
| 210 | | | | 215 | | | | 220 | | | | | | | |
| Cys | Met | Ile | Glu | Asn | Asp | Ile | Ala | Lys | Ala | Thr | Gly | Asp | Ile | Lys | Val |
| 225 | | | | 230 | | | | 235 | | | | | | 240 | |
| Thr | Asp | Ser | Glu | Val | Lys | Arg | Arg | Ser | Gln | Leu | Gln | Leu | Leu | Asn | Ser |
| | | | 245 | | | | 250 | | | | 255 | | | | |
| Gly | Pro | Ser | Pro | Cys | Val | Ser | Ser | Ala | Phe | Val | Ala | Gly | Trp | Ala | |
| | | 260 | | | | 265 | | | | 270 | | | | | |
| Leu | Leu | Ser | Leu | Ser | Cys | Cys | Leu | Met | Leu | Arg | | | | | |
| | 275 | | | | 280 | | | | | | | | | | |

```
<210> SEQ ID NO 3
<211> LENGTH: 275
<212> TYPE: PRT
<213> ORGANISM: Mus musculus

<400> SEQUENCE: 3
```

| | | | | | | | | | | | | | | | |
|---|---|---|---|---|---|---|---|---|---|---|---|---|---|---|---|
| Met | Glu | Trp | Ser | Trp | Val | Phe | Leu | Phe | Phe | Leu | Ser | Val | Thr | Thr | Gly |
| 1 | | | | 5 | | | | | 10 | | | | | 15 | |
| Val | His | Ser | Gly | Phe | Gly | Ile | Ser | Gly | Lys | His | Phe | Ile | Thr | Val | Thr |
| | | | 20 | | | | 25 | | | | 30 | | | | |
| Thr | Phe | Thr | Ser | Ala | Gly | Asn | Ile | Gly | Glu | Asp | Gly | Thr | Leu | Ser | Cys |

```
            35                  40                  45
Thr Phe Glu Pro Asp Ile Lys Leu Asn Gly Ile Val Ile Gln Trp Leu
 50                  55                  60

Lys Glu Gly Ile Lys Gly Leu Val His Glu Phe Lys Glu Gly Lys Asp
 65                  70                  75                  80

Asp Leu Ser Gln Gln His Glu Met Phe Arg Gly Arg Thr Ala Val Phe
                 85                  90                  95

Ala Asp Gln Val Val Gly Asn Ala Ser Leu Arg Leu Lys Asn Val
            100                 105                 110

Gln Leu Thr Asp Ala Gly Thr Tyr Thr Cys Tyr Ile Arg Ser Ser Lys
        115                 120                 125

Gly Lys Gly Asn Ala Asn Leu Glu Tyr Lys Thr Gly Ala Phe Ser Met
    130                 135                 140

Pro Glu Ile Asn Val Asp Tyr Asn Ala Ser Ser Glu Ser Leu Arg Cys
145                 150                 155                 160

Glu Ala Pro Arg Trp Phe Pro Gln Pro Thr Val Ala Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Asp Ser Glu Val Lys Arg Arg
225                 230                 235                 240

Ser Gln Leu Gln Leu Leu Asn Ser Gly Pro Ser Pro Cys Val Ser Ser
                245                 250                 255

Ser Ala Phe Val Ala Gly Trp Ala Leu Leu Ser Leu Ser Cys Cys Leu
            260                 265                 270

Met Leu Arg
        275

<210> SEQ ID NO 4
<211> LENGTH: 200
<212> TYPE: PRT
<213> ORGANISM: Mus musculus

<400> SEQUENCE: 4

Gly Phe Gly Ile Ser Gly Lys His Phe Ile Thr Val Thr Thr Phe Thr
 1               5                  10                  15

Ser Ala Gly Asn Ile Gly Glu Asp Gly Thr Leu Ser Cys Thr Phe Glu
            20                  25                  30

Pro Asp Ile Lys Leu Asn Gly Ile Val Ile Gln Trp Leu Lys Glu Gly
        35                  40                  45

Ile Lys Gly Leu Val His Glu Phe Lys Glu Gly Lys Asp Asp Leu Ser
    50                  55                  60

Gln Gln His Glu Met Phe Arg Gly Arg Thr Ala Val Phe Ala Asp Gln
65                  70                  75                  80

Val Val Gly Asn Ala Ser Leu Arg Leu Lys Asn Val Gln Leu Thr
                85                  90                  95

Asp Ala Gly Thr Tyr Thr Cys Tyr Ile Arg Ser Ser Lys Gly Lys Gly
            100                 105                 110

Asn Ala Asn Leu Glu Tyr Lys Thr Gly Ala Phe Ser Met Pro Glu Ile
        115                 120                 125
```

```
Asn Val Asp Tyr Asn Ala Ser Ser Glu Ser Leu Arg Cys Glu Ala Pro
    130                 135                 140

Arg Trp Phe Pro Gln Pro Thr Val Ala Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
                180                 185                 190

Asn Asn Thr Tyr Ser Cys Met Ile
            195                 200

<210> SEQ ID NO 5
<211> LENGTH: 283
<212> TYPE: PRT
<213> ORGANISM: Mus musculus

<400> SEQUENCE: 5

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Phe Thr Ser Ala Gly Asn Ile
            35                  40                  45

Gly Glu Asp Gly Thr Leu Ser Cys Thr Phe Glu Pro Asp Ile Lys Leu
        50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
            115                 120                 125

Thr Cys Tyr Ile Arg Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
            245                 250                 255

Gly Pro Ser Pro Cys Val Phe Ser Ala Phe Val Ala Gly Trp Ala
            260                 265                 270

Leu Leu Ser Leu Ser Cys Cys Leu Met Leu Arg
    275                 280

<210> SEQ ID NO 6
```

```
<211> LENGTH: 275
<212> TYPE: PRT
<213> ORGANISM: Mus musculus

<400> SEQUENCE: 6

Met Glu Trp Ser Trp Val Phe Leu Phe Phe Leu Ser Val Thr Thr Gly
1               5                   10                  15

Val His Ser Gly Phe Gly Ile Ser Gly Lys His Phe Ile Thr Val Thr
            20                  25                  30

Thr Phe Thr Ser Ala Gly Asn Ile Gly Glu Asp Gly Thr Leu Ser Cys
        35                  40                  45

Thr Phe Glu Pro Asp Ile Lys Leu Asn Gly Ile Val Ile Gln Trp Leu
50                  55                  60

Lys Glu Gly Ile Lys Gly Leu Val His Glu Phe Lys Glu Gly Lys Asp
65                  70                  75                  80

Asp Leu Ser Gln Gln His Glu Met Phe Arg Gly Arg Thr Ala Val Phe
                85                  90                  95

Ala Asp Gln Val Val Gly Asn Ala Ser Leu Arg Leu Lys Asn Val
            100                 105                 110

Gln Leu Thr Asp Ala Gly Thr Tyr Thr Cys Tyr Ile Arg Thr Ser Lys
        115                 120                 125

Gly Lys Gly Asn Ala Asn Leu Glu Tyr Lys Thr Gly Ala Phe Ser Met
130                 135                 140

Pro Glu Ile Asn Val Asp Tyr Asn Ala Ser Glu Ser Leu Arg Cys
145                 150                 155                 160

Glu Ala Pro Arg Trp Phe Pro Gln Pro Thr Val Ala Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
210                 215                 220

Lys Ala Thr Gly Asp Ile Lys Val Thr Asp Ser Glu Val Lys Arg Arg
225                 230                 235                 240

Ser Gln Leu Gln Leu Leu Asn Ser Gly Pro Ser Pro Cys Val Phe Ser
                245                 250                 255

Ser Ala Phe Val Ala Gly Trp Ala Leu Leu Ser Leu Ser Cys Cys Leu
            260                 265                 270

Met Leu Arg
        275

<210> SEQ ID NO 7
<211> LENGTH: 256
<212> TYPE: PRT
<213> ORGANISM: Mus musculus

<400> SEQUENCE: 7

Gly Phe Gly Ile Ser Gly Lys His Phe Ile Thr Val Thr Thr Phe Thr
1               5                   10                  15

Ser Ala Gly Asn Ile Gly Glu Asp Gly Thr Leu Ser Cys Thr Phe Glu
            20                  25                  30

Pro Asp Ile Lys Leu Asn Gly Ile Val Ile Gln Trp Leu Lys Glu Gly
        35                  40                  45

Ile Lys Gly Leu Val His Glu Phe Lys Glu Gly Lys Asp Asp Leu Ser
50                  55                  60
```

Gln Gln His Glu Met Phe Arg Gly Arg Thr Ala Val Phe Ala Asp Gln
65                  70                  75                  80

Val Val Val Gly Asn Ala Ser Leu Arg Leu Lys Asn Val Gln Leu Thr
                85                  90                  95

Asp Ala Gly Thr Tyr Thr Cys Tyr Ile Arg Thr Ser Lys Gly Lys Gly
            100                 105                 110

Asn Ala Asn Leu Glu Tyr Lys Thr Gly Ala Phe Ser Met Pro Glu Ile
        115                 120                 125

Asn Val Asp Tyr Asn Ala Ser Ser Glu Ser Leu Arg Cys Glu Ala Pro
    130                 135                 140

Arg Trp Phe Pro Gln Pro Thr Val Ala Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Asp Ser Glu Val Lys Arg Arg Ser Gln Leu
    210                 215                 220

Gln Leu Leu Asn Ser Gly Pro Ser Pro Cys Val Phe Ser Ser Ala Phe
225                 230                 235                 240

Val Ala Gly Trp Ala Leu Leu Ser Leu Ser Cys Cys Leu Met Leu Arg
                245                 250                 255

<210> SEQ ID NO 8
<211> LENGTH: 849
<212> TYPE: DNA
<213> ORGANISM: Homo sapiens

<400> SEQUENCE: 8
atggcttccc tggggcagat cctcttctgg agcataatta gcatcatcat tattctggct        60
ggagcaattg cactcatcat tggctttggt atttcaggga gacactccat cacagtcact       120
actgtcgcct cagctgggaa cattgggag gatggaatcc tgagctgcac ttttgaacct       180
gacatcaaac tttctgatat cgtgatacaa tggctgaagg aaggtgtttt aggcttggtc       240
catgagttca agaaggcaa agatgagctg tcggagcagg atgaaatgtt cagaggccgg       300
acagcagtgt tgctgatca agtgatagtt ggcaatgcct ctttgcggct gaaaaacgtg       360
caactcacag atgctggcac ctacaaatgt tatatcatca cttctaaagg caaggggaat       420
gctaaccttg agtataaaac tggagccttc agcatgccgg aagtgaatgt ggactataat       480
gccagctcag agaccttgcg tgtgaggct ccccgatggt tcccccagcc cacagtggtc       540
tgggcatccc aagttgacca gggagccaac ttctcggaag tctccaatac cagctttgag       600
ctgaactctg agaatgtgac catgaaggtt gtgtctgtgc tctacaatgt tacgatcaac       660
aacacatact cctgtatgat tgaaaatgac attgccaaag caacagggga tatcaaagtg       720
acagaatcgg agatcaaaag gcggagtcac ctacagctgc taaactcaaa ggcttctctg       780
tgtgtctctt cttctttgc catcagctgg gcacttctgc ctctcagccc ttacctgatg       840
ctaaaataa                                                                849

<210> SEQ ID NO 9
<211> LENGTH: 282
<212> TYPE: PRT

<213> ORGANISM: Homo sapiens

<400> SEQUENCE: 9

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280

<210> SEQ ID NO 10
<211> LENGTH: 274
<212> TYPE: PRT
<213> ORGANISM: Homo sapiens

<400> SEQUENCE: 10

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Leu Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp

```
                65                  70                  75                  80
        Glu Leu Ser Glu Gln Asp Glu Met Phe Arg Gly Arg Thr Ala Val Phe
                        85                  90                  95
        Ala Asp Gln Val Ile Val Gly Asn Ala Ser Leu Arg Leu Lys Asn Val
                        100                 105                 110
        Gln Leu Thr Asp Ala Gly Thr Tyr Lys Cys Tyr Ile Ile Thr Ser Lys
                        115                 120                 125
        Gly Lys Gly Asn Ala Asn Leu Glu Tyr Lys Thr Gly Ala Phe Ser Met
                        130                 135                 140
        Pro Glu Val Asn Val Asp Tyr Asn Ala Ser Ser Glu Thr Leu Arg Cys
        145                 150                 155                 160
        Glu Ala Pro Arg Trp Phe Pro Gln Pro Thr Val Val Trp Ala Ser Gln
                        165                 170                 175
        Val Asp Gln Gly Ala Asn Phe Ser Glu Val Ser Asn Thr Ser Phe Glu
                        180                 185                 190
        Leu Asn Ser Glu Asn Val Thr Met Lys Val Val Ser Val Leu Tyr Asn
                        195                 200                 205
        Val Thr Ile Asn Asn Thr Tyr Ser Cys Met Ile Glu Asn Asp Ile Ala
                        210                 215                 220
        Lys Ala Thr Gly Asp Ile Lys Val Thr Glu Ser Glu Ile Lys Arg Arg
        225                 230                 235                 240
        Ser His Leu Gln Leu Leu Asn Ser Lys Ala Ser Leu Cys Val Ser Ser
                        245                 250                 255
        Phe Phe Ala Ile Ser Trp Ala Leu Leu Pro Leu Ser Pro Tyr Leu Met
                        260                 265                 270
        Leu Lys

<210> SEQ ID NO 11
<211> LENGTH: 255
<212> TYPE: PRT
<213> ORGANISM: Homo sapiens

<400> SEQUENCE: 11

Gly Phe Gly Ile Ser Gly Arg His Ser Ile Thr Val Thr Thr Val Ala
        1                   5                   10                  15
        Ser Ala Gly Asn Ile Gly Glu Asp Gly Ile Leu Ser Cys Thr Phe Glu
                        20                  25                  30
        Pro Asp Ile Lys Leu Ser Asp Ile Val Ile Gln Trp Leu Lys Glu Gly
                        35                  40                  45
        Val Leu Gly Leu Val His Glu Phe Lys Glu Gly Lys Asp Glu Leu Ser
                        50                  55                  60
        Glu Gln Asp Glu Met Phe Arg Gly Arg Thr Ala Val Phe Ala Asp Gln
        65                  70                  75                  80
        Val Ile Val Gly Asn Ala Ser Leu Arg Leu Lys Asn Val Gln Leu Thr
                        85                  90                  95
        Asp Ala Gly Thr Tyr Lys Cys Tyr Ile Ile Thr Ser Lys Gly Lys Gly
                        100                 105                 110
        Asn Ala Asn Leu Glu Tyr Lys Thr Gly Ala Phe Ser Met Pro Glu Val
                        115                 120                 125
        Asn Val Asp Tyr Asn Ala Ser Ser Glu Thr Leu Arg Cys Glu Ala Pro
                        130                 135                 140
        Arg Trp Phe Pro Gln Pro Thr Val Val Trp Ala Ser Gln Val Asp Gln
        145                 150                 155                 160
        Gly Ala Asn Phe Ser Glu Val Ser Asn Thr Ser Phe Glu Leu Asn Ser
```

```
                    165                 170                 175
Glu Asn Val Thr Met Lys Val Ser Val Leu Tyr Asn Val Thr Ile
                180                 185                 190

Asn Asn Thr Tyr Ser Cys Met Ile Glu Asn Asp Ile Ala Lys Ala Thr
                195                 200                 205

Gly Asp Ile Lys Val Thr Glu Ser Glu Ile Lys Arg Arg Ser His Leu
            210                 215                 220

Gln Leu Leu Asn Ser Lys Ala Ser Leu Cys Val Ser Ser Phe Phe Ala
225                 230                 235                 240

Ile Ser Trp Ala Leu Leu Pro Leu Ser Pro Tyr Leu Met Leu Lys
                245                 250                 255

<210> SEQ ID NO 12
<211> LENGTH: 282
<212> TYPE: PRT
<213> ORGANISM: Homo sapiens

<400> SEQUENCE: 12

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Thr Val Ala Ser Ala Gly Asn Ile
            35                  40                  45

Gly Glu Asp Gly Ile Gln Ser Cys Thr Phe Glu Pro Asp Ile Lys Leu
        50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu
        130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
        210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280
```

<210> SEQ ID NO 13
<211> LENGTH: 274
<212> TYPE: PRT
<213> ORGANISM: Homo sapiens

<400> SEQUENCE: 13

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Gln Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser His Leu Gln Leu Leu Asn Ser Lys Ala Ser Leu Cys Val Ser Ser
                245                 250                 255

Phe Phe Ala Ile Ser Trp Ala Leu Leu Pro Leu Ser Pro Tyr Leu Met
            260                 265                 270

Leu Lys

<210> SEQ ID NO 14
<211> LENGTH: 255
<212> TYPE: PRT
<213> ORGANISM: Homo sapiens

<400> SEQUENCE: 14

Gly Phe Gly Ile Ser Gly Arg His Ser Ile Thr Val Thr Thr Val Ala
1               5                   10                  15

Ser Ala Gly Asn Ile Gly Glu Asp Gly Ile Gln Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser

```
            50                  55                  60
Glu Gln Asp Glu Met Phe Arg Gly Arg Thr Ala Val Phe Ala Asp Gln
 65                  70                  75                  80

Val Ile Val Gly Asn Ala Ser Leu Arg Leu Lys Asn Val Gln Leu Thr
                 85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
            130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
                180                 185                 190

Asn Asn Thr Tyr Ser Cys Met Ile Glu Asn Asp Ile Ala Lys Ala Thr
                195                 200                 205

Gly Asp Ile Lys Val Thr Glu Ser Glu Ile Lys Arg Arg Ser His Leu
            210                 215                 220

Gln Leu Leu Asn Ser Lys Ala Ser Leu Cys Val Ser Ser Phe Phe Ala
225                 230                 235                 240

Ile Ser Trp Ala Leu Leu Pro Leu Ser Pro Tyr Leu Met Leu Lys
                245                 250                 255

<210> SEQ ID NO 15
<211> LENGTH: 278
<212> TYPE: PRT
<213> ORGANISM: Pan troglodytes

<400> SEQUENCE: 15

Met Lys Pro Leu Thr Ser Arg Ile Ile Ser Ile Ile Ile Ile Leu Ala
 1                   5                  10                  15

Gly Ala Ile Ala Leu Ile Ile Gly Phe Gly Ile Ser Gly Arg His Ser
                 20                  25                  30

Ile Thr Val Thr Thr Val Ala Ser Ala Gly Asn Ile Gly Glu Asp Gly
             35                  40                  45

Ile Leu Ser Cys Thr Phe Glu Pro Asp Ile Lys Leu Ser Asp Ile Val
 50                  55                  60

Ile Gln Trp Leu Lys Glu Gly Val Leu Gly Leu Val His Glu Phe Lys
 65                  70                  75                  80

Glu Gly Lys Asp Glu Leu Ser Glu Gln Asp Glu Met Phe Arg Gly Arg
                 85                  90                  95

Thr Ala Val Phe Ala Asp Gln Val Ile Val Gly Asn Ala Ser Leu Arg
            100                 105                 110

Leu Lys Asn Val Gln Leu Thr Asp Ala Gly Thr Tyr Lys Cys Tyr Ile
            115                 120                 125

Ile Thr Ser Lys Gly Lys Gly Asn Ala Asn Leu Glu Tyr Lys Thr Gly
            130                 135                 140

Ala Phe Ser Met Pro Glu Val Asn Val Asp Tyr Asn Ala Ser Ser Glu
145                 150                 155                 160

Thr Leu Arg Cys Glu Ala Pro Arg Trp Phe Pro Gln Pro Thr Val Val
                165                 170                 175
```

```
Trp Ala Ser Gln Ile Asp Gln Gly Ala Asn Phe Ser Glu Val Ser Asn
            180                 185                 190

Thr Ser Phe Glu Leu Asn Ser Glu Asn Val Thr Met Lys Val Val Ser
        195                 200                 205

Val Leu Tyr Asn Ala Thr Ile Asn Asn Thr Tyr Ser Cys Met Ile Glu
    210                 215                 220

Asn Asp Ile Ala Lys Ala Thr Gly Asp Ile Lys Val Thr Glu Ser Glu
225                 230                 235                 240

Ile Lys Arg Arg Ser His Leu Gln Leu Leu Asn Ser Lys Ala Ser Leu
                245                 250                 255

Cys Val Ser Ser Phe Phe Ala Ile Ser Trp Ala Leu Leu Pro Leu Ser
            260                 265                 270

Pro Tyr Leu Met Leu Lys
        275

<210> SEQ ID NO 16
<211> LENGTH: 255
<212> TYPE: PRT
<213> ORGANISM: Pan troglodytes

<400> SEQUENCE: 16

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Ile Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Ala Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
    210                 215                 220

Gln Leu Leu Asn Ser Lys Ala Ser Leu Cys Val Ser Ser Phe Phe Ala
225                 230                 235                 240

Ile Ser Trp Ala Leu Leu Pro Leu Ser Pro Tyr Leu Met Leu Lys
                245                 250                 255

<210> SEQ ID NO 17
```

```
<211> LENGTH: 282
<212> TYPE: PRT
<213> ORGANISM: Macaca mulatta

<400> SEQUENCE: 17

Met Ala Ser Leu Gly Gln Ile Leu Phe Trp Ser Ile Ile Ser Ile Ile
1               5                   10                  15

Phe Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
            35                  40                  45

Gly Glu Asp Gly Ile Leu Ser Cys Thr Phe Glu Pro Asp Ile Lys Leu
50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Leu Ala Ile Ser Trp Ala Leu
                260                 265                 270

Leu Pro Leu Ala Pro Tyr Leu Met Leu Lys
            275                 280

<210> SEQ ID NO 18
<211> LENGTH: 255
<212> TYPE: PRT
<213> ORGANISM: Macaca mulatta

<400> SEQUENCE: 18

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
                20                  25                  30

Pro Asp Ile Lys Leu Ser Asp Ile Val Ile Gln Trp Leu Lys Glu Gly
            35                  40                  45

Val Ile Gly Leu Val His Glu Phe Lys Glu Gly Lys Asp Glu Leu Ser
    50                  55                  60
```

```
Glu Gln Asp Glu Met Phe Arg Gly Arg Thr Ala Val Phe Ala Asp Gln
 65                  70                  75                  80

Val Ile Val Gly Asn Ala Ser Leu Arg Leu Lys Asn Val Gln Leu Thr
                 85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
210                 215                 220

Gln Leu Leu Asn Ser Lys Ala Ser Leu Cys Val Ser Ser Phe Leu Ala
225                 230                 235                 240

Ile Ser Trp Ala Leu Leu Pro Leu Ala Pro Tyr Leu Met Leu Lys
                245                 250                 255

<210> SEQ ID NO 19
<211> LENGTH: 282
<212> TYPE: PRT
<213> ORGANISM: Macaca fascicularis

<400> SEQUENCE: 19

Met Ala Ser Leu Gly Gln Ile Leu Phe Trp Ser Ile Ile Ser Ile Ile
  1               5                  10                  15

Phe Ile Leu Ala Gly Ala Ile Ala Leu Ile Ile Gly Phe Gly Ile Ser
                 20                  25                  30

Gly Arg His Ser Ile Thr Val Thr Thr Val Ala Ser Ala Gly Asn Ile
             35                  40                  45

Gly Glu Asp Gly Ile Leu Ser Cys Thr Phe Glu Pro Asp Ile Lys Leu
         50                  55                  60

Ser Asp Ile Val Ile Gln Trp Leu Lys Glu Gly Val Ile Gly Leu Val
 65                  70                  75                  80

His Glu Phe Lys Glu Gly Lys Asp Glu Leu Ser Glu Gln Asp Glu Met
                 85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
```

```
                    180                 185                 190
Glu Val Ser Asn Thr Ser Phe Glu Leu Asn Ser Glu Asn Val Thr Met
                195                 200                 205

Lys Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Leu Ala Ile Ser Trp Ala Leu
            260                 265                 270

Pro Pro Leu Ala Pro Tyr Leu Met Leu Lys
            275                 280

<210> SEQ ID NO 20
<211> LENGTH: 255
<212> TYPE: PRT
<213> ORGANISM: Macaca fascicularis

<400> SEQUENCE: 20

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
            35                  40                  45

Val Ile Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser His Leu
        210                 215                 220

Gln Leu Leu Asn Ser Lys Ala Ser Leu Cys Val Ser Ser Phe Leu Ala
225                 230                 235                 240

Ile Ser Trp Ala Leu Pro Pro Leu Ala Pro Tyr Leu Met Leu Lys
                245                 250                 255

<210> SEQ ID NO 21
<211> LENGTH: 771
```

```
<212> TYPE: DNA
<213> ORGANISM: Mus musculus

<400> SEQUENCE: 21
atggcttcct tggggcagat catcttttgg agtattatta acatcatcat catcctggct      60
ggggccatcg cactcatcat tggctttggc atttcaggca agcacttcat cacggtcacg     120
accttcacct cagctggaaa cattggagag acgggaccc tgagctgcac ttttgaacct      180
gacatcaaac tcaacggcat cgtcatccag tggctgaaag aaggcatcaa aggtttggtc     240
cacgagttca agaaggcaa agacgacctc tcacagcagc atgagatgtt cagaggccgc      300
acagcagtgt ttgctgatca ggtggtagtt ggcaatgctt ccctgagact gaaaaacgtg     360
cagctcacgg atgctggcac ctacacatgt acatccgca cctcaaaagg caaagggaat      420
gcaaaccttg agtataagac cggagccttc agtatgccag agtaaatgt ggactataat     480
gccagttcag agagtttacg ctgcgaggct cctcggtggt tccccagcc cacagtggcc      540
tgggcatctc aagtcgacca aggagccaat ttctcagaag tctccaacac cagctttgag    600
ttgaactctg agaatgtgac catgaaggtc gtatctgtgc tctacaatgt cacaatcaac    660
aacacatact cctgtatgat tgaaaacgac attgccaaag ccaccgggga catcaaagtg    720
acagattcag aggtcaaaag gcgaagtcag ctgcagttgc tgaactctgg g             771

<210> SEQ ID NO 22
<211> LENGTH: 747
<212> TYPE: DNA
<213> ORGANISM: Mus musculus

<400> SEQUENCE: 22
atggagtggt catgggtttt tctgttcttt cttagcgtga ctacaggcgt ccattcagga     60
ttcggcataa gcggcaagca cttcatcaca gttacaacgt ttacaagtgc ggggaacatt    120
ggggaagatg gaacattgtc atgtacattt gagccagata tcaaactcaa tggaatagta    180
attcagtggc ttaaggaggg catcaagggc ctggtccacg aatttaagga ggggaaagac    240
gatctgtctc agcagcacga gatgttcagg ggcagaaccg ccgtcttcgc agaccaggtt    300
gtggtaggca acgccagttt gcggctgaaa aacgtgcagc tgactgacgc cggcacctac    360
acatgctata tccggtcctc taagggcaag gggaacgcta atctcgagta caaacaggc    420
gccttttcta tgccagagat caacgtggac tataacgcaa gctctgaaag tctgagatgc    480
gaggcgccaa ggtggttccc tcagcccacc gtcgcgtggg cttcccaggt ggatcaaggc    540
gccaactttt ctgaggtttc taacaccagc ttcgaactga cagcgaaaa tgtgacaatg    600
aaggtagtca gcgttctgta acgtgacc atcaacaata cttactcctg tatgatagaa      660
aatgatatag ccaaggctac aggagatatt aaagtgacgg attcagaagt gaaaaggagg    720
agtcaactgc aactcttgaa tagcggc                                        747

<210> SEQ ID NO 23
<211> LENGTH: 747
<212> TYPE: DNA
<213> ORGANISM: Mus musculus

<400> SEQUENCE: 23
atggagtggt catgggtttt tctgttcttt cttagcgtga ctacaggcgt ccattcagga     60
ttcggcataa gcggcaagca cttcatcaca gttacaacgt ttacaagtgc ggggaacatt    120
ggggaagatg gaacattgtc atgtacattt gagccagata tcaaactcaa tggaatagta    180
```

```
attcagtggc ttaaggaggg catcaagggc ctggtccacg aatttaagga ggggaaagac        240
gatctgtctc agcagcacga gatgttcagg ggcagaaccg ccgtcttcgc agaccaggtt        300
gtggtaggca acgccagttt gcggctgaaa acgtgcagc tgactgacgc cggcacctac        360
acatgctata tccggacctc taagggcaag gggaacgcta atctcgagta caaaacaggc        420
gccttttcta tgccagagat caacgtggac tataacgcaa gctctgaaag tctgagatgc        480
gaggcgccaa ggtggttccc tcagcccacc gtcgcgtggg cttcccaggt ggatcaaggc        540
gccaactttt ctgaggtttc taacaccagc ttcgaactga acagcgaaaa tgtgacaatg        600
aaggtagtca gcgttctgta taacgtgacc atcaacaata cttactcctg tatgatagaa        660
aatgatatag ccaaggctac aggagatatt aaagtgacgg attcagaagt gaaaaggagg        720
agtcaactgc aactcttgaa tagcggc                                            747
```

```
<210> SEQ ID NO 24
<211> LENGTH: 249
<212> TYPE: PRT
<213> ORGANISM: Mus musculus

<400> SEQUENCE: 24

Met Glu Trp Ser Trp Val Phe Leu Phe Phe Leu Ser Val Thr Thr Gly
1               5                   10                  15

Val His Ser Gly Phe Gly Ile Ser Gly Lys His Phe Ile Thr Val Thr
            20                  25                  30

Thr Phe Thr Ser Ala Gly Asn Ile Gly Glu Asp Gly Thr Leu Ser Cys
        35                  40                  45

Thr Phe Glu Pro Asp Ile Lys Leu Asn Gly Ile Val Ile Gln Trp Leu
    50                  55                  60

Lys Glu Gly Ile Lys Gly Leu Val His Glu Phe Lys Glu Gly Lys Asp
65                  70                  75                  80

Asp Leu Ser Gln Gln His Glu Met Phe Arg Gly Arg Thr Ala Val Phe
                85                  90                  95

Ala Asp Gln Val Val Val Gly Asn Ala Ser Leu Arg Leu Lys Asn Val
            100                 105                 110

Gln Leu Thr Asp Ala Gly Thr Tyr Thr Cys Tyr Ile Arg Ser Ser Lys
        115                 120                 125

Gly Lys Gly Asn Ala Asn Leu Glu Tyr Lys Thr Gly Ala Phe Ser Met
    130                 135                 140

Pro Glu Ile Asn Val Asp Tyr Asn Ala Ser Ser Glu Ser Leu Arg Cys
145                 150                 155                 160

Glu Ala Pro Arg Trp Phe Pro Gln Pro Thr Val Ala Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Asp Ser Glu Val Lys Arg Arg
225                 230                 235                 240

Ser Gln Leu Gln Leu Leu Asn Ser Gly
                245

<210> SEQ ID NO 25
<211> LENGTH: 249
```

```
<212> TYPE: PRT
<213> ORGANISM: Mus musculus

<400> SEQUENCE: 25

Met Glu Trp Ser Trp Val Phe Leu Phe Phe Leu Ser Val Thr Thr Gly
1               5                   10                  15

Val His Ser Gly Phe Gly Ile Ser Gly Lys His Phe Ile Thr Val Thr
            20                  25                  30

Thr Phe Thr Ser Ala Gly Asn Ile Gly Glu Asp Gly Thr Leu Ser Cys
        35                  40                  45

Thr Phe Glu Pro Asp Ile Lys Leu Asn Gly Ile Val Ile Gln Trp Leu
    50                  55                  60

Lys Glu Gly Ile Lys Gly Leu Val His Glu Phe Lys Glu Gly Lys Asp
65                  70                  75                  80

Asp Leu Ser Gln Gln His Glu Met Phe Arg Gly Arg Thr Ala Val Phe
                85                  90                  95

Ala Asp Gln Val Val Gly Asn Ala Ser Leu Arg Leu Lys Asn Val
            100                 105                 110

Gln Leu Thr Asp Ala Gly Thr Tyr Thr Cys Tyr Ile Arg Thr Ser Lys
        115                 120                 125

Gly Lys Gly Asn Ala Asn Leu Glu Tyr Lys Thr Gly Ala Phe Ser Met
    130                 135                 140

Pro Glu Ile Asn Val Asp Tyr Asn Ala Ser Ser Glu Ser Leu Arg Cys
145                 150                 155                 160

Glu Ala Pro Arg Trp Phe Pro Gln Pro Thr Val Ala Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Asp Ser Glu Val Lys Arg Arg
225                 230                 235                 240

Ser Gln Leu Gln Leu Leu Asn Ser Gly
                245

<210> SEQ ID NO 26
<211> LENGTH: 257
<212> TYPE: PRT
<213> ORGANISM: Mus musculus

<400> SEQUENCE: 26

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95
```

```
Phe Arg Gly Arg Thr Ala Val Phe Ala Asp Gln Val Val Gly Asn
                100                 105                 110

Ala Ser Leu Arg Leu Lys Asn Val Gln Leu Thr Asp Ala Gly Thr Tyr
            115                 120                 125

Thr Cys Tyr Ile Arg Ser Ser Lys Gly Lys Gly Asn Ala Asn Leu Glu
        130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly

<210> SEQ ID NO 27
<211> LENGTH: 257
<212> TYPE: PRT
<213> ORGANISM: Mus musculus

<400> SEQUENCE: 27

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Gly Asn
                100                 105                 110

Ala Ser Leu Arg Leu Lys Asn Val Gln Leu Thr Asp Ala Gly Thr Tyr
            115                 120                 125

Thr Cys Tyr Ile Arg Thr Ser Lys Gly Lys Gly Asn Ala Asn Leu Glu
        130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205
```

```
Lys Val Val Ser Val Leu Tyr Asn Val Thr Ile Asn Asn Thr Tyr Ser
    210                 215                 220
Cys Met Ile Glu Asn Asp Ile Ala Lys Ala Thr Gly Asp Ile Lys Val
225                 230                 235                 240
Thr Asp Ser Glu Val Lys Arg Arg Ser Gln Leu Gln Leu Leu Asn Ser
                245                 250                 255
Gly
```

<210> SEQ ID NO 28
<211> LENGTH: 230
<212> TYPE: PRT
<213> ORGANISM: Mus musculus

<400> SEQUENCE: 28

```
Gly Phe Gly Ile Ser Gly Lys His Phe Ile Thr Val Thr Thr Phe Thr
1               5                   10                  15
Ser Ala Gly Asn Ile Gly Glu Asp Gly Thr Leu Ser Cys Thr Phe Glu
                20                  25                  30
Pro Asp Ile Lys Leu Asn Gly Ile Val Ile Gln Trp Leu Lys Glu Gly
            35                  40                  45
Ile Lys Gly Leu Val His Glu Phe Lys Glu Gly Lys Asp Asp Leu Ser
50                  55                  60
Gln Gln His Glu Met Phe Arg Gly Arg Thr Ala Val Phe Ala Asp Gln
65                  70                  75                  80
Val Val Val Gly Asn Ala Ser Leu Arg Leu Lys Asn Val Gln Leu Thr
                85                  90                  95
Asp Ala Gly Thr Tyr Thr Cys Tyr Ile Arg Ser Ser Lys Gly Lys Gly
            100                 105                 110
Asn Ala Asn Leu Glu Tyr Lys Thr Gly Ala Phe Ser Met Pro Glu Ile
        115                 120                 125
Asn Val Asp Tyr Asn Ala Ser Ser Glu Ser Leu Arg Cys Glu Ala Pro
130                 135                 140
Arg Trp Phe Pro Gln Pro Thr Val Ala Trp Ala Ser Gln Val Asp Gln
145                 150                 155                 160
Gly Ala Asn Phe Ser Glu Val Ser Asn Thr Ser Phe Glu Leu Asn Ser
                165                 170                 175
Glu Asn Val Thr Met Lys Val Val Ser Val Leu Tyr Asn Val Thr Ile
            180                 185                 190
Asn Asn Thr Tyr Ser Cys Met Ile Glu Asn Asp Ile Ala Lys Ala Thr
        195                 200                 205
Gly Asp Ile Lys Val Thr Asp Ser Glu Val Lys Arg Arg Ser Gln Leu
210                 215                 220
Gln Leu Leu Asn Ser Gly
225                 230
```

<210> SEQ ID NO 29
<211> LENGTH: 230
<212> TYPE: PRT
<213> ORGANISM: Mus musculus

<400> SEQUENCE: 29

```
Gly Phe Gly Ile Ser Gly Lys His Phe Ile Thr Val Thr Thr Phe Thr
1               5                   10                  15
Ser Ala Gly Asn Ile Gly Glu Asp Gly Thr Leu Ser Cys Thr Phe Glu
                20                  25                  30
Pro Asp Ile Lys Leu Asn Gly Ile Val Ile Gln Trp Leu Lys Glu Gly
```

```
              35                  40                  45
Ile Lys Gly Leu Val His Glu Phe Lys Glu Gly Lys Asp Asp Leu Ser
 50                  55                  60

Gln Gln His Glu Met Phe Arg Gly Arg Thr Ala Val Phe Ala Asp Gln
 65                  70                  75                  80

Val Val Val Gly Asn Ala Ser Leu Arg Leu Lys Asn Val Gln Leu Thr
                 85                  90                  95

Asp Ala Gly Thr Tyr Thr Cys Tyr Ile Arg Thr Ser Lys Gly Lys Gly
                100                 105                 110

Asn Ala Asn Leu Glu Tyr Lys Thr Gly Ala Phe Ser Met Pro Glu Ile
            115                 120                 125

Asn Val Asp Tyr Asn Ala Ser Ser Glu Ser Leu Arg Cys Glu Ala Pro
        130                 135                 140

Arg Trp Phe Pro Gln Pro Thr Val Ala Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Asp Ser Glu Val Lys Arg Arg Ser Gln Leu
    210                 215                 220

Gln Leu Leu Asn Ser Gly
225                 230

<210> SEQ ID NO 30
<211> LENGTH: 387
<212> TYPE: DNA
<213> ORGANISM: Mus musculus

<400> SEQUENCE: 30
ggattcggca taagcggcaa gcacttcatc acagttacaa cgtttacaag tgcggggaac      60
attggggaag atgaacatt gtcatgtaca tttgagccag atatcaaact caatggaata     120
gtaattcagt ggcttaagga gggcatcaag ggcctggtcc acgaatttaa ggaggggaaa     180
gacgatctgt ctcagcagca cgagatgttc aggggcagaa ccgccgtctt cgcagaccag     240
gttgtggtag gcaacgccag tttgcggctg aaaaacgtgc agctgactga cgccggcacc     300
tacacatgct atatccggtc tctaaggggc aaggggaacg ctaatctcga gtacaaaaca     360
ggcgcctttt ctatgccaga gatcaac                                         387

<210> SEQ ID NO 31
<211> LENGTH: 387
<212> TYPE: DNA
<213> ORGANISM: Mus musculus

<400> SEQUENCE: 31
ggattcggca taagcggcaa gcacttcatc acagttacaa cgtttacaag tgcggggaac      60
attggggaag atgaacatt gtcatgtaca tttgagccag atatcaaact caatggaata     120
gtaattcagt ggcttaagga gggcatcaag ggcctggtcc acgaatttaa ggaggggaaa     180
gacgatctgt ctcagcagca cgagatgttc aggggcagaa ccgccgtctt cgcagaccag     240
gttgtggtag gcaacgccag tttgcggctg aaaaacgtgc agctgactga cgccggcacc     300
tacacatgct atatccggac tctaaggggc aaggggaacg ctaatctcga gtacaaaaca     360
```
ggcgcctttt ctatgccaga gatcaac 387

<210> SEQ ID NO 32
<211> LENGTH: 129
<212> TYPE: PRT
<213> ORGANISM: Mus musculus

<400> SEQUENCE: 32

Gly Phe Gly Ile Ser Gly Lys His Phe Ile Thr Val Thr Thr Phe Thr
1               5                   10                  15

Ser Ala Gly Asn Ile Gly Glu Asp Gly Thr Leu Ser Cys Thr Phe Glu
            20                  25                  30

Pro Asp Ile Lys Leu Asn Gly Ile Val Ile Gln Trp Leu Lys Glu Gly
        35                  40                  45

Ile Lys Gly Leu Val His Glu Phe Lys Glu Gly Lys Asp Asp Leu Ser
    50                  55                  60

Gln Gln His Glu Met Phe Arg Gly Arg Thr Ala Val Phe Ala Asp Gln
65                  70                  75                  80

Val Val Val Gly Asn Ala Ser Leu Arg Leu Lys Asn Val Gln Leu Thr
                85                  90                  95

Asp Ala Gly Thr Tyr Thr Cys Tyr Ile Arg Ser Ser Lys Gly Lys Gly
            100                 105                 110

Asn Ala Asn Leu Glu Tyr Lys Thr Gly Ala Phe Ser Met Pro Glu Ile
        115                 120                 125

Asn

<210> SEQ ID NO 33
<211> LENGTH: 129
<212> TYPE: PRT
<213> ORGANISM: Mus musculus

<400> SEQUENCE: 33

Gly Phe Gly Ile Ser Gly Lys His Phe Ile Thr Val Thr Thr Phe Thr
1               5                   10                  15

Ser Ala Gly Asn Ile Gly Glu Asp Gly Thr Leu Ser Cys Thr Phe Glu
            20                  25                  30

Pro Asp Ile Lys Leu Asn Gly Ile Val Ile Gln Trp Leu Lys Glu Gly
        35                  40                  45

Ile Lys Gly Leu Val His Glu Phe Lys Glu Gly Lys Asp Asp Leu Ser
    50                  55                  60

Gln Gln His Glu Met Phe Arg Gly Arg Thr Ala Val Phe Ala Asp Gln
65                  70                  75                  80

Val Val Val Gly Asn Ala Ser Leu Arg Leu Lys Asn Val Gln Leu Thr
                85                  90                  95

Asp Ala Gly Thr Tyr Thr Cys Tyr Ile Arg Thr Ser Lys Gly Lys Gly
            100                 105                 110

Asn Ala Asn Leu Glu Tyr Lys Thr Gly Ala Phe Ser Met Pro Glu Ile
        115                 120                 125

Asn

<210> SEQ ID NO 34
<211> LENGTH: 747
<212> TYPE: DNA
<213> ORGANISM: Homo sapiens

<400> SEQUENCE: 34

| | |
|---|---:|
| atggcttccc tggggcagat cctcttctgg agcataatta gcatcatcat tattctggct | 60 |
| ggagcaattg cactcatcat tggctttggt atttcaggga gacactccat cacagtcact | 120 |
| actgtcgcct cagctgggaa cattggggag gatggaatcc tgagctgcac ttttgaacct | 180 |
| gacatcaaac tttctgatat cgtgatacaa tggctgaagg aaggtgtttt aggcttggtc | 240 |
| catgagttca agaaggcaa agatgagctg tcggagcagg atgaaatgtt cagaggccgg | 300 |
| acagcagtgt tgctgatca agtgatagtt ggcaatgcct ctttgcggct gaaaaacgtg | 360 |
| caactcacag atgctggcac ctacaaatgt tatatcatca cttctaaagg caaggggaat | 420 |
| gctaaccttg agtataaaac tggagccttc agcatgccgg aagtgaatgt ggactataat | 480 |
| gccagctcag agaccttgcg cgtgtgaggct ccccgatggt tccccagcc cacagtggtc | 540 |
| tgggcatccc aagttgacca gggagccaac ttctcggaag tctccaatac cagctttgag | 600 |
| ctgaactctg agaatgtgac catgaaggtt gtgtctgtgc tctacaatgt tacgatcaac | 660 |
| aacacatact cctgtatgat tgaaaatgac attgccaaag caacagggga tatcaaagtg | 720 |
| acagaatcgg agatcaaaag gcggagt | 747 |

<210> SEQ ID NO 35
<211> LENGTH: 735
<212> TYPE: DNA
<213> ORGANISM: Homo sapiens

<400> SEQUENCE: 35

| | |
|---|---:|
| atggcttccc tggggcagat cctcttctgg agcataatta gcatcatcat tattctggct | 60 |
| ggagcaattg cactcatcat tggctttggt atttcaggga gacactccat cacagtcact | 120 |
| actgtcgcct cagctgggaa cattggggag gatggaatcc tgagctgcac ttttgaacct | 180 |
| gacatcaaac tttctgatat cgtgatacaa tggctgaagg aaggtgtttt aggcttggtc | 240 |
| catgagttca agaaggcaa agatgagctg tcggagcagg atgaaatgtt cagaggccgg | 300 |
| acagcagtgt tgctgatca agtgatagtt ggcaatgcct ctttgcggct gaaaaacgtg | 360 |
| caactcacag atgctggcac ctacaaatgt tatatcatca cttctaaagg caaggggaat | 420 |
| gctaaccttg agtataaaac tggagccttc agcatgccgg aagtgaatgt ggactataat | 480 |
| gccagctcag agaccttgcg cgtgtgaggct ccccgatggt tccccagcc cacagtggtc | 540 |
| tgggcatccc aagttgacca gggagccaac ttctcggaag tctccaatac cagctttgag | 600 |
| ctgaactctg agaatgtgac catgaaggtt gtgtctgtgc tctacaatgt tacgatcaac | 660 |
| aacacatact cctgtatgat tgaaaatgac attgccaaag caacagggga tatcaaagtg | 720 |
| acagaatcgg agatc | 735 |

<210> SEQ ID NO 36
<211> LENGTH: 777
<212> TYPE: DNA
<213> ORGANISM: Homo sapiens

<400> SEQUENCE: 36

| | |
|---|---:|
| atggcttccc tggggcagat cctcttctgg agcataatta gcatcatcat tattctggct | 60 |
| ggagcaattg cactcatcat tggctttggt atttcaggga gacactccat cacagtcact | 120 |
| actgtcgcct cagctgggaa cattggggag gatggaatcc tgagctgcac ttttgaacct | 180 |
| gacatcaaac tttctgatat cgtgatacaa tggctgaagg aaggtgtttt aggcttggtc | 240 |
| catgagttca agaaggcaa agatgagctg tcggagcagg atgaaatgtt cagaggccgg | 300 |
| acagcagtgt tgctgatca agtgatagtt ggcaatgcct ctttgcggct gaaaaacgtg | 360 |

```
caactcacag atgctggcac ctacaaatgt tatatcatca cttctaaagg caagggggaat    420 gctaaccttg agtataaaac tggagccttc agcatgccgg aagtgaatgt ggactataat    480
gccagctcag agaccttgcg gtgtgaggct ccccgatggt tcccccagcc cacagtggtc    540
tgggcatccc aagttgacca gggagccaac ttctcggaag tctccaatac cagctttgag    600
ctgaactctg agaatgtgac catgaaggtt gtgtctgtgc tctacaatgt tacgatcaac    660
aacacatact cctgtatgat tgaaaatgac attgccaaag caacagggga tatcaaagtg    720
acagaatcgg agatcaaaag gcggagtcac ctacagctgc taaactcaaa ggcttct      777
```

<210> SEQ ID NO 37
<211> LENGTH: 723
<212> TYPE: DNA
<213> ORGANISM: Homo sapiens

<400> SEQUENCE: 37

```
atggaatgga gctgggtatt tctgttttc ctgtcagtaa cgactggcgt ccattcaggc      60
ttcggcatca gtggacggca cagtatcaca gtgaccaccg tcgcctccgc tggcaatata    120
ggtgaggatg gcatccagtc ctgtacccttt gagccggaca tcaaactgtc tgacatagtg    180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaacggcgg    720
tct                                                                  723
```

<210> SEQ ID NO 38
<211> LENGTH: 711
<212> TYPE: DNA
<213> ORGANISM: Homo sapiens

<400> SEQUENCE: 38

```
atggaatgga gctgggtatt tctgttttc ctgtcagtaa cgactggcgt ccattcaggc      60
ttcggcatca gtggacggca cagtatcaca gtgaccaccg tcgcctccgc tggcaatata    120
ggtgaggatg gcatccagtc ctgtacccttt gagccggaca tcaaactgtc tgacatagtg    180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
```
aacgacatcg ccaaggcaac aggtgatatt aaggtaactg aatccgagat c        711

<210> SEQ ID NO 39
<211> LENGTH: 753
<212> TYPE: DNA
<213> ORGANISM: Homo sapiens

<400> SEQUENCE: 39
atggaatgga gctgggtatt tctgtttttc ctgtcagtaa cgactggcgt ccattcaggc        60
ttcggcatca gtggacggca cagtatcaca gtgaccaccg tcgcctccgc tggcaatata       120
ggtgaggatg gcatccagtc ctgtaccttt gagccggaca tcaaactgtc tgacatagtg       180
atacaatggc tgaaggaggg ggtgctcggt ctggtacatg agtttaagga agggaaggat       240
gaactgtccg agcaggatga gatgttccgg gggaggaccg ctgtgttcgc cgatcaggta       300
atcgtcggaa atgcaagtct cagattgaaa aatgtgcaac tgactgatgc tggcacgtat       360
aaatgctaca ttatcacaag taagggcaaa ggaaatgcta accttgagta taaaacaggc       420
gcattctcaa tgcccgaggt caatgtcgac tataatgcca gcagtgaaaac attgcgctgt       480
gaagctcccc gctggttccc ccagccaacc gtggtctggg cctctcaggt tgatcagggg       540
gctaactttt ccgaggtgag caacaccagc ttcgaactca actctgagaa tgtgaccatg       600
aaagttgtgt ctgtcctgta taatgtaaca atcaacaaca cttattcatg catgattgaa       660
aacgacatcg ccaaggcaac aggtgatatt aaggtaactg aatccgagat caaacggcgg       720
tctcacctac agctgctaaa ctcaaaggct tct                                   753

<210> SEQ ID NO 40
<211> LENGTH: 723
<212> TYPE: DNA
<213> ORGANISM: Homo sapiens

<400> SEQUENCE: 40
atggaatgga gctgggtatt tctgtttttc ctgtcagtaa cgactggcgt ccattcaggc        60
ttcggcatca gtggacggca cagtatcaca gtgaccaccg tcgcctccgc tggcaatata       120
ggtgaggatg gcatcctgtc ctgtaccttt gagccggaca tcaaactgtc tgacatagtg       180
atacaatggc tgaaggaggg ggtgctcggt ctggtacatg agtttaagga agggaaggat       240
gaactgtccg agcaggatga gatgttccgg gggaggaccg ctgtgttcgc cgatcaggta       300
atcgtcggaa atgcaagtct cagattgaaa aatgtgcaac tgactgatgc tggcacgtat       360
aaatgctaca ttatcacaag taagggcaaa ggaaatgcta accttgagta taaaacaggc       420
gcattctcaa tgcccgaggt caatgtcgac tataatgcca gcagtgaaac attgcgctgt        480
gaagctcccc gctggttccc ccagccaacc gtggtctggg cctctcaggt tgatcagggg       540
gctaactttt ccgaggtgag caacaccagc ttcgaactca actctgagaa tgtgaccatg       600
aaagttgtgt ctgtcctgta taatgtaaca atcaacaaca cttattcatg catgattgaa       660
aacgacatcg ccaaggcaac aggtgatatt aaggtaactg aatccgagat caaacggcgg       720
tct                                                                    723

<210> SEQ ID NO 41
<211> LENGTH: 711
<212> TYPE: DNA
<213> ORGANISM: Homo sapiens

<400> SEQUENCE: 41
atggaatgga gctgggtatt tctgtttttc ctgtcagtaa cgactggcgt ccattcaggc        60

```
ttcggcatca gtggacggca cagtatcaca gtgaccaccg tcgcctccgc tggcaatata      120
ggtgaggatg gcatcctgtc ctgtacccttt gagccggaca tcaaactgtc tgacatagtg     180
atacaatggc tgaaggaggg ggtgctcggt ctggtacatg agtttaagga agggaaggat      240
gaactgtccg agcaggatga gatgttccgg gggaggaccg ctgtgttcgc cgatcaggta     300
atcgtcggaa atgcaagtct cagattgaaa aatgtgcaac tgactgatgc tggcacgtat     360
aaatgctaca ttatcacaag taagggcaaa ggaaatgcta accttgagta taaaacaggc     420
gcattctcaa tgcccgaggt caatgtcgac tataatgcca gcagtgaaac attgcgctgt     480
gaagctcccc gctggttccc ccagccaacc gtggtctggg cctctcaggt tgatcagggg     540
gctaactttt ccgaggtgag caacaccagc ttcgaactca actctgagaa tgtgaccatg     600
aaagttgtgt ctgtcctgta taatgtaaca atcaacaaca cttattcatg catgattgaa     660
aacgacatcg ccaaggcaac aggtgatatt aaggtaactg aatccgagat c              711

<210> SEQ ID NO 42
<211> LENGTH: 753
<212> TYPE: DNA
<213> ORGANISM: Homo sapiens

<400> SEQUENCE: 42
atggaatgga gctgggtatt tctgttttc ctgtcagtaa cgactggcgt ccattcaggc       60
ttcggcatca gtggacggca cagtatcaca gtgaccaccg tcgcctccgc tggcaatata     120
ggtgaggatg gcatcctgtc ctgtacccttt gagccggaca tcaaactgtc tgacatagtg    180
atacaatggc tgaaggaggg ggtgctcggt ctggtacatg agtttaagga agggaaggat     240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaacggcgg    720
tctcacctac agctgctaaa ctcaaaggct tct                                  753

<210> SEQ ID NO 43
<211> LENGTH: 241
<212> TYPE: PRT
<213> ORGANISM: Homo sapiens

<400> SEQUENCE: 43

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Gln Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80
```

```
Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser

<210> SEQ ID NO 44
<211> LENGTH: 237
<212> TYPE: PRT
<213> ORGANISM: Homo sapiens

<400> SEQUENCE: 44

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Gln Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205
```

```
Val Thr Ile Asn Asn Thr Tyr Ser Cys Met Ile Glu Asn Asp Ile Ala
        210                 215                 220

Lys Ala Thr Gly Asp Ile Lys Val Thr Glu Ser Glu Ile
225                 230                 235

<210> SEQ ID NO 45
<211> LENGTH: 251
<212> TYPE: PRT
<213> ORGANISM: Homo sapiens

<400> SEQUENCE: 45

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Gln Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser His Leu Gln Leu Leu Asn Ser Lys Ala Ser
                245                 250

<210> SEQ ID NO 46
<211> LENGTH: 241
<212> TYPE: PRT
<213> ORGANISM: Homo sapiens

<400> SEQUENCE: 46

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Leu Ser Cys
        35                  40                  45
```

```
Thr Phe Glu Pro Asp Ile Lys Leu Ser Asp Ile Val Ile Gln Trp Leu
 50                  55                  60

Lys Glu Gly Val Leu Gly Leu Val His Glu Phe Lys Glu Gly Lys Asp
 65                  70                  75                  80

Glu Leu Ser Glu Gln Asp Glu Met Phe Arg Gly Arg Thr Ala Val Phe
                 85                  90                  95

Ala Asp Gln Val Ile Val Gly Asn Ala Ser Leu Arg Leu Lys Asn Val
                100                 105                 110

Gln Leu Thr Asp Ala Gly Thr Tyr Lys Cys Tyr Ile Ile Thr Ser Lys
            115                 120                 125

Gly Lys Gly Asn Ala Asn Leu Glu Tyr Lys Thr Gly Ala Phe Ser Met
130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser

<210> SEQ ID NO 47
<211> LENGTH: 237
<212> TYPE: PRT
<213> ORGANISM: Homo sapiens

<400> SEQUENCE: 47

Met Glu Trp Ser Trp Val Phe Leu Phe Phe Leu Ser Val Thr Thr Gly
 1               5                  10                  15

Val His Ser Gly Phe Gly Ile Ser Gly Arg His Ser Ile Thr Val Thr
                20                  25                  30

Thr Val Ala Ser Ala Gly Asn Ile Gly Glu Asp Gly Ile Leu Ser Cys
            35                  40                  45

Thr Phe Glu Pro Asp Ile Lys Leu Ser Asp Ile Val Ile Gln Trp Leu
 50                  55                  60

Lys Glu Gly Val Leu Gly Leu Val His Glu Phe Lys Glu Gly Lys Asp
 65                  70                  75                  80

Glu Leu Ser Glu Gln Asp Glu Met Phe Arg Gly Arg Thr Ala Val Phe
                 85                  90                  95

Ala Asp Gln Val Ile Val Gly Asn Ala Ser Leu Arg Leu Lys Asn Val
                100                 105                 110

Gln Leu Thr Asp Ala Gly Thr Tyr Lys Cys Tyr Ile Ile Thr Ser Lys
            115                 120                 125

Gly Lys Gly Asn Ala Asn Leu Glu Tyr Lys Thr Gly Ala Phe Ser Met
130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175
```

-continued

Val Asp Gln Gly Ala Asn Phe Ser Glu Val Ser Asn Thr Ser Phe Glu
                180                 185                 190

Leu Asn Ser Glu Asn Val Thr Met Lys Val Val Ser Val Leu Tyr Asn
            195                 200                 205

Val Thr Ile Asn Asn Thr Tyr Ser Cys Met Ile Glu Asn Asp Ile Ala
        210                 215                 220

Lys Ala Thr Gly Asp Ile Lys Val Thr Glu Ser Glu Ile
225                 230                 235

<210> SEQ ID NO 48
<211> LENGTH: 251
<212> TYPE: PRT
<213> ORGANISM: Homo sapiens

<400> SEQUENCE: 48

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Leu Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser His Leu Gln Leu Leu Asn Ser Lys Ala Ser
                245                 250

<210> SEQ ID NO 49
<211> LENGTH: 249
<212> TYPE: PRT
<213> ORGANISM: Homo sapiens

<400> SEQUENCE: 49

Met Ala Ser Leu Gly Gln Ile Leu Phe Trp Ser Ile Ile Ser Ile Ile
1               5                   10                  15

```
Ile Ile Leu Ala Gly Ala Ile Ala Leu Ile Ile Gly Phe Gly Ile Ser
             20                  25                  30

Gly Arg His Ser Ile Thr Val Thr Val Ala Ser Ala Gly Asn Ile
         35                  40                  45

Gly Glu Asp Gly Ile Gln Ser Cys Thr Phe Glu Pro Asp Ile Lys Leu
 50                  55                  60

Ser Asp Ile Val Ile Gln Trp Leu Lys Glu Gly Val Leu Gly Leu Val
 65                  70                  75                  80

His Glu Phe Lys Glu Gly Lys Asp Glu Leu Ser Glu Gln Asp Glu Met
             85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser
                245

<210> SEQ ID NO 50
<211> LENGTH: 245
<212> TYPE: PRT
<213> ORGANISM: Homo sapiens

<400> SEQUENCE: 50

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
             20                  25                  30

Gly Arg His Ser Ile Thr Val Thr Val Ala Ser Ala Gly Asn Ile
         35                  40                  45

Gly Glu Asp Gly Ile Gln Ser Cys Thr Phe Glu Pro Asp Ile Lys Leu
 50                  55                  60

Ser Asp Ile Val Ile Gln Trp Leu Lys Glu Gly Val Leu Gly Leu Val
 65                  70                  75                  80

His Glu Phe Lys Glu Gly Lys Asp Glu Leu Ser Glu Gln Asp Glu Met
             85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
```

```
            130                 135                 140
Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                    180                 185                 190

Glu Val Ser Asn Thr Ser Phe Glu Leu Asn Ser Glu Asn Val Thr Met
                195                 200                 205

Lys Val Val Ser Val Leu Tyr Asn Val Thr Ile Asn Asn Thr Tyr Ser
                210                 215                 220

Cys Met Ile Glu Asn Asp Ile Ala Lys Ala Thr Gly Asp Ile Lys Val
225                 230                 235                 240

Thr Glu Ser Glu Ile
                245

<210> SEQ ID NO 51
<211> LENGTH: 259
<212> TYPE: PRT
<213> ORGANISM: Homo sapiens

<400> SEQUENCE: 51

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
                35                  40                  45

Gly Glu Asp Gly Ile Gln Ser Cys Thr Phe Glu Pro Asp Ile Lys Leu
            50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
                115                 120                 125

Lys Cys Tyr Ile Ile Thr Ser Lys Gly Lys Gly Asn Ala Asn Leu Glu
            130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                    180                 185                 190

Glu Val Ser Asn Thr Ser Phe Glu Leu Asn Ser Glu Asn Val Thr Met
                195                 200                 205

Lys Val Val Ser Val Leu Tyr Asn Val Thr Ile Asn Asn Thr Tyr Ser
                210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255
```

<210> SEQ ID NO 52
<211> LENGTH: 249
<212> TYPE: PRT
<213> ORGANISM: Homo sapiens

<400> SEQUENCE: 52

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser
                245
```

<210> SEQ ID NO 53
<211> LENGTH: 245
<212> TYPE: PRT
<213> ORGANISM: Homo sapiens

<400> SEQUENCE: 53

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
50                  55                  60

Ser Asp Ile Val Ile Gln Trp Leu Lys Glu Gly Val Leu Gly Leu Val
```

```
                65                  70                  75                  80
His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile
                245

<210> SEQ ID NO 54
<211> LENGTH: 259
<212> TYPE: PRT
<213> ORGANISM: Homo sapiens

<400> SEQUENCE: 54

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
            35                  40                  45

Gly Glu Asp Gly Ile Leu Ser Cys Thr Phe Glu Pro Asp Ile Lys Leu
        50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190
```

```
Glu Val Ser Asn Thr Ser Phe Glu Leu Asn Ser Glu Asn Val Thr Met
            195                 200                 205

Lys Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
            245                 250                 255

Lys Ala Ser

<210> SEQ ID NO 55
<211> LENGTH: 222
<212> TYPE: PRT
<213> ORGANISM: Homo sapiens

<400> SEQUENCE: 55

Gly Phe Gly Ile Ser Gly Arg His Ser Ile Thr Val Thr Val Ala
1               5                   10                  15

Ser Ala Gly Asn Ile Gly Glu Asp Gly Ile Gln Ser Cys Thr Phe Glu
                20                  25                  30

Pro Asp Ile Lys Leu Ser Asp Ile Val Ile Gln Trp Leu Lys Glu Gly
            35                  40                  45

Val Leu Gly Leu Val His Glu Phe Lys Glu Gly Lys Asp Glu Leu Ser
50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser
210                 215                 220

<210> SEQ ID NO 56
<211> LENGTH: 222
<212> TYPE: PRT
<213> ORGANISM: Homo sapiens

<400> SEQUENCE: 56

Gly Phe Gly Ile Ser Gly Arg His Ser Ile Thr Val Thr Val Ala
1               5                   10                  15

Ser Ala Gly Asn Ile Gly Glu Asp Gly Ile Leu Ser Cys Thr Phe Glu
                20                  25                  30

Pro Asp Ile Lys Leu Ser Asp Ile Val Ile Gln Trp Leu Lys Glu Gly
```

```
                35                  40                  45
Val Leu Gly Leu Val His Glu Phe Lys Glu Gly Lys Asp Glu Leu Ser
 50                  55                  60
Glu Gln Asp Glu Met Phe Arg Gly Arg Thr Ala Val Phe Ala Asp Gln
65                  70                  75                  80
Val Ile Val Gly Asn Ala Ser Leu Arg Leu Lys Asn Val Gln Leu Thr
                85                  90                  95
Asp Ala Gly Thr Tyr Lys Cys Tyr Ile Ile Thr Ser Lys Gly Lys Gly
            100                 105                 110
Asn Ala Asn Leu Glu Tyr Lys Thr Gly Ala Phe Ser Met Pro Glu Val
        115                 120                 125
Asn Val Asp Tyr Asn Ala Ser Ser Glu Thr Leu Arg Cys Glu Ala Pro
    130                 135                 140
Arg Trp Phe Pro Gln Pro Thr Val Val Trp Ala Ser Gln Val Asp Gln
145                 150                 155                 160
Gly Ala Asn Phe Ser Glu Val Ser Asn Thr Ser Phe Glu Leu Asn Ser
                165                 170                 175
Glu Asn Val Thr Met Lys Val Val Ser Val Leu Tyr Asn Val Thr Ile
            180                 185                 190
Asn Asn Thr Tyr Ser Cys Met Ile Glu Asn Asp Ile Ala Lys Ala Thr
        195                 200                 205
Gly Asp Ile Lys Val Thr Glu Ser Glu Ile Lys Arg Arg Ser
    210                 215                 220

<210> SEQ ID NO 57
<211> LENGTH: 218
<212> TYPE: PRT
<213> ORGANISM: Homo sapiens

<400> SEQUENCE: 57

Gly Phe Gly Ile Ser Gly Arg His Ser Ile Thr Val Thr Thr Val Ala
1               5                   10                  15
Ser Ala Gly Asn Ile Gly Glu Asp Gly Ile Gln Ser Cys Thr Phe Glu
                20                  25                  30
Pro Asp Ile Lys Leu Ser Asp Ile Val Ile Gln Trp Leu Lys Glu Gly
            35                  40                  45
Val Leu Gly Leu Val His Glu Phe Lys Glu Gly Lys Asp Glu Leu Ser
 50                  55                  60
Glu Gln Asp Glu Met Phe Arg Gly Arg Thr Ala Val Phe Ala Asp Gln
65                  70                  75                  80
Val Ile Val Gly Asn Ala Ser Leu Arg Leu Lys Asn Val Gln Leu Thr
                85                  90                  95
Asp Ala Gly Thr Tyr Lys Cys Tyr Ile Ile Thr Ser Lys Gly Lys Gly
            100                 105                 110
Asn Ala Asn Leu Glu Tyr Lys Thr Gly Ala Phe Ser Met Pro Glu Val
        115                 120                 125
Asn Val Asp Tyr Asn Ala Ser Ser Glu Thr Leu Arg Cys Glu Ala Pro
    130                 135                 140
Arg Trp Phe Pro Gln Pro Thr Val Val Trp Ala Ser Gln Val Asp Gln
145                 150                 155                 160
Gly Ala Asn Phe Ser Glu Val Ser Asn Thr Ser Phe Glu Leu Asn Ser
                165                 170                 175
Glu Asn Val Thr Met Lys Val Val Ser Val Leu Tyr Asn Val Thr Ile
            180                 185                 190
```

Asn Asn Thr Tyr Ser Cys Met Ile Glu Asn Asp Ile Ala Lys Ala Thr
            195                 200                 205

Gly Asp Ile Lys Val Thr Glu Ser Glu Ile
    210                 215

<210> SEQ ID NO 58
<211> LENGTH: 218
<212> TYPE: PRT
<213> ORGANISM: Homo sapiens

<400> SEQUENCE: 58

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile
    210                 215

<210> SEQ ID NO 59
<211> LENGTH: 232
<212> TYPE: PRT
<213> ORGANISM: Homo sapiens

<400> SEQUENCE: 59

Gly Phe Gly Ile Ser Gly Arg His Ser Ile Thr Val Thr Thr Val Ala
1               5                   10                  15

Ser Ala Gly Asn Ile Gly Glu Asp Gly Ile Gln Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
            130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser His Leu
            210                 215                 220

Gln Leu Leu Asn Ser Lys Ala Ser
225                 230

<210> SEQ ID NO 60
<211> LENGTH: 232
<212> TYPE: PRT
<213> ORGANISM: Homo sapiens

<400> SEQUENCE: 60

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
            35                  40                  45

Val Leu Gly Leu Val His Glu Phe Lys Glu Gly Lys Asp Glu Leu Ser
50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
            130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser His Leu
            210                 215                 220

Gln Leu Leu Asn Ser Lys Ala Ser
225                 230

<210> SEQ ID NO 61
<211> LENGTH: 387
<212> TYPE: DNA
<213> ORGANISM: Homo sapiens

<400> SEQUENCE: 61
ggcttcggca tcagtggacg gcacagtatc acagtgacca ccgtcgcctc cgctggcaat      60
ataggtgagg atggcatcca gtcctgtacc tttgagccgg acatcaaact gtctgacata     120
gtgatacaat ggctgaagga gggggtgctc ggtctggtac atgagtttaa ggaagggaag     180
gatgaactgt ccgagcagga tgagatgttc cgggggagga ccgctgtgtt cgccgatcag     240
gtaatcgtcg gaaatgcaag tctcagattg aaaaatgtgc aactgactga tgctggcacg     300
tataaatgct acattatcac aagtaagggc aaaggaaatg ctaaccttga gtataaaaca     360
ggcgcattct caatgcccga ggtcaat                                         387

<210> SEQ ID NO 62
<211> LENGTH: 387
<212> TYPE: DNA
<213> ORGANISM: Homo sapiens

<400> SEQUENCE: 62
ggcttcggca tcagtggacg gcacagtatc acagtgacca ccgtcgcctc cgctggcaat      60
ataggtgagg atggcatcct gtcctgtacc tttgagccgg acatcaaact gtctgacata     120
gtgatacaat ggctgaagga gggggtgctc ggtctggtac atgagtttaa ggaagggaag     180
gatgaactgt ccgagcagga tgagatgttc cgggggagga ccgctgtgtt cgccgatcag     240
gtaatcgtcg gaaatgcaag tctcagattg aaaaatgtgc aactgactga tgctggcacg     300
tataaatgct acattatcac aagtaagggc aaaggaaatg ctaaccttga gtataaaaca     360
ggcgcattct caatgcccga ggtcaat                                         387

<210> SEQ ID NO 63
<211> LENGTH: 129
<212> TYPE: PRT
<213> ORGANISM: Homo sapiens

<400> SEQUENCE: 63

Gly Phe Gly Ile Ser Gly Arg His Ser Ile Thr Val Thr Val Ala
1               5                   10                  15

Ser Ala Gly Asn Ile Gly Glu Asp Gly Ile Gln Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn

<210> SEQ ID NO 64
<211> LENGTH: 129
<212> TYPE: PRT
<213> ORGANISM: Homo sapiens

<400> SEQUENCE: 64

```
Gly Phe Gly Ile Ser Gly Arg His Ser Ile Thr Val Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
            35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125
```

Asn

<210> SEQ ID NO 65
<211> LENGTH: 245
<212> TYPE: PRT
<213> ORGANISM: Pan troglodytes

<400> SEQUENCE: 65

```
Met Lys Pro Leu Thr Ser Arg Ile Ile Ser Ile Ile Ile Leu Ala
1               5                   10                  15

Gly Ala Ile Ala Leu Ile Ile Gly Phe Gly Ile Ser Gly Arg His Ser
            20                  25                  30

Ile Thr Val Thr Thr Val Ala Ser Ala Gly Asn Ile Gly Glu Asp Gly
        35                  40                  45

Ile Leu Ser Cys Thr Phe Glu Pro Asp Ile Lys Leu Ser Asp Ile Val
    50                  55                  60

Ile Gln Trp Leu Lys Glu Gly Val Leu Gly Leu Val His Glu Phe Lys
65                  70                  75                  80

Glu Gly Lys Asp Glu Leu Ser Glu Gln Asp Glu Met Phe Arg Gly Arg
                85                  90                  95

Thr Ala Val Phe Ala Asp Gln Val Ile Val Gly Asn Ala Ser Leu Arg
            100                 105                 110

Leu Lys Asn Val Gln Leu Thr Asp Ala Gly Thr Tyr Lys Cys Tyr Ile
        115                 120                 125

Ile Thr Ser Lys Gly Lys Gly Asn Ala Asn Leu Glu Tyr Lys Thr Gly
    130                 135                 140

Ala Phe Ser Met Pro Glu Val Asn Val Asp Tyr Asn Ala Ser Ser Glu
145                 150                 155                 160

Thr Leu Arg Cys Glu Ala Pro Arg Trp Phe Pro Gln Pro Thr Val Val
                165                 170                 175

Trp Ala Ser Gln Ile Asp Gln Gly Ala Asn Phe Ser Glu Val Ser Asn
```

```
                180                 185                 190
Thr Ser Phe Glu Leu Asn Ser Glu Asn Val Thr Met Lys Val Val Ser
            195                 200                 205
Val Leu Tyr Asn Ala Thr Ile Asn Asn Thr Tyr Ser Cys Met Ile Glu
        210                 215                 220
Asn Asp Ile Ala Lys Ala Thr Gly Asp Ile Lys Val Thr Glu Ser Glu
225                 230                 235                 240
Ile Lys Arg Arg Ser
            245

<210> SEQ ID NO 66
<211> LENGTH: 241
<212> TYPE: PRT
<213> ORGANISM: Pan troglodytes

<400> SEQUENCE: 66

Met Lys Pro Leu Thr Ser Arg Ile Ile Ser Ile Ile Ile Ile Leu Ala
1               5                   10                  15

Gly Ala Ile Ala Leu Ile Ile Gly Phe Gly Ile Ser Gly Arg His Ser
            20                  25                  30

Ile Thr Val Thr Thr Val Ala Ser Ala Gly Asn Ile Gly Glu Asp Gly
        35                  40                  45

Ile Leu Ser Cys Thr Phe Glu Pro Asp Ile Lys Leu Ser Asp Ile Val
    50                  55                  60

Ile Gln Trp Leu Lys Glu Gly Val Leu Gly Leu Val His Glu Phe Lys
65                  70                  75                  80

Glu Gly Lys Asp Glu Leu Ser Glu Gln Asp Glu Met Phe Arg Gly Arg
                85                  90                  95

Thr Ala Val Phe Ala Asp Gln Val Ile Val Gly Asn Ala Ser Leu Arg
            100                 105                 110

Leu Lys Asn Val Gln Leu Thr Asp Ala Gly Thr Tyr Lys Cys Tyr Ile
        115                 120                 125

Ile Thr Ser Lys Gly Lys Gly Asn Ala Asn Leu Glu Tyr Lys Thr Gly
    130                 135                 140

Ala Phe Ser Met Pro Glu Val Asn Val Asp Tyr Asn Ala Ser Ser Glu
145                 150                 155                 160

Thr Leu Arg Cys Glu Ala Pro Arg Trp Phe Pro Gln Pro Thr Val Val
                165                 170                 175

Trp Ala Ser Gln Ile Asp Gln Gly Ala Asn Phe Ser Glu Val Ser Asn
            180                 185                 190

Thr Ser Phe Glu Leu Asn Ser Glu Asn Val Thr Met Lys Val Val Ser
        195                 200                 205

Val Leu Tyr Asn Ala Thr Ile Asn Asn Thr Tyr Ser Cys Met Ile Glu
    210                 215                 220

Asn Asp Ile Ala Lys Ala Thr Gly Asp Ile Lys Val Thr Glu Ser Glu
225                 230                 235                 240

Ile

<210> SEQ ID NO 67
<211> LENGTH: 255
<212> TYPE: PRT
<213> ORGANISM: Pan troglodytes

<400> SEQUENCE: 67

Met Lys Pro Leu Thr Ser Arg Ile Ile Ser Ile Ile Ile Ile Leu Ala
1               5                   10                  15
```

```
Gly Ala Ile Ala Leu Ile Ile Gly Phe Gly Ile Ser Gly Arg His Ser
             20                  25                  30

Ile Thr Val Thr Thr Val Ala Ser Ala Gly Asn Ile Gly Glu Asp Gly
         35                  40                  45

Ile Leu Ser Cys Thr Phe Glu Pro Asp Ile Lys Leu Ser Asp Ile Val
 50                  55                  60

Ile Gln Trp Leu Lys Glu Gly Val Leu Gly Leu Val His Glu Phe Lys
 65                  70                  75                  80

Glu Gly Lys Asp Glu Leu Ser Glu Gln Asp Glu Met Phe Arg Gly Arg
                 85                  90                  95

Thr Ala Val Phe Ala Asp Gln Val Ile Val Gly Asn Ala Ser Leu Arg
             100                 105                 110

Leu Lys Asn Val Gln Leu Thr Asp Ala Gly Thr Tyr Lys Cys Tyr Ile
         115                 120                 125

Ile Thr Ser Lys Gly Lys Gly Asn Ala Asn Leu Glu Tyr Lys Thr Gly
130                 135                 140

Ala Phe Ser Met Pro Glu Val Asn Val Asp Tyr Asn Ala Ser Ser Glu
145                 150                 155                 160

Thr Leu Arg Cys Glu Ala Pro Arg Trp Phe Pro Gln Pro Thr Val Val
                 165                 170                 175

Trp Ala Ser Gln Ile Asp Gln Gly Ala Asn Phe Ser Glu Val Ser Asn
             180                 185                 190

Thr Ser Phe Glu Leu Asn Ser Glu Asn Val Thr Met Lys Val Val Ser
         195                 200                 205

Val Leu Tyr Asn Ala Thr Ile Asn Asn Thr Tyr Ser Cys Met Ile Glu
210                 215                 220

Asn Asp Ile Ala Lys Ala Thr Gly Asp Ile Lys Val Thr Glu Ser Glu
225                 230                 235                 240

Ile Lys Arg Arg Ser His Leu Gln Leu Leu Asn Ser Lys Ala Ser
                 245                 250                 255

<210> SEQ ID NO 68
<211> LENGTH: 222
<212> TYPE: PRT
<213> ORGANISM: Pan troglodytes

<400> SEQUENCE: 68

Gly Phe Gly Ile Ser Gly Arg His Ser Ile Thr Val Thr Thr Val Ala
 1               5                  10                  15

Ser Ala Gly Asn Ile Gly Glu Asp Gly Ile Leu Ser Cys Thr Phe Glu
             20                  25                  30

Pro Asp Ile Lys Leu Ser Asp Ile Val Ile Gln Trp Leu Lys Glu Gly
         35                  40                  45

Val Leu Gly Leu Val His Glu Phe Lys Glu Gly Lys Asp Glu Leu Ser
 50                  55                  60

Glu Gln Asp Glu Met Phe Arg Gly Arg Thr Ala Val Phe Ala Asp Gln
 65                  70                  75                  80

Val Ile Val Gly Asn Ala Ser Leu Arg Leu Lys Asn Val Gln Leu Thr
                 85                  90                  95

Asp Ala Gly Thr Tyr Lys Cys Tyr Ile Ile Thr Ser Lys Gly Lys Gly
             100                 105                 110

Asn Ala Asn Leu Glu Tyr Lys Thr Gly Ala Phe Ser Met Pro Glu Val
         115                 120                 125

Asn Val Asp Tyr Asn Ala Ser Ser Glu Thr Leu Arg Cys Glu Ala Pro
```

```
            130                 135                 140
Arg Trp Phe Pro Gln Pro Thr Val Val Trp Ala Ser Gln Ile Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Ala Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser
        210                 215                 220

<210> SEQ ID NO 69
<211> LENGTH: 218
<212> TYPE: PRT
<213> ORGANISM: Pan troglodytes

<400> SEQUENCE: 69

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Ile Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Ala Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile
    210                 215

<210> SEQ ID NO 70
<211> LENGTH: 232
<212> TYPE: PRT
<213> ORGANISM: Macaca mulatta

<400> SEQUENCE: 70

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
```

```
                20              25              30
    Pro Asp Ile Lys Leu Ser Asp Ile Val Ile Gln Trp Leu Lys Glu Gly
                 35                  40                  45

Val Leu Gly Leu Val His Glu Phe Lys Glu Gly Lys Asp Glu Leu Ser
     50                  55                  60

Glu Gln Asp Glu Met Phe Arg Gly Arg Thr Ala Val Phe Ala Asp Gln
     65                  70                  75                  80

Val Ile Val Gly Asn Ala Ser Leu Arg Leu Lys Asn Val Gln Leu Thr
                         85                  90                  95

Asp Ala Gly Thr Tyr Lys Cys Tyr Ile Ile Thr Ser Lys Gly Lys Gly
                    100                 105                 110

Asn Ala Asn Leu Glu Tyr Lys Thr Gly Ala Phe Ser Met Pro Glu Val
                115                 120                 125

Asn Val Asp Tyr Asn Ala Ser Ser Glu Thr Leu Arg Cys Glu Ala Pro
            130                 135                 140

Arg Trp Phe Pro Gln Pro Thr Val Val Trp Ala Ser Gln Ile Asp Gln
    145                 150                 155                 160

Gly Ala Asn Phe Ser Glu Val Ser Asn Thr Ser Phe Glu Leu Asn Ser
                        165                 170                 175

Glu Asn Val Thr Met Lys Val Val Ser Val Leu Tyr Asn Ala Thr Ile
                    180                 185                 190

Asn Asn Thr Tyr Ser Cys Met Ile Glu Asn Asp Ile Ala Lys Ala Thr
                195                 200                 205

Gly Asp Ile Lys Val Thr Glu Ser Glu Ile Lys Arg Arg Ser His Leu
            210                 215                 220

Gln Leu Leu Asn Ser Lys Ala Ser
    225                 230

<210> SEQ ID NO 71
<211> LENGTH: 249
<212> TYPE: PRT
<213> ORGANISM: Macaca mulatta

<400> SEQUENCE: 71

Met Ala Ser Leu Gly Gln Ile Leu Phe Trp Ser Ile Ile Ser Ile Ile
     1               5                  10                  15

Phe Ile Leu Ala Gly Ala Ile Ala Leu Ile Ile Gly Phe Gly Ile Ser
                    20                  25                  30

Gly Arg His Ser Ile Thr Val Thr Thr Val Ala Ser Ala Gly Asn Ile
                 35                  40                  45

Gly Glu Asp Gly Ile Leu Ser Cys Thr Phe Glu Pro Asp Ile Lys Leu
     50                  55                  60

Ser Asp Ile Val Ile Gln Trp Leu Lys Glu Gly Val Ile Gly Leu Val
     65                  70                  75                  80

His Glu Phe Lys Glu Gly Lys Asp Glu Leu Ser Glu Gln Asp Glu Met
                         85                  90                  95

Phe Arg Gly Arg Thr Ala Val Phe Ala Asp Gln Val Ile Val Gly Asn
                    100                 105                 110

Ala Ser Leu Arg Leu Lys Asn Val Gln Leu Thr Asp Ala Gly Thr Tyr
                115                 120                 125

Lys Cys Tyr Ile Ile Thr Ser Lys Gly Lys Gly Asn Ala Asn Leu Glu
            130                 135                 140

Tyr Lys Thr Gly Ala Phe Ser Met Pro Glu Val Asn Val Asp Tyr Asn
    145                 150                 155                 160
```

Ala Ser Ser Glu Thr Leu Arg Cys Glu Ala Pro Arg Trp Phe Pro Gln
            165                 170                 175

Pro Thr Val Val Trp Ala Ser Gln Val Asp Gln Gly Ala Asn Phe Ser
        180                 185                 190

Glu Val Ser Asn Thr Ser Phe Glu Leu Asn Ser Glu Asn Val Thr Met
    195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser
            245

<210> SEQ ID NO 72
<211> LENGTH: 245
<212> TYPE: PRT
<213> ORGANISM: Macaca mulatta

<400> SEQUENCE: 72

Met Ala Ser Leu Gly Gln Ile Leu Phe Trp Ser Ile Ser Ile Ile
1               5                   10                  15

Phe Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
            35                  40                  45

Gly Glu Asp Gly Ile Leu Ser Cys Thr Phe Glu Pro Asp Ile Lys Leu
50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile
                245

<210> SEQ ID NO 73
<211> LENGTH: 259
<212> TYPE: PRT
<213> ORGANISM: Macaca mulatta

<400> SEQUENCE: 73

Met Ala Ser Leu Gly Gln Ile Leu Phe Trp Ser Ile Ile Ser Ile Ile
1               5                   10                  15

Phe Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser

<210> SEQ ID NO 74
<211> LENGTH: 222
<212> TYPE: PRT
<213> ORGANISM: Macaca mulatta

<400> SEQUENCE: 74

Gly Phe Gly Ile Ser Gly Arg His Ser Ile Thr Val Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Ile Gly Leu Val His Glu Phe Lys Glu Gly Lys Asp Glu Leu Ser
50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
        130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser
        210                 215                 220

<210> SEQ ID NO 75
<211> LENGTH: 218
<212> TYPE: PRT
<213> ORGANISM: Macaca mulatta

<400> SEQUENCE: 75

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Ile Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
        130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile
        210                 215

<210> SEQ ID NO 76
<211> LENGTH: 232
<212> TYPE: PRT
<213> ORGANISM: Macaca fascicularis

<400> SEQUENCE: 76

```
Gly Phe Gly Ile Ser Gly Arg His Ser Ile Thr Val Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Ile Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65              70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Val Asp Gln
145             150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
    210                 215                 220

Gln Leu Leu Asn Ser Lys Ala Ser
225                 230
```

<210> SEQ ID NO 77
<211> LENGTH: 249
<212> TYPE: PRT
<213> ORGANISM: Macaca fascicularis

<400> SEQUENCE: 77

```
Met Ala Ser Leu Gly Gln Ile Leu Phe Trp Ser Ile Ile Ser Ile Ile
1               5                   10                  15

Phe Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Ile Gly Leu Val
65              70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125
```

```
Lys Cys Tyr Ile Ile Thr Ser Lys Gly Lys Gly Asn Ala Asn Leu Glu
            130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser
                245

<210> SEQ ID NO 78
<211> LENGTH: 245
<212> TYPE: PRT
<213> ORGANISM: Macaca fascicularis

<400> SEQUENCE: 78

Met Ala Ser Leu Gly Gln Ile Leu Phe Trp Ser Ile Ile Ser Ile Ile
1               5                   10                  15

Phe Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
            35                  40                  45

Gly Glu Asp Gly Ile Leu Ser Cys Thr Phe Glu Pro Asp Ile Lys Leu
        50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu
            130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Glu Ser Glu Ile
```

<210> SEQ ID NO 79
<211> LENGTH: 259
<212> TYPE: PRT
<213> ORGANISM: Macaca fascicularis

<400> SEQUENCE: 79

Met Ala Ser Leu Gly Gln Ile Leu Phe Trp Ser Ile Ile Ser Ile Ile
1               5                   10                  15

Phe Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
            35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser

<210> SEQ ID NO 80
<211> LENGTH: 222
<212> TYPE: PRT
<213> ORGANISM: Macaca fascicularis

<400> SEQUENCE: 80

Gly Phe Gly Ile Ser Gly Arg His Ser Ile Thr Val Thr Val Ala
1               5                   10                  15

Ser Ala Gly Asn Ile Gly Glu Asp Gly Ile Leu Ser Cys Thr Phe Glu
                20                  25                  30

Pro Asp Ile Lys Leu Ser Asp Ile Val Ile Gln Trp Leu Lys Glu Gly
            35                  40                  45

Val Ile Gly Leu Val His Glu Phe Lys Glu Gly Lys Asp Glu Leu Ser
        50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
            85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
            130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
            165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser
            210                 215                 220

<210> SEQ ID NO 81
<211> LENGTH: 218
<212> TYPE: PRT
<213> ORGANISM: Macaca fascicularis

<400> SEQUENCE: 81

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
            35                  40                  45

Val Ile Gly Leu Val His Glu Phe Lys Glu Gly Lys Asp Glu Leu Ser
50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
            85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
            130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
            165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile
            210                 215

<210> SEQ ID NO 82
<211> LENGTH: 232
<212> TYPE: PRT
<213> ORGANISM: Macaca fascicularis

<400> SEQUENCE: 82

```
Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Ile Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser His Leu
    210                 215                 220

Gln Leu Leu Asn Ser Lys Ala Ser
225                 230
```

<210> SEQ ID NO 83
<211> LENGTH: 129
<212> TYPE: PRT
<213> ORGANISM: Pan troglodytes

<400> SEQUENCE: 83

```
Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
```

```
                    85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn

<210> SEQ ID NO 84
<211> LENGTH: 129
<212> TYPE: PRT
<213> ORGANISM: Macaca mulatta

<400> SEQUENCE: 84

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Ile Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn

<210> SEQ ID NO 85
<211> LENGTH: 129
<212> TYPE: PRT
<213> ORGANISM: Macaca fascicularis

<400> SEQUENCE: 85

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Ile Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn
```

<210> SEQ ID NO 86
<211> LENGTH: 696
<212> TYPE: DNA
<213> ORGANISM: Homo sapiens

<400> SEQUENCE: 86

```
gagcctaagt catgtgacaa gacccatacg tgcccaccct gtcccgctcc agaactgctg      60
gggggaccta gcgttttctt gttcccccca agcccaagg acaccctcat gatctcacgg      120
actcccgaag taacatgcgt agtagtcgac gtgagccacg aggatcctga agtgaagttt      180
aattggtacg tggacggagt cgaggtgcat aatgccaaaa ctaaacctcg ggaggagcag      240
tataacagta cctaccgcgt ggtatccgtc ttgacagtgc tccaccagga ctggctgaat      300
ggtaaggagt ataaatgcaa ggtcagcaac aaagctcttc ccgccccaat gaaaagact      360
atcagcaagg ccaagggaca accccgcgag ccccaggttt acacccttcc accttcacga      420
gacgagctga ccaagaacca ggtgtctctg acttgtctgg tcaaaggttt ctatccttcc      480
gacatcgcag tggagtggga gtcaaacggg cagcctgaga taactacaa gaccacaccc      540
ccagtgcttg atagcgatgg gagcttttc ctctacagta agctgactgt ggacaaatcc      600
cgctggcagc agggaaacgt tttctcttgt agcgtcatgc atgaggccct ccacaaccat      660
tatactcaga aaagcctgag tctgagtccc ggcaaa                               696
```

<210> SEQ ID NO 87
<211> LENGTH: 681
<212> TYPE: DNA
<213> ORGANISM: Homo sapiens

<400> SEQUENCE: 87

```
gacaagaccc atacgtgccc accctgtccc gctccagaac tgctgggggg acctagcgtt      60
ttcttgttcc ccccaaagcc caaggacacc ctcatgatct cacggactcc cgaagtaaca      120
tgcgtagtag tcgacgtgag ccacgaggat cctgaagtga gtttaattg gtacgtggac      180
ggagtcgagg tgcataatgc caaaactaaa cctcgggagg agcagtataa cagtacctac      240
cgcgtggtat ccgtcttgac agtgctccac caggactggc tgaatggtaa ggagtataaa      300
tgcaaggtca gcaacaaagc tcttcccgcc ccaattgaaa agactatcag caaggccaag      360
ggacaacccc gcgagcccca ggtttacacc cttccacctt cacgagacga gctgaccaag      420
aaccaggtgt ctctgacttg tctggtcaaa ggtttctatc cttccgacat cgcagtggag      480
tgggagtcaa acgggcagcc tgagaataac tacaagacca ccccccagt gcttgatagc      540
gatgggagct tttcctcta cagtaagctg actgtggaca atcccgctg gcagcaggga      600
aacgttttct cttgtagcgt catgcatgag gccctccaca accattatac tcagaaaagc      660
ctgagtctga gtcccggcaa a                                                681
```

<210> SEQ ID NO 88
<211> LENGTH: 232
<212> TYPE: PRT
<213> ORGANISM: Homo sapiens

<400> SEQUENCE: 88

```
Glu Pro Lys Ser Cys Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
```

Val Asp Val Ser His Glu Asp Pro Glu Val Lys Phe Asn Trp Tyr Val
             50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 89
<211> LENGTH: 227
<212> TYPE: PRT
<213> ORGANISM: Homo sapiens

<400> SEQUENCE: 89

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val

```
                180               185                190
Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 90
<211> LENGTH: 699
<212> TYPE: DNA
<213> ORGANISM: Mus musculus

<400> SEQUENCE: 90
gagccaagag gtcctacgat caagccctgc ccgccttgta aatgcccagc tccaaatttg      60
ctgggtggac cgtcagtctt tatcttcccg ccaaagataa aggacgtctt gatgattagt     120
ctgagcccca tcgtgacatg cgttgtggtg gatgtttcag aggatgaccc cgacgtgcaa     180
atcagttggt tcgttaacaa cgtggaggtg cataccgctc aaacccagac ccacagagag     240
gattataaca gcaccctgcg ggtagtgtcc gccctgccga tccagcatca ggattggatg     300
agcgggaaag agttcaagtg taaggtaaac aacaaagatc tgccagcgcc gattgaacga     360
accattagca gccgaaagg gagcgtgcgc gcacctcagg tttacgtcct tcctccacca     420
gaagaggaga tgacgaaaaa gcaggtgacc ctgacatgca tggtaactga ctttatgcca     480
gaagatattt acgtggaatg gactaataac ggaaagacag agctcaatta caagaacact     540
gagcctgttc tggattctga tggcagctac tttatgtact ccaaattgag ggtcgagaag     600
aagaattggg tcgagagaaa cagttatagt tgctcagtgg tgcatgaggg cctccataat     660
catcacacca caaagtcctt cagccgaacg cccgggaaa                            699

<210> SEQ ID NO 91
<211> LENGTH: 233
<212> TYPE: PRT
<213> ORGANISM: Artificial Sequence
<220> FEATURE:
<223> OTHER INFORMATION: Synthetic fusion protein

<400> SEQUENCE: 91

Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Glu Glu Glu Met
    130                 135                 140
```

```
Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
            165                 170                 175

Tyr Lys Asn Thr Glu Pro Val Leu Asp Ser Asp Gly Tyr Phe Met
        180                 185                 190

Tyr Ser Lys Leu Arg Val Glu Lys Lys Asn Trp Val Glu Arg Asn Ser
            195                 200                 205

Tyr Ser Cys Ser Val Val His Glu Gly Leu His Asn His His Thr Thr
        210                 215                 220

Lys Ser Phe Ser Arg Thr Pro Gly Lys
225                 230

<210> SEQ ID NO 92
<211> LENGTH: 4
<212> TYPE: PRT
<213> ORGANISM: Artificial Sequence
<220> FEATURE:
<223> OTHER INFORMATION: Synthetic linker sequence

<400> SEQUENCE: 92

Asp Ser Gly Ser
1

<210> SEQ ID NO 93
<211> LENGTH: 4
<212> TYPE: PRT
<213> ORGANISM: Artificial Sequence
<220> FEATURE:
<223> OTHER INFORMATION: Synthetic linker peptide

<400> SEQUENCE: 93

Gly Gly Gly Ser
1

<210> SEQ ID NO 94
<211> LENGTH: 15
<212> TYPE: PRT
<213> ORGANISM: Artificial Sequence
<220> FEATURE:
<223> OTHER INFORMATION: Synthetic linker peptide

<400> SEQUENCE: 94

Gly Gly Gly Gly Ser Gly Gly Gly Ser Gly Gly Gly Ser
1               5                   10                  15

<210> SEQ ID NO 95
<211> LENGTH: 20
<212> TYPE: PRT
<213> ORGANISM: Artificial Sequence
<220> FEATURE:
<223> OTHER INFORMATION: Synthetic linker peptide

<400> SEQUENCE: 95

Gly Gly Gly Gly Ser Gly Gly Gly Ser Gly Gly Gly Ser Gly
1               5                   10                  15

Gly Gly Gly Ser
            20

<210> SEQ ID NO 96
<211> LENGTH: 1470
<212> TYPE: DNA
<213> ORGANISM: Artificial Sequence
```

<220> FEATURE:
<223> OTHER INFORMATION: Synthetic fusion nucleotide

<400> SEQUENCE: 96

```
atggcttcct tggggcagat catcttttgg agtattatta acatcatcat catcctggct      60
ggggccatcg cactcatcat tggctttggc atttcaggca agcacttcat cacggtcacg     120
accttcacct cagctggaaa cattggagag acgggaccc tgagctgcac ttttgaacct      180
gacatcaaac tcaacggcat cgtcatccag tggctgaaag aaggcatcaa aggtttggtc     240
cacgagttca agaaggcaa agacgacctc tcacagcagc atgagatgtt cagaggccgc      300
acagcagtgt ttgctgatca ggtggtagtt ggcaatgctt ccctgagact gaaaaacgtg     360
cagctcacgg atgctggcac ctacacatgt acatccgca cctcaaaagg caaagggaat      420
gcaaaccttg agtataagac cggagccttc agtatgccag agataaatgt ggactataat     480
gccagttcag agagtttacg ctgcgaggct cctcggtggt tcccccagcc cacagtggcc     540
tgggcatctc aagtcgacca aggagccaat ttctcagaag tctccaacac cagctttgag     600
ttgaactctg agaatgtgac catgaaggtc gtatctgtgc tctacaatgt cacaatcaac     660
aacacatact cctgtatgat tgaaaacgac attgccaaag ccaccgggga catcaaagtg     720
acagattcag aggtcaaaag gcgaagtcag ctgcagttgc tgaactctgg ggagccaaga     780
ggtcctacga tcaagcctg cccgccttgt aaatgcccag ctccaaattt gctgggtgga     840
ccgtcagtct ttatcttccc gccaaagata aggacgtct tgatgattag tctgagcccc     900
atcgtgacat gcgttgtggt ggatgtttca gaggatgacc ccgacgtgca aatcagttgg    960
ttcgttaaca acgtggaggt gcataccgct caaacccaga cccacagaga ggattataac    1020
agcaccctgc gggtagtgtc cgccctgccg atccagcatc aggattggat gagcgggaaa    1080
gagttcaagt gtaaggtaaa caacaaagat ctgccagcgc cgattgaacg aaccattagc    1140
aagccgaaag ggagcgtgcg cgcacctcag gtttacgtcc ttcctccacc agaagaggag    1200
atgacgaaaa agcaggtgac cctgacatgc atggtaactg actttatgcc agaagatatt    1260
tacgtggaat ggactaataa cggaaagaca gagctcaatt acaagaacac tgagcctgtt    1320
ctggattctg atggcagcta ctttatgtac tccaaattga gggtcgagaa gaagaattgg    1380
gtcgagagaa acagttatag ttgctcagtg gtgcatgagg gcctccataa tcatcacacc    1440
acaaagtcct tcagccgaac gcccgggaaa                                     1470
```

<210> SEQ ID NO 97
<211> LENGTH: 1446
<212> TYPE: DNA
<213> ORGANISM: Artificial Sequence
<220> FEATURE:
<223> OTHER INFORMATION: Synthetic fusion nucleotide

<400> SEQUENCE: 97

```
atggagtggt catgggtttt tctgttcttt cttagcgtga ctacaggcgt ccattcagga      60
ttcggcataa gcggcaagca cttcatcaca gttacaacgt ttacaagtgc ggggaacatt     120
ggggaagatg gaacattgtc atgtacattt gagccagata tcaaactcaa tggaatagta     180
attcagtggc ttaaggaggg catcaagggc ctggtccacg aatttaagga ggggaaagac     240
gatctgtctc agcagcacga gatgttcagg gcagaaccg ccgtcttcgc agaccaggtt      300
gtggtaggca acgccagttt gcggctgaaa aacgtcagc tgactgacgc cggcacctac      360
acatgctata tccggtcctc taagggcaag gggaacgcta atctcgagta caaaacaggc    420
```

```
gccttttcta tgccagagat caacgtggac tataacgcaa gctctgaaag tctgagatgc      480
gaggcgccaa ggtggttccc tcagcccacc gtcgcgtggg cttcccaggt ggatcaaggc      540
gccaactttt ctgaggtttc taacaccagc ttcgaactga acagcgaaaa tgtgacaatg      600
aaggtagtca gcgttctgta taacgtgacc atcaacaata cttactcctg tatgatagaa      660
aatgatatag ccaaggctac aggagatatt aaagtgacgg attcagaagt gaaaaggagg      720
agtcaactgc aactcttgaa tagcggcgag ccaagaggtc ctacgatcaa gccctgcccg      780
ccttgtaaat gcccagctcc aaatttgctg ggtggaccgt cagtctttat cttcccgcca      840
aagataaagg acgtcttgat gattagtctg agccccatcg tgacatgcgt tgtggtggat      900
gtttcagagg atgaccccga cgtgcaaatc agttggttcg ttaacaacgt ggaggtgcat      960
accgctcaaa cccagaccca cagagaggat tataacagca ccctgcgggt agtgtccgcc     1020
ctgccgatcc agcatcagga ttggatgagc gggaagagt tcaagtgtaa ggtaaacaac     1080
aaagatctgc cagcgccgat tgaacgaacc attagcaagc cgaaagggag cgtgcgcgca     1140
cctcaggttt acgtccttcc tccaccagaa gaggagatga cgaaaaagca ggtgaccctg     1200
acatgcatgg taactgactt tatgccagaa gatatttacg tggaatggac taataacgga     1260
aagacagagc tcaattacaa gaacactgag cctgttctgg attctgatgg cagctacttt     1320
atgtactcca aattgagggt cgagaagaag aattgggtcg agagaaacag ttatagttgc     1380
tcagtggtgc atgagggcct ccataatcat cacaccacaa gtccttcag ccgaacgccc     1440 gggaaa                                                                1446
```

<210> SEQ ID NO 98
<211> LENGTH: 1446
<212> TYPE: DNA
<213> ORGANISM: Artificial Sequence
<220> FEATURE:
<223> OTHER INFORMATION: Synthetic fusion nucleotide

<400> SEQUENCE: 98

```
atggagtggt catgggtttt tctgttctt cttagcgtga ctacaggcgt ccattcagga       60
ttcggcataa gcggcaagca cttcatcaca gttacaacgt ttacaagtgc ggggaacatt      120
ggggaagatg gaacattgtc atgtacattt gagccagata tcaaactcaa tggaatagta      180
attcagtggc ttaaggaggg catcaagggc ctggtccacg aatttaagga ggggaaagac      240
gatctgtctc agcagcacga gatgttcagg ggcagaaccg ccgtcttcgc agaccaggtt      300
gtggtaggca cgccagtttt gcggctgaaa acgtcagc tgactgacgc cggcacctac       360
acatgctata tccggacctc taagggcaag gggaacgcta atctcgagta caaacaggc      420 gccttttcta tgccagagat caacgtggac tataacgcaa gctctgaaag tctgagatgc      480
gaggcgccaa ggtggttccc tcagcccacc gtcgcgtggg cttcccaggt ggatcaaggc      540
gccaactttt ctgaggtttc taacaccagc ttcgaactga acagcgaaaa tgtgacaatg      600
aaggtagtca gcgttctgta taacgtgacc atcaacaata cttactcctg tatgatagaa      660
aatgatatag ccaaggctac aggagatatt aaagtgacgg attcagaagt gaaaaggagg      720
agtcaactgc aactcttgaa tagcggcgag ccaagaggtc ctacgatcaa gccctgcccg      780
ccttgtaaat gcccagctcc aaatttgctg ggtggaccgt cagtctttat cttcccgcca      840
aagataaagg acgtcttgat gattagtctg agccccatcg tgacatgcgt tgtggtggat      900
gtttcagagg atgaccccga cgtgcaaatc agttggttcg ttaacaacgt ggaggtgcat      960
accgctcaaa cccagaccca cagagaggat tataacagca ccctgcgggt agtgtccgcc     1020
```

```
ctgccgatcc agcatcagga ttggatgagc gggaaagagt tcaagtgtaa ggtaaacaac    1080
aaagatctgc cagcgccgat tgaacgaacc attagcaagc cgaaagggag cgtgcgcgca    1140
cctcaggttt acgtccttcc tccaccagaa gaggagatga cgaaaaagca ggtgaccctg    1200
acatgcatgg taactgactt tatgccagaa gatatttacg tggaatggac taataacgga    1260
aagacagagc tcaattacaa gaacactgag cctgttctgg attctgatgg cagctacttt    1320
atgtactcca aattgagggt cgagaagaag aattgggtcg agagaaacag ttatagttgc    1380
tcagtggtgc atgagggcct ccataatcat cacaccacaa agtccttcag ccgaacgccc    1440
gggaaa                                                               1446
```

<210> SEQ ID NO 99
<211> LENGTH: 490
<212> TYPE: PRT
<213> ORGANISM: Artificial Sequence
<220> FEATURE:
<223> OTHER INFORMATION: Synthetic fusion protein

<400> SEQUENCE: 99

```
Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Ser Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Glu Pro Arg Gly Pro Thr Ile Lys Pro Cys Pro Pro Cys Lys Cys
            260                 265                 270

Pro Ala Pro Asn Leu Leu Gly Gly Pro Ser Val Phe Ile Phe Pro Pro
```

```
              275                 280                 285
Lys Ile Lys Asp Val Leu Met Ile Ser Leu Ser Pro Ile Val Thr Cys
            290                 295                 300
Val Val Val Asp Val Ser Glu Asp Pro Asp Val Gln Ile Ser Trp
305                 310                 315                 320
Phe Val Asn Asn Val Glu Val His Thr Ala Gln Thr Gln Thr His Arg
                325                 330                 335
Glu Asp Tyr Asn Ser Thr Leu Arg Val Val Ser Ala Leu Pro Ile Gln
                340                 345                 350
His Gln Asp Trp Met Ser Gly Lys Glu Phe Lys Cys Lys Val Asn Asn
                355                 360                 365
Lys Asp Leu Pro Ala Pro Ile Glu Arg Thr Ile Ser Lys Pro Lys Gly
            370                 375                 380
Ser Val Arg Ala Pro Gln Val Tyr Val Leu Pro Pro Pro Glu Glu Glu
385                 390                 395                 400
Met Thr Lys Lys Gln Val Thr Leu Thr Cys Met Val Thr Asp Phe Met
                405                 410                 415
Pro Glu Asp Ile Tyr Val Glu Trp Thr Asn Asn Gly Lys Thr Glu Leu
                420                 425                 430
Asn Tyr Lys Asn Thr Glu Pro Val Leu Asp Ser Asp Gly Ser Tyr Phe
            435                 440                 445
Met Tyr Ser Lys Leu Arg Val Glu Lys Lys Asn Trp Val Glu Arg Asn
            450                 455                 460
Ser Tyr Ser Cys Ser Val Val His Glu Gly Leu His Asn His His Thr
465                 470                 475                 480
Thr Lys Ser Phe Ser Arg Thr Pro Gly Lys
                485                 490

<210> SEQ ID NO 100
<211> LENGTH: 490
<212> TYPE: PRT
<213> ORGANISM: Artificial Sequence
<220> FEATURE:
<223> OTHER INFORMATION: Synthetic fusion protein

<400> SEQUENCE: 100

Met Ala Ser Leu Gly Gln Ile Ile Phe Trp Ser Ile Ile Asn Ile Ile
1               5                   10                  15
Ile Leu Ala Gly Ala Ile Ala Leu Ile Ile Gly Phe Gly Ile Ser
                20                  25                  30
Gly Lys His Phe Ile Thr Val Thr Thr Phe Thr Ser Ala Gly Asn Ile
            35                  40                  45
Gly Glu Asp Gly Thr Leu Ser Cys Thr Phe Glu Pro Asp Ile Lys Leu
        50                  55                  60
Asn Gly Ile Val Ile Gln Trp Leu Lys Glu Gly Ile Lys Gly Leu Val
65                  70                  75                  80
His Glu Phe Lys Glu Gly Lys Asp Asp Leu Ser Gln Gln His Glu Met
                85                  90                  95
Phe Arg Gly Arg Thr Ala Val Phe Ala Asp Gln Val Val Val Gly Asn
                100                 105                 110
Ala Ser Leu Arg Leu Lys Asn Val Gln Leu Thr Asp Ala Gly Thr Tyr
            115                 120                 125
Thr Cys Tyr Ile Arg Thr Ser Lys Gly Lys Gly Asn Ala Asn Leu Glu
        130                 135                 140
Tyr Lys Thr Gly Ala Phe Ser Met Pro Glu Ile Asn Val Asp Tyr Asn
```

```
                145                 150                 155                 160
Ala Ser Ser Glu Ser Leu Arg Cys Glu Ala Pro Arg Trp Phe Pro Gln
                    165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
        210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Glu Pro Arg Gly Pro Thr Ile Lys Pro Cys Pro Pro Cys Lys Cys
            260                 265                 270

Pro Ala Pro Asn Leu Leu Gly Gly Pro Ser Val Phe Ile Phe Pro Pro
        275                 280                 285

Lys Ile Lys Asp Val Leu Met Ile Ser Leu Ser Pro Ile Val Thr Cys
    290                 295                 300

Val Val Val Asp Val Ser Glu Asp Asp Pro Asp Val Gln Ile Ser Trp
305                 310                 315                 320

Phe Val Asn Asn Val Glu Val His Thr Ala Gln Thr Gln Thr His Arg
                325                 330                 335

Glu Asp Tyr Asn Ser Thr Leu Arg Val Val Ser Ala Leu Pro Ile Gln
            340                 345                 350

His Gln Asp Trp Met Ser Gly Lys Glu Phe Lys Cys Lys Val Asn Asn
        355                 360                 365

Lys Asp Leu Pro Ala Pro Ile Glu Arg Thr Ile Ser Lys Pro Lys Gly
    370                 375                 380

Ser Val Arg Ala Pro Gln Val Tyr Val Leu Pro Pro Pro Glu Glu Glu
385                 390                 395                 400

Met Thr Lys Lys Gln Val Thr Leu Thr Cys Met Val Thr Asp Phe Met
                405                 410                 415

Pro Glu Asp Ile Tyr Val Glu Trp Thr Asn Asn Gly Lys Thr Glu Leu
            420                 425                 430

Asn Tyr Lys Asn Thr Glu Pro Val Leu Asp Ser Asp Gly Ser Tyr Phe
        435                 440                 445

Met Tyr Ser Lys Leu Arg Val Glu Lys Lys Asn Trp Val Glu Arg Asn
    450                 455                 460

Ser Tyr Ser Cys Ser Val Val His Glu Gly Leu His Asn His His Thr
465                 470                 475                 480

Thr Lys Ser Phe Ser Arg Thr Pro Gly Lys
                485                 490

<210> SEQ ID NO 101
<211> LENGTH: 482
<212> TYPE: PRT
<213> ORGANISM: Artificial Sequence
<220> FEATURE:
<223> OTHER INFORMATION: Synthetic fusion protein

<400> SEQUENCE: 101

Met Glu Trp Ser Trp Val Phe Leu Phe Phe Leu Ser Val Thr Thr Gly
1               5                   10                  15

Val His Ser Gly Phe Gly Ile Ser Gly Lys His Phe Ile Thr Val Thr
```

-continued

```
                20                  25                  30
Thr Phe Thr Ser Ala Gly Asn Ile Gly Glu Asp Gly Thr Leu Ser Cys
            35                  40                  45
Thr Phe Glu Pro Asp Ile Lys Leu Asn Gly Ile Val Ile Gln Trp Leu
 50                  55                  60
Lys Glu Gly Ile Lys Gly Leu Val His Glu Phe Lys Glu Gly Lys Asp
 65                  70                  75                  80
Asp Leu Ser Gln Gln His Glu Met Phe Arg Gly Arg Thr Ala Val Phe
                85                  90                  95
Ala Asp Gln Val Val Val Gly Asn Ala Ser Leu Arg Leu Lys Asn Val
            100                 105                 110
Gln Leu Thr Asp Ala Gly Thr Tyr Thr Cys Tyr Ile Arg Ser Ser Lys
        115                 120                 125
Gly Lys Gly Asn Ala Asn Leu Glu Tyr Lys Thr Gly Ala Phe Ser Met
    130                 135                 140
Pro Glu Ile Asn Val Asp Tyr Asn Ala Ser Ser Glu Ser Leu Arg Cys
145                 150                 155                 160
Glu Ala Pro Arg Trp Phe Pro Gln Pro Thr Val Ala Trp Ala Ser Gln
                165                 170                 175
Val Asp Gln Gly Ala Asn Phe Ser Glu Val Ser Asn Thr Ser Phe Glu
            180                 185                 190
Leu Asn Ser Glu Asn Val Thr Met Lys Val Val Ser Val Leu Tyr Asn
        195                 200                 205
Val Thr Ile Asn Asn Thr Tyr Ser Cys Met Ile Glu Asn Asp Ile Ala
    210                 215                 220
Lys Ala Thr Gly Asp Ile Lys Val Thr Asp Ser Glu Val Lys Arg Arg
225                 230                 235                 240
Ser Gln Leu Gln Leu Leu Asn Ser Gly Glu Pro Arg Gly Pro Thr Ile
                245                 250                 255
Lys Pro Cys Pro Pro Cys Lys Cys Pro Ala Pro Asn Leu Leu Gly Gly
            260                 265                 270
Pro Ser Val Phe Ile Phe Pro Pro Lys Ile Lys Asp Val Leu Met Ile
        275                 280                 285
Ser Leu Ser Pro Ile Val Thr Cys Val Val Val Asp Val Ser Glu Asp
    290                 295                 300
Asp Pro Asp Val Gln Ile Ser Trp Phe Val Asn Asn Val Glu Val His
305                 310                 315                 320
Thr Ala Gln Thr Gln Thr His Arg Glu Asp Tyr Asn Ser Thr Leu Arg
                325                 330                 335
Val Val Ser Ala Leu Pro Ile Gln His Gln Asp Trp Met Ser Gly Lys
            340                 345                 350
Glu Phe Lys Cys Lys Val Asn Asn Lys Asp Leu Pro Ala Pro Ile Glu
        355                 360                 365
Arg Thr Ile Ser Lys Pro Lys Gly Ser Val Arg Ala Pro Gln Val Tyr
    370                 375                 380
Val Leu Pro Pro Pro Glu Glu Glu Met Thr Lys Lys Gln Val Thr Leu
385                 390                 395                 400
Thr Cys Met Val Thr Asp Phe Met Pro Glu Asp Ile Tyr Val Glu Trp
                405                 410                 415
Thr Asn Asn Gly Lys Thr Glu Leu Asn Tyr Lys Asn Thr Glu Pro Val
            420                 425                 430
Leu Asp Ser Asp Gly Ser Tyr Phe Met Tyr Ser Lys Leu Arg Val Glu
        435                 440                 445
```

```
Lys Lys Asn Trp Val Glu Arg Asn Ser Tyr Ser Cys Ser Val Val His
            450                 455                 460

Glu Gly Leu His Asn His Thr Thr Lys Ser Phe Ser Arg Thr Pro
465                 470                 475                 480

Gly Lys

<210> SEQ ID NO 102
<211> LENGTH: 482
<212> TYPE: PRT
<213> ORGANISM: Artificial Sequence
<220> FEATURE:
<223> OTHER INFORMATION: Synthetic fusion protein

<400> SEQUENCE: 102

Met Glu Trp Ser Trp Val Phe Leu Phe Phe Leu Ser Val Thr Thr Gly
1               5                   10                  15

Val His Ser Gly Phe Gly Ile Ser Gly Lys His Phe Ile Thr Val Thr
                20                  25                  30

Thr Phe Thr Ser Ala Gly Asn Ile Gly Glu Asp Gly Thr Leu Ser Cys
            35                  40                  45

Thr Phe Glu Pro Asp Ile Lys Leu Asn Gly Ile Val Ile Gln Trp Leu
        50                  55                  60

Lys Glu Gly Ile Lys Gly Leu Val His Glu Phe Lys Glu Gly Lys Asp
65                  70                  75                  80

Asp Leu Ser Gln Gln His Glu Met Phe Arg Gly Arg Thr Ala Val Phe
                85                  90                  95

Ala Asp Gln Val Val Gly Asn Ala Ser Leu Arg Leu Lys Asn Val
                100                 105                 110

Gln Leu Thr Asp Ala Gly Thr Tyr Thr Cys Tyr Ile Arg Thr Ser Lys
            115                 120                 125

Gly Lys Gly Asn Ala Asn Leu Glu Tyr Lys Thr Gly Ala Phe Ser Met
        130                 135                 140

Pro Glu Ile Asn Val Asp Tyr Asn Ala Ser Ser Glu Ser Leu Arg Cys
145                 150                 155                 160

Glu Ala Pro Arg Trp Phe Pro Gln Pro Thr Val Ala Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Asp Ser Glu Val Lys Arg Arg
225                 230                 235                 240

Ser Gln Leu Gln Leu Leu Asn Ser Gly Glu Pro Arg Gly Pro Thr Ile
                245                 250                 255

Lys Pro Cys Pro Pro Cys Lys Cys Pro Ala Pro Asn Leu Leu Gly Gly
            260                 265                 270

Pro Ser Val Phe Ile Phe Pro Pro Lys Ile Lys Asp Val Leu Met Ile
        275                 280                 285

Ser Leu Ser Pro Ile Val Thr Cys Val Val Val Asp Val Ser Glu Asp
    290                 295                 300

Asp Pro Asp Val Gln Ile Ser Trp Phe Val Asn Asn Val Glu Val His
305                 310                 315                 320
```

```
Thr Ala Gln Thr Gln Thr His Arg Glu Asp Tyr Asn Ser Thr Leu Arg
            325                 330                 335

Val Val Ser Ala Leu Pro Ile Gln His Gln Asp Trp Met Ser Gly Lys
        340                 345                 350

Glu Phe Lys Cys Lys Val Asn Asn Lys Asp Leu Pro Ala Pro Ile Glu
        355                 360                 365

Arg Thr Ile Ser Lys Pro Lys Gly Ser Val Arg Ala Pro Gln Val Tyr
    370                 375                 380

Val Leu Pro Pro Pro Glu Glu Met Thr Lys Lys Gln Val Thr Leu
385                 390                 395                 400

Thr Cys Met Val Thr Asp Phe Met Pro Glu Asp Ile Tyr Val Glu Trp
                405                 410                 415

Thr Asn Asn Gly Lys Thr Glu Leu Asn Tyr Lys Asn Thr Glu Pro Val
            420                 425                 430

Leu Asp Ser Asp Gly Ser Tyr Phe Met Tyr Ser Lys Leu Arg Val Glu
        435                 440                 445

Lys Lys Asn Trp Val Glu Arg Asn Ser Tyr Ser Cys Ser Val Val His
    450                 455                 460

Glu Gly Leu His Asn His His Thr Thr Lys Ser Phe Ser Arg Thr Pro
465                 470                 475                 480

Gly Lys
```

<210> SEQ ID NO 103
<211> LENGTH: 463
<212> TYPE: PRT
<213> ORGANISM: Artificial Sequence
<220> FEATURE:
<223> OTHER INFORMATION: Synthetic fusion protein

<400> SEQUENCE: 103

```
Gly Phe Gly Ile Ser Gly Lys His Phe Ile Thr Val Thr Thr Phe Thr
1               5                   10                  15

Ser Ala Gly Asn Ile Gly Glu Asp Gly Thr Leu Ser Cys Thr Phe Glu
            20                  25                  30

Pro Asp Ile Lys Leu Asn Gly Ile Val Ile Gln Trp Leu Lys Glu Gly
        35                  40                  45

Ile Lys Gly Leu Val His Glu Phe Lys Glu Gly Lys Asp Asp Leu Ser
    50                  55                  60

Gln Gln His Glu Met Phe Arg Gly Arg Thr Ala Val Phe Ala Asp Gln
65                  70                  75                  80

Val Val Val Gly Asn Ala Ser Leu Arg Leu Lys Asn Val Gln Leu Thr
                85                  90                  95

Asp Ala Gly Thr Tyr Thr Cys Tyr Ile Arg Ser Ser Lys Gly Lys Gly
            100                 105                 110

Asn Ala Asn Leu Glu Tyr Lys Thr Gly Ala Phe Ser Met Pro Glu Ile
        115                 120                 125

Asn Val Asp Tyr Asn Ala Ser Ser Glu Ser Leu Arg Cys Glu Ala Pro
    130                 135                 140

Arg Trp Phe Pro Gln Pro Thr Val Ala Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
```

```
                195                 200                 205
Gly Asp Ile Lys Val Thr Asp Ser Glu Val Lys Arg Arg Ser Gln Leu
    210                 215                 220

Gln Leu Leu Asn Ser Gly Glu Pro Arg Gly Pro Thr Ile Lys Pro Cys
225                 230                 235                 240

Pro Pro Cys Lys Cys Pro Ala Pro Asn Leu Leu Gly Gly Pro Ser Val
                245                 250                 255

Phe Ile Phe Pro Pro Lys Ile Lys Asp Val Leu Met Ile Ser Leu Ser
            260                 265                 270

Pro Ile Val Thr Cys Val Val Val Asp Val Ser Glu Asp Asp Pro Asp
                275                 280                 285

Val Gln Ile Ser Trp Phe Val Asn Asn Val Glu Val His Thr Ala Gln
    290                 295                 300

Thr Gln Thr His Arg Glu Asp Tyr Asn Ser Thr Leu Arg Val Val Ser
305                 310                 315                 320

Ala Leu Pro Ile Gln His Gln Asp Trp Met Ser Gly Lys Glu Phe Lys
                325                 330                 335

Cys Lys Val Asn Asn Lys Asp Leu Pro Ala Pro Ile Glu Arg Thr Ile
            340                 345                 350

Ser Lys Pro Lys Gly Ser Val Arg Ala Pro Gln Val Tyr Val Leu Pro
        355                 360                 365

Pro Pro Glu Glu Glu Met Thr Lys Lys Gln Val Thr Leu Thr Cys Met
    370                 375                 380

Val Thr Asp Phe Met Pro Glu Asp Ile Tyr Val Glu Trp Thr Asn Asn
385                 390                 395                 400

Gly Lys Thr Glu Leu Asn Tyr Lys Asn Thr Glu Pro Val Leu Asp Ser
                405                 410                 415

Asp Gly Ser Tyr Phe Met Tyr Ser Lys Leu Arg Val Glu Lys Lys Asn
            420                 425                 430

Trp Val Glu Arg Asn Ser Tyr Ser Cys Ser Val Val His Glu Gly Leu
        435                 440                 445

His Asn His His Thr Thr Lys Ser Phe Ser Arg Thr Pro Gly Lys
    450                 455                 460

<210> SEQ ID NO 104
<211> LENGTH: 463
<212> TYPE: PRT
<213> ORGANISM: Artificial Sequence
<220> FEATURE:
<223> OTHER INFORMATION: Synthetic fusion protein

<400> SEQUENCE: 104

Gly Phe Gly Ile Ser Gly Lys His Phe Ile Thr Val Thr Thr Phe Thr
1               5                   10                  15

Ser Ala Gly Asn Ile Gly Glu Asp Gly Thr Leu Ser Cys Thr Phe Glu
                20                  25                  30

Pro Asp Ile Lys Leu Asn Gly Ile Val Ile Gln Trp Leu Lys Glu Gly
            35                  40                  45

Ile Lys Gly Leu Val His Glu Phe Lys Glu Gly Lys Asp Asp Leu Ser
        50                  55                  60

Gln Gln His Glu Met Phe Arg Gly Arg Thr Ala Val Phe Ala Asp Gln
65                  70                  75                  80

Val Val Val Gly Asn Ala Ser Leu Arg Leu Lys Asn Val Gln Leu Thr
                85                  90                  95

Asp Ala Gly Thr Tyr Thr Cys Tyr Ile Arg Thr Ser Lys Gly Lys Gly
```

```
                100              105              110
Asn Ala Asn Leu Glu Tyr Lys Thr Gly Ala Phe Ser Met Pro Glu Ile
            115                  120              125
Asn Val Asp Tyr Asn Ala Ser Ser Glu Ser Leu Arg Cys Glu Ala Pro
        130                  135              140
Arg Trp Phe Pro Gln Pro Thr Val Ala Trp Ala Ser Gln Val Asp Gln
145                  150              155                  160
Gly Ala Asn Phe Ser Glu Val Ser Asn Thr Ser Phe Glu Leu Asn Ser
                165                  170              175
Glu Asn Val Thr Met Lys Val Val Ser Val Leu Tyr Asn Val Thr Ile
            180                  185              190
Asn Asn Thr Tyr Ser Cys Met Ile Glu Asn Asp Ile Ala Lys Ala Thr
        195                  200              205
Gly Asp Ile Lys Val Thr Asp Ser Glu Val Lys Arg Arg Ser Gln Leu
    210                  215              220
Gln Leu Leu Asn Ser Gly Glu Pro Arg Gly Pro Thr Ile Lys Pro Cys
225                  230              235                  240
Pro Pro Cys Lys Cys Pro Ala Pro Asn Leu Leu Gly Gly Pro Ser Val
                245                  250              255
Phe Ile Phe Pro Pro Lys Ile Lys Asp Val Leu Met Ile Ser Leu Ser
            260                  265              270
Pro Ile Val Thr Cys Val Val Asp Val Ser Glu Asp Asp Pro Asp
        275                  280              285
Val Gln Ile Ser Trp Phe Val Asn Asn Val Glu Val His Thr Ala Gln
    290                  295              300
Thr Gln Thr His Arg Glu Asp Tyr Asn Ser Thr Leu Arg Val Val Ser
305                  310              315                  320
Ala Leu Pro Ile Gln His Gln Asp Trp Met Ser Gly Lys Glu Phe Lys
                325                  330              335
Cys Lys Val Asn Asn Lys Asp Leu Pro Ala Pro Ile Glu Arg Thr Ile
            340                  345              350
Ser Lys Pro Lys Gly Ser Val Arg Ala Pro Gln Val Tyr Val Leu Pro
        355                  360              365
Pro Pro Glu Glu Glu Met Thr Lys Lys Gln Val Thr Leu Thr Cys Met
    370                  375              380
Val Thr Asp Phe Met Pro Glu Asp Ile Tyr Val Glu Trp Thr Asn Asn
385                  390              395                  400
Gly Lys Thr Glu Leu Asn Tyr Lys Asn Thr Glu Pro Val Leu Asp Ser
                405                  410              415
Asp Gly Ser Tyr Phe Met Tyr Ser Lys Leu Arg Val Glu Lys Lys Asn
            420                  425              430
Trp Val Glu Arg Asn Ser Tyr Ser Cys Ser Val Val His Glu Gly Leu
        435                  440              445
His Asn His His Thr Thr Lys Ser Phe Ser Arg Thr Pro Gly Lys
    450                  455              460

<210> SEQ ID NO 105
<211> LENGTH: 1443
<212> TYPE: PRT
<213> ORGANISM: Artificial Sequence
<220> FEATURE:
<223> OTHER INFORMATION: Synthetic fusion protein

<400> SEQUENCE: 105

Ala Thr Gly Gly Cys Thr Thr Cys Cys Cys Thr Gly Gly Gly Gly Cys
```

-continued

```
1               5                   10                  15

Ala Gly Ala Thr Cys Cys Thr Cys Thr Thr Cys Thr Gly Gly Ala Gly
            20                  25                  30

Cys Ala Thr Ala Ala Thr Thr Ala Gly Cys Ala Thr Cys Ala Thr Cys
        35                  40                  45

Ala Thr Thr Ala Thr Thr Cys Thr Gly Gly Cys Thr Gly Gly Ala Gly
    50                  55                  60

Cys Ala Ala Thr Thr Gly Cys Ala Cys Thr Cys Ala Thr Cys Ala Thr
65                  70                  75                  80

Thr Gly Gly Cys Thr Thr Thr Gly Gly Thr Ala Thr Thr Thr Cys Ala
                85                  90                  95

Gly Gly Gly Ala Gly Ala Cys Ala Cys Thr Cys Cys Ala Thr Cys Ala
            100                 105                 110

Cys Ala Gly Thr Cys Ala Cys Thr Ala Cys Thr Gly Thr Cys Gly Cys
        115                 120                 125

Cys Thr Cys Ala Gly Cys Thr Gly Gly Gly Ala Ala Cys Ala Thr Thr
    130                 135                 140

Gly Gly Gly Gly Ala Gly Gly Ala Thr Gly Gly Ala Ala Thr Cys Cys
145                 150                 155                 160

Thr Gly Ala Gly Cys Thr Gly Cys Ala Cys Thr Thr Thr Thr Gly Ala
                165                 170                 175

Ala Cys Cys Thr Gly Ala Cys Ala Thr Cys Ala Ala Ala Cys Thr Thr
            180                 185                 190

Thr Cys Thr Gly Ala Thr Ala Thr Cys Gly Thr Gly Ala Thr Ala Cys
        195                 200                 205

Ala Ala Thr Gly Gly Cys Thr Gly Ala Ala Gly Gly Ala Ala Gly Gly
    210                 215                 220

Thr Gly Thr Thr Thr Thr Ala Gly Gly Cys Thr Thr Gly Gly Thr Cys
225                 230                 235                 240

Cys Ala Thr Gly Ala Gly Thr Thr Cys Ala Ala Ala Gly Ala Ala Gly
                245                 250                 255

Gly Cys Ala Ala Ala Gly Ala Thr Gly Ala Gly Cys Thr Gly Thr Cys
            260                 265                 270

Gly Gly Ala Gly Cys Ala Gly Gly Ala Thr Gly Ala Ala Ala Thr Gly
        275                 280                 285

Thr Thr Cys Ala Gly Ala Gly Gly Cys Cys Gly Gly Ala Cys Ala Gly
    290                 295                 300

Cys Ala Gly Thr Gly Thr Thr Thr Gly Cys Thr Gly Ala Thr Cys Ala
305                 310                 315                 320

Ala Gly Thr Gly Ala Thr Ala Gly Thr Thr Gly Gly Cys Ala Ala Thr
                325                 330                 335

Gly Cys Cys Thr Cys Thr Thr Thr Gly Cys Gly Gly Cys Thr Gly Ala
            340                 345                 350

Ala Ala Ala Ala Cys Gly Thr Gly Cys Ala Ala Cys Thr Cys Ala Cys
        355                 360                 365

Ala Gly Ala Thr Gly Cys Thr Gly Gly Cys Ala Cys Cys Thr Ala Cys
    370                 375                 380

Ala Ala Ala Thr Gly Thr Thr Ala Thr Ala Thr Cys Ala Thr Cys Ala
385                 390                 395                 400

Cys Thr Thr Cys Thr Ala Ala Ala Gly Gly Cys Ala Ala Gly Gly Gly
                405                 410                 415

Gly Ala Ala Thr Gly Cys Thr Ala Ala Cys Cys Thr Thr Gly Ala Gly
            420                 425                 430
```

```
Thr Ala Thr Ala Ala Ala Ala Cys Thr Gly Gly Ala Gly Cys Cys Thr
        435                 440                 445

Thr Cys Ala Gly Cys Ala Thr Gly Cys Cys Gly Gly Ala Ala Gly Thr
    450                 455                 460

Gly Ala Ala Thr Gly Thr Gly Gly Ala Cys Thr Ala Thr Ala Ala Thr
465                 470                 475                 480
Gly Cys Cys Ala Gly Cys Thr Cys Ala Gly Ala Gly Ala Cys Cys Thr
                485                 490                 495
Thr Gly Cys Gly Gly Thr Gly Thr Gly Ala Gly Gly Cys Thr Cys Cys
            500                 505                 510

Cys Cys Gly Ala Thr Gly Gly Thr Thr Cys Cys Cys Cys Cys Ala Gly
        515                 520                 525

Cys Cys Cys Ala Cys Ala Gly Thr Gly Gly Thr Cys Thr Gly Gly Gly
    530                 535                 540

Cys Ala Thr Cys Cys Cys Ala Ala Gly Thr Thr Gly Ala Cys Cys Ala
545                 550                 555                 560
Gly Gly Gly Ala Gly Cys Cys Ala Ala Cys Thr Thr Cys Thr Cys Gly
                565                 570                 575
Gly Ala Ala Gly Thr Cys Thr Cys Cys Ala Ala Thr Ala Cys Cys Ala
            580                 585                 590
Gly Cys Thr Thr Thr Gly Ala Gly Cys Thr Gly Ala Ala Cys Thr Cys
        595                 600                 605

Thr Gly Ala Gly Ala Ala Thr Gly Thr Gly Ala Cys Cys Ala Thr Gly
    610                 615                 620

Ala Ala Gly Gly Thr Thr Gly Thr Gly Thr Cys Thr Gly Thr Gly Cys
625                 630                 635                 640
Thr Cys Thr Ala Cys Ala Ala Thr Gly Thr Thr Ala Cys Gly Ala Thr
                645                 650                 655
Cys Ala Ala Cys Ala Ala Cys Ala Cys Ala Thr Ala Cys Thr Cys Cys
            660                 665                 670

Thr Gly Thr Ala Thr Gly Ala Thr Thr Gly Ala Ala Ala Ala Thr Gly
        675                 680                 685

Ala Cys Ala Thr Thr Gly Cys Cys Ala Ala Ala Gly Cys Ala Ala Cys
    690                 695                 700

Ala Gly Gly Gly Gly Ala Thr Ala Thr Cys Ala Ala Ala Gly Thr Gly
705                 710                 715                 720
Ala Cys Ala Gly Ala Ala Thr Cys Gly Gly Ala Gly Ala Thr Cys Ala
                725                 730                 735

Ala Ala Ala Gly Gly Cys Gly Gly Ala Gly Thr Gly Ala Gly Cys Cys
            740                 745                 750

Thr Ala Ala Gly Thr Cys Ala Thr Gly Thr Gly Ala Cys Ala Ala Gly
        755                 760                 765

Ala Cys Cys Cys Ala Thr Ala Cys Gly Thr Gly Cys Cys Cys Ala Cys
    770                 775                 780

Cys Cys Thr Gly Thr Cys Cys Cys Gly Cys Thr Cys Cys Ala Gly Ala
785                 790                 795                 800

Ala Cys Thr Gly Cys Thr Gly Gly Gly Gly Gly Gly Ala Cys Cys Thr
                805                 810                 815

Ala Gly Cys Gly Thr Thr Thr Thr Cys Thr Thr Gly Thr Thr Cys Cys
            820                 825                 830

Cys Cys Cys Cys Ala Ala Ala Gly Cys Cys Cys Ala Ala Gly Gly Ala
        835                 840                 845
```

```
Cys Ala Cys Cys Cys Thr Cys Ala Thr Gly Ala Thr Cys Thr Cys Ala
    850                 855                 860

Cys Gly Gly Ala Cys Thr Cys Cys Cys Gly Ala Ala Gly Thr Ala Ala
865                 870                 875                 880
Cys Ala Thr Gly Cys Gly Thr Ala Gly Thr Ala Gly Thr Cys Gly Ala
                885                 890                 895

Cys Gly Thr Gly Ala Gly Cys Cys Ala Cys Gly Ala Gly Gly Ala Thr
            900                 905                 910

Cys Cys Thr Gly Ala Ala Gly Thr Gly Ala Ala Gly Thr Thr Thr Ala
        915                 920                 925
Ala Thr Thr Gly Gly Thr Ala Cys Gly Thr Gly Gly Ala Cys Gly Gly
    930                 935                 940

Ala Gly Thr Cys Gly Ala Gly Gly Thr Gly Cys Ala Thr Ala Ala Thr
945                 950                 955                 960
Gly Cys Cys Ala Ala Ala Ala Cys Thr Ala Ala Ala Cys Cys Thr Cys
                965                 970                 975

Gly Gly Gly Ala Gly Gly Ala Gly Cys Ala Gly Thr Ala Thr Ala Ala
            980                 985                 990

Cys Ala Gly Thr Ala Cys Cys Thr  Ala Cys Cys Gly Cys  Gly Thr Gly
        995                 1000                1005

Gly Thr  Ala Thr Cys Cys Gly  Thr Cys Thr Thr Gly  Ala Cys Ala
    1010                1015                1020

Gly Thr  Gly Cys Thr Cys Cys  Ala Cys Cys Ala Gly  Gly Ala Cys
    1025                1030                1035

Thr Gly  Gly Cys Thr Gly Ala  Ala Thr Gly Gly Thr  Ala Ala Gly
    1040                1045                1050

Gly Ala  Gly Thr Ala Thr Ala  Ala Ala Thr Gly Cys  Ala Ala Gly
    1055                1060                1065

Gly Thr  Cys Ala Gly Cys Ala  Ala Cys Ala Ala Ala  Gly Cys Thr
    1070                1075                1080

Cys Thr  Thr Cys Cys Cys Gly  Cys Cys Cys Cys Ala  Ala Thr Thr
    1085                1090                1095

Gly Ala  Ala Ala Ala Gly Ala  Cys Thr Ala Thr Cys  Ala Gly Cys
    1100                1105                1110

Ala Ala  Gly Gly Cys Cys Ala  Ala Gly Gly Gly Ala  Cys Ala Ala
    1115                1120                1125

Cys Cys  Cys Cys Gly Cys Gly  Ala Gly Cys Cys Cys  Cys Ala Gly
    1130                1135                1140

Gly Thr  Thr Thr Ala Cys Ala  Cys Cys Cys Thr Thr  Cys Cys Ala
    1145                1150                1155

Cys Cys  Thr Thr Cys Ala Cys  Gly Ala Gly Ala Cys  Gly Ala Gly
    1160                1165                1170

Cys Thr  Gly Ala Cys Cys Ala  Ala Gly Ala Ala Cys  Cys Ala Gly
    1175                1180                1185

Gly Thr  Gly Thr Cys Thr Cys  Thr Gly Ala Cys Thr  Thr Gly Thr
    1190                1195                1200

Cys Thr  Gly Gly Thr Cys Ala  Ala Ala Gly Gly Thr  Thr Thr Cys
    1205                1210                1215

Thr Ala  Thr Cys Cys Thr Thr  Cys Cys Gly Ala Cys  Ala Thr Cys
    1220                1225                1230

Gly Cys  Ala Gly Thr Gly Gly  Ala Gly Thr Gly Gly  Gly Ala Gly
    1235                1240                1245

Thr Cys  Ala Ala Ala Cys Gly  Gly Gly Cys Ala Gly  Cys Cys Thr
```

-continued

| | 1250 | | | 1255 | | | 1260 | | |
|---|---|---|---|---|---|---|---|---|---|

Gly Ala Gly Ala Ala Thr Ala Cys Thr Ala Cys Ala Ala Gly
        1265               1270              1275

Ala Cys Cys Ala Cys Ala Cys Cys Cys Cys Ala Gly Thr Gly
        1280               1285              1290

Cys Thr Thr Gly Ala Thr Ala Gly Cys Gly Ala Thr Gly Gly
        1295               1300              1305

Ala Gly Cys Thr Thr Thr Thr Thr Cys Thr Cys Thr Ala Cys
        1310               1315              1320

Ala Gly Thr Ala Ala Gly Cys Thr Gly Ala Cys Thr Gly Thr
        1325               1330              1335

Gly Ala Cys Ala Ala Thr Cys Cys Gly Cys Thr Gly Gly
        1340               1345              1350

Cys Ala Gly Cys Ala Gly Gly Ala Ala Cys Gly Thr Thr
        1355               1360              1365

Thr Thr Cys Thr Cys Thr Thr Gly Thr Ala Gly Cys Gly Thr Cys
        1370               1375              1380

Ala Thr Gly Cys Ala Thr Gly Ala Gly Gly Cys Cys Cys Thr Cys
        1385               1390              1395

Cys Ala Cys Ala Ala Cys Cys Ala Thr Thr Ala Thr Ala Cys Thr
        1400           &nb

```
cagtataaca gtacctaccg cgtggtatcc gtcttgacag tgctccacca ggactggctg    1020
aatggtaagg agtataaatg caaggtcagc aacaaagctc ttcccgcccc aattgaaaag    1080
actatcagca aggccaaggg acaaccccgc gagccccagg tttacaccct tccaccttca    1140
cgagacgagc tgaccaagaa ccaggtgtct ctgacttgtc tggtcaaagg tttctatcct    1200
tccgacatcg cagtggagtg ggagtcaaac gggcagcctg agaataacta caagaccaca    1260
cccccagtgc ttgatagcga tgggagcttt ttcctctaca gtaagctgac tgtggacaaa    1320
tcccgctggc agcagggaaa cgttttctct gtagcgtca tgcatgaggc cctccacaac    1380
cattatactc agaaaagcct gagtctgagt cccggcaaa                          1419
```

<210> SEQ ID NO 107
<211> LENGTH: 1404
<212> TYPE: DNA
<213> ORGANISM: Artificial Sequence
<220> FEATURE:
<223> OTHER INFORMATION: Synthetic fusion nucleotide

<400> SEQUENCE: 107

```
atggaatgga gctgggtatt tctgttttc ctgtcagtaa cgactggcgt ccattcaggc      60
ttcggcatca gtgacggca cagtatcaca gtgaccaccg tcgcctccgc tggcaatata     120
ggtgaggatg gcatccagtc ctgtacccttt gagccggaca tcaaactgtc tgacatagtg    180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa atgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta atgtaaca atcaacaaca ttattcatg catgattgaa    660 aacgacatcg ccaaggcaac aggtgatatt aaggtaactg aatccgagat caaacggcgg    720
tctgacaaga cccatacgtg cccacccctgt cccgctccag aactgctggg gggacctagc    780
gttttcttgt tccccccaaa gcccaaggac accctcatga tctcacggac tcccgaagta    840
acatgcgtag tagtcgacgt gagccacgag gatcctgaag tgaagtttaa ttggtacgtg    900
gacggagtcg aggtgcataa tgccaaaact aaacctcggg aggagcagta taacagtacc    960
taccgcgtgg tatccgtctt gacagtgctc caccaggact ggctgaatgg taaggagtat    1020
aaatgcaagg tcagcaacaa agctcttccc gccccaattg aaaagactat cagcaaggcc    1080
aagggacaac cccgcgagcc ccaggtttac acccttccac cttcacgaga cgagctgacc    1140
aagaaccagg tgtctctgac ttgtctggtc aaaggtttct atccttccga catcgcagtg    1200
gagtgggagt caaacgggca gcctgagaat aactacaaga ccacaccccc agtgcttgat    1260
agcgatggga ctttttcct ctacagtaag ctgactgtgg acaaatcccg ctggcagcag    1320
ggaaacgttt ctcttgtag cgtcatgcat gaggccctcc acaaccatta tactcagaaa    1380
agcctgagtc tgagtcccgg caaa                                           1404
```

<210> SEQ ID NO 108
<211> LENGTH: 1392
<212> TYPE: DNA

<213> ORGANISM: Artificial Sequence
<220> FEATURE:
<223> OTHER INFORMATION: Synthetic fusion nucleotide

<400> SEQUENCE: 108

| | |
|---|---|
| atggaatgga gctgggtatt tctgttttc ctgtcagtaa cgactggcgt ccattcaggc | 60 |
| ttcggcatca gtggacggca cagtatcaca gtgaccaccg tcgcctccgc tggcaatata | 120 |
| ggtgaggatg gcatccagtc ctgtaccttt gagccggaca tcaaactgtc tgacatagtg | 180 |
| atacaatggc tgaaggaggg ggtgctcggt ctggtacatg agtttaagga agggaaggat | 240 |
| gaactgtccg agcaggatga gatgttccgg gggaggaccg ctgtgttcgc cgatcaggta | 300 |
| atcgtcggaa atgcaagtct cagattgaaa aatgtgcaac tgactgatgc tggcacgtat | 360 |
| aaatgctaca ttatcacaag taagggcaaa ggaaatgcta accttgagta taaaacaggc | 420 |
| gcattctcaa tgcccgaggt caatgtcgac tataatgcca gcagtgaaac attgcgctgt | 480 |
| gaagctcccc gctggttccc ccagccaacc gtggtctggg cctctcaggt tgatcagggg | 540 |
| gctaactttt ccgaggtgag caacaccagc ttcgaactca actctgagaa tgtgaccatg | 600 |
| aaagttgtgt ctgtcctgta taatgtaaca atcaacaaca cttattcatg catgattgaa | 660 |
| aacgacatcg ccaaggcaac aggtgatatt aaggtaactg aatccgagat cgacaagacc | 720 |
| catacgtgcc caccctgtcc cgctccagaa ctgctggggg gacctagcgt tttcttgttc | 780 |
| cccccaaagc ccaaggacac cctcatgatc tcacggactc ccgaagtaac atgcgtagta | 840 |
| gtcgacgtga gccacgagga tcctgaagtg aagtttaatt ggtacgtgga cggagtcgag | 900 |
| gtgcataatg ccaaaactaa acctcgggag gagcagtata cagtaccta ccgcgtggta | 960 |
| tccgtcttga cagtgctcca ccaggactgg ctgaatggta aggagtataa atgcaaggtc | 1020 |
| agcaacaaag ctcttcccgc cccaattgaa aagactatca gcaaggccaa gggacaaccc | 1080 |
| cgcgagcccc aggtttacac ccttccacct tcacgagacg agctgaccaa gaaccaggtg | 1140 |
| tctctgactt gtctggtcaa aggtttctat ccttccgaca tcgcagtgga gtgggagtca | 1200 |
| aacgggcagc ctgagaataa ctacaagacc acacccccag tgcttgatag cgatgggagc | 1260 |
| ttttcctct acagtaagct gactgtggac aaatcccgct ggcagcaggg aaacgttttc | 1320 |
| tcttgtagcg tcatgcatga ggccctccac aaccattata ctcagaaaag cctgagtctg | 1380 |
| agtcccggca aa | 1392 |

<210> SEQ ID NO 109
<211> LENGTH: 1428
<212> TYPE: DNA
<213> ORGANISM: Artificial Sequence
<220> FEATURE:
<223> OTHER INFORMATION: Synthetic fusion nucleotide

<400> SEQUENCE: 109

| | |
|---|---|
| atggaatgga gctgggtatt tctgttttc ctgtcagtaa cgactggcgt ccattcaggc | 60 |
| ttcggcatca gtggacggca cagtatcaca gtgaccaccg tcgcctccgc tggcaatata | 120 |
| ggtgaggatg gcatccagtc ctgtaccttt gagccggaca tcaaactgtc tgacatagtg | 180 |
| atacaatggc tgaaggaggg ggtgctcggt ctggtacatg agtttaagga agggaaggat | 240 |
| gaactgtccg agcaggatga gatgttccgg gggaggaccg ctgtgttcgc cgatcaggta | 300 |
| atcgtcggaa atgcaagtct cagattgaaa aatgtgcaac tgactgatgc tggcacgtat | 360 |
| aaatgctaca ttatcacaag taagggcaaa ggaaatgcta accttgagta taaaacaggc | 420 |
| gcattctcaa tgcccgaggt caatgtcgac tataatgcca gcagtgaaac attgcgctgt | 480 |

```
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaacggcgg    720
tctcacctgc agctgctgaa ctccaaggac aagacccata cgtgcccacc ctgtcccgct    780
ccagaactgc tggggggacc tagcgttttc ttgttccccc caaagcccaa ggacaccctc    840
atgatctcac ggactcccga gtaacatgc gtagtagtcg acgtgagcca cgaggatcct     900
gaagtgaagt taattggta cgtggacgga gtcgaggtgc ataatgccaa aactaaacct     960
cgggaggagc agtataacag tacctaccgc gtggtatccg tcttgacagt gctccaccag    1020
gactggctga atggtaagga gtataaatgc aaggtcagca acaaagctct tcccgcccca    1080
attgaaaaga ctatcagcaa ggccaaggga caaccccgcg agccccaggt ttacaccctt    1140
ccaccttcac gagacgagct gaccaagaac caggtgtctc tgacttgtct ggtcaaaggt    1200
ttctatcctt ccgacatcgc agtggagtgg gagtcaaacg ggcagcctga gaataactac    1260
aagaccacac ccccagtgct tgatagcgat gggagctttt tcctctacag taagctgact    1320
gtggacaaat cccgctggca gcagggaaac gttttctctt gtagcgtcat gcatgaggcc    1380
ctccacaacc attatactca gaaaagcctg agtctgagtc ccggcaaa               1428

<210> SEQ ID NO 110
<211> LENGTH: 1419
<212> TYPE: DNA
<213> ORGANISM: Artificial Sequence
<220> FEATURE:
<223> OTHER INFORMATION: Synthetic fusion nucleotide

<400> SEQUENCE: 110
atggaatgga gctgggtatt tctgttttc ctgtcagtaa cgactggcgt ccattcaggc       60
ttcggcatca gtggacggca cagtatcaca gtgaccaccg tcgcctccgc tggcaatata     120
ggtgaggatg gcatcctgtc ctgtacctttt gagccggaca tcaaactgtc tgacatagtg    180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaaac attgcgctgt    480 gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaacggcgg    720
tctgagccta agtcatgtga caagacccat acgtgcccac cctgtcccgc tccagaactg    780 ctgggggac ctagcgtttt cttgttcccc ccaaagccca aggacaccct catgatctca     840
cggactcccg aagtaacatg cgtagtagtc gacgtgagcc acgaggatcc tgaagtgaag    900
tttaattggt acgtggacgg agtcgaggtg cataatgcca aaactaaacc tcgggaggag    960
cagtataaca gtacctaccg cgtggtatcc gtcttgacag tgctccacca ggactggctg    1020
aatggtaagg agtataaatg caaggtcagc aacaaagctc ttcccgcccc aattgaaaag    1080
```

| actatcagca aggccaaggg acaaccccgc gagccccagg tttacaccct tccaccttca | 1140 |
| cgagacgagc tgaccaagaa ccaggtgtct ctgacttgtc tggtcaaagg tttctatcct | 1200 |
| tccgacatcg cagtggagtg ggagtcaaac gggcagcctg agaataacta caagaccaca | 1260 |
| cccccagtgc ttgatagcga tgggagcttt ttcctctaca gtaagctgac tgtggacaaa | 1320 |
| tcccgctggc agcagggaaa cgttttctct tgtagcgtca tgcatgaggc cctccacaac | 1380 |
| cattatactc agaaaagcct gagtctgagt cccggcaaa | 1419 |

```
<210> SEQ ID NO 111
<211> LENGTH: 1404
<212> TYPE: DNA
<213> ORGANISM: Artificial Sequence
<220> FEATURE:
<223> OTHER INFORMATION: Synthetic fusion nucleotide

<400> SEQUENCE: 111
```

| atggaatgga gctgggtatt tctgtttttc ctgtcagtaa cgactggcgt ccattcaggc | 60 |
| ttcggcatca gtggacggca cagtatcaca gtgaccaccg tcgcctccgc tggcaatata | 120 |
| ggtgaggatg gcatcctgtc ctgtacccttt gagccggaca tcaaactgtc tgacatagtg | 180 |
| atacaatggc tgaaggaggg ggtgctcggt ctggtacatg agtttaagga agggaaggat | 240 |
| gaactgtccg agcaggatga gatgttccgg ggaggaccgc tgtgttcgc gatcaggta | 300 |
| atcgtcggaa atgcaagtct cagattgaaa aatgtgcaac tgactgatgc tggcacgtat | 360 |
| aaatgctaca ttatcacaag taagggcaaa ggaaatgcta accttgagta taaaacaggc | 420 |
| gcattctcaa tgcccgaggt caatgtcgac tataatgcca gcagtgaaac attgcgctgt | 480 |
| gaagctcccc gctggttccc ccagccaacc gtggtctggg cctctcaggt tgatcagggg | 540 |
| gctaactttt ccgaggtgag caacaccagc ttcgaactca actctgagaa tgtgaccatg | 600 |
| aaagttgtgt ctgtcctgta taatgtaaca atcaacaaca cttattcatg catgattgaa | 660 |
| aacgacatcg ccaaggcaac aggtgatatt aaggtaactg aatccgagat caaacggcgg | 720 |
| tctgacaaga cccatacgtg cccaccctgt cccgctccag aactgctggg gggacctagc | 780 |
| gttttcttgt tccccccaaa gcccaaggac accctcatga tctcacggac tcccgaagta | 840 |
| acatgcgtag tagtcgacgt gagccacgag gatcctgaag tgaagtttaa ttggtacgtg | 900 |
| gacggagtcg aggtgcataa tgccaaaact aaacctcggg aggagcagta taacagtacc | 960 |
| taccgcgtgg tatccgtctt gacagtgctc caccaggact ggctgaatgg taaggagtat | 1020 |
| aaatgcaagg tcagcaacaa agctcttccc gccccaattg aaaagactat cagcaaggcc | 1080 |
| aagggacaac cccgcgagcc ccaggtttac acccttccac cttcacgaga cgagctgacc | 1140 |
| aagaaccagg tgtctctgac ttgtctggtc aaaggttttct atccttccga catcgcagtg | 1200 |
| gagtgggagt caaacgggca gcctgagaat aactacaaga ccacaccccc agtgcttgat | 1260 |
| agcgatggga gcttttttcct ctacagtaag ctgactgtgg acaaatcccg ctggcagcag | 1320 |
| ggaaacgttt tctcttgtag cgtcatgcat gaggccctcc acaaccatta tactcagaaa | 1380 |
| agcctgagtc tgagtcccgg caaa | 1404 |

```
<210> SEQ ID NO 112
<211> LENGTH: 1392
<212> TYPE: DNA
<213> ORGANISM: Artificial Sequence
<220> FEATURE:
<223> OTHER INFORMATION: Synthetic fusion nucleotide

<400> SEQUENCE: 112
```

```
atggaatgga gctgggtatt tctgtttttc ctgtcagtaa cgactggcgt ccattcaggc    60
ttcggcatca gtgacggca cagtatcaca gtgaccaccg tcgcctccgc tggcaatata   120
ggtgaggatg gcatcctgtc ctgtacctttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccg ctgtgttcgc cgatcaggta   300
atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
aaagttgtgt ctgtcctgta atgtaaca atcaacaaca cttattcatg catgattgaa   660
aacgacatcg ccaaggcaac aggtgatatt aaggtaactg aatccgagat cgacaagacc   720
catacgtgcc caccctgtcc cgctccagaa ctgctggggg gacctagcgt tttcttgttc   780
cccccaaagc ccaaggacac cctcatgatc tcacggactc ccgaagtaac atgcgtagta   840
gtcgacgtga gccacgagga tcctgaagtg aagtttaatt ggtacgtgga cggagtcgag   900
gtgcataatg ccaaaactaa acctcgggag gagcagtata cagtaccta ccgcgtggta   960
tccgtcttga cagtgctcca ccaggactgg ctgaatggta aggagtataa atgcaaggtc  1020
agcaacaaag ctcttcccgc cccaattgaa aagactatca gcaaggccaa gggacaaccc  1080
cgcgagcccc aggtttacac ccttccacct tcacgagacg agctgaccaa gaaccaggtg  1140
tctctgactt gtctggtcaa aggtttctat ccttccgaca tcgcagtgga gtgggagtca  1200
aacgggcagc ctgagaataa ctacaagacc acacccccag tgcttgatag cgatgggagc  1260
ttttcctct acagtaagct gactgtggac aaatcccgct ggcagcaggg aaacgttttc  1320
tcttgtagcg tcatgcatga ggccctccac aaccattata ctcagaaaag cctgagtctg  1380
agtcccggca aa                                                      1392
```

<210> SEQ ID NO 113
<211> LENGTH: 1428
<212> TYPE: DNA
<213> ORGANISM: Artificial Sequence
<220> FEATURE:
<223> OTHER INFORMATION: Synthetic fusion nucleotide

<400> SEQUENCE: 113

```
atggaatgga gctgggtatt tctgtttttc ctgtcagtaa cgactggcgt ccattcaggc    60
ttcggcatca gtgacggca cagtatcaca gtgaccaccg tcgcctccgc tggcaatata   120
ggtgaggatg gcatcctgtc ctgtaccttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccg ctgtgttcgc cgatcaggta   300
atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
```

```
aaagttgtgt ctgtcctgta taatgtaaca atcaacaaca cttattcatg catgattgaa    660
aacgacatcg ccaaggcaac aggtgatatt aaggtaactg aatccgagat caaacggcgg    720
tctcacctgc agctgctgaa ctccaaggac aagacccata cgtgcccacc ctgtcccgct    780
ccagaactgc tggggggacc tagcgttttc ttgttccccc caaagcccaa ggacaccctc    840
atgatctcac ggactcccga agtaacatgc gtagtagtcg acgtgagcca cgaggatcct    900
gaagtgaagt taattggta cgtggacgga gtcgaggtgc ataatgccaa aactaaacct    960
cgggaggagc agtataacag tacctaccgc gtggtatccg tcttgacagt gctccaccag   1020
gactggctga atggtaagga gtataaatgc aaggtcagca caaagctct tcccgcccca   1080 attgaaaaga ctatcagcaa ggccaaggga caaccccgcg agccccaggt ttacacccct   1140
ccaccttcac gagacgagct gaccaagaac caggtgtctc tgacttgtct ggtcaaaggt   1200
ttctatcctt ccgacatcgc agtggagtgg gagtcaaacg ggcagcctga gaataactac   1260
aagaccacac ccccagtgct tgatagcgat gggagctttt tcctctacag taagctgact   1320
gtggacaaat cccgctggca gcagggaaac gttttctctt gtagcgtcat gcatgaggcc   1380
ctccacaacc attatactca gaaaagcctg agtctgagtc ccggcaaa               1428
```

<210> SEQ ID NO 114
<211> LENGTH: 481
<212> TYPE: PRT
<213> ORGANISM: Artificial Sequence
<220> FEATURE:
<223> OTHER INFORMATION: Synthetis fusion protein

<400> SEQUENCE: 114

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Gln Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220
```

```
Cys Met Ile Glu Asn Asp Ile Ala Lys Ala Thr Gly Asp Ile Lys Val
225                 230                 235                 240

Thr Glu Ser Glu Ile Lys Arg Arg Ser Glu Pro Lys Ser Cys Asp Lys
            245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
            275                 280                 285

Arg Thr Pro Glu Val Thr Cys Val Val Val Asp Val Ser His Glu Asp
            290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
            325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
            355                 360                 365

Thr Ile Ser Lys Ala Lys Gly Gln Pro Arg Glu Pro Gln Val Tyr Thr
370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
            405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
            435                 440                 445

Ser Arg Trp Gln Gln Gly Asn Val Phe Ser Cys Ser Val Met His Glu
            450                 455                 460

Ala Leu His Asn His Tyr Thr Gln Lys Ser Leu Ser Leu Ser Pro Gly
465                 470                 475                 480

Lys

<210> SEQ ID NO 115
<211> LENGTH: 536
<212> TYPE: PRT
<213> ORGANISM: Artificial Sequence
<220> FEATURE:
<223> OTHER INFORMATION: Synthetic fusion protein

<400> SEQUENCE: 115

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
            35                  40                  45

Gly Glu Asp Gly Ile Gln Ser Cys Thr Phe Glu Pro Met Ala Ser Leu
50                  55                  60

Gly Gln Ile Leu Phe Trp Ser Ile Ile Ser Ile Ile Ile Ile Leu Ala
65                  70                  75                  80

Gly Ala Ile Ala Leu Ile Ile Gly Phe Gly Ile Ser Gly Arg His Ser
            85                  90                  95
```

```
Ile Thr Val Thr Thr Val Ala Ser Ala Gly Asn Ile Gly Glu Asp Gly
            100                 105                 110
Ile Gln Ser Cys Thr Phe Glu Pro Asp Ile Lys Leu Ser Asp Ile Val
            115                 120                 125
Ile Gln Trp Leu Lys Glu Gly Val Leu Gly Leu Val His Glu Phe Lys
        130                 135                 140
Glu Gly Lys Asp Glu Leu Ser Glu Gln Asp Glu Met Phe Arg Gly Arg
145                 150                 155                 160
Thr Ala Val Phe Ala Asp Gln Val Ile Val Gly Asn Ala Ser Leu Arg
                165                 170                 175
Leu Lys Asn Val Gln Leu Thr Asp Ala Gly Thr Tyr Lys Cys Tyr Ile
            180                 185                 190
Ile Thr Ser Lys Gly Lys Gly Asn Ala Asn Leu Glu Tyr Lys Thr Gly
        195                 200                 205
Ala Phe Ser Met Pro Glu Val Asn Val Asp Tyr Asn Ala Ser Ser Glu
    210                 215                 220
Thr Leu Arg Cys Glu Ala Pro Arg Trp Phe Pro Gln Pro Thr Val Val
225                 230                 235                 240
Trp Ala Ser Gln Val Asp Gln Gly Ala Asn Phe Ser Glu Val Ser Asn
                245                 250                 255
Thr Ser Phe Glu Leu Asn Ser Glu Asn Val Thr Met Lys Val Val Ser
            260                 265                 270
Val Leu Tyr Asn Val Thr Ile Asn Asn Thr Tyr Ser Cys Met Ile Glu
        275                 280                 285
Asn Asp Ile Ala Lys Ala Thr Gly Asp Ile Lys Val Thr Glu Ser Glu
    290                 295                 300
Ile Lys Arg Arg Ser Asp Lys Thr His Thr Cys Pro Pro Cys Pro Ala
305                 310                 315                 320
Pro Glu Leu Leu Gly Gly Pro Ser Val Phe Leu Phe Pro Pro Lys Pro
                325                 330                 335
Lys Asp Thr Leu Met Ile Ser Arg Thr Pro Glu Val Thr Cys Val Val
            340                 345                 350
Val Asp Val Ser His Glu Asp Pro Glu Val Lys Phe Asn Trp Tyr Val
        355                 360                 365
Asp Gly Val Glu Val His Asn Ala Lys Thr Lys Pro Arg Glu Glu Gln
    370                 375                 380
Tyr Asn Ser Thr Tyr Arg Val Val Ser Val Leu Thr Val Leu His Gln
385                 390                 395                 400
Asp Trp Leu Asn Gly Lys Glu Tyr Lys Cys Lys Val Ser Asn Lys Ala
                405                 410                 415
Leu Pro Ala Pro Ile Glu Lys Thr Ile Ser Lys Ala Lys Gly Gln Pro
            420                 425                 430
Arg Glu Pro Gln Val Tyr Thr Leu Pro Pro Ser Arg Asp Glu Leu Thr
        435                 440                 445
Lys Asn Gln Val Ser Leu Thr Cys Leu Val Lys Gly Phe Tyr Pro Ser
    450                 455                 460
Asp Ile Ala Val Glu Trp Glu Ser Asn Gly Gln Pro Glu Asn Asn Tyr
465                 470                 475                 480
Lys Thr Thr Pro Pro Val Leu Asp Ser Asp Gly Ser Phe Phe Leu Tyr
                485                 490                 495
Ser Lys Leu Thr Val Asp Lys Ser Arg Trp Gln Gln Gly Asn Val Phe
            500                 505                 510
Ser Cys Ser Val Met His Glu Ala Leu His Asn His Tyr Thr Gln Lys
```

-continued

```
             515                 520                 525
Ser Leu Ser Leu Ser Pro Gly Lys
    530                 535
```

<210> SEQ ID NO 116
<211> LENGTH: 472
<212> TYPE: PRT
<213> ORGANISM: Artificial Sequence
<220> FEATURE:
<223> OTHER INFORMATION: Synthetic fusion protein

<400> SEQUENCE: 116

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Gln Ser Cys Thr Phe Glu Pro Asp Ile Lys Leu
50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
```

```
                340             345             350
Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
        370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 117
<211> LENGTH: 484
<212> TYPE: PRT
<213> ORGANISM: Artificial Sequence
<220> FEATURE:
<223> OTHER INFORMATION: Synthetic fusion protein

<400> SEQUENCE: 117

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Gln Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
```

```
                225                 230                 235                 240
Thr Glu Ser Glu Ile Lys Arg Arg Ser His Leu Gln Leu Leu Asn Ser
                    245                 250                 255

Lys Asp Lys Thr His Thr Cys Pro Pro Cys Pro Ala Pro Glu Leu Leu
                    260                 265                 270

Gly Gly Pro Ser Val Phe Leu Phe Pro Pro Lys Pro Lys Asp Thr Leu
                    275                 280                 285

Met Ile Ser Arg Thr Pro Glu Val Thr Cys Val Val Val Asp Val Ser
                    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                    325                 330                 335

Tyr Arg Val Val Ser Val Leu Thr Val Leu His Gln Asp Trp Leu Asn
                    340                 345                 350

Gly Lys Glu Tyr Lys Cys Lys Val Ser Asn Lys Ala Leu Pro Ala Pro
                    355                 360                 365

Ile Glu Lys Thr Ile Ser Lys Ala Lys Gly Gln Pro Arg Glu Pro Gln
                    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                    405                 410                 415

Glu Trp Glu Ser Asn Gly Gln Pro Glu Asn Asn Tyr Lys Thr Thr Pro
                    420                 425                 430

Pro Val Leu Asp Ser Asp Gly Ser Phe Phe Leu Tyr Ser Lys Leu Thr
                    435                 440                 445

Val Asp Lys Ser Arg Trp Gln Gln Gly Asn Val Phe Ser Cys Ser Val
                    450                 455                 460

Met His Glu Ala Leu His Asn His Tyr Thr Gln Lys Ser Leu Ser Leu
465                 470                 475                 480

Ser Pro Gly Lys

<210> SEQ ID NO 118
<211> LENGTH: 481
<212> TYPE: PRT
<213> ORGANISM: Artificial Sequence
<220> FEATURE:
<223> OTHER INFORMATION: Synthetic fusion protein

<400> SEQUENCE: 118

Met Ala Ser Leu Gly Gln Ile Leu Phe Trp Ser Ile Ser Ile Ile
1               5                   10                  15

Ile Ile Leu Ala Gly Ala Ile Ala Leu Ile Ile Gly Phe Gly Ile Ser
                    20                  25                  30

Gly Arg His Ser Ile Thr Val Thr Thr Val Ala Ser Ala Gly Asn Ile
                    35                  40                  45

Gly Glu Asp Gly Ile Leu Ser Cys Thr Phe Glu Pro Asp Ile Lys Leu
                    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                    85                  90                  95

Phe Arg Gly Arg Thr Ala Val Phe Ala Asp Gln Val Ile Val Gly Asn
                    100                 105                 110
```

```
Ala Ser Leu Arg Leu Lys Asn Val Gln Leu Thr Asp Ala Gly Thr Tyr
            115                 120                 125
Lys Cys Tyr Ile Ile Thr Ser Lys Gly Lys Gly Asn Ala Asn Leu Glu
130                 135                 140
Tyr Lys Thr Gly Ala Phe Ser Met Pro Glu Val Asn Val Asp Tyr Asn
145                 150                 155                 160
Ala Ser Ser Glu Thr Leu Arg Cys Glu Ala Pro Arg Trp Phe Pro Gln
            165                 170                 175
Pro Thr Val Val Trp Ala Ser Gln Val Asp Gln Gly Ala Asn Phe Ser
            180                 185                 190
Glu Val Ser Asn Thr Ser Phe Glu Leu Asn Ser Glu Asn Val Thr Met
            195                 200                 205
Lys Val Val Ser Val Leu Tyr Asn Val Thr Ile Asn Asn Thr Tyr Ser
            210                 215                 220
Cys Met Ile Glu Asn Asp Ile Ala Lys Ala Thr Gly Asp Ile Lys Val
225                 230                 235                 240
Thr Glu Ser Glu Ile Lys Arg Arg Ser Glu Pro Lys Ser Cys Asp Lys
                245                 250                 255
Thr His Thr Cys Pro Pro Cys Pro Ala Pro Glu Leu Leu Gly Gly Pro
            260                 265                 270
Ser Val Phe Leu Phe Pro Pro Lys Pro Lys Asp Thr Leu Met Ile Ser
            275                 280                 285
Arg Thr Pro Glu Val Thr Cys Val Val Val Asp Val Ser His Glu Asp
            290                 295                 300
Pro Glu Val Lys Phe Asn Trp Tyr Val Asp Gly Val Glu Val His Asn
305                 310                 315                 320
Ala Lys Thr Lys Pro Arg Glu Glu Gln Tyr Asn Ser Thr Tyr Arg Val
                325                 330                 335
Val Ser Val Leu Thr Val Leu His Gln Asp Trp Leu Asn Gly Lys Glu
            340                 345                 350
Tyr Lys Cys Lys Val Ser Asn Lys Ala Leu Pro Ala Pro Ile Glu Lys
            355                 360                 365
Thr Ile Ser Lys Ala Lys Gly Gln Pro Arg Glu Pro Gln Val Tyr Thr
            370                 375                 380
Leu Pro Pro Ser Arg Asp Glu Leu Thr Lys Asn Gln Val Ser Leu Thr
385                 390                 395                 400
Cys Leu Val Lys Gly Phe Tyr Pro Ser Asp Ile Ala Val Glu Trp Glu
                405                 410                 415
Ser Asn Gly Gln Pro Glu Asn Asn Tyr Lys Thr Thr Pro Pro Val Leu
            420                 425                 430
Asp Ser Asp Gly Ser Phe Phe Leu Tyr Ser Lys Leu Thr Val Asp Lys
            435                 440                 445
Ser Arg Trp Gln Gln Gly Asn Val Phe Ser Cys Ser Val Met His Glu
            450                 455                 460
Ala Leu His Asn His Tyr Thr Gln Lys Ser Leu Ser Leu Ser Pro Gly
465                 470                 475                 480
Lys
```

<210> SEQ ID NO 119
<211> LENGTH: 476
<212> TYPE: PRT
<213> ORGANISM: Artificial Sequence
<220> FEATURE:
<223> OTHER INFORMATION: Synthetic fusion protein

<400> SEQUENCE: 119

```
Met Ala Ser Leu Gly Gln Ile Leu Phe Trp Ser Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
```

```
              405                 410                 415
Glu Asn Asn Tyr Lys Thr Thr Pro Val Leu Asp Ser Asp Gly Ser
            420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
            450                 455                 460

Tyr Thr Gln Lys Ser Leu Ser Leu Ser Pro Gly Lys
465                 470                 475

<210> SEQ ID NO 120
<211> LENGTH: 472
<212> TYPE: PRT
<213> ORGANISM: Artificial Sequence
<220> FEATURE:
<223> OTHER INFORMATION: Synthetic fusion protein

<400> SEQUENCE: 120

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
```

```
                290             295             300
Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Leu Pro Pro Ser Arg Asp Glu Leu Thr
                370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460

Ser Leu Ser Leu Ser Pro Gly Lys
465                 470

<210> SEQ ID NO 121
<211> LENGTH: 484
<212> TYPE: PRT
<213> ORGANISM: Artificial Sequence
<220> FEATURE:
<223> OTHER INFORMATION: Synthetic fusion protein

<400> SEQUENCE: 121

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Thr Val Ala Ser Ala Gly Asn Ile
                35                  40                  45

Gly Glu Asp Gly Ile Leu Ser Cys Thr Phe Glu Pro Asp Ile Lys Leu
50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
                115                 120                 125

Lys Cys Tyr Ile Ile Thr Ser Lys Gly Lys Gly Asn Ala Asn Leu Glu
                130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
```

```
              180                 185                 190
Glu Val Ser Asn Thr Ser Phe Glu Leu Asn Ser Glu Asn Val Thr Met
        195                 200                 205

Lys Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Lys

<210> SEQ ID NO 122
<211> LENGTH: 473
<212> TYPE: PRT
<213> ORGANISM: Artificial Sequence
<220> FEATURE:
<223> OTHER INFORMATION: Synthetic fusion protein

<400> SEQUENCE: 122

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Gln Ser Cys
        35                  40                  45

Thr Phe Glu Pro Asp Ile Lys Leu Ser Asp Ile Val Ile Gln Trp Leu
    50                  55                  60
```

```
Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
210                 215                 220

Lys Ala Thr Gly Asp Ile Lys Val Thr Glu Ser Glu Ile Lys Arg Arg
225                 230                 235                 240

Ser Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470
```

```
<210> SEQ ID NO 123
<211> LENGTH: 468
<212> TYPE: PRT
<213> ORGANISM: Artificial Sequence
<220> FEATURE:
<223> OTHER INFORMATION: Synthetic fusion protein

<400> SEQUENCE: 123

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Gln Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365
```

```
Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 124
<211> LENGTH: 464
<212> TYPE: PRT
<213> ORGANISM: Artificial Sequence
<220> FEATURE:
<223> OTHER INFORMATION: Synthetic fusion protein

<400> SEQUENCE: 124

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
                20                  25                  30

Thr Val Ala Ser Ala Gly Asn Ile Gly Glu Asp Gly Ile Gln Ser Cys
            35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
    115                 120                 125

Gly Lys Gly Asn Ala Asn Leu Glu Tyr Lys Thr Gly Ala Phe Ser Met
130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
    195                 200                 205

Val Thr Ile Asn Asn Thr Tyr Ser Cys Met Ile Glu Asn Asp Ile Ala
210                 215                 220

Lys Ala Thr Gly Asp Ile Lys Val Thr Glu Ser Glu Ile Asp Lys Thr
225                 230                 235                 240

His Thr Cys Pro Pro Cys Pro Ala Pro Glu Leu Leu Gly Gly Pro Ser
                245                 250                 255
```

```
Val Phe Leu Phe Pro Pro Lys Pro Lys Asp Thr Leu Met Ile Ser Arg
            260                 265                 270

Thr Pro Glu Val Thr Cys Val Val Asp Val Ser His Glu Asp Pro
        275                 280                 285

Glu Val Lys Phe Asn Trp Tyr Val Asp Gly Val Glu Val His Asn Ala
        290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
                340                 345                 350

Ile Ser Lys Ala Lys Gly Gln Pro Arg Glu Pro Gln Val Tyr Thr Leu
            355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 125
<211> LENGTH: 476
<212> TYPE: PRT
<213> ORGANISM: Artificial Sequence
<220> FEATURE:
<223> OTHER INFORMATION: Synthetic fusion protein

<400> SEQUENCE: 125

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Gln Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140

Pro Glu Val Asn Val Asp Tyr Asn Ala Ser Ser Glu Thr Leu Arg Cys
145                 150                 155                 160
```

```
Glu Ala Pro Arg Trp Phe Pro Gln Pro Thr Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Ser Val Leu Tyr Asn
            195                 200                 205

Val Thr Ile Asn Asn Thr Tyr Ser Cys Met Ile Glu Asn Asp Ile Ala
            210                 215                 220

Lys Ala Thr Gly Asp Ile Lys Val Thr Glu Ser Glu Ile Lys Arg Arg
225                 230                 235                 240

Ser His Leu Gln Leu Leu Asn Ser Lys Asp Lys Thr His Thr Cys Pro
                245                 250                 255

Pro Cys Pro Ala Pro Glu Leu Leu Gly Gly Pro Ser Val Phe Leu Phe
                260                 265                 270

Pro Pro Lys Pro Lys Asp Thr Leu Met Ile Ser Arg Thr Pro Glu Val
                275                 280                 285

Thr Cys Val Val Val Asp Val Ser His Glu Asp Pro Glu Val Lys Phe
                290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
                340                 345                 350

Ser Asn Lys Ala Leu Pro Ala Pro Ile Glu Lys Thr Ile Ser Lys Ala
                355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
                420                 425                 430

Phe Phe Leu Tyr Ser Lys Leu Thr Val Asp Lys Ser Arg Trp Gln Gln
                435                 440                 445

Gly Asn Val Phe Ser Cys Ser Val Met His Glu Ala Leu His Asn His
                450                 455                 460

Tyr Thr Gln Lys Ser Leu Ser Leu Ser Pro Gly Lys
465                 470                 475

<210> SEQ ID NO 126
<211> LENGTH: 473
<212> TYPE: PRT
<213> ORGANISM: Artificial Sequence
<220> FEATURE:
<223> OTHER INFORMATION: Synthetic fusion protein

<400> SEQUENCE: 126

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
                20                  25                  30

Thr Val Ala Ser Ala Gly Asn Ile Gly Glu Asp Gly Ile Leu Ser Cys
            35                  40                  45
```

```
Thr Phe Glu Pro Asp Ile Lys Leu Ser Asp Ile Val Ile Gln Trp Leu
 50                  55                  60

Lys Glu Gly Val Leu Gly Leu Val His Glu Phe Lys Glu Gly Lys Asp
 65                  70                  75                  80

Glu Leu Ser Glu Gln Asp Glu Met Phe Arg Gly Arg Thr Ala Val Phe
                 85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
210                 215                 220

Lys Ala Thr Gly Asp Ile Lys Val Thr Glu Ser Glu Ile Lys Arg Arg
225                 230                 235                 240

Ser Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
```

-continued

```
                465                 470

<210> SEQ ID NO 127
<211> LENGTH: 468
<212> TYPE: PRT
<213> ORGANISM: Artificial Sequence
<220> FEATURE:
<223> OTHER INFORMATION: Synthetic fusion protein

<400> SEQUENCE: 127

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
            20                  25                  30

Thr Val Ala Ser Ala Gly Asn Ile Gly Glu Asp Gly Ile Leu Ser Cys
        35                  40                  45

Thr Phe Glu Pro Asp Ile Lys Leu Ser Asp Ile Val Ile Gln Trp Leu
    50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140

Pro Glu Val Asn Val Asp Tyr Asn Ala Ser Ser Glu Thr Leu Arg Cys
145                 150                 155                 160

Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
```

```
                  355                 360                 365
Val Tyr Thr Leu Pro Pro Ser Arg Asp Glu Leu Thr Lys Asn Gln Val
            370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
            435                 440                 445
Met His Glu Ala Leu His Asn His Tyr Thr Gln Lys Ser Leu Ser Leu
450                 455                 460
Ser Pro Gly Lys
465

<210> SEQ ID NO 128
<211> LENGTH: 464
<212> TYPE: PRT
<213> ORGANISM: Artificial Sequence
<220> FEATURE:
<223> OTHER INFORMATION: Synthetic fusion protein

<400> SEQUENCE: 128

Met Glu Trp Ser Trp Val Phe Leu Phe Phe Leu Ser Val Thr Thr Gly
1               5                   10                  15
Val His Ser Gly Phe Gly Ile Ser Gly Arg His Ser Ile Thr Val Thr
            20                  25                  30
Thr Val Ala Ser Ala Gly Asn Ile Gly Glu Asp Gly Ile Leu Ser Cys
        35                  40                  45
Thr Phe Glu Pro Asp Ile Lys Leu Ser Asp Ile Val Ile Gln Trp Leu
    50                  55                  60
Lys Glu Gly Val Leu Gly Leu Val His Glu Phe Lys Glu Gly Lys Asp
65                  70                  75                  80
Glu Leu Ser Glu Gln Asp Glu Met Phe Arg Gly Arg Thr Ala Val Phe
                85                  90                  95
Ala Asp Gln Val Ile Val Gly Asn Ala Ser Leu Arg Leu Lys Asn Val
            100                 105                 110
Gln Leu Thr Asp Ala Gly Thr Tyr Lys Cys Tyr Ile Ile Thr Ser Lys
        115                 120                 125
Gly Lys Gly Asn Ala Asn Leu Glu Tyr Lys Thr Gly Ala Phe Ser Met
    130                 135                 140
Pro Glu Val Asn Val Asp Tyr Asn Ala Ser Ser Glu Thr Leu Arg Cys
145                 150                 155                 160
Glu Ala Pro Arg Trp Phe Pro Gln Pro Thr Val Val Trp Ala Ser Gln
                165                 170                 175
Val Asp Gln Gly Ala Asn Phe Ser Glu Val Ser Asn Thr Ser Phe Glu
            180                 185                 190
Leu Asn Ser Glu Asn Val Thr Met Lys Val Val Ser Val Leu Tyr Asn
        195                 200                 205
Val Thr Ile Asn Asn Thr Tyr Ser Cys Met Ile Glu Asn Asp Ile Ala
    210                 215                 220
Lys Ala Thr Gly Asp Ile Lys Val Thr Glu Ser Glu Ile Asp Lys Thr
225                 230                 235                 240
His Thr Cys Pro Pro Cys Pro Ala Pro Glu Leu Leu Gly Gly Pro Ser
```

245                 250                 255
Val Phe Leu Phe Pro Lys Pro Lys Asp Thr Leu Met Ile Ser Arg
            260                 265                 270

Thr Pro Glu Val Thr Cys Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 129
<211> LENGTH: 476
<212> TYPE: PRT
<213> ORGANISM: Artificial Sequence
<220> FEATURE:
<223> OTHER INFORMATION: Synthetic fusion protein

<400> SEQUENCE: 129

Met Glu Trp Ser Trp Val Phe Leu Phe Phe Leu Ser Val Thr Thr Gly
1               5                   10                  15

Val His Ser Gly Phe Gly Ile Ser Gly Arg His Ser Ile Thr Val Thr
                20                  25                  30

Thr Val Ala Ser Ala Gly Asn Ile Gly Glu Asp Gly Ile Leu Ser Cys
            35                  40                  45

Thr Phe Glu Pro Asp Ile Lys Leu Ser Asp Ile Val Ile Gln Trp Leu
        50                  55                  60

Lys Glu Gly Val Leu Gly Leu Val His Glu Phe Lys Glu Gly Lys Asp
65                  70                  75                  80

Glu Leu Ser Glu Gln Asp Glu Met Phe Arg Gly Arg Thr Ala Val Phe
                85                  90                  95

Ala Asp Gln Val Ile Val Gly Asn Ala Ser Leu Arg Leu Lys Asn Val
            100                 105                 110

Gln Leu Thr Asp Ala Gly Thr Tyr Lys Cys Tyr Ile Ile Thr Ser Lys
        115                 120                 125

Gly Lys Gly Asn Ala Asn Leu Glu Tyr Lys Thr Gly Ala Phe Ser Met
    130                 135                 140

Pro Glu Val Asn Val Asp Tyr Asn Ala Ser Ser Glu Thr Leu Arg Cys

```
            145                 150                 155                 160
Glu Ala Pro Arg Trp Phe Pro Gln Pro Thr Val Val Trp Ala Ser Gln
                165                 170                 175

Val Asp Gln Gly Ala Asn Phe Ser Glu Val Ser Asn Thr Ser Phe Glu
            180                 185                 190

Leu Asn Ser Glu Asn Val Thr Met Lys Val Ser Val Leu Tyr Asn
        195                 200                 205

Val Thr Ile Asn Asn Thr Tyr Ser Cys Met Ile Glu Asn Asp Ile Ala
    210                 215                 220

Lys Ala Thr Gly Asp Ile Lys Val Thr Glu Ser Glu Ile Lys Arg Arg
225                 230                 235                 240

Ser His Leu Gln Leu Leu Asn Ser Lys Asp Lys Thr His Thr Cys Pro
                245                 250                 255

Pro Cys Pro Ala Pro Glu Leu Leu Gly Gly Pro Ser Val Phe Leu Phe
                260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
        290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 130
<211> LENGTH: 454
<212> TYPE: PRT
<213> ORGANISM: Artificial Sequence
<220> FEATURE:
<223> OTHER INFORMATION: Synthetic fusion protein

<400> SEQUENCE: 130

Gly Phe Gly Ile Ser Gly Arg His Ser Ile Thr Val Thr Val Ala
1               5                   10                  15

Ser Ala Gly Asn Ile Gly Glu Asp Gly Ile Gln Ser Cys Thr Phe Glu
            20                  25                  30

Pro Asp Ile Lys Leu Ser Asp Ile Val Ile Gln Trp Leu Lys Glu Gly
```

```
                35                  40                  45
Val Leu Gly Leu Val His Glu Phe Lys Glu Gly Lys Asp Glu Leu Ser
 50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
                100                 105                 110

Asn Ala Asn Leu Glu Tyr Lys Thr Gly Ala Phe Ser Met Pro Glu Val
                115                 120                 125

Asn Val Asp Tyr Asn Ala Ser Ser Glu Thr Leu Arg Cys Glu Ala Pro
                130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
                180                 185                 190

Asn Asn Thr Tyr Ser Cys Met Ile Glu Asn Asp Ile Ala Lys Ala Thr
                195                 200                 205

Gly Asp Ile Lys Val Thr Glu Ser Glu Ile Lys Arg Arg Ser Glu Pro
                210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Asn
                290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Lys
                450
```

<210> SEQ ID NO 131
<211> LENGTH: 449
<212> TYPE: PRT
<213> ORGANISM: Artificial Sequence
<220> FEATURE:
<223> OTHER INFORMATION: Synthetic fusion protein

<400> SEQUENCE: 131

```
Gly Phe Gly Ile Ser Gly Arg His Ser Ile Thr Val Thr Val Ala
1               5                   10                  15

Ser Ala Gly Asn Ile Gly Glu Asp Gly Ile Gln Ser Cys Thr Phe Glu
            20                  25                  30

Pro Asp Ile Lys Leu Ser Asp Ile Val Ile Gln Trp Leu Lys Glu Gly
            35                  40                  45

Val Leu Gly Leu Val His Glu Phe Lys Glu Gly Lys Asp Glu Leu Ser
        50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
        130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 132
<211> LENGTH: 445
<212> TYPE: PRT
<213> ORGANISM: Artificial Sequence
<220> FEATURE:
<223> OTHER INFORMATION: Synthetic fusion protein

<400> SEQUENCE: 132

Gly Phe Gly Ile Ser Gly Arg His Ser Ile Thr Val Thr Thr Val Ala
1               5                   10                  15

Ser Ala Gly Asn Ile Gly Glu Asp Gly Ile Gln Ser Cys Thr Phe Glu
                20                  25                  30

Pro Asp Ile Lys Leu Ser Asp Ile Val Ile Gln Trp Leu Lys Glu Gly
            35                  40                  45

Val Leu Gly Leu Val His Glu Phe Lys Glu Gly Lys Asp Glu Leu Ser
50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270
```

```
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 133
<211> LENGTH: 457
<212> TYPE: PRT
<213> ORGANISM: Artificial Sequence
<220> FEATURE:
<223> OTHER INFORMATION: Synthetic fusion protein

<400> SEQUENCE: 133

Gly Phe Gly Ile Ser Gly Arg His Ser Ile Thr Val Thr Thr Val Ala
1               5                   10                  15
Ser Ala Gly Asn Ile Gly Glu Asp Gly Ile Gln Ser Cys Thr Phe Glu
                20                  25                  30
Pro Asp Ile Lys Leu Ser Asp Ile Val Ile Gln Trp Leu Lys Glu Gly
            35                  40                  45
Val Leu Gly Leu Val His Glu Phe Lys Glu Gly Lys Asp Glu Leu Ser
        50                  55                  60
Glu Gln Asp Glu Met Phe Arg Gly Arg Thr Ala Val Phe Ala Asp Gln
65                  70                  75                  80
Val Ile Val Gly Asn Ala Ser Leu Arg Leu Lys Asn Val Gln Leu Thr
                85                  90                  95
Asp Ala Gly Thr Tyr Lys Cys Tyr Ile Ile Thr Ser Lys Gly Lys Gly
            100                 105                 110
Asn Ala Asn Leu Glu Tyr Lys Thr Gly Ala Phe Ser Met Pro Glu Val
        115                 120                 125
Asn Val Asp Tyr Asn Ala Ser Ser Glu Thr Leu Arg Cys Glu Ala Pro
    130                 135                 140
Arg Trp Phe Pro Gln Pro Thr Val Val Trp Ala Ser Gln Val Asp Gln
145                 150                 155                 160
Gly Ala Asn Phe Ser Glu Val Ser Asn Thr Ser Phe Glu Leu Asn Ser
                165                 170                 175
Glu Asn Val Thr Met Lys Val Val Ser Val Leu Tyr Asn Val Thr Ile
            180                 185                 190
```

```
Asn Asn Thr Tyr Ser Cys Met Ile Glu Asn Asp Ile Ala Lys Ala Thr
            195                 200                 205

Gly Asp Ile Lys Val Thr Glu Ser Glu Ile Lys Arg Arg Ser His Leu
210                 215                 220

Gln Leu Leu Asn Ser Lys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
            355                 360                 365

Thr Lys Asn Gln Val Ser Leu Thr Cys Leu Val Lys Gly Phe Tyr Pro
            370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
        450                 455

<210> SEQ ID NO 134
<211> LENGTH: 454
<212> TYPE: PRT
<213> ORGANISM: Artificial Sequence
<220> FEATURE:
<223> OTHER INFORMATION: Synthetic fusion protein

<400> SEQUENCE: 134

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
        35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95
```

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
            115                 120                 125

Asn Val Asp Tyr Asn Ala Ser Ser Glu Thr Leu Arg Cys Glu Ala Pro
        130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 135
<211> LENGTH: 449
<212> TYPE: PRT
<213> ORGANISM: Artificial Sequence
<220> FEATURE:
<223> OTHER INFORMATION: Synthetic fusion protein

<400> SEQUENCE: 135

```
Gly Phe Gly Ile Ser Gly Arg His Ser Ile Thr Val Thr Val Ala
1               5                   10                  15

Ser Ala Gly Asn Ile Gly Glu Asp Gly Ile Leu Ser Cys Thr Phe Glu
            20                  25                  30

Pro Asp Ile Lys Leu Ser Asp Ile Val Ile Gln Trp Leu Lys Glu Gly
                35                  40                  45

Val Leu Gly Leu Val His Glu Phe Lys Glu Gly Lys Asp Glu Leu Ser
    50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Lys Arg Arg Ser Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
                     420                 425                 430
Ala Leu His Asn His Tyr Thr Gln Lys Ser Leu Ser Leu Ser Pro Gly
            435                 440                 445
Lys

<210> SEQ ID NO 136
<211> LENGTH: 445
<212> TYPE: PRT
<213> ORGANISM: Artificial Sequence
<220> FEATURE:
<223> OTHER INFORMATION: Synthetic fusion protein

<400> SEQUENCE: 136

Gly Phe Gly Ile Ser Gly Arg His Ser Ile Thr Val Thr Val Ala
1               5                   10                  15

Ser Ala Gly Asn Ile Gly Glu Asp Gly Ile Leu Ser Cys Thr Phe Glu
                20                  25                  30

Pro Asp Ile Lys Leu Ser Asp Ile Val Ile Gln Trp Leu Lys Glu Gly
            35                  40                  45

Val Leu Gly Leu Val His Glu Phe Lys Glu Gly Lys Asp Glu Leu Ser
50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
            100                 105                 110

Asn Ala Asn Leu Glu Tyr Lys Thr Gly Ala Phe Ser Met Pro Glu Val
        115                 120                 125

Asn Val Asp Tyr Asn Ala Ser Ser Glu Thr Leu Arg Cys Glu Ala Pro
    130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
            180                 185                 190

Asn Asn Thr Tyr Ser Cys Met Ile Glu Asn Asp Ile Ala Lys Ala Thr
        195                 200                 205

Gly Asp Ile Lys Val Thr Glu Ser Glu Ile Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335
```

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 137
<211> LENGTH: 457
<212> TYPE: PRT
<213> ORGANISM: Artificial Sequence
<220> FEATURE:
<223> OTHER INFORMATION: Synthetic fusion protein

<400> SEQUENCE: 137

Gly Phe Gly Ile Ser Gly Arg His Ser Ile Thr Val Thr Thr Val Ala
1               5                   10                  15

Ser Ala Gly Asn Ile Gly Glu Asp Gly Ile Leu Ser Cys Thr Phe Glu
                20                  25                  30

Pro Asp Ile Lys Leu Ser Asp Ile Val Ile Gln Trp Leu Lys Glu Gly
                35                  40                  45

Val Leu Gly Leu Val His Glu Phe Lys Glu Gly Lys Asp Glu Leu Ser
                50                  55                  60

Glu Gln Asp Glu Met Phe Arg Gly Arg Thr Ala Val Phe Ala Asp Gln
65                  70                  75                  80

Val Ile Val Gly Asn Ala Ser Leu Arg Leu Lys Asn Val Gln Leu Thr
                85                  90                  95

Asp Ala Gly Thr Tyr Lys Cys Tyr Ile Ile Thr Ser Lys Gly Lys Gly
                100                 105                 110

Asn Ala Asn Leu Glu Tyr Lys Thr Gly Ala Phe Ser Met Pro Glu Val
                115                 120                 125

Asn Val Asp Tyr Asn Ala Ser Ser Glu Thr Leu Arg Cys Glu Ala Pro
                130                 135                 140

Arg Trp Phe Pro Gln Pro Thr Val Val Trp Ala Ser Gln Val Asp Gln
145                 150                 155                 160

Gly Ala Asn Phe Ser Glu Val Ser Asn Thr Ser Phe Glu Leu Asn Ser
                165                 170                 175

Glu Asn Val Thr Met Lys Val Val Ser Val Leu Tyr Asn Val Thr Ile
                180                 185                 190

Asn Asn Thr Tyr Ser Cys Met Ile Glu Asn Asp Ile Ala Lys Ala Thr
                195                 200                 205

Gly Asp Ile Lys Val Thr Glu Ser Glu Ile Lys Arg Arg Ser His Leu
                210                 215                 220

Gln Leu Leu Asn Ser Lys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

-continued

```
Pro Lys Asp Thr Leu Met Ile Ser Arg Thr Pro Glu Val Thr Cys Val
            260                 265                 270
Val Val Asp Val Ser His Glu Asp Pro Glu Val Lys Phe Asn Trp Tyr
        275                 280                 285
Val Asp Gly Val Glu Val His Asn Ala Lys Thr Lys Pro Arg Glu Glu
    290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Ala Leu Pro Ala Pro Ile Glu Lys Thr Ile Ser Lys Ala Lys Gly Gln
            340                 345                 350
Pro Arg Glu Pro Gln Val Tyr Thr Leu Pro Pro Ser Arg Asp Glu Leu
        355                 360                 365
Thr Lys Asn Gln Val Ser Leu Thr Cys Leu Val Lys Gly Phe Tyr Pro
    370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Gln Gly Asn Val
            420                 425                 430
Phe Ser Cys Ser Val Met His Glu Ala Leu His Asn His Tyr Thr Gln
        435                 440                 445
Lys Ser Leu Ser Leu Ser Pro Gly Lys
    450                 455

<210> SEQ ID NO 138
<211> LENGTH: 17
<212> TYPE: PRT
<213> ORGANISM: Artificial Sequence
<220> FEATURE:
<223> OTHER INFORMATION: OVA323-339 Peptide

<400> SEQUENCE: 138

Ile Ser Gln Ala Val His Ala Ala His Ala Glu Ile Asn Glu Ala Gly
1               5                   10                  15
Arg

<210> SEQ ID NO 139
<211> LENGTH: 13
<212> TYPE: PRT
<213> ORGANISM: Artificial Sequence
<220> FEATURE:
<223> OTHER INFORMATION: PLP130-151 Peptide

<400> SEQUENCE: 139

His Ser Leu Gly Lys Trp Leu Gly His Pro Asp Lys Phe
1               5                   10

<210> SEQ ID NO 140
<211> LENGTH: 14
<212> TYPE: PRT
<213> ORGANISM: Artificial Sequence
<220> FEATURE:
<223> OTHER INFORMATION: PLP130-151 Peptide

<400> SEQUENCE: 140

Asn Thr Trp Thr Thr Cys Gln Ser Ile Ala Phe Pro Ser Lys
```

```
<210> SEQ ID NO 141
<211> LENGTH: 21
<212> TYPE: PRT
<213> ORGANISM: Artificial Sequence
<220> FEATURE:
<223> OTHER INFORMATION: MOG35-55 Peptide

<400> SEQUENCE: 141

Met Glu Val Gly Trp Tyr Arg Ser Pro Phe Ser Arg Val Val His Leu
1               5                   10                  15

Tyr Arg Asn Gly Lys
            20
```

METHODS AND COMPOSITIONS FOR THE INHIBITION OF TRANSPLANT REJECTION

CROSS REFERENCE TO RELATED APPLICATIONS

This application claims priority to U.S. Provisional Patent Application No. 61/238,605 filed on Aug. 31, 2009, U.S. Provisional Patent Application No. 61/266,854, filed on Dec. 4, 2009, U.S. Provisional Patent Application No. 61/254,930 filed on Oct. 26, 2009, U.S. Provisional Patent Application No. 61/286,537 filed on Dec. 15, 2009, and U.S. Provisional Patent Application No. 61/378,361 filed Aug. 30, 2010.

FIELD OF THE INVENTION

The field of the invention is generally in area of immunology, in particular to methods and compositions for treating transplant rejection.

BACKGROUND OF THE INVENTION

Continued advances in surgical techniques and immunosuppressive therapy have allowed organ transplantation to become an extremely successful treatment option for patients in need of transplants. Beginning with the revolutionary discovery of cyclosporine in the 1970s, immunosuppressive regimens have evolved greatly and lead to a significant increase in the survival rates for many types of organ and tissue transplants, such as heart, kidney and bone marrow. For example, current statistics confirm one-year liver graft survival rates in excess of 80% (Pillai et al., *World J Gastroenterol*, 15(34): 4225-4233 (2009)).

The success of surgical transplantation of organs and tissue is largely dependent on the ability of the clinician to modulate the immune response of the transplant recipient. The immunological response directed against the transplanted foreign tissue must be controlled if the tissue is to survive and function. During transplant rejection, the normally functioning immune system of the transplant recipient recognizes the transplanted organ as "non-self" tissue and thereafter mounts an immune response to the transplanted organ. Left unchecked, the immune response will generate a multitude of cells and proteins that will ultimately result in loss of biological functioning or death of the transplanted organ and can also lead to other severe toxic side effects in the transplant recipient.

Transplant rejection remains the leading impediment to long term graft survival in humans.

T cells play a central role in transplant rejection (Gandhi, A., et al., *Curr Opin Organ Transplant*, 13:622-626 (2008)). Most therapies for preventing transplant rejection focus on inhibiting T cell activation. Naïve T cells require 2 signals for their full activation (Vincennti, F., et al., *J Allergy Clin Immunol*, 121(2):299-306). The first signal is antigen-specific and is provided by the T cell receptor interacting with the MHC and antigenic peptide complex on the antigen presenting cell (APC). The second signal, or costimulatory signal, is provided by the interactions between molecules such as CD80 and CD86 on the APC with cognate receptors on naïve T cells. The presence of cytokines including IL-2 stimulates the process of activation resulting in T cell proliferation. If the T cell does not receive a costimulation signal because of blockade of this pathway, it becomes anergic and undergoes apoptosis.

CD80 (B7-1) and CD86 (B7-2) are members of the B7 superfamily of co-stimulatory molecules that each can engage the stimulatory CD28 receptor and the inhibitory CTLA-4 (CD152) receptor. In conjunction with signaling through the T cell receptor, CD28 ligation increases antigen-specific proliferation of T cells, enhances production of cytokines, stimulates differentiation and effector function, and promotes survival of T cells (Lenshow, et al., *Annu. Rev. Immunol.*, 14:233-258 (1996); Chambers and Allison, *Curr. Opin. Immunol.*, 9:396-404 (1997); and Rathmell and Thompson, *Annu. Rev. Immunol.*, 17:781-828 (1999)). In contrast, signaling through CTLA-4 is thought to deliver a negative signal that inhibits T cell proliferation, IL-2 production, and cell cycle progression (Krummel and Allison, *J Exp. Med.*, 183:2533-2540 (1996); and Walunas, et al., *J. Exp. Med.*, 183:2541-2550 (1996)).

Current immunosuppressive agents include calcineurin inhibitors such as cyclosporine and tacrolimus. These agents inhibit the intracellular protease calcineurin which is not exclusive to T cells. Because calcineurin in present in other cell types, calcineurin inhibitors cause side effects in other tissues. mTOR inhibitors such as sirolimus similarly have side effects in other tissues because they inhibit a signal transduction pathway which is not specific to T cells. (Emamaullee, J. et al., *Expert Opin. Biol. Ther.* 9(6):789-796 (2009)). Antibody-based agents that bind to receptors on T cells provide more selectivity than calcineurin inhibitors but often provide a more potent inhibitory effect on the immune system that can last for several months.

CTLA-4 is expressed after T cell activation and acts to downregulate the T cell response. CTLA-4 binds with higher avidity to the CD80 and CD86 ligands than CD28 and competes with CD28 to downregulate T cell activity. Fusion proteins with the extracellular domain of CTLA-4 have been shown to selectively prevent activation of T cells through CD28 (Alegre, M., et al., *Current Pharmacoloical Design*, 12:149-160).

Therefore, it is an object of the invention to provide methods and compositions for inhibiting or reducing transplant rejection.

It is another object of the invention to provide methods and compositions for prolonging allograft survival.

It is another object of the invention to provide methods and compositions for inhibiting or reducing graft versus host disease.

It is another object of the invention to provide immunosuppressive agents specific for T cells.

It is another object of the invention to provide methods and compositions for inhibiting transplant rejection by inhibiting the development of naïve T cells into any of Th1, Th17 or Th22 cells.

It is another object of the invention to provide methods and compositions for inhibiting transplant rejection by inhibiting or reducing the production of proinflammatory molecules and thereby inhibit or reduce transplant rejection.

It is an object of the invention to provide methods and compositions for inhibiting transplant rejection that inhibit the proliferation of T cells, decrease or inhibit production of pro-inflammatory molecules by T cells, decrease or inhibit differentiation and effector function of Th1, Th17 or Th22 cells, and decrease or inhibit survival of Th1, Th17 or Th22 cells.

It is another object of the invention to provide methods and compositions for inhibiting transplant rejection by enhancing the suppressive effect of Tregs.

It is another object of the invention to provide methods and compositions for inhibiting transplant rejection by enhancing the suppressive effect of Tregs on the Th1, Th17 and Th22 pathways, to reduce the level of IFN-gamma, IL-17 and other inflammatory molecules produced and thereby inhibit or reduce inflammation, alloreactivity and transplant rejection.

It is another object of the invention to provide methods and compositions for inhibiting transplant rejection by administering an agent that acts directly on Tregs to promote or enhance production of IL-10 to further suppress the production of inflammatory molecules and thereby inhibit or reduce transplant rejection.

It is another object of the invention to provide methods and compositions for inhibiting transplant rejection that increase or promote the activity of Tregs, increase the differentiation of naïve T cells into Tregs, increase the number of Tregs, or increase the survival of Tregs.

It is another object of the invention to provide compositions and methods for modulating the proinflammatory activity of Th1, Th17 or Th22 T cells while simultaneously increasing or promoting the activity of Tregs.

It is another object of the invention to provide combination therapies for inhibiting transplant rejection.

SUMMARY OF THE INVENTION

Methods for modulating immune responses in a subject are provided. A preferred embodiment provides methods and compositions for reducing or inhibiting transplant rejection in a subject, preferably a human subject, by administering an effective amount of a B7-H4 polypeptide or fragment, or fusion protein thereof to inhibit or reduce the biological activity of an immune cell or to reduce the amounts of proinflammatory molecules, for example, proinflammatory cytokines. The most preferred embodiment is a B7-H4-Ig fusion protein. Exemplary proinflammatory molecules include, but are not limited to, IL-1β, TNF-α, TGF-beta, IFN-γ, IL-17, IL-6, IL-23, IL-22, IL-21, and MMPs. Th1, Th17 and Th22 are exemplary T cells that can be targeted for inhibition by B7-H4 polypeptides, fusion proteins or fragments thereof to inhibit or reduce inflammation. B7-H4 polypeptides or fragments, or fusion proteins thereof can also be used to target other cells that secrete, or cause other cells to secrete, inflammatory molecules. Additionally, B7-H4 polypeptides, fusion proteins or fragments thereof can target Tregs to cause an enhanced suppressive effect on production of inflammatory molecules such as IL-17. B7-H4 polypeptides or fragments or fusions thereof can also act directly on Tregs to promote or enhance production of IL-10 to further suppress the production of inflammatory molecules, or to enhance the suppressive effects of Tregs and thereby inhibit or reduce transplant rejection.

B7-H4 polypeptides or fragments, or fusions thereof act at multiple points in multiple pathways. For example, they can inhibit the development of naïve T cells into Th1, Th17, Th22 or other cells that secrete, or cause other cells to secrete, inflammatory molecules. Alternatively, they can interact with Th1, Th17, Th22 and/or other cells, to inhibit or reduce the production of proinflammatory molecules or inhibit proliferation of Th1, Th17 and Th22 cells. Additionally, they can work with Tregs to cause an enhanced suppressive effect on Th1, Th17 and/or Th22 cells to reduce the level of IFN-γ and/or IL-17 produced. They can also act directly on Tregs to promote or enhance production of IL-10 to suppress the Th1 and/or Th17 pathway. Additionally they can work by enhancing the differentiation, recruitment and/or expansion of Treg cells in the region of engrafted tissue.

The transplanted material to be treated can be cells, tissues, organs, limbs, digits or a portion of the body, preferably the human body. The transplants are typically allogenic or xenogenic. B7-H4 polypeptides or fragments, or fusions thereof can be administered systemically or locally. In some embodiments, B7-H4 polypeptides, fragments, or fusions thereof are administered to a site of transplantation prior to, at the time of, or following transplantation. In one embodiment, the B7-H4 polypeptides, fragments or fusions thereof are administered to a site of transplantation parenterally, such as by subcutaneous injection. In other embodiments, B7-H4 polypeptides or fragments, or fusions thereof are administered ex vivo directly to cells, tissue or organs to be transplanted. In one embodiment, the transplant material is contacted with B7-H4 polypeptides or fragments, or fusions thereof prior to transplantation, after transplantion, or both. In other embodiments, B7-H4 polypeptides or fragments, or fusions thereof are administered to immune tissues or organs, such as lymph nodes or the spleen. Vectors encoding B7-H4 polypeptides are also provided. These vectors can be used to deliver B7-H4 locally in vivo or ex vivo, for example to islet cells. An exemplary vector is an adenoviral vector.

B7-H4 polypeptides or fragments, or fusions thereof can be administered in combination with one or more additional therapeutic agents, including, but not limited to, antibodies against other lymphocyte surface markers (e.g., CD40) or against cytokines, other fusion proteins, e.g., CTLA-4-Ig (Orencia®), TNFR-Ig (Enbrel®), or other immunosuppressive drugs, anti-proliferatives, cytotoxic agents, or other compounds that may assist in immunosuppression. In one embodiment, the additional therapeutic agent is a CTLA-4 fusion protein, such as CTLA-4 Ig (abatacept). In a preferred embodiment, the additional therapeutic agent is a CTLA-4-Ig fusion protein known as belatacept that contains two amino acid substitutions (L104E and A29Y) that markedly increase its avidity to CD86 in vivo.

Still another embodiment provides methods and compositions for treating one or more symptoms of graft versus host disease (GVHD) in a subject in need thereof by administering an effective amount of B7-H4 polypeptides or fragments, or fusions thereof to alleviate one or more symptoms associated with GVHD.

Another embodiment provides a method for treating diabetes by transplanting insulin producing cells into a subject in need thereof and administering an effective amount of B7-H4 polypeptides, fusions thereof, or vectors encoding the B7-H4 polypeptides or B7-H4 fusion proteins to inhibit or reduce transplant rejection of the insulin-producing cells.

A method for inhibiting or reducing chronic transplant rejection is also provided. The method includes administering to a subject in need thereof an effective amount of a B7-H4 polypeptides or fragments, or fusions thereof thereof to inhibit or reduce chronic rejection of a transplant relative to a control.

BRIEF DESCRIPTION OF THE DRAWINGS

FIG. 3 is a schematic diagram of an experimental design for a graft versus host disease assay. Four groups of mice were subjected to bone marrow transplants. Group I had syngeneic bone marrow transplants. Group II had allogenic bone marrow transplants and were treated with control IgG (0.5 mg) on Days 0, 1, 7 and 14. Group III had allogenic bone marrow transplants and were treated with B7-H4-Ig (0.5 mg) on Days 0, 1, 7, and 14. Group IV had allogenic bone marrow transplants and were treated with phosphate buffered saline (PBS) on Days 0, 1, 7, and 14.

FIG. 4A is a bar graph showing diarrhea clinical score of the Group II and III mice treated in FIG. 3. Control IgG (solid shading). B7-H4-Ig (open box). FIG. 4B is a bar graph showing percent weight loss of the mice treated in FIG. 3 Control IgG (solid shading).

DETAILED DESCRIPTION OF THE INVENTION

I. Definitions

Figure 1:
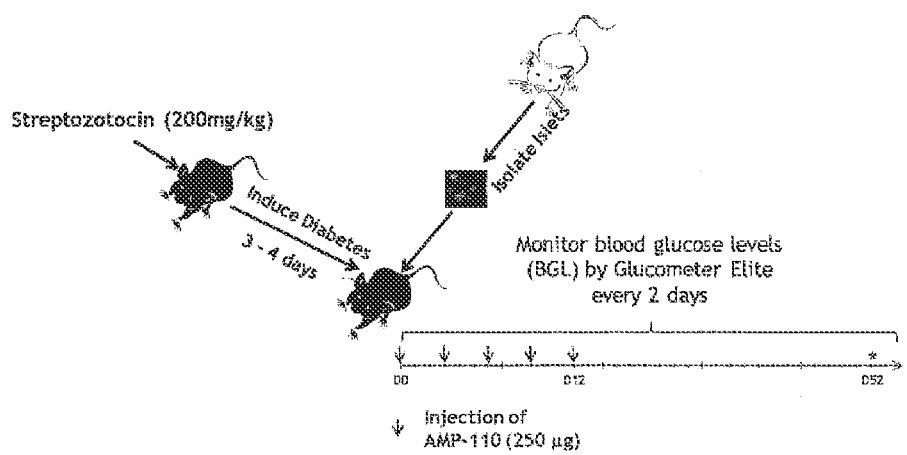
FIG. 1 is a schematic illustration of diabetes induction and treatment with allogeneic islet transplantation and administration of B7-H4-Ig (0.25 mg) on Days 0, 2, 4, 6, and 8.

The term "syngeneic" refers to genetically identical or closely related organisms, cells, tissues, organs, and the like.

The term "allogeneic" refers to organisms, cells, tissues, organs, and the like from, or derived from, individuals of the same species, but wherein the organisms, cells, tissues, organs, and the like are genetically different one from another.

The term "xenograft" refers to a transplant in which the donor and recipient are of different species.

The term "transplant rejection" refers to a partial or complete destruction of a transplanted cell, tissue, organ, or the like on or in the transplant recipient.

The term "host" or "subject" refers to an organism (preferably the organism is a mammal), a tissue, organ, or the like that is the recipient of a transplanted cell, tissue, organ, or the like. The terms "host", "recipient", or "subject" when referring to transplant hosts, subjects or recipients are used interchangeably herein.

An "amount therapeutically effective to inhibit transplant rejection" refers to an amount of B7-H4-Ig that when administered to a transplant recipient, inhibits, either partially or completely, rejection of the transplant relative to an untreated control.

As used herein, "inflammatory molecules" refers to cytokines, metelloproteases and other molecules including, but not limited to IL-1β, TNF-α, TGF-beta, IFN-γ, IL-17, IL-6, IL-23, IL-22, IL-21, and MMPs.

II. B7-H4 and Fusion Proteins Thereof

A. B7-H4

B7-H4 is a member of the B7 family of proteins and is involved in T cell signaling pathways. Naïve T cells require 2 signals for their full activation (Vincennti, F., et al., J Allergy Clin Immunol, 121(2):299-306). The first signal is antigen-specific and is provided by the T cell receptor interacting with the MHC and antigenic peptide complex on the antigen presenting cell (APC). The second signal, or costimulatory signal, is provided by the interactions between molecules such as CD80 and CD86 on the APC with cognate receptors such as CD28 on naïve T cells. The most extensively characterized T cell costimulatory pathway is B7-CD28, in which B7-1 (CD80) and B7-2 (CD86) each can engage the stimulatory CD28 receptor and the inhibitory CTLA-4 (CD152) receptor. In conjunction with signaling through the T cell receptor, CD28 ligation increases antigen-specific proliferation of T cells, enhances production of cytokines, stimulates differentiation and effector function, and promotes survival of T cells (Lenshow, et al., *Annu. Rev. Immunol.*, 14:233-258 (1996); Chambers and Allison, *Curr. Opin. Immunol.*, 9:396-404 (1997); and Rathmell and Thompson, *Annu. Rev. Immunol.*, 17:781-828 (1999)). In contrast, signaling through CTLA-4 is thought to deliver a negative signal that inhibits T cell proliferation, IL-2 production, and cell cycle progression (Krummel and Allison, *J. Exp. Med.*, 183:2533-2540 (1996); and Walunas, et al., *J. Exp. Med.*, 183:2541-2550 (1996)). Other members of the B7 family include B7-H1 (Dong, et al., *Nature Med.*, 5:1365-1369 (1999); and Freeman, et al., *J. Exp. Med.*, 192:1-9 (2000)), B7-DC (Tseng, et al., *J. Exp. Med.*, 193:839-846 (2001); and Latchman, et al., *Nature Immunol.*, 2:261-268 (2001)), B7-H2 (Wang, et al., *Blood*, 96:2808-2813 (2000); Swallow, et al., *Immunity*, 11:423-432 (1999); and Yoshinaga, et al., *Nature*, 402:827-832 (1999)), and B7-H3 (Chapoval, et al., *Nature Immunol.*, 2:269-274 (2001)) and B7-H4 (Choi, et al., *J. Immunol.*, 171:4650-4654 (2003); Sica, et al., *Immunity*, 18:849-861 (2003); Prasad, et al., *Immunity*, 18:863-873 (2003); and Zang, et al., *Proc. Natl. Acad. Sci. U.S.A.*, 100:10388-10392 (2003)). B7-H1 and B7-DC are ligands for PD-1, B7-H2 is a ligand for ICOS, and B7-H3 and B7-H4 remain orphan ligands at this time (Dong, et al., *Immunol. Res.*, 28:39-48 (2003)).

B7-H4 is a negative regulator of T cell responses. Human and mouse B7-H4 share 87% amino acid identity suggesting an important evolutionarily conserved function. Human and mouse B7-H4 mRNAs are expressed broadly in both lymphoid (spleen and thymus) and nonlymphoid organs (including lung, liver, testis, ovary, placenta, skeletal muscle, pancreas, and small intestine), however B7-H4 protein is not detected in normal human tissues by immunohistochemistry.

Limited studies of B7-H4 protein expression indicate that B7-H4 is not expressed on freshly isolated human T cells, B cells, DC, and monocytes, but it can be induced on these cell types after in vitro stimulation Immunohistochemical staining shows that B7-H4 is highly expressed in tumors of the lung, ovaries, and head and neck, and reverse-transcriptase polymerase chain reaction (RT-PCR) analyses indicate that mouse B7-H4 also is highly expressed in a number of tumor cell lines, including prostate, lung, and colon carcinomas.

Functional studies using B7-H4 transfectants and immobilized B7-H4-Ig fusion proteins demonstrate that B7-H4 delivers a signal that inhibits TCR-mediated CD4+ and CD8+ T proliferation, cell-cycle progression and IL-2 production. B7-1 costimulation cannot overcome B7-H4-Ig-induced inhibition. In agreement with the in vitro activity, B7-H4 knock-out mice develop autoimmunity.

B. Exemplary B7-H4 Polypeptides and Fusion Proteins

Fusion proteins containing B7-H4 polypeptides coupled to other polypeptides to form fusion proteins are provided. B7-H4 fusion polypeptides have a first fusion partner comprising all or a part of a B7-H4 protein fused (i) directly to a second polypeptide or, (ii) optionally, fused to a linker peptide sequence that is fused to the second polypeptide. The fusion proteins optionally contain a domain that functions to dimerize or multimerize two or more fusion proteins. The peptide/polypeptide linker domain can either be a separate domain, or alternatively can be contained within one of one of the other domains (B7-H4 polypeptide or second polypeptide) of the fusion protein. Similarly, the domain that functions to dimerize or multimerize the fusion proteins can either be a separate domain, or alternatively can be contained within one of one of the other domains (B7-H4 polypeptide, second polypeptide or peptide/polypeptide linker domain) of the fusion protein. In one embodiment, the dimerization/multimerization domain and the peptide/polypeptide linker domain are the same.

Fusion proteins disclosed herein are of formula I:

$$N\text{-}R_1\text{-}R_2\text{-}R_3\text{-}C$$

wherein "N" represents the N-terminus of the fusion protein, "C" represents the C-terminus of the fusion protein, "$R_1$" is a B7-H4 polypeptide, "$R_2$" is an optional peptide/polypeptide linker domain, and "$R_3$" is a second polypeptide. Alternatively, $R_3$ may be the B7-H4 polypeptide and $R_1$ may be the second polypeptide.

The fusion proteins can be dimerized or multimerized. Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

A. B7-H4 Polypeptides

In a preferred embodiment the B7-H4 polypeptide is from a mammalian species. In the most preferred embodiment, the B7-H4 polypeptide is of murine, non-human primate (*Pan troglodytes, Macaca mulatta* or *Macaca fascicularis*), or human origin. Useful murine B7-H4 polypeptides have at least about 80, 85, 90, 95 or 100% sequence identity to the B7-H4 polypeptide encoded by the nucleic acid having GenBank Accession Number NM_178594 or AY280973. Useful murine B7-H4 polypeptides have at least about 80, 85, 90, 95 or 100% sequence identity to the B7-H4 polypeptide according to GenBank Accession Number AAH32925.1 or NP_848709.2. Useful human B7-H4 polypeptides have at least about 80, 85, 90, 95 or 100% sequence identity to the B7-H4 polypeptide encoded by the nucleic acid having GenBank Accession Number AK026071. Useful human B7-H4 polypeptides have at least about 80, 85, 90, 95 or 100% sequence identity to the B7-H4 polypeptide according to GenBank Accession Number NP_078902.2 or BAB15349.1.

Murine B7-H4 polypeptides can be encoded by a nucleotide sequence having at least 80%, 85%, 90%, 95%, 99%, or 100% sequence identity to:

```
                                                          (SEQ ID NO: 1)
atggcttcct tggggcagat catcttttgg agtattatta acatcatcat catcctggct      60
ggggccatcg cactcatcat tggctttggc atttcaggca agcacttcat cacggtcacg     120
accttcacct cagctggaaa cattggagag gacgggaccc tgagctgcac ttttgaacct     180
gacatcaaac tcaacggcat cgtcatccag tggctgaaag aaggcatcaa aggtttggtc     240
cacgagttca aagaaggcaa agacgacctc tcacagcagc atgagatgtt cagaggccgc     300
acagcagtgt ttgctgatca ggtggtagtt ggcaatgctt ccctgagact gaaaaacgtg     360
cagctcacgg atgctggcac ctacacatgt tacatccgca cctcaaaagg caaagggaat     420
gcaaaccttg agtataagac cggagccttc agtatgccag agataaatgt ggactataat     480
gccagttcag agagtttacg ctgcgaggct cctcggtggt tcccccagcc cacagtggcc     540
tgggcatctc aagtcgacca aggagccaat ttctcagaag tctccaacac cagctttgag     600
ttgaactctg agaatgtgac catgaaggtc gtatctgtgc tctacaatgt cacaatcaac     660
aacacatact cctgtatgat tgaaaacgac attgccaaag ccaccgggga catcaaagtg     720
acagattcag aggtcaaaag gcgaagtcag ctgcagttgc tgaactctgg gccttccccg     780
tgtgtttttt cttctgcctt tgtggctggc tgggcactcc tatctctctc ctgttgcctg     840
atgctaagat ga.                                                        852
```

Murine B7-H4 polypeptides can have at least 80%, 85%, 90%,95%,

-continued

99%, or 100% sequence identity to:

(SEQ ID NO: 2)
```
MASLGQIIEW SIINIIIILA GAIALIIGFG ISGKHFITVT TFTSAGNIGE DGTLSCTFEP    60
DIKLNGIVIQ WLKEGIKGLV HEFKEGKDDL SQQHEMFRGR TAVFADQVVV GNASLRLKNV   120
QLTDAGTYTC YIRSSKGKGN ANLEYKTGAF SMPEINVDYN ASSESLRCEA PRWFPQPTVA   180
WASQVDQGAN FSEVSNTSFE LNSENVTMKV VSVLYNVTIN NTYSCMIEND IAKATGDIKV   240
TDSEVKRRSQ LQLLNSGPSP CVSSSAFVAG WALLSLSCCL MLR,                    283
```

(SEQ ID NO: 3)
```
MEWSWVFLFF LSVTTGVHSG FGISGKHFIT VTTFTSAGNI GEDGTLSCTF EPDIKLNGIV    60
IQWLKEGIKG LVHEFKEGKD DLSQQHEMFR GRTAVFADQV VVGNASLRLK NVQLTDAGTY   120
TCYIRSSKGK GNANLEYKTG AFSMPEINVD YNASSESLRC EAPRWFPQPT VAWASQVDQG   180
ANFSEVSNTS FELNSENVIM KVVSVLYNVT INNTYSCMIE NDIAKATGDI KVIDSEVXRR   240
SQLQLLNSGP SPCVSSSAFV AGWALLSLSC CLMLR,                             275
```

(SEQ ID NO: 4)
```
GFGISGKHFI TVTTFTSAGN IGEDGTLSCT FEPDIKLNGI VIQWLKEGIK GLVHEFKEGK    60
DDLSQQHEMF RGRTAVFADQ VVVGNASLRL KNVQLTDAGT YTCYIRSSKG KGNANLEYKT   120
GAFSMPEINV DYNASSESLR CEAPRWFPQP TVAWASQVDQ GANFSEVSNT SFELNSENVT   180
MKVVSVLYNV TINNTYSCMI ENDIAKATGD IKVTDSEVKR RSQLQLLNSG PSPCVSSSAF   240
VAGWALLSLS CCLMLR,                                                  256
```

(SEQ ID NO: 5)
```
MASLGQIIFW SIINIIIILA GAIALIIGFG ISGKHFITVT TFTSAGNIGE DGTLSCTFEP    60
DIKLNGIVIQ WLKEGIKGLV HEFKEGKDDL SQQHEMFRGR TAVFADQVVV GNASLRLKNV   120
QLTDAGTYTC YIRSSKGKGN ANLEYKTGAF SMPEINVDYN ASSESLRCEA PRWFPQPIVA   180
WASQVDQGAN FSEVSNTSFE LNSENVTMKV VSVLYNVTIN NTYSCMIEND IAKATGDIKV   240
TDSEVKRRSQ LQLLNSGPSP CVFSSAFVAG WALLSLSCCL MLR,                    283
```

(SEQ ID NO: 6)
```
MEWSWVFLFF LSVTTGVHSG FGISGKHFIT VTTFTSAGNI GEDGTLSCTF EPDIKLNGIV    60
IQWLKEGIKG LVHEFKEGKD DLSQQHEMFR GRTAVFADQV VVGNASLRLK NVQLTDAGTY   120
TCYIRTSKGK GNANLEYKTG AFSMPEINVD YNASSESLRC EAPRWFPQPT VAWASQVDQG   180
ANFSEVSNTS FELNSENVTM KVVSVLYNVT INNTYSCMIE NDIAKATGDI KVTDSEVKRR   240
SQLQLLNSGP SPCVSSSAFV AGWALLSLSC CLMLR,                             275
```
or (SEQ ID NO: 7)
```
GEGISGKHFI TVTTFTSAGN IGEDGTLSCT FEPDIKLNGI VIQWLKEGIK GLVHEFKEGK    60
DDLSQQHEMF RGRTAVFADQ VVVGNASLRL KNVQLTDAGT YTCYIRSSKG KGNANLEYKT   120
GAFSMPEINV DYNASSESLR CEAPRWFPQP TVAWASQVDQ GANFSEVSNT SFELNSENVT   180
MKVVSVLYNV TINNTYSCMI ENDIAKATGD IKVIDSEVKR RSQLQLLNSG PSPCVFSSAF   240
VAGWALLSLS CCLMLR.                                                  256
```

Human B7-H4 polypeptides can be encoded by a nucleotide sequence
having at least 80%, 85%, 90%, 95%, 99%, or 100% sequence identity to:

(SEQ ID NO: 8)
```
atggcttccc tggggcagat cctcttctgg agcataatta gcatcatcat tattctggot    60
ggagcaattg cactcatcat tggctttggt atttcaggga cactccat  cacagtcact   120
actgtcgcct cagctgggaa cattggggag gatggaatcc tgagctgcac ttttgaacct   180
gacatcaaac tttctgatat cgtgataaca tggctgaagg aagtgttttt aggcttggtc   240
catgagttca aagaaggcaa agatgagctg toggagcagg atgaaatgtt cagaggccgg   300
```

```
acagcagtgt tgctgatca agtgatagtt ggcaatgcct ctttgcggct gaaaaacgtg    360
caactcacag atgctggcac ctacaaatgt tatatcatca cttctaaagg caagggaat    420 gctaaccttg agtataaaac tggagccttc agcatgccgg aagtgaatgt ggactataat    480
gccagctcag agaccttgcg tgtgaggct ccccgatggt tcccccagcc cacagtggtc    540
tgggcatccc aagttgacca gggagccaac ttctcggaag tctccaatac cagctttgag    600
ctgaactctg agaatgtgac catgaaggtt gtgtctgtgc tctacaatgt tacgatcaac    660
aacacatact cctgtatgat tgaaaatgac attgccaaag caacagggga tatcaaagtg    720
acagaatcgg agatcaaaag gcggagtcac ctacagctgc taaactcaaa ggcttctctg    780
tgtgtctctt ctttctttgc catcagctgg gcacttctgc ctctcagccc ttacctgatg    840 ctaaaataa.                                                          849
```

Human B7-H4 polypeptides can have at least 80%, 85%, 90%, 95%, 99%, or 100% sequence identity to:

```
                                                      (SEQ ID NO: 9)
MASLGQILFW SIISIIIILA GAIALIIGFG ISGRHSITVT TVASAGNIGE DGILSCTFEP     60

DIKLSDIVIQ WLKEGVLGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIKRRSH LQLLNSKASL CVSSFFAISW ALLPLSPYLM LK,                      282

(SEQ ID NO: 10)
MEWSWVFLFF LSVTTGVHSG FGISGRHSIT VTTVASAGNI GEDGILSCTF EPDIKLSDIV     60

IQWLKEGVLG LVHEFKEGKD ELSEQDEMFR GRTAVFADQV IVGNASLRIK NVQLTDAGTY    120

KCYIITSKGK GNANLEYKTG AFSMPEVNVD YNASSETLRC EAPRWFPQPT VVWASQVDQG    180

ANFSEVSNTS FELNSENVTM KVVSVLYNVT INNTYSCMIE NDIAKATGDI KVTESEIKRR    240

SHLQLLNSKA SLCVSSFFAI SWALLPLSPY LMLK,                               274

(SEQ ID NO: 11)
GFGISGRHSI TVTTVASAGN IGEDGILSCT FEPDIKLSDI VIQWLKEGVL GLVHEFKEGK     60

DELSEQDEMF RGRTAVFADQ VIVGNASLRL KNVQLTDAGT YKCYIITSKG KGNANLEYKT    120

GAFSMPEVNV DYNASSETLR CEAPRWFPQP TVVWASQVDQ GANFSEVSNT SFELNSENVT    180

MKVVSVLYNV TINNTYSCMI ENDIAKATGD IKVTESEIKR RSHLQLLNSK ASLCVSSFFA    240

ISWALLPLSP YLMLK,                                                    255

(SEQ ID NO: 12)
MASLGQILFW SIISIIFILA GAIALIIGFG ISGRHSITVT TVASAGNIGE DGIQSCTFEP     60

DIKLSDIVIQ WLKEGVLGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIKRRSH LQLLNSKASL CVSSFFAISW ALLPLAPYLM LK,                      282

(SEQ ID NO: 13)
MEWSWVFLFF LSVTTGVHSG EGISGRHSIT VTTVASAGNI GEDGIQSCTF EFDIKLSDIV     60

IQWLKEGVLG LVHEFKEGKD ELSEQDEMFR GRTAVFADQV IVGNASLRLK NVQLTDAGTY    120

KCYIITSKGK GNANLEYKTG AFSMPEVNVD YNASSETLRC EAPRWFPQPT VVWASQVDQG    180

ANFSEVSNTS FELNSENVTM KVVSVLYNVT INNTYSCMIE NDIAKATGDI KVTESEIKRR    240

SHLQLLNSKA SLCVSSFFAI SWALLPLSPY LMLK,                               274
or
                                                      (SEQ ID NO: 14)
GFGISGRHSI TVTTVASAGN IGEDGIQSCT FEPDIKLSDI VIQWLKEGVL GLVHEFKEGK     60
```

```
DELSEQDEMF RGRTAVFADQ VIVGNASLRL KNVQLTDAGT YKCYIITSKG KGNANLEYKT    120

GAFSMPEVNV DYNASSETLR CEAPRWFPQP TVVWASQVDQ GANFSEVSNT SFELNSENVT    180

MKVVSVLYNV TINNTYSCMI ENDIAKATGD IKVTESEIKR RSHLQLLNSK ASLCVSSFFA    240

ISWALLPLSP YLMLK.                                                   255

Non-human primate B7-H4 polypeptides can have at least 80%, 85%,
90%, 95%, 99%, or 100% sequence identity to:
                                                          (SEQ ID NO: 15)
MKPLTSRIIS IIIILAGAIA LIIGFGISGR HSITVTTVAS AGNIGEDGIL SCTFEPDIKL     60

SDIVIQWLKE GVLGLVHEFK EGKDELSEQD EMERGRTAVF ADQVIVGNAS LRLKNVQLTD    120

AGTYKCYIIT SKGKGNANLE YKTGAFSMPE VNVDYNASSE TLRCEAPRWF POPTVVWASQ   180

IDQGANFSEV SNTSFELNSE NVTMKVVSVL YNATINNTYS CMIENDIAKA TGDIKVTESE    240

IKRRSHLQLL NSKASLCVSS FFAISWALLP LSPYLMLK,                          278
or
                                                          (SEQ ID NO: 16)
GFGISGRHSI TVTTVASAGN IGEDGILSCT FEPDIKLSDI VIQWLKEGVL GLVHEFKEGK     60

DELSEQDEMF RGRTAVFADQ VIVGNASLRL KNVQLTDAGT YKCYIITSKG KGNANLEYKT    120

GAFSMPEVNV DYNASSETLR CEAPRWFPQP TVVWASQIDQ GANFSEVSNT SFELNSENVT    180

MKVVSVLYNA TINNTYSCMI ENDIAKATGD IKVTESEIKR RSHLQLLNSK ASLCVSSFFA    240

ISWALLPLSP YLMLK,                                                   255
or
                                                          (SEQ ID NO: 17)
MASLGOILFW SIISIIFILA GAIALIIGFG ISGRHSITVT TVASAGNIGE DGILSCTFEP     60

DIKLSDIVIQ WLKEGVIGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIKRRSH LQLLNSKASL CVSSFLAISW ALLPLAPYLM LK,                      282
or
                                                          (SEQ ID NO: 18)
GFGISGRHSI TVTTVASAGN IGEDGILSCT FEPDIKLSDI VIQWLKEGVI GLVHEFKEGK     60

DELSEQDEMF RGRTAVFADQ VIVGNASLRL KNVQLTDAGT YKCYIITSKG KGNANLEYKT    120

GAFSMPEVNV DYNASSETLR CEAPRWFPQP TVVWASQVDQ GANFSEVSNT SFELNSENVT    180

MKVVSVLYNV TINNTYSCMI ENDIAKATGD IKVTESEIKR RSHLQUNSK ASLCVSSFLA     240

ISWALLPLAP YLMLK,                                                   255
or
                                                          (SEQ ID NO: 19)
MASLGQILFW SIISIIFILA GAIALIIGFG ISGRHSITVT TVASAGNIGE DGILSCTFEP     60

DIKLSDIVIQ WLKEGVIGLV HEFKEGKDEL SEQDEMERGR TAVFADQVIV GNASLRLKNV    120

QLTDAGTYKC YIITSKGKGN ANLEYKTGAF SMPEVNVDYN ASSETLRCER PRWFPQPTVV    180

WASQVDQGAN FSEVSNTSFE LNSENVTMKV VSVLYNVTIN NTYSCMIEND IAKATGDIKV    240

TESEIKRRSH LQLLNSKASL CVSSFLAISW ALPPLAPYLM LK,                      282
or
                                                          (SEQ ID NO: 20)
GFGISGRHSI TVTTVASAGN IGEDGILSCT FEPDIKLSDI VIQWLKEGVI GLVHEEKEGK     60

DELSEQDEMF RGRTAVFADQ VIVGNASLRL KNVQLTDAGT YKCYIITSKG KGNANLEYKT    120

GAFSMPEVNV DYNASSETLR CEAPRWEPQP TVVWASQVDQ GANFSEVSNT SFELNSENVT    180

MKVVSVLYNV TINNTYSCMI ENDIAKATGD IKVTESEIKR RSHLQLLNSK ASLCVSSFLA    240

ISWALPPLAP YLMLK,                                                   255
``` where SEQ ID NOs:15 and 16 are chimpanzee (*Pan troglodytes*) polypeptide sequences, SEQ ID NOs:17 and 18 are rhesus monkey (*Macaca mulatta*) polypeptide sequences, and SEQ ID NOs:19 and 20 are cynomolgus monkey (*Macaca fascicularis*) polypeptide sequences.

Nucleic acids encoding B7-H4 polypeptides may be optimized for expression in the expression host of choice. Codons may be substituted with alternative codons encoding the same amino acid to account for differences in codon usage between the mammal from which the B7-H4 nucleic acid sequence is derived and the expression host. In this manner, the nucleic acids may be synthesized using expression host-preferred codons.

1. Fragments of B7-H4 Polypeptides

The B7-H4 proteins contain two immunoglobulin domains within the extracellular, the IgV domain (or V domain) and the IgC domain (or C domain), which are related to the variable and constant domains of antibodies. The domains can be identified by anyone skilled in the art by searching against family and domain databases. The IgV domain is believed to be responsible for receptor binding, based on functional data from the isolated IgV domain as well as by analogy to the other B7 family members. Each Ig domain of extracellular domain includes one disulfide bond formed between intradomain cystein residues, as is typical for this fold and may be important for structure-function. In SEQ ID NOS: 2, 5, 9 and 12 these cysteines are located at residues 56 and 130 for the IgV domain, and 168 and 225 for the IgC domain. In addition, there is one predicted N-linked glycosylation site in the IgV domain and six glycosylation sites in the IgC domain, which are conserved between mouse and human B7-H4 sequences.

In one embodiment, the first fusion partner is a fragment of B7-H4. As used herein, a fragment of B7-H4 refers to any subset of the polypeptide that is at least one amino acid shorter than full length protein. Useful fragments are those that retain the ability to bind to their natural receptor or receptors. A B7-H4 polypeptide that is a fragment of full-length B7-H4 typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural receptor(s) as compared to full-length B7-H4.

Fragments of B7-H4 polypeptides include soluble fragments. Soluble B7-H4 polypeptide fragments are fragments of B7-H4 polypeptides that may be shed, secreted or otherwise extracted from the producing cells. Soluble fragments of B7-H4 polypeptides include some or all of the extracellular domain of the receptor polypeptide, and lack some or all of the intracellular and/or transmembrane domains. In one embodiment, B7-H4 polypeptide fragments include the entire extracellular domain of the B7-H4 polypeptide. In other embodiments, the soluble fragments of B7-H4 polypeptides include fragments of the extracellular domain that retain B7-H4 biological activity. The extracellular domain can include 1, 2, 3, 4, or 5 contiguous amino acids from the transmembrane domain, and/or 1, 2, 3, 4, or 5 contiguous amino acids from the signal sequence. Alternatively, the extracellular domain can have 1, 2, 3, 4, 5 or more amino acids removed from the C-terminus, N-terminus, or both. In some embodiments the extracellular domain is only the IgV domain, or the region between the conserved cysteines of the IgV domain located at residues 56 and 130 of the full-length protein.

Generally, the B7-H4 polypeptides or fragments thereof are expressed from nucleic acids that include sequences that encode a signal sequence. The signal sequence is generally cleaved from the immature polypeptide to produce the mature polypeptide lacking the signal sequence. SEQ ID NOs: 4, 7, 11, 14, 16, 18 and 20 each lack a signal peptide. The signal sequence of B7-H4 can be replaced by the signal sequence of another polypeptide using standard molecule biology techniques to affect the expression levels, secretion, solubility, or other property of the polypeptide. The signal sequence that is used to replace the B7-H4 signal sequence can be any known in the art. SEQ ID NOs: 2, 3, 5, 6, 9, 10, 12, 13, 15, 17 and 19 each contain a signal peptide.

In a preferred embodiment, the fusion protein includes the extracellular domain of B7-H4, or a fragment thereof fused to an Ig Fc region. Recombinant B7-H4-Ig fusion proteins can be prepared by fusing the coding region of the extracellular domain of B7-H4 or a fragment thereof to the Fc region of human IgG1 or mouse IgG2a, as described previously (Chapoval, et al., *Methods Mol. Med.*, 45:247-255 (2000)).

a. Murine B7-DC Extracellular Domain Fusion Partners

In one embodiment, the first fusion partner of the fusion protein includes the extracellular domain of murine B7-H4 or a fragment thereof. The first fusion partner can be encoded by a nucleotide sequence having at least 80%, 85%, 90%, 95%, 99%, or 100% sequence identity to:

```
                                                           (SEQ ID NO: 21)
         atggcttcct tggggcagat catctttgg agtattatta acatcatcat catcctggct    60
ggggccatcg cactcatcat tggctttggc atttcaggca agcacttcat cacggtcacg   120
accttcacct cagctggaaa cattggagag gacgggaccc tgagctgcac ttttgaacct   180
gacatcaaac tcaacggcat cgtcatccag tggctgaaag aaggcatcaa aggtttggtc   240
cacgagttca aagaaggcaa agacgacctc tcacagcagc atgagatgtt cagaggccgc   300
acagcagtgt ttgctgatca ggtggtagtt ggcaatgctt ccctgagact gaaaaacgtg   360
cagctcacgg atgctggcac ctacacatgt tacatccgca cctcaaaagg caaagggaat   420
gcaaaccttg agtataagac cggagccttc agtatgccag agataaatgt ggactataat   480
gccagttcag agagtttacg ctgcgaggct cctcggtggt tcccccagcc cacagtggcc   540
tgggcatctc aagtcgacca aggagccaat ttctcagaag tctccaacac cagctttgag   600
ttgaactctg agaatgtgac catcaagggc gtatctgtgc tctacaatgt cacaatcaac   660
aacacatact cctgtatgat tgaaaacgac attgccaaag ccaccgggga catcaaagtg   720
```

```
acagattcag aggtcaaaag gcgaagtcag ctgcagttgc tgaactctgg g,        771
```

```
                                                     (SEQ ID NO: 22)
atggagtggt catgggtttt tctgttcttt cttagcgtga ctacaggcgt ccattcagga  60
ttcggcataa gcggcaagca cttcatcaca gttacaacgt ttacaagtgc ggggaacatt 120
ggggaagatg gaacattgtc atgtacattt gagccagata tcaaactcaa tggaatagta 180
attcagtggc ttaaggaggg catcaagggc ctggtccacg aatttaagga ggggaaagac 240
gatctgtctc agcagcacga gatgttcagg ggcagaaccg ccgtcttcgc agaccaggtt 300
gtggtaggca acgccagttt gcggctgaaa aacgtgcagc tgactgacgc cggcacctac 360
acatgctata tccggtcctc taagggcaag gggaacgcta atctcgagta caaaacaggc 420
gccttttcta tgccagagat caacgtggac tataacgcaa gctctgaaag tctgagatgc 480
gaggcgccaa ggtggttccc tcagcccacc gtcgcgtggg cttcccaggt ggatcaaggc 540
gccaactttt ctgaggtttc taacaccagc ttcgaactga acagcgaaaa tgtgacaatg 600
aaggtagtca gcgttctgta taacgtgacc atcaacaata cttactcctg tatgatagaa 660
aatgatatag ccaaggctac aggagatatt aaagtgacgg attcagaagt gaaaaggagg 720
agtcaactgc aactcttgaa tagcggc                                   747
``` or

```
                                                     (SEQ ID NO: 23)
atggagtggt catgggtttt tctgttcttt cttagcgtga ctacaggcgt ccattcagga  60
ttcggcataa gcggcaagca cttcatcaca gttacaacgt ttacaagtgc ggggaacatt 120
ggggaagatg gaacattgtc atgtacattt gagccagata tcaaactcaa tggaatagta 180
attcagtggc ttaaggaggg catcaagggc ctggtccacg aatttaagga ggggaaagac 240
gatctgtctc agcagcacga gatgttcagg ggcagaaccg ccgtcttcgc agaccaggtt 300
gtggtaggca acgccagttt gcggctgaaa aacgtgcagc tgactgacgc cggcacctac 360
acatgctata tccggacctc taagggcaag gggaacgcta atctcgagta caaaacaggc 420
gccttttcta tgccagagat caacgtggac tataacgcaa gctctgaaag tctgagatgc 480
gaggcgccaa ggtggttccc tcagcccacc gtcgcgtggg cttcccaggt ggatcaaggc 540
gccaactttt ctgaggtttc taacaccagc ttcgaactga acagcgaaaa tgtgacaatg 600
aaggtagtca gcgttctgta taacgtgacc atcaacaata cttactcctg tatgatagaa 660
aatgatatag ccaaggctac aggagatatt aaagtgacgg attcagaagt gaaaaggagg 720
agtcaactgc aactcttgaa tagcggc.                                  747
```

In another embodiment, the first fusion partner can have at least 80%, 85%, 90%, 95%, 99%, or 100% sequence identity to the murine amino acid sequence:

```
                                                     (SEQ ID NO: 24)
MEWSWVFLFF LSVTTGVHSG FGISGKHFIT VTTFTSAGNI GEDGTLSCTF EPDIKLNGIV  60
IQWLKEGIKG LVHEFKEGKD DLSQQHEMFR GRTAVFADQV VVGNASLRLK NVQLTDAGTY 120
TCYIRSSKGK GNANLEYKTG AFSMPEINVD YNASSESLRC EAPRWFPQPT VAWASQVDQG 180
ANFSEVSNTS FELNSENVTM KVVSVLYNVT INNTYSCMIE NDIAKATGDI RVTDSEVKRR 240
SQLQLLNSG,                                                      249
```

```
                                                     (SEQ ID NO: 25)
MEWSWVFLFF LSVTTGVHSG FGISGKHFIT VTTFTSAGNI GEDGTLSCTF EPDIKLNGIV  60
IQWLKEGIKG LVHEFKEGKD DLSQQHEMFR GRTAVFADQV VVGNASLRLK NVQLTDAGTY 120
```

```
                                                            (SEQ ID NO: 26)
TCYIRTSKGK GNANLEYKTG AFSMPEINVD YNASSESLRC EAPRWFPQPT VAWASQVDQG  180

ANFSEVSNTS FELNSENVTM KVVSVLYNVT INNTYSCMIE NDIAKATGDI KVTDSEVKRR  240

SQLQLLNSG,                                                        249

(SEQ ID NO: 26)
MASLGQIIFW SIINIIIILA GAIALIIGFG ISGKHFITVT TFTSAGNIGE DGTLSCTFEP   60

DIKLNGIVIQ WLKEGIKGLV HEFKEGKDDL SQQHEMFRGR TAVFADQVVV GNASLRLKNV  120

QLTDAGTYTC YIRSSKGKGN ANLEYKTGAF SMPEINVDYN ASSESLRCEA PRWFPQPTVA  180

WASQVDQGAN FSEVSNTSFE LNSENVTMKV VSVLYNVTIN NTYSCMIEND TAKATGDIKV  240

TDSEVKRRSQ LQLLNSG,                                               257
or
                                                            (SEQ ID NO:27)
MASLGQIIEW SIINIIIILA GAIALIIGFG ISGKHFITVT TFTSAGNIGE DGTLSCTFEP   60

DIKLNGIVIQ WLKEGIKGLV HEFKEGKDDL SQQHEMFRGR TAVFADQVVV GNASLRLKNV  120

QLTDAGTYTC YIRTSKGKGN ANLEYKTGAF SMPEINVDYN ASSESLRCEA PRWFPUTVA   180

WASQVDQGAN FSEVSNTSFE LNSENVTMKV VSVLYNVTIN NTYSCMIEND IAKATGDIKV  240

TDSEVKRRSQ LQLLNSG.                                               257
```

The signal sequence is removed in the mature protein. Additionally, signal peptides from other polypeptides or organisms can be used to enhance the secretion of the fusion protein from a host during manufacture. SEQ ID NO:28 provides the murine amino acid sequence of SEQ ID NO:24 and SEQ ID NO:26 without the signal sequence:

```
                                                            (SEQ ID NO: 28)
GFGISGKHFI TVTTFTSAGN IGEDGTLSCT FEPDIKLNGI VIQWLKEGIK GLVHEFKEGK   60

DDLSQQHEMF RGRTAVFADQ VVVGNASLRL KNVQLTDAGT YTCYIRSSKG KGNANLEYKT  120

GAFSMPEINV DYNASSESLR CEAPRWFPQP TVAWASQVDQ GANFSEVSNT SFELNSENVT  180

MKVVSVLYNV TINNTYSCMI ENDIAKATGD IKVTDSEVKR RSQLQLLNSG.            230
```

SEQ ID NO:29 provides the murine amino acid sequence of SEQ ID NO:25 and SEQ ID NO:27 without the signal sequence:

```
                                                            (SEQ ID NO: 29)
GFGISGKHFI TVTTFTSAGN IGEDGTLSCT FEEDIKLNGI VIQWLKEGIK GLVHEFKEGK   60

DDLSQQHEMF RGRTAVFADQ VVVGNASLRL KNVQLTDAGT YTCYIRTSKG KGNANLEYKT  120

GAFSMPEINV DYNASSESLR CEAPRWFPQP TVAWASQVDQ GANFSEVSNT SFELNSENVT  180

MKVVSVLYNV TINNTYSCMI ENDIAKATGD IKVTDSEVKR RSQLQLLNSG            230
```

In another embodiment, the first fusion partner of the fusion protein includes the IgV domain of murine B7-H4. In one embodiment, the IgV domain includes at least from the cysteine at position 56 of SEQ ID NO:2 or SEQ ID NO:5 to the cysteine at position 130 of SEQ ID NO:2 or SEQ ID NO:5. In another embodiment, the IgV domain contains a fragment of at least 25 or 50 amino acids of the polypeptide defined by this amino acid range.

The first fusion partner can be encoded by a nucleotide sequence having at least 80%, 85%, 90%, 95%, 99%, or 100% sequence identity to the following nucleotide sequence encoding an exemplary IgV domain:

```
                                                            (SEQ ID NO: 30)
           ggattcggca taagcggcaa gcacttcatc acagttacaa cgtttacaag tgcggggaac   60
attggggaag atggaacatt gtcatgtaca tttgagccag atatcaaact caatggaata  120
gtaattcagt ggcttaagga gggcatcaag ggcctggtcc acgaatttaa ggaggggaaa  180
```

```
gacgatctgt ctcagcagca cgagatgttc aggggcagaa ccgccgtctt cgcagaccag  240
gttgtggtag gcaacgccag tttgcggctg aaaaacgtgc agctgactga cgccggcacc  300
tacacatgct atatccggtc ctctaagggc aaggggaacg ctaatctcga gtacaaaaca  360 ggcgccttt ctatgccaga gatcaac                                       387
or
                                                     (SEQ ID NO: 31)
ggattcggca taagcggcaa gcacttcatc acagttacaa cgtttacaag tgcggggaac   60
attggggaag atggaacatt gtcatgtaca tttgagccag atatcaaact caatggaata  120
gtaattcagt ggcttaagga gggcatcaag ggcctggtcc acgaatttaa ggagggggaaa 180 gacgatctgt ctcagcagca cgagatgttc aggggcagaa ccgccgtctt cgcagaccag  240
gttgtggtag gcaacgccag tttgcggctg aaaaacgtgc agctgactga cgccggcacc  300
tacacatgct atatccggac ctctaagggc aaggggaacg ctaatctcga gtacaaaaca  360 ggcgccttt ctatgccaga gatcaac.                                      387
```

The first fusion partner can have at least 80%, 85%, 90%, 95%, 99%, or 100% sequence identity to the murine amino acid sequence:

```
                                                     (SEQ ID NO: 32)
GFGISGKHFI TVTTFTSAGN IGEDGTLSCT FEPDIKLNGI VIQWLKEGIK GLVHEFKEGK   60

DDLSQQHEMF RGRTAVFADQ VVVGNASLRL KNVQLTDAGT YTCYIRSSKG KGNANLEYKT  120

GAFSMPEIN,                                                         129
or
                                                     (SEQ ID NO: 33)
GFGISGKHFI TVTTFTSAGN IGEDGTLSCT FEPDIKLNGI VIQWLKEGIK GLVHEFKEGK   60

DDLSQQHEMF RGRTAVFADQ VVVGNASLRL KNVQLTDAGT YTCYIRTSKG KGNANLEYKT  120

GAFSMPEIN.                                                         129
``` b. Human Extracellular Domain Fusion Partners

In another embodiment, the first fusion partner of the fusion protein includes the extracellular domain of human B7-H4 or a fragment thereof. The first fusion partner can be encoded by a nucleotide sequence having at least 80%, 85%, 90%, 95%, 99%, or 100% sequence identity to:

```
                                                     (SEQ ID NO: 34)
atggcttccc tggggcagat cctcttctgg agcataatta gcatcatcat tattctggct   60
ggagcaattg cactcatcat tggctttggt atttcaggga gacactccat cacagtcact  120
actgtcgcct cagctgggaa cattggggag gatgaatcc tgagctgcac ttttgaacct  180
gacatcaaac tttctgatat cgtgatacaa tggctgaagg aaggtgtttt aggcttggtc  240
catgagttca agaaggcaa agatgagctg tcggagcagg atgaaatgtt cagaggccgg  300
acagcagtgt ttgctgatca agtgatagtt ggcaatgcct ctttgcggct gaaaaacgtg  360
caactcacag atgctggcac ctacaaatgt tatatcatca cttctaaagg caaggggaat  420
gctaaccttg agtataaaac tggagccttc agcatgccgg aagtgaatgt ggactataat  480
gccagctcag agaccttgcg gtgtgaggct ccccgatggt tcccccagcc cacagtggtc  540
tgggcatccc aagttgacca gggagccaac ttctcggaag tctccaatac cagctttgag  600
ctgaactctg agaatgtgac catgaaggtt gtgtctgtgc tctacaatgt tacgataaac  660
aacacatact cctgtatgat tgaaaatgac attgccaaag caacaggga tatcaaagtg  720 acagaatcgg agatcaaaag gcggagt,                                     747
                                                     (SEQ ID NO: 35)
atggcttccc tggggcagac cctcttctgg agcataatta gcatcatcat tattctggct   60
```

```
ggagcaattg cactcatcat tggctttggt atttcaggga cactccat cacagtcact    120 actgtcgcct cagctgggaa cattggggag atggaatcc tgagctgcac ttttgaacct    180
gacatcaaac ttcctgatat cgtgatacaa tggctgaagg aaggtgtttt aggcttggtc    240
catgagttca agaaggcaa agatgagctg tcggagcagg atgaaatgtt cagaggccgg    300
acagcagtgt tgctgatca agtgatagtt ggcaatgcct ctttgcggct gaaaaacgtg    360
caactcacag atgctggcec ctacaaatgt tatatcatca cttctaaagg caaggggaat    420
gctaaccttg agtataaaac tggagccttc agcatgccgg aagtgaatgt ggactataat    480
gccagctcag agaccttgcg gtgtgaggct ccccgatggt tcccccagcc cacagtggtc    540
tgggcatccc aagttgacca gggagccaac ttctcggaag tctccaatac cagctttgag    600
ctgaactctg agaatgtgac catgaaggtt gtgtctgtgc tctacaatgt tacgatcaac    660
aacacatact cctgtatgat tgaaaatgac attgccaaag caacagggga tatcaaagtg    720
acagaatcgg agatc,                                                    735

(SEQ ID NO: 36)
atggcttccc tggggcagat cctcttctgg agcataatta gcatcatcat tattctggct    60
ggagcaattg cactcatcat tggctttggt atttcaggga cactccat cacagtcact    120 actgtcgcct cagctgggaa cattggggag atggaatcc tgagctgcac ttttgaacct    180
gacatcaaac tttctgatat cgtgatacaa tggctgaagg aaggtgtttt aggcttggtc    240
catgagttca agaaggcaa agatgagctg tcggagcagg atgaaatgtt cagaggccgg    300
acagcagtgt tgctgatca agtgatagtt ggcaatgcct ctttgcggct gaaaaacgtg    360
caactcacag atgctggcac ctacaaatgt tatatcatca cttctaaagg caaggggaat    420
gctaaccttg agtataaaac tggagccttc agcatgccgg aagtgaatgt ggactataat    480
gccagctcag agaccttgcg gtgtgaggct ccccgatggt tcccccagcc cacagtggtc    540
tgggcatccc aagttgacca gggagecaac ttctcggaag tctccaatac cagctttgag    600
ctgaactctg agaatgtgac catgaaggtt gtgtctgtgc tctacaatgt tacgatcaac    660
aacacatact cctgtatgat tgaaaatgac attgccaaag caacagggga tatcaaagtg    720
acagaatcgg agatcaaaag gcggagtcac ctacagctgc taaactcaaa ggcttct,     777

(SEQ ID NO: 37)
atggaatgga gctgggtatt tctgtttttc ctgtcagtaa cgactggcgt ccattcaggc    60
ttcggcatca gtggacggca cagtatcaca gtgaccaccg tcgcctccgc tggcaatata    120
ggtgaggatg gcatccagtc ctgtacccttt gagcceggaca tcaaactgtc tgacatagtg    180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300 atcgtccggaa atgcaagtct cagattgaaa aatgtgcaac tgactgatgc tggcaegtat    360 aaatgctaca ttatcacaag taagggcaaa ggaaatgcta accttgagta taaaacaggc    420
gcattctcaa tgcccgaggt caatgtcgac tataatgcea gcagtgaaac attgegctgt    480 gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaaeggegg    720 tct,                                                                 723

(SEQ ID NO: 38)
atggaatgga gctgggtatt tctgtttttc ctgtcagtaa cgactggcgt ccattcaggc    60
```

-continued

```
ttcggcatca gtggacggca cagtatcaca gtgaccaccg tcgcctccgc tggcaatata    120
ggtgaggatg gcatccagtc ctgtacccttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccc tgtgttcgc cgatcaggta    300 atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaaac attgcgctgt   480 gaagctcccc gctggttccc ccagccaacc gtggtctggg cctctcaggt tgatcagggg   540 gctaacttttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat c,            711
```

(SEQ ID NO: 39)
```
atggaatgga gctgggtatt tctgtttttc ctgtcagtaa cgactggcgt ccattcaggc    60
ttcggcatca gtggacggca cagtatcaca gtgaccaccg tcgcctccgc tggcaatata    120
ggtgaggatg gcatccagtc ctgtacccttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccc tgtgttcgc cgatcaggta    300 atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaaac attgcgctgt   480 gaagctcccc gctggttccc ccagccaacc gtggtctggg cctctcaggt tgatcagggg   540 gctaacttttt ccgaggtgag caacaccagc ttcgaactca actctgagaa tgtgaccatg   600 oeagttgtgt ctgtcctgta taatgtaaca atcaacaaca cttattcatg catgattgaa   660
aacgacatcg ccaaggcaac aggtgatatt aaggtaactg aatccgagat caaacggcgg   720
tctcacctac agctgctaaa ctcaaaggct tct,                                753
```

(SEQ ID NO: 40)
```
atggaatgga gctgggtatt tctgtttttc ctgtcagtaa cgactggcgt ccattcaggc    60
ttcggcatca gtggacggca cagtatcaca gtgaccaccg tcgcctccgc tggcaatata    120
ggtgaggatg gcatcctgtc ctgtacccttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccg tgtgttcgc cgatcaggta    300 atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaaac attgcgctgt   480 gaagctcccc gctggttccc ccagccaacc gtggtctggg cctctcaggt tgatcagggg   540 gctaacttttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat caaacggcgg   720 tct,                                                                 723
```

(SEQ ID NO: 41)
```
atggaatgga gctgggtatt tctgtttttc ctgtcagtaa cgactggcgt ccattcaggc    60
ttcggcatca gtggacggca cagtatcaca gtgaccaccg tcgcctccgc tggcaatata    120
```

```
ggtgaggatg gcatcctgtc ctgtacctttt gagccggaca tcaaactgtc tgacatagtg    180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat c,            711
or
                                                (SEQ ID NO: 42)
atggaatgga gctgggtatt tctgttttc ctgtcagtaa cgactggcgt ccattcaggc      60
ttcggcatca gtggacggca cagtatcaca gtgaccaccg tcgcctccgc tggcaatata    120
ggtgaggatg gcatcctgtc ctgtacctttt gagccggaca tcaaactgtc tgacatagtg    180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaacggcgg    720
tctcacctac agctgctaaa ctcaaaggct tct.                                753
```

In another embodiment, the first fusion partner can have at least 80%, 85%, 90%, 95%, 99%, or 100% sequence identity to the human amino acid sequence:

```
                                                (SEQ ID NO: 43)
MEWSWVFLFF LSVTTGVHSG FGISGRHSIT VTTVASAGNI GEDGIQSCTF EPDIKLSDIV     60

IQWLKEGVLG LVHEFKEGKD ELSEQDEMFR GRTAVFADQV IVGNASLRLK NVQLTDAGTY    120

KCYIITSKGK GNANLEYKTG AFSMPEVNVD YNASSETLRC EAPRWFPQPT VVWASQVDQG    180

ANFSEVSNTS FELNSENVTM KVVSVLYNVT INNTYSCMIE NDIAKATGDI KVTESEIKRR    240

S                                                                    241
                                                (SEQ ID NO: 44)
MEWSWVFLFF LSVTTGVHSG FGISGRHSIT VTTVASAGNI GEDGIQSCTF EPDIKLSDIV     60

IQWLKEGVLG LVHEFKEGKD ELSEQDEMFR GRTAVFADQV IVGNASLRLK NVQLTDAGTY    120

KCYIITSKGK GNANLEYKTG AFSMPEVNVD YNASSETLRC EAPRWFPQPT VVWASQVDQG    180

ANFSEVSNTS FELNSENVTM KVVSVLYNVT INNTYSCMIE NDIAKATGDI KVTESEI,      237

(SEQ ID NO: 45)
MEWSWVFLFF LSVTTGVHSG FGISGRHSIT VTTVASAGNI GEDGIQSCTF EPDIKLSDIV     60

IQWLKEGVLG LVHEFKEGKD ELSEQDEMFR GRTAVFADQV IVGNASLRLK NVQLTDAGTY    120
```

```
                                                        -continued
KCYIITSKGK GNANLEYKTG AFSMPEVNVD YNASSETLRC EAPRWFPQPT VVWASQVDQG       180

ANFSEVSNTS FELNSENVTM KVVSVLYNVT INNTYSCMIE NDIAKATGDI KVTESEIKRR       240

SHLQLLNSKA S,                                                          251

(SEQ ID NO: 46)
MEWSWVFLFF LSVTTGVHSG FGISGRHSIT VTTVASAGNI GEDGILSCTF EPDIKLSDIV        60

IQWLKEGVLG LVHEFKEGKD ELSEQDEMFR GRTAVFADQV IVGNASLRLK NVQLTDAGTY       120

KCYIITSKGK GNANLEYKTG AFSMPEVNVD YNASSETLRC EAPRWFPQPT VVWASQVDQG       180

ANFSEVSNTS FELNSENVTM KVVSVLYNVT INNTYSCMIE NDIAKATGDI KVTESEIKRR       240

S,                                                                     241

(SEQ ID NO: 47)
MEWSWVFLEF LSVTTGVHSG FGISGRHSIT VTTVASAGNI GEDGILSCTF EPDIKLSDIV        60

IQWLKEGVLG LVHEFKEGKD ELSEQDEMFR GRTAVFADQV IVGNASLRLK NVQLTDAGTY       120

KCYIITSKGK GNANLEYKTG AFSMPEVNVD YNASSETLRC EAPRWFPQPT VVWASQVDQG       180

ANFSEVSNTS FELNSENVTM KVVSVLYNVT INNTYSCMIE NDIAKATGDI KVTESEI,        237

(SEQ ID NO: 48)
MEWSWVFLFF LSVTTGVHSG FGISGRHSIT VTTVASAGNI GEDGILSCTF EPDIKLSDIV        60

IQWLKEGVLG LVHEFKEGKD ELSEQDEMFR GRTAVFADQV IVGNASLRLK NVQLTDAGTY       120

KCYIITSKGK GNANLEYKTG AFSMPEVNVD YNASSETLRC EAPRWFPQPT VVWASQVDQG       180

ANFSEVSNTS FELNSENVTM KVVSVLYNVT INNTYSCMIE NDIAKATGDI KVTESEIKRR       240

SHLQLLNSKA S,                                                          251

(SEQ ID NO: 49)
MASLGQILFW SIISIIIILA GAIALIIGFG ISGRHSITVT TVASAGNIGE DGIQSCTFEP        60

DIKLSDIVIQ WLKEGVLGLV HEFKEGKDEL SEQDEMFRGR TAVFADQVIV GNASLRLKNV       120

QLTDAGTYKC YIITSKGKGN ANLEYKTGAF SMPEVNVDYN ASSETLRCEA PRWFPQPTVV       180

WASQVDQGAN FSEVSNTSFE LNSENVTMKV VSVLYNVTIN NTYSCMIEND IAKATGDIKV       240

TESEIKRRS,                                                             249

(SEQ ID NO: 50)
MASLGQILFW SIISIIIILA GAIALIIGFG ISGRHSITVT TVASAGNIGE DGIQSCTFEP        60

DIKLSDIVIQ WLKEGVLGLV HEFKEGKDEL SEQDEMFRGR TAVFADQVIV GNASLRLKNV       120

QLTDAGTYKC YIITSKGKGN ANLEYKTGAF SMPEVNVDYN ASSETLRCEA PRWFPQPTVV       180

WASQVDQGAN FSEVSNTSFE LNSENVTMKV VSVLYNVTIN NTYSCMIEND IAKATGDIKV       240

TESEI,                                                                 245

(SEQ ID NO: 51)
MASLGQILFW SIISIIIILA GAIALIIGFG ISGRHSITVT TVASAGNIGE DGIQSCTFEP        60

DIKLSDIVIQ WLKEGVLGLV HEFKEGKDEL SEQDEMFRGR TAVFADQVIV GNASLRLKNV       120

QLTDAGTYKC YIITSKGKGN ANLEYKTGAF SMPEVNVDYN ASSETLRCEA PRWFPQPTVV       180

WASQVDQGAN FSEVSNTSFE LNSENVTMKV VSVLYNVTIN NTYSCMIEND IAKATGDIKV       240

TESEIKRRSH LQLLNSKAS,                                                  259

(SEQ ID NO: 52)
MASLGQILFW SIISIIIILA GAIALIIGFG ISGRHSITVT TVASAGNIGE DGILSCTFEP        60

DIKLSDIVIQ WLKEGVLGLV HEFKEGKDEL SEQDEMFRGR TAVFADQVIV GNASLRLKNV       120

QLTDAGTYKC YIITSKGKGN ANLEYKTGAF SMPEVNVDYN ASSETLRCEA PRWFPQPTVV       180

WASQVDQGAN FSEVSNTSFE LNSENVTMKV VSVLYNVTIN NTYSCMIEND IAKATGDIKV       240

TESEIKRRS,                                                             249
```

-continued

```
                                                     (SEQ ID NO: 53)
MASLGQILFW SIISIIIILA GAIALIIGFG ISGRHSITVT TVASAGNIGE DGILSCTFEP    60

DIKLSDIVIQ WLKEGVLGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEI,                                                              245
``` or

```
                                                     (SEQ ID NO: 54)
MASLGQILFW SIISIIIILA GAIALIIGFG ISGRHSITVT TVASAGNIGE DGILSCTFEP    60

DIKLSDIVIQ WLKEGVLGLV HEFKEGRDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEIKRRSH LQLLNSKAS.                                               259
```

The signal sequence will be removed in the mature protein. Additionally, signal peptides from other polypeptides or organisms can be used to enhance the secretion of the fusion protein from a host during manufacture. SEQ ID NO:55 provides the human amino acid sequence of SEQ ID NO:43 and SEQ ID NO:49 without the signal sequence:

```
                                                     (SEQ ID NO: 55)
GEGISGRHSI TVTTVASAGN IGEDGIQSCT FERDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDO GANFSEVSNT SFELNSENVT   180

MKVVSVLYNV TINNTYSCMI ENDIAKATGD IKVTESEIKR RS.                     222
```

SEQ ID NO:56 provides the human amino acid sequence of SEQ ID NO:46 and SEQ ID NO:52 without the signal sequence:

```
                                                     (SEQ ID NO: 56)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEIKR RS.                     222
```

SEQ ID NO:57 provides the human amino acid sequence of SEQ ID NO:44 and SEQ ID NO:50 without the signal sequence:

```
                                                     (SEQ ID NO: 57)
GEGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEI.                          218
```

SEQ ID NO:58 provides the human amino acid sequence of SEQ ID NO:47 and SEQ ID NO:53 without the signal sequence:

```
                                                        (SEQ ID NO: 58)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANESEVSNT SFELNSENVT   180

MKVVSVLYNV TINNTYSCMI ENDIAKATGD IKVTESEI.                         218
```

SEQ ID NO:59 provides the human amino acid sequence of SEQ ID NO:45 and SEQ ID NO:51 without the signal sequence:

```
                                                        (SEQ ID NO: 59)
GFGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEIKR RSHLQLLNSK AS.          232
```

SEQ ID NO:60 provides the human amino acid sequence of SEQ ID NO:48 and SEQ ID NO:54 without the signal sequence:

```
                                                        (SEQ ID NO: 60)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD TKVTESEIKR PSHLQLLNSK AS.          232
```

In other embodiments the final alanine and serine residues are removed from SEQ ID NOS: 45, 48, 51, 54, 59, and 60.

In another embodiment, the first fusion partner of the fusion protein includes the IgV domain of human B7-H4. In one embodiment, the IgV domain includes at least from the cysteine at position 56 of SEQ ID NO:9 or SEQ ID NO:12 to the cysteine at position 130 of SEQ ID NO:9 or SEQ ID NO:12. In another embodiment, the IgV domain contains a fragment of at least 25 or 50 amino acids of the polypeptide defined by this amino acid range.

The first fusion partner can be encoded by a nucleotide sequence having at least 80%, 85%, 90%, 95%, 99%, or 100% sequence identity to the following nucleotide sequence encoding an exemplary IgV domain:

```
                                                        (SEQ ID NO: 61)
             ggcttcggca tcagtggacg gcacagtatc acagtgacca ccgtcgcctc cgctggcaat    60
ataggtgagg atggcatcca gtcctgtacc tttgagccgg acatcaaact gtctgacata   120
gtgatacaat ggctgaagga gggggtgctc ggtctggtac atgagtttaa ggaagggaag   180
gatgaactgt ccgagcagga tgagatgttc cggggagga ccgctgtgtt cgccgatcag    240
gtaatcgtcg gaaatgcaag tctcagattg aaaaatgtgc aactgactga tgctggcacg   300
tataaatgct acattatcac aagtaagggc aaggaaatg ctaaccttga gtataaaaca    360
ggcgcattct caatgcccga ggtcaat                                       387
or
```

```
                                                        (SEQ ID NO: 62)
             ggcttcggca tcagtggacg gcacagtatc acagtgacca ccgtcgcctc cgctggcaat    60
ataggtgagg atggcatcct gtcctgtacc tttgagccgg acatcaaact gtctgacata   120
gtgatacaat ggctgaagga gggggtgctc ggtctggtac atgagtttaa ggaagggaag   180
gatgaactgt ccgagcagga tgagatgttc cggggagga ccgctgtgtt cgccgatcag    240
gtaatcgtcg gaaatgcaag tctcagattg aaaaatgtgc aactgactga tgctggcacg   300
```

-continued

```
tataaatgct acattatcac aagtaagggc aaaggaaatg ctaaccttga gtataaaaca   360
ggcgcattct caatgcccga ggtcaat.                                      387
```

The first fusion partner can have at least 80%, 85%, 90%, 95%, 99%, or 100% sequence identity to the human amino acid sequence:

```
                                                        (SEQ ID NO: 63)
GFGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVN,                                                         129
or
                                                        (SEQ ID NO: 64)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVN.                                                         129
``` c. Non-Human Primate Extracellular Domain Fusion Partners

In another embodiment, the first fusion partner of the fusion protein includes the extracellular domain of non-human primate B7-H4 or a fragment thereof. Exemplary non-human primates include, but are not limited to, chimpanzee (*Pan troglodytes*), rhesus monkey (*Macaca mulatta*) and cynomolgus monkey (*Macaca fascicularis*).

The first fusion partner can have at least 80%, 85%, 90%, 95%, 99%, or 100% sequence identity to the chimapanzee (*Pan troglodytes*) amino acid sequence:

```
                                                        (SEQ ID NO: 65)
MKPLTSRIIS IIIILAGAIA LIIGFGISGR HSITVTTVAS AGNIGEDGIL SCTFEPDIKL    60

SDIVIQWLKE GVLGLVHEFK EGKDELSEQD EMFRGRTAVF ADQVIVGNAS LRLKNVQLTD   120

AGTYKCYIIT SKGKGNANLE YKTGAFSMPE VNVDYNASSE TLRCEAPRWF PQPTVVWASQ   180

IDQGANFSEV SNTSFELNSE NVTMKVVSVL YNATINNTYS CMIENDIAKA TGDIKVTESE   240

IKRRS,                                                             245

(SEQ ID NO: 66)
MKPLTSRIIS IIIILAGAIA LIIGFGISGR HSITVTTVAS AGNIGEDGIL SCTFEPDIKL    60

SDIVIQWLKE GVLGLVHEFK EGKDELSEQD EMFRGRTAVF ADQVIVGNAS LRLKNVQLTD   120

AGTYKCYIIT SKGKGNANLE YKTGAFSMPE VNVDYNASSE TLRCEAPRWF PQPTVVWASQ   180

IDQGANFSEV SNTSFELNSE NVTMKVVSVL YNATINNTYS CMIENDIAKA TGDIKVTESE   240

I,                                                                 241
or
                                                        (SEQ ID NO: 67)
MKPLTSRIIS IIIILAGAIA LIIGFGISGR HSITVTTVAS AGNIGEDGIL SCTFEPDIKL    60

SDIVIQWLKE GVLGLVHEFK EGKDELSEQD EMFRGRTAVF ADQVIVGNAS LRLKNVQLTD   120

AGTYKCYIIT SKGKGNANLE YKTGAFSMPE VNVDYNASSE TLRCEAPRWF PQPTVVWASQ   180

IDQGANFSEV SNTSFELNSE MVTMKVVSVL YNATINNTYS CMIENDIAKA TGDIKVTESE   240

IKRRSHLQLL NSKAS.                                                  255
```

The signal sequence will be removed in the mature protein. Additionally, signal peptides from other polypeptides or organisms can be used to enhance the secretion of the fusion protein from a host during manufacture.

SEQ ID NO:68 provides the chimapanzee amino acid sequence of SEQ ID NO:65 without the signal sequence:

```
                                                              (SEQ ID NO: 68)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQIDQ GANFSEVSNT SFELNSENVT   180

MKVVSVLYNA TINNTYSCMI ENDIAKATGD IKVTESEIKR RS.                    222
```

SEQ ID NO:69 provides the chimapanzee amino acid sequence of SEQ ID NO:66 without the signal sequence:

```
                                                              (SEQ ID NO: 69)
GEGTSGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYTITSKG KGNANLEYKT   120

GAFSMPEVNV DYNASSETLR CEAPRWFPQP TVVWASQIDQ GANFSEVSNT SFELNSENVT   180

MKVVSVLYNA TINNTYSCMI ENDIRKATGD IKVTESEI.                         218
```

SEQ ID NO:70 provides the chimapanzee amino acid sequence of SEQ ID NO:67 without the signal sequence:

```
                                                              (SEQ ID NO: 70)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQIDQ GANFSEVSNT SFELNSENVT   180

MKVVSVLYNA TINNTYSCMI ENDIAKATGD IKVTESEIKR RSHLQLLNSK AS.         232
```

The first fusion partner can have at least 80%, 85%, 90%, 95%, 99%, or 100% sequence identity to the rhesus monkey (*Macaca mulatta*) amino acid sequence:

```
                                                              (SEQ ID NO: 71)
MASLGQILFW SIISIIFILA GAIALIIGFG ISGRHSITVT TVASAGNIGE DGILSCTFEP    60

DIKLSDIVIQ WLKEGVIGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWMPTVV    180

WASQVDQGAN FSEVSNTSFE LNSENVTMKV VSVLYNVTIN NTYSCMIEND IAKATGDIKV   240

TESEIKRRS,                                                         249
```

```
                                                              (SEQ ID NO: 72)
MASLGQILFW SIISIIFILA GAIALIIGFG ISGRHSITVT TVASAGNIGE DGILSCTFEP    60

DIKLSDIVIQ WLKEGVIGLV HEFKEGKDEL SEQDEMFRGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEI,                                                             245
or
```

```
                                                              (SEQ ID NO: 73)
MASLGQILFW SIISIIFILA GAIALIIGFG ISGRHSITVT TVASAGNIGE DGILSCTFEP    60

DIKLSDIVIQ WLKEGVIGLV HEFKEGKDEL SEQDEMERGR TAVFADQVIV GNASLRLKNV   120

QLTDAGTYKC YIITSKGKGN ANLEYKTGAF SMPEVNVDYN ASSETLRCEA PRWFPQPTVV   180

WASQVDQGAN FSEVSNTSFE LNSENVTMKV VSVLYNVTIN NTYSCMIEND IAKATGDIKV   240

TESEIKRRSH LQLLNSKAS.                                              259
```

The signal sequence will be removed in the mature protein. Additionally, signal peptides from other polypeptides or organisms can be used to enhance the secretion of the fusion protein from a host during manufacture.

SEQ ID NO:74 provides the rhesus monkey amino acid sequence of SEQ ID NO:71 without the signal sequence:

```
                                                    (SEQ ID NO: 74)
GFGISGRHSI TVTTVASAGN IGEDGILSCT FEPDIKLSDI VIQWLKEGVI GLVHEFKEGK   60

DELSEQDEMF RGRTAVFADQ VIVGNASLRL KNVQLTDAGT YKCYIITSKG KGNANLEYKT  120

GAFSMPEVNV DYNASSETLR CEAPRWFPQP TVVWASQVDQ GANFSEVSNT SFELNSENVT  180

MKVVSVLYNV TINNTYSCMI ENDIAKATGD IKVISSEIKR RS.                   222
```

SEQ ID NO:75 provides the rhesus monkey amino acid sequence of SEQ ID NO:72 without the signal sequence:

```
                                                    (SEQ ID NO: 75)
GFGISGRHSI TVTTVASAGN IGEDGILSCT FEPDIKLSDI VIQWLKEGVI GLVHEFKEGK   60

DELSEQDEMF RGRTAVFADQ VIVGNASLRL KNVQLTDAGT YKCYIITSKG KGNANLEYKT  120

GAFSMPEVNV DYNASSETLR CEAPRWFPQP TVVWASQVDQ GANFSEVSNT SFELNSENVT  180

MKVVSVLYNV TINNTYSCMI ENDIAKATGD IKVTESEI.                        218
```

SEQ ID NO:76 provides the rhesus monkey amino acid sequence of SEQ ID NO:73 without the signal sequence:

```
                                                    (SEQ ID NO: 76)
GFGISGRHSI TVTTVASAGN IGEDGILSCT FEPDIKLSDI VIQWLKEGVI GLVHEFKEGK   60

DELSEQDEMF RGRTAVFADQ VIVGNASLRL KNVQLTDAGT YKCYIITSKG KGNANLEYKT  120

GAFSMPEVNV DYNASSETLR CEAPRWFPQP TVVWASQVDQ GANFSEVSNT SFELNSENVT  180

MKVVSVLYNV TINNTYSCMI ENDIAKATGD IKVTESEIKR RSHLQLLNSK AS.        232
```

The first fusion partner can have at least 80%, 85%, 90%, 95%, 99%, or 100% sequence identity to the cynomolgus monkey (*Macaca fascicularis*) amino acid sequence:

```
                                                    (SEQ ID NO: 77)
MASLGQILFW SIISIIFILA GAIALIIGFG ISGRHSITVT TVASAGNIGE DGILSCTFEP   60

DIKLSDIVIQ WLKEGVIGLV HEFKEGKDEL SEQDEMFRGR TAVFADQVIV GNASLRLKNV  120

QLTDAGTYKC YIITSKGKGN ANLEYKTGAF SMPEVNVDYN ASSETLRCEA PRWFPQPIVV  180

WASQVDQGAN FSEVSNTSFE LNSENVTMKV VSVLYNVTIN NTYSCMIEND IAKATGDIKV  240

TESEIKRRS,                                                        249

(SEQ ID NO: 78)
MASLGQILFW SIISIIFILA GAIALIIGFG ISGRHSITVT TVASAGNIGE DGILSCTFEP   60

DIKLSDIVIQ WLKEGVIGLV HEFKEGKDEL SEQDEMFRGR TAVFADQVIV GNASLRLKNV  120

QLTDAGTYKC YIITSKGKGN ANLEYKTGAF SMPEVNVDYN ASSETLRCEA PRWFPQPIVV  180

WASQVDQGAN FSEVSNTSFE LNSENVTMKV VSVLYNVTIN NTYSCMIEND IAKATGDIKV  240

TESEI,                                                            245
or (SEQ ID NO: 79)
MASLGQILFW SIISIIFILA GAIALIIGFG ISGRHSITVT TVASAGNIGE DGILSCTFEP   60

DIKLSDIVIQ WLKEGVIGLV HEFKEGKDEL SEQDEMFRGR TAVFADQVIV GNASLRLKNV  120

QLTDAGTYKC YIITSKGKGN ANLEYKTGAF SMPEVNVDYN ASSETLRCEA PRWFPQPTVV  180

WASQVDQGAN FSEVSNTSFE LNSENVTMKV VSVLYNVTIN NTYSCMIEND IAKATGDIKV  240

TESEIKRRSH LQLLNSKAS.                                             259
```

The signal sequence will be removed in the mature protein. Additionally, signal peptides from other polypeptides or organisms can be used to enhance the secretion of the fusion protein from a host during manufacture.

SEQ ID NO:80 provides the cynomolgus monkey amino acid sequence of SEQ ID NO:77 without the signal sequence:

```
                                                         (SEQ ID NO: 80)
GEGISGRHSI TVTTVASAGN IGEDGILSCT FEPDIKLSDI VIQWLKEGVI GLVHEFKEGK    60

DELSEQDEMF RGRTAVFADQ VIVGHASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEIKR RS.                    222
```

SEQ ID NO:81 provides the cynomolgus monkey amino acid sequence of SEQ ID NO:78 without the signal sequence:

```
                                                         (SEQ ID NO: 81)
GFGISGRHSI TVTTVASAGN IGEDGILSCT FEPDIKLSDI VIQWLKEGVI GLVHEFKEGK    60

DELSEQDRMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEI.                         218
```

SEQ ID NO:82 provides the cynomolgus monkey amino acid sequence of SEQ ID NO:79 without the signal sequence:

```
                                                         (SEQ ID NO: 82)
GFGISGRHSI TVTTVASAGN IGEDGILSCT FEPDIKLSDI VIQWLKEGVI GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIARATGD IKVTESEIKR RSHLQLLNSK AS.          232
```

In other embodiments the final alanine and serine residues are removed from SEQ ID NOS:67, 70, 73, 76, 79, and 82.

In another embodiment, the first fusion partner of the fusion protein includes the IgV domain of chimpanzee B7-H4. In another embodiment, the IgV domain includes at least from the cysteine at position 52 of SEQ ID NO:15 to the cysteine at position 126 of SEQ ID NO:15. In another embodiment, the IgV domain contains a fragment of at least 25 or 50 amino acids of the polypeptide defined by this amino acid range.

The first fusion partner can have at least 80%, 85%, 90%, 95%, 99%, or 100% sequence identity to the following chimpanzee amino acid sequence of the following exemplary IgV domain:

```
                                                         (SEQ ID NO: 83)
GEGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVN.                                                         129
```

In another embodiment, the first fusion partner of the fusion protein includes the IgV domain of rhesus monkey B7-H4. In one embodiment, the IgV domain includes at least from the cysteine at position 56 of SEQ ID NO:17 to the cysteine at position 130 of SEQ ID NO:17. In another embodiment, the IgV domain contains a fragment of at least 25 or 50 amino acids of the polypeptide defined by this amino acid range.

The first fusion protein can have at least 80%, 85%, 90%, 95%, 99%, or 100% sequence identity to the rhesus monkey amino acid sequence of the following exemplary IgV domain:

```
                                                         (SEQ ID NO: 84)
GEGISGRHSI TVTTVASAGN IGEDGILSCT FEPDIKLSDI VIQWLKEGVI GLVHEFKEGK    60

DELSEQDEMF RGRTAVFADQ VIVGNASLRL KNVQLTDAGT YKCYIITSKG KGNANLEYKT   120

GAFSMPEVN.                                                         129
```

In another embodiment, the first fusion partner of the fusion protein includes the IgV domain of cynomolgus monkey B7-H4. In one embodiment, the IgV domain includes at least from the cysteine at position 56 of SEQ ID NO:19 to the cysteine at position 130 of SEQ ID NO:19. In another embodiment, the IgV domain contains a fragment of at least 25 or 50 amino acids of the polypeptide defined by this amino acid range.

The first fusion protein can have at least 80%, 85%, 90%, 95%, 99%, or 100% sequence identity to the cynomolgus monkey amino acid sequence of the following exemplary IgV domain:

```
                                                        (SEQ ID NO: 85)
GFGISGRHSI TVTTVASAGN IGEDGILSCT FEPDIKLSDI VIQWLKEGVI GLVHEFKEGK    60

DELSEQDEMF RGRTAVFADQ VIVGNASLRL KNVQLTDAGT YKCYIITSKG KGNANLEYKT   120

GAFSMPEVN.                                                         129
``` d. B7-H4 Extracellular Domain Fragments

The B7-H4 extracellular domain can contain one or more amino acids from the signal peptide or the putative transmembrane domain of B7-H4. During secretion, the number of amino acids of the signal peptide that are cleaved can vary depending on the expression system and the host. Additionally, fragments of B7-H4 extracellular domain missing one or more amino acids from the C-terminus or the N-terminus that retain the ability to bind to the B7-H4 receptor can be used as a fusion partner for the disclosed fusion proteins.

For example, suitable fragments of murine B7-H4 that can be used as a first fusion partner include, but are not limited to, the following:
32-257, 32-256, 32-255, 32-254, 32-253, 32-252, 32-251, 32-250, 32-249, 31-257, 31-256, 31-255, 31-254, 31-253, 31-252, 31-251, 31-250, 31-249, 30-257, 30-256, 30-255, 30-254, 30-253, 30-252, 30-251, 30-250, 30-249, 29-257, 29-256, 29-255, 29-254, 29-253, 29-252, 29-251, 29-250, 29-249, 28-257, 28-256, 28-255, 28-254, 28-253, 28-252, 28-251, 28-250, 28-249, 27-257, 27-256, 27-255, 27-254, 27-253, 27-252, 27-251, 27-250, 27-249, 26-257, 26-256, 26-255, 26-254, 26-253, 26-252, 26-251, 26-250, 26-249, 25-257, 25-256, 25-255, 25-254, 25-253, 25-252, 25-251, 25-250, 25-249, 24-257, 24-256, 24-255, 24-254, 24-253, 24-252, 24-251, 24-250, 24-249, of SEQ ID NO:26 or SEQ ID NO:27, or 24-249, 24-248, 24-247, 24-246, 24-245, 24-244, 24-243, 24-242, 24-241, 23-249, 23-248, 23-247, 23-246, 23-245, 23-244, 23-243, 23-242, 23-241, 22-249, 22-248, 22-247, 22-246, 22-245, 22-244, 22-243, 22-242, 22-241, 21-249, 21-248, 21-247, 21-246, 21-245, 21-244, 21-243, 21-242, 21-241, 20-249, 20-248, 20-247, 20-246, 20-245, 20-244, 20-243, 20-242, 20-241, 19-249, 19-248, 19-247, 19-246, 19-245, 19-244, 19-243, 19-242, 19-241, 18-249, 18-248, 18-247, 18-246, 18-245, 18-244, 18-243, 18-242, 18-241, 17-249, 17-248, 17-247, 17-246, 17-245, 17-244, 17-243, 17-242, 17-241, 16-249, 16-248, 16-247, 16-246, 16-245, 16-244, 16-243, 16-242, 16-241, of SEQ ID NO:24 or SEQ ID NO:25.

Additional suitable fragments of murine B7-H4 include, but are not limited to, the following:
28-257, 28-258, 28-259, 28-260, 28-261, 28-262, 28-263, 29-257, 29-258, 29-259, 29-260, 29-261, 29-262, 29-263, 30-257, 30-258, 30-259, 30-260, 30-261, 30-262, 30-263, 31-257, 31-258, 31-259, 31-260, 31-261, 31-262, 31-263, 32-257, 32-258, 32-259, 32-260, 32-261, 32-262, 32-263, of SEQ ID NO:2 or SEQ ID NO:5, optionally with one to five amino acids of a signal peptide attached to the N-terminal end. The signal peptide may be any disclosed herein, including those contained within SEQ ID NOs:2, 3, 5, 6, 9, 10, 12, 13, 15, 17 and 19, or may be any signal peptide known in the art.

Additional suitable fragments of murine B7-H4 include, but are not limited to, fragments containing at least 25, 20, 75, 100 or 125 amino acids of the IgV domain as set forth in SEQ ID NO:32 or SEQ ID NO:33.

Exemplary fragments include, but are not limited to:
16-144, 16-145, 16-146, 16-147, 16-148, 16-149, 16-150, 16-151, 16-152,
17-144, 17-145, 17-146, 17-147, 17-148, 17-149, 17-150, 17-151, 17-152,
18-144, 18-145, 18-146, 18-147, 18-148, 18-149, 18-150, 18-151, 18-152,
19-144, 19-145, 19-146, 19-147, 19-148, 19-149, 19-150, 19-151, 19-152,
20-144, 20-145, 20-146, 20-147, 20-148, 20-149, 20-150, 20-151, 20-152,
21-144, 21-145, 21-146, 21-147, 21-148, 21-149, 21-150, 21-151, 21-152,
22-144, 22-145, 22-146, 22-147, 22-148, 22-149, 22-150, 22-151, 22-152,
23-144, 23-145, 23-146, 23-147, 23-148, 23-149, 23-150, 23-151, 23-152,
24-144, 24-145, 24-146, 24-147, 24-148, 24-149, 24-150, 24-151, 24-152,
of SEQ ID NO:24 or SEQ ID NO:25, or
24-152, 24-153, 24-154, 24-155, 24-156, 24-157, 24-158, 24-159, 24-160,
25-152, 25-153, 25-154, 25-155, 25-156, 25-157, 25-158, 25-159, 25-160,
26-152, 26-153, 26-154, 26-155, 26-156, 26-157, 26-158, 26-159, 26-160,
27-152, 27-153, 27-154, 27-155, 27-156, 27-157, 27-158, 27-159, 27-160,
28-152, 28-153, 28-154, 28-155, 28-156, 28-157, 28-158, 28-159, 28-160,
29-152, 29-153, 29-154, 29-155, 29-156, 29-157, 29-158, 29-159, 29-160,
30-152, 30-153, 30-154, 30-155, 30-156, 30-157, 30-158, 30-159, 30-160,
31-152, 31-153, 31-154, 31-155, 31-156, 31-157, 31-158, 31-159, 31-160,
32-152, 32-153, 32-154, 32-155, 32-156, 32-157, 32-158, 32-159, 32-160,
of SEQ ID NO:26 or SEQ ID NO:27, optionally with one to five amino acids of a signal peptide attached to the N-terminal end. The signal peptide may be any disclosed herein, including those contained within SEQ ID NOs:2, 3, 5, 6, 9, 10, 12, 13, 15, 17 and 19, or may be any signal peptide known in the art.

Exemplary suitable fragments of human B7-H4 that can be used as a first fusion partner include, but are not limited to, the following:
32-249, 32-248, 32-247, 32-246, 32-245, 32-244, 32-243, 32-242, 32-241, 31-249, 31-248, 31-247, 31-246, 31-245, 31-244, 31-243, 31-242, 31-241,
30-249, 30-248, 30-247, 30-246, 30-245, 30-244, 30-243, 30-242, 30-241,
29-249, 29-248, 29-247, 29-246, 29-245, 29-244, 29-243, 29-242, 29-241,
28-249, 28-248, 28-247, 28-246, 28-245, 28-244, 28-243, 28-242, 28-241,
27-249, 27-248, 27-247, 27-246, 27-245, 27-244, 27-243, 27-242, 27-241,
26-249, 26-248, 26-247, 26-246, 26-245, 26-244, 26-243, 26-242, 26-241,
25-249, 25-248, 25-247, 25-246, 25-245, 25-244, 25-243, 25-242, 25-241,
24-249, 24-248, 24-247, 24-246, 24-245, 24-244, 24-243, 24-242, 24-241,
of SEQ ID NO:49, or SEQ ID NO:52, or
32-245, 32-244, 32-243, 32-242, 32-241, 32-240, 32-239, 32-238, 32-237,
31-245, 31-244, 31-243, 31-242, 31-241, 31-240, 31-239, 31-238, 31-237,
30-245, 30-244, 30-243, 30-242, 30-241, 30-240, 30-239, 30-238, 30-237,
29-245, 29-244, 29-243, 29-242, 29-241, 29-240, 29-239, 29-238, 29-237,
28-245, 28-244, 28-243, 28-242, 28-241, 28-240, 28-239, 28-238, 28-237,
27-245, 27-244, 27-243, 27-242, 27-241, 27-240, 27-239, 27-238, 27-237,
26-245, 26-244, 26-243, 26-242, 26-241, 26-240, 26-239, 26-238, 26-237,
25-245, 25-244, 25-243, 25-242, 25-241, 25-240, 25-239, 25-238, 25-237,
24-245, 24-244, 24-243, 24-242, 24-241, 24-240, 24-239, 24-238, 24-237,
of SEQ ID NO:50 or SEQ ID NO:53, or
32-259, 32-258, 32-257, 32-256, 32-255, 32-254, 32-253, 32-252, 32-251,
31-259, 31-258, 31-257, 31-256, 31-255, 31-254, 31-253, 31-252, 31-251,
30-259, 30-258, 30-257, 30-256, 30-255, 30-254, 30-253, 30-252, 30-251,
29-259, 29-258, 29-257, 29-256, 29-255, 29-254, 29-253, 29-252, 29-251,
28-259, 28-258, 28-257, 28-256, 28-255, 28-254, 28-253, 28-252, 28-251,
27-259, 27-258, 27-257, 27-256, 27-255, 27-254, 27-253, 27-252, 27-251,
26-259, 26-258, 26-257, 26-256, 26-255, 26-254, 26-253, 26-252, 26-251,
25-259, 25-258, 25-257, 25-256, 25-255, 25-254, 25-253, 25-252, 25-251,
24-259, 24-258, 24-257, 24-256, 24-255, 24-254, 24-253, 24-252, 24-251,
of SEQ ID NO:51 or SEQ ID NO:54, or
24-241, 24-240, 24-239, 24-238, 24-237, 24-236, 24-235, 24-234, 24-233,
23-241, 23-240, 23-239, 23-238, 23-237, 23-236, 23-235, 23-234, 23-233,
22-241, 22-240, 22-239, 22-238, 22-237, 22-236, 22-235, 22-234, 22-233,
21-241, 21-240, 21-239, 21-238, 21-237, 21-236, 21-235, 21-234, 21-233,
20-241, 20-240, 20-239, 20-238, 20-237, 20-236, 20-235, 20-234, 20-233,
19-241, 19-240, 19-239, 19-238, 19-237, 19-236, 19-235, 19-234, 19-233,
18-241, 18-240, 18-239, 18-238, 18-237, 18-236, 18-235, 18-234, 18-233,
17-241, 17-240, 17-239, 17-238, 17-237, 17-236, 17-235, 17-234, 17-233,
16-241, 16-240, 16-239, 16-238, 16-237, 16-236, 16-235, 16-234, 16-233,
of SEQ ID NO:43 or SEQ ID NO:46, or
24-237, 24-236, 24-235, 24-234, 24-233, 24-232, 24-231, 24-230, 24-229,
23-237, 23-236, 23-235, 23-234, 23-233, 23-232, 23-231, 23-230, 23-229,
22-237, 22-236, 22-235, 22-234, 22-233, 22-232, 22-231, 22-230, 22-229,
21-237, 21-236, 21-235, 21-234, 21-233, 21-232, 21-231, 21-230, 21-229,
20-237, 20-236, 20-235, 20-234, 20-233, 20-232, 20-231, 20-230, 20-229,
19-237, 19-236, 19-235, 19-234, 19-233, 19-232, 19-231, 19-230, 19-229,
18-237, 18-236, 18-235, 18-234, 18-233, 18-232, 18-231, 18-230, 18-229,
17-237, 17-236, 17-235, 17-234, 17-233, 17-232, 17-231, 17-230, 17-229,
16-237, 16-236, 16-235, 16-234, 16-233, 16-232, 16-231, 16-230, 16-229,
of SEQ ID NO:44 or SEQ ID NO:47, or
24-251, 24-250, 24-249, 24-248, 24-247, 24-246, 24-245, 24-244, 24-243,
23-251, 23-250, 23-249, 23-248, 23-247, 23-246, 23-245, 23-244, 23-243,
22-251, 22-250, 22-249, 22-248, 22-247, 22-246, 22-245, 22-244, 22-243,
21-251, 21-250, 21-249, 21-248, 21-247, 21-246, 21-245, 21-244, 21-243,
20-251, 20-250, 20-249, 20-248, 20-247, 20-246, 20-245, 20-244, 20-243,
19-251, 19-250, 19-249, 19-248, 19-247, 19-246, 19-245, 19-244, 19-243,
18-251, 18-250, 18-249, 18-248, 18-247, 18-246, 18-245, 18-244, 18-243,
17-251, 17-250, 17-249, 17-248, 17-247, 17-246, 17-245, 17-244, 17-243,
16-251, 16-250, 16-249, 16-248, 16-247, 16-246, 16-245, 16-244, 16-243,
of SEQ ID NO:45 or SEQ ID NO:48.

Additional suitable fragments of human B7-H4 include, but are not limited to, the following:
27-249, 27-250, 27-251, 27-252, 27-253, 27-254, 27-255, 27-256, 27-257, 27-259, 27-260,
28-249, 28-250, 28-251, 28-252, 28-253, 28-254, 28-255, 28-256, 28-257, 28-259, 28-260,
29-249, 29-250, 29-251, 29-252, 29-253, 29-254, 29-255, 29-256, 29-257, 29-259, 29-260,
30-249, 30-250, 30-251, 30-252, 30-253, 30-254, 30-255, 30-256, 30-257, 30-259, 30-260,
31-249, 31-250, 31-251, 31-252, 31-253, 31-254, 31-255, 31-256, 31-257, 31-259, 31-260,
32-249, 32-250, 32-251, 32-252, 32-253, 32-254, 32-255, 32-256, 32-257, 32-259, 32-260
of SEQ ID NO:9 or SEQ ID NO:12, optionally with one to five amino acids of a signal peptide attached to the N-terminal end. The signal peptide may be any disclosed herein, including those contained within SEQ ID NOs:2, 3, 5, 6, 9, 10, 12, 13, 15, 17 and 19, or may be any signal peptide known in the art.

Additional suitable fragments of human B7-H4 include, but are not limited to, fragments containing at least 25, 20, 75, 100 or 125 amino acids of the IgV domain as set forth in SEQ ID NO:63 or SEQ ID NO:64. Exemplary fragments include, but are not limited to:
16-144, 16-145, 16-146, 16-147, 16-148, 16-149, 16-150, 16-151, 16-152,
17-144, 17-145, 17-146, 17-147, 17-148, 17-149, 17-150, 17-151, 17-152,
18-144, 18-145, 18-146, 18-147, 18-148, 18-149, 18-150, 18-151, 18-152,
19-144, 19-145, 19-146, 19-147, 19-148, 19-149, 19-150, 19-151, 19-152,
20-144, 20-145, 20-146, 20-147, 20-148, 20-149, 20-150, 20-151, 20-152,
21-144, 21-145, 21-146, 21-147, 21-148, 21-149, 21-150, 21-151, 21-152,
22-144, 22-145, 22-146, 22-147, 22-148, 22-149, 22-150, 22-151, 22-152,
23-144, 23-145, 23-146, 23-147, 23-148, 23-149, 23-150, 23-151, 23-152,
24-144, 24-145, 24-146, 24-147, 24-148, 24-149, 24-150, 24-151, 24-152,
of any of SEQ ID NO:43, SEQ ID NO:44, SEQ ID NO:45, SEQ ID NO:46, SEQ ID NO:47, or SEQ ID NO:48, or
24-152, 24-153, 24-154, 24-155, 24-156, 24-157, 24-158, 24-159, 24-160,
25-152, 25-153, 25-154, 25-155, 25-156, 25-157, 25-158, 25-159, 25-160,
26-152, 26-153, 26-154, 26-155, 26-156, 26-157, 26-158, 26-159, 26-160,
27-152, 27-153, 27-154, 27-155, 27-156, 27-157, 27-158, 27-159, 27-160,
28-152, 28-153, 28-154, 28-155, 28-156, 28-157, 28-158, 28-159, 28-160,
29-152, 29-153, 29-154, 29-155, 29-156, 29-157, 29-158, 29-159, 29-160,
30-152, 30-153, 30-154, 30-155, 30-156, 30-157, 30-158, 30-159, 30-160,
31-152, 31-153, 31-154, 31-155, 31-156, 31-157, 31-158, 31-159, 31-160,
32-152, 32-153, 32-154, 32-155, 32-156, 32-157, 32-158, 32-159, 32-160,
of any of SEQ ID NO:49, SEQ ID NO:50, SEQ ID NO:51, SEQ ID NO:52, SEQ ID NO:53, or SEQ ID NO:54, optionally with one to five amino acids of a signal peptide attached to the N-terminal end. The signal peptide may be any disclosed herein, including those contained within SEQ ID NOs: 2, 3, 5, 6, 9, 10, 12, 13, 15, 17 and 19, or may be any signal peptide known in the art.

Exemplary suitable fragments of non-human primate B7-H4 that can be used as a first fusion partner include, but are not limited to, the following:
32-249, 32-248, 32-247, 32-246, 32-245, 32-244, 32-243, 32-242, 32-241,
31-249, 31-248, 31-247, 31-246, 31-245, 31-244, 31-243, 31-242, 31-241,
30-249, 30-248, 30-247, 30-246, 30-245, 30-244, 30-243, 30-242, 30-241,
29-249, 29-248, 29-247, 29-246, 29-245, 29-244, 29-243, 29-242, 29-241,
28-249, 28-248, 28-247, 28-246, 28-245, 28-244, 28-243, 28-242, 28-241,
27-249, 27-248, 27-247, 27-246, 27-245, 27-244, 27-243, 27-242, 27-241,
26-249, 26-248, 26-247, 26-246, 26-245, 26-244, 26-243, 26-242, 26-241,
25-249, 25-248, 25-247, 25-246, 25-245, 25-244, 25-243, 25-242, 25-241,
24-249, 24-248, 24-247, 24-246, 24-245, 24-244, 24-243, 24-242, 24-241,
of SEQ ID NO:71, or SEQ ID NO:77, or
32-245, 32-244, 32-243, 32-242, 32-241, 32-240, 32-239, 32-238, 32-237,
31-245, 31-244, 31-243, 31-242, 31-241, 31-240, 31-239, 31-238, 31-237,
30-245, 30-244, 30-243, 30-242, 30-241, 30-240, 30-239, 30-238, 30-237,
29-245, 29-244, 29-243, 29-242, 29-241, 29-240, 29-239, 29-238, 29-237,
28-245, 28-244, 28-243, 28-242, 28-241, 28-240, 28-239, 28-238, 28-237,
27-245, 27-244, 27-243, 27-242, 27-241, 27-240, 27-239, 27-238, 27-237,
26-245, 26-244, 26-243, 26-242, 26-241, 26-240, 26-239, 26-238, 26-237,
25-245, 25-244, 25-243, 25-242, 25-241, 25-240, 25-239, 25-238, 25-237,
24-245, 24-244, 24-243, 24-242, 24-241, 24-240, 24-239, 24-238, 24-237,
of SEQ ID NO:72 or SEQ ID NO:78, or
32-259, 32-258, 32-257, 32-256, 32-255, 32-254, 32-253, 32-252, 32-251,
31-259, 31-258, 31-257, 31-256, 31-255, 31-254, 31-253, 31-252, 31-251,
30-259, 30-258, 30-257, 30-256, 30-255, 30-254, 30-253, 30-252, 30-251,
29-259, 29-258, 29-257, 29-256, 29-255, 29-254, 29-253, 29-252, 29-251,
28-259, 28-258, 28-257, 28-256, 28-255, 28-254, 28-253, 28-252, 28-251,
27-259, 27-258, 27-257, 27-256, 27-255, 27-254, 27-253, 27-252, 27-251,
26-259, 26-258, 26-257, 26-256, 26-255, 26-254, 26-253, 26-252, 26-251,
25-259, 25-258, 25-257, 25-256, 25-255, 25-254, 25-253, 25-252, 25-251,
24-259, 24-258, 24-257, 24-256, 24-255, 24-254, 24-253, 24-252, 24-251,
of SEQ ID NO:73 or SEQ ID NO:79, or
28-245, 28-244, 28-243, 28-242, 28-241, 28-240, 28-239, 28-238, 28-237,
27-245, 27-244, 27-243, 27-242, 27-241, 27-240, 27-239, 27-238, 27-237,
26-245, 26-244, 26-243, 26-242, 26-241, 26-240, 26-239, 26-238, 26-237,
25-245, 25-244, 25-243, 25-242, 25-241, 25-240, 25-239, 25-238, 25-237,
24-245, 24-244, 24-243, 24-242, 24-241, 24-240, 24-239, 24-238, 24-237,
23-245, 23-244, 23-243, 23-242, 23-241, 23-240, 23-239, 23-238, 23-237,
22-245, 22-244, 22-243, 22-242, 22-241, 22-240, 22-239, 22-238, 22-237,
21-245, 21-244, 21-243, 21-242, 21-241, 21-240, 21-239, 21-238, 21-237,
20-245, 20-244, 20-243, 20-242, 20-241, 20-240, 20-239, 20-238, 20-237,
of SEQ ID NO:65, or
28-241, 28-240, 28-239, 28-238, 28-237, 28-236, 28-235, 28-234, 28-233,
27-241, 27-240, 27-239, 27-238, 27-237, 27-236, 27-235, 27-234, 27-233,
26-241, 26-240, 26-239, 26-238, 26-237, 26-236, 26-235, 26-234, 26-233, 25-241, 25-240, 25-239, 25-238, 25-237, 25-236, 25-235, 25-234, 25-233,
24-241, 24-240, 24-239, 24-238, 24-237, 24-236, 24-235, 24-234, 24-233,
23-241, 23-240, 23-239, 23-238, 23-237, 23-236, 23-235, 23-234, 23-233,
22-241, 22-240, 22-239, 22-238, 22-237, 22-236, 22-235, 22-234, 22-233,
21-241, 21-240, 21-239, 21-238, 21-237, 21-236, 21-235, 21-234, 21-233,
20-241, 20-240, 20-239, 20-238, 20-237, 20-236, 20-235, 20-234, 20-233,
of SEQ ID NO:66, or
28-255, 28-254, 28-253, 28-252, 28-251, 28-250, 28-249, 28-248, 28-247,
27-255, 27-254, 27-253, 27-252, 27-251, 27-250, 27-249, 27-248, 27-247,
26-255, 26-254, 26-253, 26-252, 26-251, 26-250, 26-249, 26-248, 26-247,
25-255, 25-254, 25-253, 25-252, 25-251, 25-250, 25-249, 25-248, 25-247,
24-255, 24-254, 24-253, 24-252, 24-251, 24-250, 24-249, 24-248, 24-247,
23-255, 23-254, 23-253, 23-252, 23-251, 23-250, 23-249, 23-248, 23-247,
22-255, 22-254, 22-253, 22-252, 22-251, 22-250, 22-249, 22-248, 22-247,
21-255, 21-254, 21-253, 21-252, 21-251, 21-250, 21-249, 21-248, 21-247,
20-255, 20-254, 20-253, 20-252, 20-251, 20-250, 20-249, 20-248, 20-247,
of SEQ ID NO:67.

Additional suitable fragments of non-human primate B7-H4 include, but are not limited to, the following:
27-249, 27-250, 27-251, 27-252, 27-253, 27-254, 27-255, 27-256, 27-257, 27-259, 27-260,
28-249, 28-250, 28-251, 28-252, 28-253, 28-254, 28-255, 28-256, 28-257, 28-259, 28-260,
29-249, 29-250, 29-251, 29-252, 29-253, 29-254, 29-255, 29-256, 29-257, 29-259, 29-260,
30-249, 30-250, 30-251, 30-252, 30-253, 30-254, 30-255, 30-256, 30-257, 30-259, 30-260,
31-249, 31-250, 31-251, 31-252, 31-253, 31-254, 31-255, 31-256, 31-257, 31-259, 31-260,
32-249, 32-250, 32-251, 32-252, 32-253, 32-254, 32-255, 32-256, 32-257, 32-259, 32-260
of SEQ ID NO:17 or SEQ ID NO:19, optionally with one to five amino acids of a signal peptide attached to the N-terminal end. The signal peptide may be any disclosed herein, including those contained within SEQ ID NOs:2, 3, 5, 6, 9, 10, 12, 13, 15, 17 and 19, or may be any signal peptide known in the art.

Additional suitable fragments of non-human primate B7-H4 include, but are not limited to, the following:
23-245, 23-246, 23-247, 23-248, 23-249, 23-250, 23-251, 23-252, 23-253, 23-254, 23-255,
24-245, 24-246, 24-247, 24-248, 24-249, 24-250, 24-251, 24-252, 24-253, 24-254, 24-255,
25-245, 25-246, 25-247, 25-248, 25-249, 25-250, 25-251, 25-252, 25-253, 25-254, 25-255,
26-245, 26-246, 26-247, 26-248, 26-249, 26-250, 26-251, 26-252, 26-253, 26-254, 26-255,
27-245, 27-246, 27-247, 27-248, 27-249, 27-250, 27-251, 27-252, 27-253, 27-254, 27-255,
28-245, 28-246, 28-247, 28-248, 28-249, 28-250, 28-251, 28-252, 28-253, 28-254, 28-255
of SEQ ID NO:15, optionally with one to five amino acids of a signal peptide attached to the N-terminal end. The signal peptide may be any disclosed herein, including those contained within SEQ ID NOs:2, 3, 5, 6, 9, 10, 12, 13, 15, 17 and 19, or may be any signal peptide known in the art.

Additional suitable fragments of non-human primate B7-H4 include, but are not limited to, fragments containing at least 25, 20, 75, 100 or 125 amino acids of the IgV domain as set forth in SEQ ID NO:83, SEQ ID NO:84 or SEQ ID NO:85. Exemplary fragments include, but are not limited to:
20-148, 20-149, 20-150, 20-151, 20-152, 20-153, 20-154, 20-155, 20-156,
21-148, 21-149, 21-150, 21-151, 21-152, 21-153, 21-154, 21-155, 21-156,
22-148, 22-149, 22-150, 22-151, 22-152, 22-153, 22-154, 22-155, 22-156,
23-148, 23-149, 23-150, 23-151, 23-152, 23-153, 23-154, 23-155, 23-156,
24-148, 24-149, 24-150, 24-151, 24-152, 24-153, 24-154, 24-155, 20-156,
25-148, 25-149, 25-150, 25-151, 25-152, 25-153, 25-154, 25-155, 25-156,
26-148, 26-149, 26-150, 26-151, 26-152, 26-153, 26-154, 26-155, 26-156,
27-148, 27-149, 27-150, 27-151, 27-152, 27-153, 27-154, 27-155, 27-156,
28-148, 28-149, 28-150, 28-151, 28-152, 28-153, 28-154, 28-155, 28-156,
of any of SEQ ID NO:65, SEQ ID NO:66, or SEQ ID NO:67, or
24-152, 24-153, 24-154, 24-155, 24-156, 24-157, 24-158, 24-159, 24-160,
25-152, 25-153, 25-154, 25-155, 25-156, 25-157, 25-158, 25-159, 25-160,
26-152, 26-153, 26-154, 26-155, 26-156, 26-157, 26-158, 26-159, 26-160,
27-152, 27-153, 27-154, 27-155, 27-156, 27-157, 27-158, 27-159, 27-160,
28-152, 28-153, 28-154, 28-155, 28-156, 28-157, 28-158, 28-159, 28-160,
29-152, 29-153, 29-154, 29-155, 29-156, 29-157, 29-158, 29-159, 29-160,
30-152, 30-153, 30-154, 30-155, 30-156, 30-157, 30-158, 30-159, 30-160,
31-152, 31-153, 31-154, 31-155, 31-156, 31-157, 31-158, 31-159, 31-160,
32-152, 32-153, 32-154, 32-155, 32-156, 32-157, 32-158, 32-159, 32-160,
of any of SEQ ID NO:71, SEQ ID NO:72, SEQ ID NO:73, SEQ ID NO:77, SEQ ID NO:78, or SEQ ID NO:79, optionally with one to five amino acids of a signal peptide attached to the N-terminal end. The signal peptide may be any disclosed herein, including those contained within SEQ ID NOs: 2, 3, 5, 6, 9, 10, 12, 13, 15, 17 and 19, or may be any signal peptide known in the art.

2. Variants of B7-H4 Polypeptides

Useful variants include those that increase biological activity, as indicated by any of the assays described herein, or that increase half life or stability of the protein. The B7-H4 polypeptides and B7-H4 fragments, or fusions thereof having B7-H4 activity, can be engineered to increase biological activity. In a preferred embodiment, the B7-H4 polypeptide or fusion protein has been modified with at least one amino acid substitution, deletion, or insertion that increases the binding of the molecule to an immune cell, for example a T cell, and transmits an inhibitory signal into the T cell.

Other preferred variants are those B7-H4 polypeptides that are engineered to selectively bind to one type of T cell versus other immune cells. For example, the B7-H4 polypeptide can be engineered to bind preferentially to Tregs, Th0, Th1, Th17, or Th22 cells. Preferential binding refers to binding that is at least 10%, 20%, 30%, 40%, 50%, 60%, 70%, 80%, 90%, 95%, or greater for one type of cell over another type of cell.

Still other variants of B7-H4 can be engineered to have reduced binding to immune cells relative to wildtype B7-H4. These variants can be used in combination with variants having stronger binding properties to modulate the immune response with a moderate impact.

Finally, variant B7-H4 polypeptides can be engineered to have an increased half-life relative to wildtype. These variants typically are modified to resist enzymatic degradation. Exemplary modifications include modified amino acid residues and modified peptide bonds that resist enzymatic degradation. Various modifications to achieve this are known in the art. For example, the juxtamembrane region of B7-H4 includes a dibasic motif, KRRS, which could potentially be recognized and cleaved, for example by a member of the proprotein convertase family of proteases. This motif (KRRS) can be removed to increase half life. The variants can be modified to adjust for effects of affinity for the receptor on the half life of B7-H4 polypeptides, fragments, or fusions thereof at serum and endosomal pH.

B. Second Polypeptide

The B7-H4 polypeptide may be fused to a second polypeptide. The presence of the second polypeptide can alter the solubility, stability, affinity and/or valency of the B7-H4 fusion polypeptide. As used herein, "valency" refers to the number of binding sites available per molecule. In one embodiment the second polypeptide is a polypeptide from a different source or different protein.

In one embodiment, the second polypeptide contains one or more domains of an immunoglobulin heavy chain constant region, preferably having an amino acid sequence corresponding to the hinge, $C_H2$ and $C_H3$ regions of a human immunoglobulin $C_\gamma1$ chain or to the hinge, $C_H2$ and $C_H3$ regions of a murine immunoglobulin Cγ2a chain. SEQ ID NOS: 88 and 89 provide exemplary sequences for the hinge, $C_H2$ and $C_H3$ regions of a human immunoglobulin $C_\gamma1$.

In a preferred dimeric fusion protein, the dimer results from the covalent bonding of Cys residue in the hinge region of two of the Ig heavy chains that are the same Cys residues that are disulfide linked in dimerized normal Ig heavy chains. Such proteins are referred to as B7-H4-Ig.

In one embodiment, the immunoglobulin constant domain may contain one or more amino acid insertions, deletions or substitutions that enhance binding to specific cell types, increase the bioavailability, or increase the stability of the B7-H4 polypeptides, fusion proteins, or fragments thereof. Suitable amino acid substitutions include conservative and non-conservative substitutions, as described above.

In another embodiment the second polypeptide may have a conjugation domain through which additional molecules can be bound to the B7-H4 fusion proteins. In one such embodiment, the conjugated molecule is capable of targeting the fusion protein to a particular organ or tissue. In another such embodiment the conjugated molecule is another immunomodulatory agent that can enhance or augment the effects of the B7-H4 fusion protein. In another embodiment the conjugated molecule is Polyethylene Glycol (PEG).

The Fc portion of the fusion protein may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, et al., Mol. Immun., 34(6):441-452 (1997), Swann, et al., Cur. Opin. Immun., 20:493-499 (2008), and Presta, Cur. Opin. Immun. 20:460-470 (2008). In some embodiments the Fc region is the native IgG1, IgG2, or IgG4 Fc region. In some embodiments the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG 1 with altered pH-dependent binding to FcRn. The Fc region may include the entire hinge region, or less than the entire hinge region.

The therapeutic outcome in patients treated with rituximab (a chimeric mouse/human IgG1 monoclonal antibody against CD20) for non-Hodgkin's lymphoma or Waldenstrom's macroglobulinemia correlated with the individual's expression of allelic variants of Fcγ receptors with distinct intrinsic affinities for the Fc domain of human IgG1. In particular, patients with high affinity alleles of the low affinity activating Fc receptor CD16A (FcγRIIIA) showed higher response rates and, in the cases of non-Hodgkin's lymphoma, improved progression-free survival. In another embodiment, the Fc domain may contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA)

Another embodiment includes IgG2-4 hybrids and IgG4 mutants that have reduce binding to FcR which increase their half life. Representative IG2-4 hybrids and IgG4 mutants are described in Angal, S. et al., Molecular Immunology, 30(1): 105-108 (1993); Mueller, J. et al., Molecular Immonology, 34(6): 441-452 (1997); and U.S. Pat. No. 6,982,323 to Wang et al. In some embodiments the IgG1 and/or IgG2 domain is deleted for example, Angal et al. describe IgG1 and IgG2 having serine 241 replaced with a proline.

In a preferred embodiment, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, et al., Cancer Res., 57(18):8882-90 (2007). Exemplary variants of human IgG1 Fc domains with reduced binding to CD32B and/or increased binding to CD16A contain F243L, R929P, Y300L, V305I or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297Q substitution, as this mutation abolishes FcR binding.

C. Peptide or Polypeptide Linker Domain

The disclosed B7-H4 fusion proteins optionally contain a peptide or polypeptide linker domain that separates the B7-H4 polypeptide from the second polypeptide.

1. Hinge Region of Antibodies

In one embodiment, the linker domain contains the hinge region of an immunoglobulin. In a preferred embodiment, the hinge region is derived from a human immunoglobulin. Suitable human immunoglobulins that the hinge can be derived from include IgG, IgD and IgA. In a preferred embodiment, the hinge region is derived from human IgG. Amino acid sequences of immunoglobulin hinge regions and other domains are well known in the art.

In one embodiment, B7-H4 fusion polypeptides contain the hinge, $C_H2$ and $C_H3$ regions of a human immunoglobulin Cγ1 chain encoded by a nucleic acid having at least 80%, 85%, 90%, 95%, 99% or 100% sequence identity to:

```
                                                    (SEQ ID NO: 86)
gagcctaagt catgtgacaa gacccatacg tgcccaccct gtcccgctcc agaactgctg    60
gggggaccta gcgttttctt gttcccccca aagcccaagg acaccctcat gatctcacgg   120
actcccgaag taacatgcgt agtagtcgac gtgagccacg aggatcctga agtgaagttt   180
aattggtacg tggacggagt cgaggtgcat aatgccaaaa ctaaacctcg ggaggagcag   240
tataacagta cctaccgcgt ggtatccgtc ttgacagtgc tccaccagga ctggctgaat   300
ggtaaggagt ataaatgcaa ggtcagcaac aaagctcttc ccgccccaat tgaaaagact   360
atcagcaagg ccaagggaca accccgcgag ccccaggttt acacccttcc accttcacga   420
gacgagctga ccaagaacca ggtgtctctg acttgtctgg tcaaaggttt ctatccttcc   480
gacatcgcag tggagtggga gtcaaacggg cagcctgaga ataactacaa gaccacaccc   540
ccagtgcttg atagcgatgg gagcttttc ctctacagta agctgactgt ggacaaatcc   600
cgctggcagc agggaaacgt tttctcttgt agcgtcatgc atgaggccct ccacaaccat   660
tatactcaga aaagcctgag tctgagtccc ggcaaa,                            696
or
                                                    (SEQ ID NO: 87)
gacaagaccc atacgtgccc accctgtccc gctccagaac tgctggggg acctagcgtt     60 ttcttgttcc ccccaaagcc caaggacacc ctcatgatct cacggactcc cgaagtaaca   120
tgcgtagtag tcgacgtgag ccacgaggat cctgaagtga agtttaattg gtacgtggac   180
ggagtcgagg tgcataatgc caaaactaaa cctcgggagg agcagtataa cagtacctac   240
cgcgtggtat ccgtcttgac agtgctccac caggactggc tgaatggtaa ggagtataaa   300
tgcaaggtca gcaacaaagc tcttcccgcc ccaattgaaa agactatcag caaggccaag   360
ggacaacccc gcgagcccca ggtttacacc cttccaccct cacgagacga gctgaccaag   420
aaccaggtgt ctctgacttg tctggtcaaa ggtttctatc cttccgacat cgcagtggag   480
tgggagtcaa acgggcagcc tgagaataac tacaagacca cccccagt gcttgatagc   540 gatgggagct ttttcctcta cagtaagctg actgtggaca atcccgctg gcagcaggga   600 aacgttttct cttgtagcgt catgcatgag gccctccaca accattatac tcagaaaagc   660
ctgagtctga gtcccggcaa a.                                            681
```

The hinge, $C_H2$ and $C_H3$ regions of a human immunoglobulin Cγ1 chain encoded by SEQ ID NO:86 has the following amino acid sequence:

```
                                                    (SEQ ID NO: 88)
EPKSCDKTHT CPPCPAPELL GGPSVFLFPP KPKDTLMISR TPEVTCVVVD VSHEDPEVKF     60

NWYVDGVEVH NAKTKPREEQ YNSTYRVVSV LTVLHQDWLN GKEYKCKVSN KALPAPIEKT   120

ISKAKGQPRE PQVYTLPPSR DELTKNQVSL TCLVKGFYPS DIAVEWESNG QPENNYKTTP   180

PVLDSDGSFF LYSKLTVDFS RWQQGNVFSC SVMBEALHNH YTQKSLSLSP GK.          232
```

The hinge, CH2 and CH3 regions of a human immunoglobulin Cγ1 chain encoded by SEQ ID NO:87 has the following amino acid sequence:

```
                                                        (SEQ ID NO: 89)
DKTHTCPPCP APELLGGPSV FLFPPKPKDT LMISRTPEVT CVVVDVSHED PEVKFNWYVD    60

GVEVHNAKTK PREEQYNSTY RVVSVLTVLH QDWLNGKEYK CKVSNKALPA PIEKTISKAK   120

GQPREPQVYT LPPSRDELTK NQVSLTCLVK GFYPSDIAVE WESNGQPENN YKTTPPVLDS   180

DGSFFLYSKL TVDKSRWQQG NVFSCSVNHE ALHNHYTQKS LSLSPGK.                227
```

The hinge can be further shortened to remove amino acids 1, 2, 3, 4, 5, or combinations thereof of SEQ ID NO:89. In one embodiment, amino acids 1 and 2 of SEQ ID NO:89 are deleted.

In another embodiment, the B7-H4 fusion polypeptides contain the hinge, $C_H2$ and $C_H3$ regions of a murine immunoglobulin Cγ2a chain encoded by a nucleic acid having at least 80%, 85%, 90%, 95%, 99% or 100% sequence identity to:

```
                                                        (SEQ ID NO: 90)
gagccaagag gtcctacgat caagccctgc ccgccttgta aatgcccagc tccaaatttg    60
ctgggtggac cgtcagtctt tatcttcccg ccaaagataa aggacgtctt gatgattagt   120
ctgagcccca tcgtgacatg cgttgtggtg gatgtttcag aggatgaccc cgacgtgcaa   180
atcagttggt tcgttaacaa cgtggaggtg cataccgctc aaacccagac ccacagagag   240
gattataaca gcaccctgcg ggtagtgtcc gccctgccga tccagcatca ggattggatg   300
agcgggaaag agttcaagtg taaggtaaac aacaaagatc tgccagcgcc gattgaacga   360
accattagca agccgaaagg gagcgtgcgc gcacctcagg tttacgtcct tcctccacca   420
gaagaggaga tgacgaaaaa gcaggtgacc ctgacatgca tggtaactga ctttatgcca   480
gaagatattt acgtggaatg gactaataac ggaaagacag agctcaatta caagaacact   540
gagcctgttc tggattctga tggcagctac tttatgtact ccaaattgag ggtcgagaag   600
aagaattggg tcgagagaaa cagttatagt tgctcagtgg tgcatgaggg cctccataat   660
catcacacca caaagtcctt cagccgaacg cccgggaaa                          699
```

The hinge, $C_H2$ and $C_H3$ regions of a murine immunoglobulin Cγ2a chain encoded by SEQ ID NO:90 has the following amino acid sequence:

```
                                                        (SEQ ID NO: 91)
EPRGPTIKPC PPCKCPAPNL LGGPSVFIFP PKIKDVLMIS LSPIVTCVVV DVSEDDPDVQ    60

ISWFVNNVEV HTAQTQIHRE DYNSTLRVVS ALPIQHQDWM SGKEFKCKVN NKDLPAPIER   120

TISKPKGSVR APQVYVLPPP EEEMTEKQVT LTCMVTDFMP EDIYVEWTNN GKTELNYKNT   180

EPVLDSDGSY FMYSKLEVEK KNWVERNSYS CSVVHEGLHN HHTTKSFSRT PGK          233
```

In another embodiment, the linker domain contains a hinge region of an immunoglobulin as described above, and further includes one or more additional immunoglobulin domains.

2. Other Peptide/Polypeptide Linker Domains

Other suitable peptide/polypeptide linker domains include naturally occurring or non-naturally occurring peptides or polypeptides. Peptide linker sequences are at least 2 amino acids in length. Preferably the peptide or polypeptide domains are flexible peptides or polypeptides. A "flexible linker" herein refers to a peptide or polypeptide containing two or more amino acid residues joined by peptide bond(s) that provides increased rotational freedom for two polypeptides linked thereby than the two linked polypeptides would have in the absence of the flexible linker. Such rotational freedom allows two or more antigen binding sites joined by the flexible linker to each access target antigen(s) more efficiently. Exemplary flexible peptides/polypeptides include, but are not limited to, the amino acid sequences Gly-Ser, Gly-Ser-Gly-Ser (SEQ ID NO:92), Ala-Ser, Gly-Gly-Gly-Ser (SEQ ID NO:93), (Gly$_4$-Ser)$_3$ (SEQ ID NO:94) and (Gly$_4$-Ser)$_4$ (SEQ ID NO:95). Additional flexible peptide/polypeptide sequences are well known in the art.

D. Dimerization, Multimerization and Targeting Domains

The fusion proteins disclosed herein optionally contain a dimerization or multimerization domain that functions to dimerize or multimerize two or more fusion proteins. The domain that functions to dimerize or multimerize the fusion proteins can either be a separate domain, or alternatively can be contained within one of the other domains (B7-H4 polypeptide, second polypeptide, or peptide/polypeptide linker domain) of the fusion protein.

1. Dimerization Domains

A "dimerization domain" is formed by the association of at least two amino acid residues or of at least two peptides or polypeptides (which may have the same, or different, amino acid sequences). The peptides or polypeptides may interact with each other through covalent and/or non-covalent association(s). Preferred dimerization domains contain at least one cysteine that is capable of forming an intermolecular disulfide bond with a cysteine on the partner fusion protein. The dimerization domain can contain one or more cysteine residues such that disulfide bond(s) can form between the partner fusion proteins. In one embodiment, dimerization domains contain one, two or three to about ten cysteine residues. In a preferred embodiment, the dimerization domain is the hinge region of an immunoglobulin.

Additional exemplary dimerization domain can be any known in the art and include, but not limited to, coiled coils, acid patches, zinc fingers, calcium hands, a $C_H1$-$C_L$ pair, an "interface" with an engineered "knob" and/or "protruberance" as described in U.S. Pat. No. 5,821,333, leucine zippers (e.g., from jun and/or fos) (U.S. Pat. No. 5,932,448), SH2 (src homology 2), SH3 (src Homology 3) (Vidal, et al., *Biochemistry*, 43, 7336-44 ((2004)), phosphotyrosine binding (PTB) (Zhou, et al., *Nature*, 378:584-592 (1995)), WW (Sudol, *Prog. Biochys. Mol. Bio.*, 65:113-132 (1996)), PDZ (Kim, et al., *Nature*, 378: 85-88 (1995); Komau, et al., *Science*, 269: 1737-1740 (1995)) 14-3-3, WD40 (Hu, et al., *J Biol Chem.*, 273, 33489-33494 (1998)) EH, Lim, an isoleucine zipper, a receptor dimer pair (e.g., interleukin-8 receptor (IL-8R); and integrin heterodimers such as LFA-1 and GPIIIb/IIIa), or the dimerization region(s) thereof, dimeric ligand polypeptides (e.g. nerve growth factor (NGF), neurotrophin-3 (NT-3), interleukin-8 (IL-8), vascular endothelial growth factor (VEGF), VEGF-C, VEGF-D, PDGF members, and brain-derived neurotrophic factor (BDNF) (Arakawa, et al., *J. Biol. Chem.*, 269(45): 27833-27839 (1994) and Radziejewski, et al., *Biochem.*, 32(48): 1350 (1993)) and can also be variants of these domains in which the affinity is altered. The polypeptide pairs can be identified by methods known in the art, including yeast two hybrid screens. Yeast two hybrid screens are described in U.S. Pat. Nos. 5,283,173 and 6,562,576. Affinities between a pair of interacting domains can be determined using methods known in the art, including as described in Katahira, et al., *J. Biol. Chem.*, 277, 9242-9246 (2002)). Alternatively, a library of peptide sequences can be screened for heterodimerization, for example, using the methods described in WO 01/00814. Useful methods for protein-protein interactions are also described in U.S. Pat. No. 6,790,624.

2. Multimerization Domains

A "multimerization domain" is a domain that causes three or more peptides or polypeptides to interact with each other through covalent and/or non-covalent association(s). Suitable multimerization domains include, but are not limited to, coiled-coil domains. A coiled-coil is a peptide sequence with a contiguous pattern of mainly hydrophobic residues spaced 3 and 4 residues apart, usually in a sequence of seven amino acids (heptad repeat) or eleven amino acids (undecad repeat), which assembles (folds) to form a multimeric bundle of helices. Coiled-coils with sequences including some irregular distribution of the 3 and 4 residues spacing are also contemplated. Hydrophobic residues are in particular the hydrophobic amino acids Val, Ile, Leu, Met, Tyr, Phe and Trp. "Mainly hydrophobic" means that at least 50% of the residues must be selected from the mentioned hydrophobic amino acids.

The coiled coil domain may be derived from laminin. In the extracellular space, the heterotrimeric coiled coil protein laminin plays an important role in the formation of basement membranes. Apparently, the multifunctional oligomeric structure is required for laminin function. Coiled coil domains may also be derived from the thrombospondins in which three (TSP-1 and TSP-2) or five (TSP-3, TSP-4 and TSP-5) chains are connected, or from COMP (COMPcc) (Guo, et al., *EMBO J.*, 1998, 17: 5265-5272) which folds into a parallel five-stranded coiled coil (Malashkevich, et al., *Science*, 274: 761-765 (1996)).

Additional coiled-coil domains derived from other proteins, and other domains that mediate polypeptide multimerization are known in the art and are suitable for use in the disclosed fusion proteins.

In another embodiment, B7-H4 polypeptides, fusion proteins, or fragments thereof can be induced to form multimers by binding to a second multivalent polypeptide, such as an antibody. Antibodies suitable for use to multimerize B7-H4 polypeptides, fusion proteins, or fragments thereof include, but are not limited to, IgM antibodies and cross-linked, multivalent IgG, IgA, IgD, or IgE complexes.

3. Targeting Domains

The B7-H4 polypeptides and fusion proteins can contain a targeting domain to target the molecule to specific sites in the body. Preferred targeting domains target the molecule to areas of inflammation. Exemplary targeting domains are antibodies, or antigen binding fragments thereof that are specific for inflamed tissue or to a proinflammatory cytokine including but not limited to IL17, IL-4, IL-6, IL-12, IL-21, IL-22, and IL-23. In the case of neurological disorders such as Multiple Sclerosis, the targeting domain may target the molecule to the CNS or may bind to VCAM-1 on the vascular epithelium. Additional targeting domains can be peptide aptamers specific for a proinflammatory molecule. In other embodiments, the B7-H4 fusion protein can include a binding partner specific for a polypeptide displayed on the surface of an immune cell, for example a T cell. In still other embodiments, the targeting domain specifically targets activated immune cells. Preferred immune cells that are targeted include Th0, Th1, Th17 and Th22 T cells, other cells that secrete, or cause other cells to secrete inflammatory molecules including, but not limited to, IL-1β, TNF-α, TGF-beta, IFN-γ, IL-17, IL-6, IL-23, IL-22, IL-21, and MMPs, and Tregs. For example, a targeting domain for Tregs may bind specifically to CD25.

In another embodiment, the B7-H4 polypeptides, fragments, or fusions thereof can contain a targeting domain to target the molecule to an organ or tissue that is being transplanted. For example, the targeting domain can be an antibody, antigen binding fragment thereof, or another binding partner specific for a polypeptide displayed on the surface of cells specific to the type of organ or tissue being transplanted.

E. Exemplary Fusion Proteins

A representative murine B7-H4 fusion protein is encoded by a nucleic acid having at least 80%, 85%, 90%, 95%, 99% or 100% sequence identity to:

(SEQ ID NO: 96)
```
atggcttcct tggggcagat catcttttgg agtattatta acatcatcat catcctggct   60
ggggccatcg cactcatcat tggctttggc atttcaggca agcacttcat cacggtcacg  120
accttcacct cagctggaaa cattggagag gacgggaccc tgagctgcac ttttgaacct  180
gacatcaaac tcaacggcat cgtcatccag tggctgaaag aaggcatcaa aggtttggtc  240
cacgagttca agaaggcaa agacgacctc tcacagcagc atgagatgtt cagaggccgc  300
```

```
acagcagtgt tgctgatca ggtggtagtt ggcaatgctt ccctgagact gaaaaacgtg   360
cagctcacgg atgctggcac ctacacatgt tacatccgca cctcaaaagg caagggaat   420
gcaaaccttg agtataagac cggagccttc agtatgccag agataaatgt ggactataat   480
gccagttcag agagtttacg ctgcgaggct cctcggtggt tcccccagcc acagtggcc   540
tgggcatctc aagtcgacca aggagccaat ttctcagaag tctccaacac cagctttgag   600
ttgaactctg agaatgtgac catgaaggtc gtatctgtgc tctacaatgt cacaatcaac   660
aacacatact cctgtatgat tgaaaacgac attgccaaag ccaccgggga catcaaagtg   720
acagattcag aggtcaaaag gcgaagtcag ctgcagttgc tgaactctgg ggagccaaga   780
ggtcctacga tcaagccctg cccgccttgt aaatgcccag ctccaaattt gctgggtgga   840
ccgtcagtct ttatcttccc gccaaagata aggacgtct tgatgattag tctgagcccc   900
atcgtgacat gcgttgtggt ggatgtttca gaggatgacc ccgacgtgca aatcagttgg   960
ttcgttaaca acgtggaggt gcataccgct caaacccaga cccacagaga ggattataac  1020
agcaccctgc gggtagtgtc cgccctgccg atccagcatc aggattggat gagcgggaaa  1080
gagttcaagt gtaaggtaaa caacaaagat ctgccagcgc cgattgaacg aaccattagc  1140
aagccgaaag ggagcgtgcg cgcacctcag gtttacgtcc ttcctccacc agaagaggag  1200
atgacgaaaa agcaggtgac cctgacatgc atggtaactg actttatgcc agaagatatt  1260
tacgtggaat ggactaataa cggaaagaca gagctcaatt acaagaacac tgagcctgtt  1320
ctggattctg atggcagcta ctttatgtac tccaaattga gggtcgagaa gaagaattgg  1380
gtcgagagaa acagttatag ttgctcagtg gtgcatgagg cctccataa tcatcacacc  1440
acaaagtcct tcagccgaac gcccgggaaa,                                 1470
                                                       (SEQ ID NO: 97)
atggagtggt catgggtttt tctgttcttt cttagcgtga ctacaggcgt ccattcagga    60
ttcggcataa gcgcaagca cttcatcaca gttacaacgt ttacaagtgc ggggaacatt   120
ggggaagatg gaacattgtc atgtacattt gagccagata tcaaactcaa tggaatagta   180
attcagtggc ttaaggaggg catcaagggc tggtccacg aatttaagga ggggaaagac   240
gatctgtctc agcagcacga gatgttcagg ggcagaaccg ccgtcttcgc agaccaggtt   300
gtggtaggca cgccagtttt gcggctgaaa aacgtcagc tgactgacgc cggcacctac   360
acatgctata tccggtcctc taagggcaag gggaacgcta atctcgagta caaaacaggc   420
gccttttcta tgccagagat caacgtggac tataacgcaa gctctgaaag tctgagatgc   480
gaggcgccaa ggtggttccc tcagcccacc gtcgcgtggg cttcccaggt ggatcaaggc   540
gccaactttt ctgaggtttc taacaccagc ttcgaactga acagcgaaaa tgtgacaatg   600
aaggtagtca gcgttctgta aacgtgacc atcaacaata cttactcctg tatgatagaa   660
aatgatatag ccaaggctac aggagatatt aaagtgacgg attcagaagt gaaaggagg   720
agtcaactgc aactcttgaa tagcggcgag ccaagaggtc ctacgatcaa gcctgcccg   780
ccttgtaaat gcccagctcc aaatttgctg ggtggaccgt cagtctttat cttcccgcca   840
aagataaagg acgtcttgat gattagtctg agccccatcg tgcatgcgt tgtggtggat   900
gtttcagagg atgaccccga cgtgcaaatc agttggttcg ttaacaacgt ggaggtgcat   960
accgctcaaa cccagaccca cagagaggat ataacagca cctgcgggt agtgtccgcc  1020
ctgccgatcc agcatcagga ttggatgagc gggaaagagt tcaagtgtaa ggtaaacaac  1080
aaagatctgc cagcgccgat tgaacgaacc attagcaagc cgaagggag cgtgcgcgca  1140
cctcaggttt acgtccttcc tccaccagaa gaggagatga cgaaaaagca ggtgaccctg  1200
```

```
acatgcatgg taactgactt tatgccagaa gatatttacg tggaatggac taataacgga 1260
aagacagagc tcaattacaa gaacactgag cctgttctgg attctgatgg cagctacttt 1320
atgtactcca aattgagggt cgagaagaag aattgggtcg agagaaacag ttatagttgc 1380
tcagtggtgc atgagggcct ccataatcat cacaccacaa agtccttcag ccgaacgccc 1440
gggaaa                                                             1446
or
                                                    (SEQ ID NO: 98)
atggagtggt catgggtttt tctgttcttt cttagcgtga ctacaggcgt ccattcagga   60
ttcggcataa gcggcaagca cttcatcaca gttacaacgt ttacaagtgc ggggaacatt  120
ggggaagatg gaacattgtc atgtacattt gagccagata tcaaactcaa tggaatagta  180
attcagtggc ttaaggaggg catcaagggc ctggtccacg aatttaagga ggggaaagac  240
gatctgtctc agcagcacga gatgttcagg gcagaaccg ccgtcttcgc agaccaggtt  300
gtggtaggca cgccagttt gcggctgaaa aacgtgcagc tgactgacgc cggcacctac  360
acatgctata tccggaccct caagggcaag gggaacgcta atctcgagta caaaacaggc  420
gcctttccta tgccagagat caacgtggac tataacgcaa gctctgaaag tctgagatgc  480
gaggcgccaa ggtggttccc tcagcccacc gtcgcgtggg cttcccaggt ggatcaaggc  540
gccaactttt ctgaggtttc taacaccagc ttcgaactga acagcgaaaa tgtgacaatg  600
aaggtagtca gcgttctgta taacgtgacc atcaacaata cttactcctg tatgatagaa  660
aatgatatag ccaaggctac aggagatatt aaagtgacgg attcagaagt gaaaaggagg  720
agtcaactgc aactcttgaa tagcggcgag ccaagaggtc ctacgatcaa gccctgcccg  780
ccttgtaaat gcccagctcc aaatttgctg ggtggaccgt cagtctttat cttccgcca   840 aagataaagg acgtcttgat gattagtctg agccccatcg tgacatgcgt tgtggtggat  900
gtttcagagg atgaccccga cgtgcaaatc agttggttcg ttaacaacgt ggaggtgcat  960
accgctcaaa cccagaccca cagagaggat tataacagca ccctgcgggt agtgtccgcc 1020
ctgccgatcc agcatcagga ttggatgagc gggaaagagt tcaagtgtaa ggtaaacaac 1080
aaagatctgc cagcgccgat tgaacgaacc attagcaagc cgaagggag cgtgcgcgca 1140 cctcaggttt acgtccttcc tccaccagaa gaggagatga cgaaaaagca ggtgaccctg 1200
acatgcatgg taactgactt tatgccagaa gatatttacg tggaatggac taataacgga 1260
aagacagagc tcaattacaa gaacactgag cctgttctgg attctgatgg cagctacttt 1320
atgtactcca aattgagggt cgagaagaag aattgggtcg agagaaacag ttatagttgc 1380
tcagtggtgc atgagggcct ccataatcat cacaccacaa agtccttcag ccgaacgccc 1440
gggaaa                                                             1446
```

In another embodiment, a representative murine B7-H4 fusion protein has at least 80%, 85%, 90%, 95%, 99% or 100% sequence identity to:

```
                                                    (SEQ ID NO: 99)
MASLGQIIFW SIINIIIILA GAIALIIGFG ISGKHFITVT TFTSAGNIGE DGTLSCTFEP   60

DIKLNGIVIQ WLKEGIKGLV HEETEGKDDL SQQHEMFRGR TAVFADQVVV GNASLRLKNV  120

QLTDAGTYTC YIRSSKGKGN ANLEYKTGAF SMPEINVDYN ASSESLRCEA PRWFPQPTVA  180

WASQVDQGAN FSEVSNTSFE LNSENVTMKV VSVLYNVTIN NTYSCMIEND IAKATGDIKV  240

TDSEVKRRSQ LQLLNSGEPR GPTIKPCPPC KCPAPNLIGG PSVFIFPPKI KDVLMISLSP  300
```

```
                                                                    (SEQ ID NO: 100)
IVTCVVVDVS EDDPDVQISW FVNNVEVHTA QTQTHREDYN STLRVVSALP IQHQDWMSGK        360

EFKCKVNNKD LPAPIERTIS KPKGSVRAPQ VYVLPPPEEE MTKKQVTLTC MVTDFMPEDI        420

YVEWTNNGKT ELNYKNTEPV LDSDGSYFMY SKLRVEKKNW VERNSYSCSV VHEGLHNHHT        480

TKSFSRTPGK,                                                             490

(SEQ ID NO: 100)
MASLGQIIFW SIINIIIILA GAIALIIGFG ISGKHFITVT TFTSAGNIGE DGTLSCTFEP         60

DIKLNGIVIQ WLKEGIKGLV HEFKEGKDDL SQQHEMFRGR TAVFADQVVV GNASLRLKNV        120

QLTDAGTYTC YIRTSKGXGN ANLEYKTGAF SMPEINVDYN ASSESLRCEA PRWFPQPTVA        180

WASQVDQGAN FSEVSNTSFE LNSENVTMKV VSVLYNVTIN NTYSCMIEND IAKATGDIKV        240

TDSEVKRRSQ LQLLNSGEPR GPTIKPCPPC KCPAPNLLGG PSVFIFPPKI KDVLMISLSP        300

IVTCVVVDVS EDDPDVQISW FVNNVEVHTA QTQTHREDYN STLRVVSALP IQHQDWMSGK        360

EFKCKVNNKD LPAPIERTIS KPKGSVRAPQ VYVLPPPEEE MTKKQVTLTC MVTDEMPEDI        420

YVEWTNNGKT ELNYKNTEPV LDSDGSYFMY SKLRVEKKNW VERNSYSCSV VHEGLHNHHT        480

TKSFSRTPGK,                                                             490

(SEQ ID NO:101)
MEWSWVELFF LSVTTGVHSG FGISGKHFIT VTTFTSAGNI GEDGTLSCTF EPDIKLNGIV         60

IQWLKEGIKG LVHEFKEGKD LSQQHEMFR GRTAVFADQV VVGNASLRLK NVQLTDAGTY         120

TCYIRSSKGK GNANLEYKTG AFSMPEINVD YNASSESLRC EAPRWFPQPT VAWASQVDQG        180

ANFSEVSNTS FELNSENVTM KVVSVLYNVT INNTYSCMIE NDIAKATGDI KVTDSEVKRR        240

SQLQLLNSGE PRGPTIKPCP PCKCPAPNLL GGPSVFIFPP KIKDVLMISL SPIVTCVVVD        300

VSEDDPDVQI SWFVNNVEVH TAQTQTHRED YNSTLRVVSA LPIQHQDWMS GKEFKCKVNN        360

KDLPAPIERT ISKPKGSVRA PQVYVLPPPE EEMTKKQVTL TCMVTDFMPE DIYVEWTNNG        420

KTELNYKNTE PVLDSDGSYF MYSKLRVEKK NWVERNSYSC SVVHEGLHNH HTTKSFSRTP        480

GK                                                                      482
or
                                                                    (SEQ ID NO: 102)
MEWSWVFLFF LSVTTGVHSG FGISGKHFIT VTTFTSAGNI GEDGTLSCTF EPDIKLNGIV         60

IQWLKEGIKG LVHEFKEGKD LSQQHEMFR GRTAVFADQV VVGNASLRLK NVQLTDAGTY         120

TCYIRTSKGK GNANLEYKTG AFSMPEINVD YNASSESLRC EAPRWFPQPT VAWASQVDQG        180

ANFSEVSNTS FELNSENVTM KVVSVLYNVT INNTYSCMIE NDIAKATGDI KVTDSEVKRR        240

SQLQIINSGE PRGPTIKPCP PCKCPAPNLL GGPSVFIFPP KIKDVLMISL SPIVTCVVVD        300

VSEDDPDVQI SWFVNNVEVH TAQTQTHRED YNSTLRVVSA LPIQHQDWMS GKEFKCKVNN        360

KDLPAPIERT ISKPKGSVRA PQVYVLPPPE EEMTKKQVTL TCMVTDFMPE DTYVEWTNNG        420

KTELNYKNTE PVLDSDGSYT MYSKLRVEKK NWVERNSYSC SVVHEGLHNH HTTKSFSRTP        480

GK.                                                                     482
```

The amino acid sequence of the murine B7-H4 fusion protein of SEQ ID NO:99 and SEQ ID NO:101 without the signal sequence is:

```
                                                                    (SEQ ID NO: 103)
GFGISGKHFI TVTTFTSAGN IGEDGTLSCT FEPDIKLNGI VIQWLKEGIK GLVHEFKEGK         60

DDLSQQHEMF RGRTAVFADQ VVVGNASLRL KNVQLTDAGT YTCYIRSSKG KGNANLEYKT        120

GAFSMPEINV DYNASSESLR CEAPRWFPQP TVAWASQVDQ GANFSEVSNT SFELNSENVT        180

MKVVSVLYNV TINNTYSCMI ENDIAKATGD IKVTDSEVKR RSQLQLLNSG EPRGPTIKPC        240
```

```
PPCKCPAPNL LGGGPSVFIFP PKIKDVLMIS LSPIVTCVVV DVSEDDPDVQ ISWFVNNVEV      300

HTAQTQTHRE DYNSTLRVVS ALPIQHQDWM SGKEFKCKVN NKDLPAPIER TISKPKGSVR      360

APQVYVLPPP EEEMTKKQVT LTCMVTDFMP EDIYVEWTNN GKTELNYKNT EPVLDSDGSY      420

EMYSKLRVEK KNWVERNSYS CSVVHEGLHN HHTTKSFSRT PGK.                      463
```

The amino acid sequence of the murine B7-H4 fusion protein of SEQ ID NO:100 and SEQ ID NO:102 without the signal sequence is:

```
                                                              (SEQ ID NO: 104)
GFGISGKHFI TVTTFTSAGN IGEDGTLSCT FEPDIKLNGI VIQWLKEGIK GLVHEFKEGK       60

DDLSQQHEMF RGRTAVFADQ VVVGNASLRL KNVQLTDAGT YTCYIRTSKG KGNANLEYKT      120

GAFSMPEINV DYNASSESLR CEAPRWFPQP TVAWASQVDQ GANFSEVSNT SFELNSENVT      180

MKVVSVLYNV TINNTYSCMI ENDIAKATGD IKVTDSEVKR RSQLQLLNSG EPRGPTIKPC      240

PPCKCPAPNL LGGPSVFIFP PKIKDVLMIS LSPIVTCVVV DVSEDDPDVQ ISWFVNNVEV      300

HTAQTQTHRE DYNSTLRVVS ALPIQHQDWM SGREFKCKVN NKDLPAPIER TISKPKGSVR      360

APQVYVLPPP EEEMTKKQVT LTCMVTDFMP EDIYVEWTNN GKTELNYKNT EPVLDSDGSY      420

FMYSKLRVEK KNWVERNSYS CSVVHEGLHN HHTTRSFSRT PGK.                      463
```

A representative human B7-H4 fusion protein is encoded by a nucleic acid having at least 80%, 85%, 90%, 95%, 99% or 100% sequence identity to:

```
                                                              (SEQ ID NO: 105)
atggcttccc tgggcagat ccctcttctgg agcataatta gcatcatcat tattctggct       60
ggagcaattg cactcatcat tggctttggt atttcaggga gacactccat cacagtcact      120
actgtcgcct cagctgggaa cattggggag atggaatcc tgagctgcac ttttgaacct      180
gacatcaaaC tttctgatat cgtgatacaa tggctgaagg aaggtgtttt aggcttggtc      240
catgagttca agaaggcaa agatgagctg tcggagcagg atgaaatgtt cagaggccgg      300
acagcagtgt ttgctgatca agtgatagtt ggcaatgcct ctttgcggct gaaaaacgtg      360
caactcacag atgctggcac ctacaaatgt tatatcatca cttctaaagg caaggggaat      420
gctaaccttg agtataaaac tggagccttc agcatgccgg aagtgaatgt ggactataat      480
gccagctcag agaccttgcg tgtgaggct ccccgatggt tcccccagcc cacagtggtc      540
tgggcatccc aagttgacca gggagccaac ttctcggaag tctccaatac cagctttgag      600
ctgaactctg agaatgtgac catgaaggtt gtgtctgtgc tctacaatgt tacgatcaac      660
aacacatact cctgtatgat tgaaaatgac attgccaaag caacaggga tatcaaagtg      720 acagaatcgg agatcaaaag gcggagtgag cctaagtcat gtgacaagac ccatacgtgc      780
ccaccctgtc ccgctccaga actgctgggg ggacctagcg ttttcttgtt cccccccaaag     840 cccaaggaca ccctcatgat ctcacggact cccgaagtaa catgcgtagt agtcgacgtg      900
agccacgagg atcctgaagt gaagtttaat tggtacgtgg acggagtcga ggtgcataat      960
gccaaaacta aacctcggga ggagcagtat aacagtacct accgcgtggt atccglcttg    1020 acagtgctcc accaggactg gctgaatggt aaggagtata atgcaaggt cagcaacaaa    1080 gctcttcccg ccccaattga aaagactatc agcaaggca agggacaacc ccgcgagccc    1140 caggttaca cccttccacc ttcacgagac gagctgacca gaaccaggt gtctctgact    1200 tgtctggtca aaggtttcta tccttccgac atcgcagtgg agtgggagtc aaacgggcag    1260
```

-continued

```
cctgagaata actacaagac cacacccca gtgcttgata gcgatgggag cttttcctc      1320 tacagtaagc tgactgtgga caaatcccgc tggcagcagg gaaacgtttt ctcttgtagc    1380
gtcatgcatg aggccctcca caaccattat actcagaaaa gcctgagtct gagtcccggc    1440 aaa,                                                                 1443
                                                         (SEQ ID NO: 106)
atggaatgga gctgggtatt tctgtttttc ctgtcagtaa cgactggcgt ccattcaggc      60
ttcggcatca gtggacggca cagtatcaca gtgaccaccg tcgcctccgc tggcaatata     120
ggtgaggatg gcatccagtc ctgtaccttt gagccggaca tcaaactgtc tgacatagtg     180
atacaatggc tgaaggaggg ggtgctcggt ctggtacatg agtttaagga agggaaggat     240
gaactgtccg agcaggatga gatgttccgg gcgaggaccg ctgtgttcgc cgatcaggta     300
atcgtcggaa atgcaagtct cagattgaaa aatgtgcaac tgactgatgc tggcacgtat     360
aaatgctaca ttatcacaag taagggcaaa ggaaatgcta accttgagta taaaacaggc     420
gcattctcaa tgcccgaggt caatgtcgac tataatgcca gcagtgaaac attgcgctgt     480
gaagctcccc gctggttccc ccagccaacc gtggtctggg cctctcaggt tgatcagggg     540
gctaactttt ccgaggtgag caacaccagc ttcgaactca actctgagaa tgtgaccatg     600
aaagttgtgt ctgtcctgta taatgtaaca atcaacaaca cttattcatg catgattgaa     660
aacgacatcg ccaaggcaac aggtgatatt aaggtaactg aatccgagat caaacggcgg     720
tctgagccta agtcatgtga caagacccat acgtgcccac cctgtcccgc tccagaactg     780 ctgggggac ctagcgtttt cttgttcccc caaagccca aggacaccct catgatctca      840
cggactcccg aagtaacatg cgtagtagtc gacgtgagcc acgaggatcc tgaagtgaag     900
tttaattggt acgtggacgg agtcgaggtg cataatgcca aaactaaacc tcgggaggag     960
cagtataaca gtacctaccg cgtggtatcc gtcttgacag tgctccacca ggactggctg    1020
aatggtaagg agtataaatg caaggtcagc aacaaagctc ttcccgcccc aattgaaaag    1080
actatcagca aggccaaggg acaaccccgc gagccccagg tttacaccct tccaccttca    1140
cgagacgagc tgaccaagaa ccaggtgtct ctgacttgtc tggtcaaagg tttctatcct    1200
tccgacatcg cagtggagtg ggagtcaaac gggcagcctg agaataacta caagaccaca    1260
cccccagtgc ttgatagcga tgggagcttt tcctctaca gtaagctgac tgtggacaaa     1320
tcccgctggc agcagggaaa cgttttctct tgtagcgtca tgcatgaggc cctccacaac    1380
cattatactc agaaaagcct gagtctgagt cccggcaaa,                          1419
                                                         (SEQ ID NO:107)
atggaatgga gctgggtatt tctgtttttc ctgtcagtaa cgactggcgt ccattcaggc      60
ttcggcatca gtggacggca cagtatcaca gtgaccaccg tcgcctccgc tggcaatata     120
ggtgaggatg gcatccagtc ctgtaccttt gagccggaca tcaaactgtc tgacatagtg     180
atacaatggc tgaaggaggg ggtgctcggt ctggtacatg agtttaagga agggaaggat     240
gaactgtccg agcaggatga gatgttccgg gggaggaccg ctgtgttcgc cgatcaggta     300
atcgtcggaa atgcaagtct cagattgaaa aatgtgcaac tgactgatgc tggcacgtat     360
aaatgctaca ttatcacaag taagggcaaa ggaaatgcta accttgagta taaaacaggc     420
gcattctcaa tgcccgaggt caatgtcgac tataatgcca gcagtgaaac attgcgctgt     480
gaagctcccc gctggttccc ccagccaacc gtggtctggg cctctcaggt tgatcagggg     540
gctaactttt ccgaggtgag caacaccagc ttcgaactca actctgagaa tgtgaccatg     600
aaagttgtgt ctgtcctgta taatgtaaca atcaacaaca cttattcatg catgattgaa     660
```

```
                                                            -continued
aacgacatcg ccaaggcaac aggtgatatt aajgtaactg aatccgagat caaacggcgg    720
tctgacaaga cccatacgtg cccaccctgt ccsgctccag aactgctggg gggacctagc    780
gttttcttgt tccccccaaa gcccaaggac accctcatga tctcacggac tcccgaagta    840
acatgcgtag tagtcgacgt gagccacgag gatcctgaag tgaagtttaa ttggtacgtg    900
gacggagtcg aggtgcataa tgccaaaact aaacctcggg aggagcagta taacagtacc    960
taccgcgtgg tatccgtctt gacagtgctc caccaggact ggctgaatgg taaggagtat   1020
aaatgcaagg tcagcaacaa agctcttccc gccccaattg aaaagactat cagcaaggcc   1080
aagggacaac cccgcgagcc ccaggtttac acccttccac cttcacgaga cgagctgacc   1140
aagaaccagg tgtctctgac ttgtctggtc aaaggtttct atccttccga catcgcagtg   1200
gagtgggagt caaacgggca gcctgagaat aactacaaga ccacacccccc agtgcttgat   1260 agcgatggga gcttttttcct ctacagtaag ctgactgtgg acaaatcccg ctggcagcag   1320
ggaaacgttt tctcttgtag cgtcatgcat gaggccctcc acaaccatta tactcagaaa   1380
agcctgagtc tgagtcccgg caaa,                                          1404

(SEQ ID NO: 108)
atggaatgga gctgggtatt tctgtttttc ctgtcagtaa cgactggcgt ccattcaggc     60
ttcggcatca gtggacggca cagtatcaca gtgaccaccg tcgcctccgc tggcaatata    120
ggtgaggatg gcatccagtc ctgtaccttt gagccggaca tcaaactgtc tgacatagtg    180
atacaatggc cgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa gcaaatgcta accttgagta taaaacaggc    420
gcattctcaa tgcccgaggt caatgtcgac tataatgcca gcagtgaaaac attgcgctgt    480 gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat cgacaagacc    720
catacgtgcc caccctgtcc cgctccagaa ctgctggggg gacctagcgt tttcttgttc    780
cccccaaagc ccaaggacac cctcatgatc tcacggactc cgaagtaac atgcgtagta    840 gtcgacgtga gccacgagga tcctgaagtg aagtttaatt ggtacgtgga cggagtcgag    900
gtgcataatg ccaaaactaa acctcggagg agcagtata acagtaccta ccgcgtggta    960
tccgtcttga cagtgctcca ccaggactgg ctgaatggta aggagtataa atgcaaggtc   1020
agcaacaaag ctcttcccgc cccaattgaa aagactatca gcaaggccaa gggacaaccc   1080
cgcgagcccc aggtttacac ccttccacct tcacgagacg agctgaccaa gaaccaggtg   1140
tctctgactt gtctggtcaa aggtttctat ccttccgaca tcgcagtgga gtgggagtca   1200
aacgggcagc ctgagaataa ctacaagacc acacccccag tgcttgatag cgatgggagc   1260 ttttcctct acagtaagct gactgtggac aaatcccgct ggcagcaggg aaacgttttc   1320
tcttgtagcg tcatgcatga ggccctccac aaccattata ctcagaaaag cctgagtctg   1380
agtcccggca aa,                                                      1392

(SEQ ID NO: 109)
atggaatgga gctgggtatt tctgtttttc ctgtcagtaa cgactggcgt ccattcaggc     60
ttcggcatca gtggacggca cagtatcaca gtgaccaccg tcgcctccgc tggcaatata    120
ggtgaggatg gcatccagtc ctgtaccttt gagccggaca tcaaactgtc tgacatagtg    180
```

-continued

```
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aggtgatatt aaggtaactg aatccgagat caaacggcgg    720
tctcacctgc agctgctgaa ctccaaggac aegacccata cgtgcccacc ctgtcccgct    780
ccagaactgc tgggggggacc tagcgttttc ttgttccccc caaagcccaa ggacaccctc    840
atgatctcac ggactcccga agtaacatgc gtagtagtcg acgtgagcca cgaggatcct    900
gaagtgaagt ttaattggta cgtggacgga gtcgaggtgc ataatgccaa aactaaacct    960
cgggaggagc agtataacag tacctaccgc gtggtatccg tcttgacagt gctccaccag   1020
gactggctga atggtaagga gtataaatgc aaggtcagca acaaagctct tcccgcccca   1080
attgaaaaga ctatcagcaa ggccaaggga caaccccgcg agcccccaggt ttacacccctt   1140 ccaccttcac gagacgagct gaccaagaac caggtgtctc tgacttgtct ggtcaaaggt   1200
ttctatccct tccgacatcgc agtggagtgg gagtcaaacg gcagcctga gaataactac   1260 aagaccacac ccccagtgct tgatagcgat gggagctttt tcctctacag taagctgact   1320
gtggacaaat cccgctggca gcagggaaac gttttccctt gtagcgtcat gcatgaggcc   1380
ctccacaacc attatactca gaaaagcctg agtctgagtc ccggcaaa,                1428

(SEQ ID NO: 110)
atggaatgga gctgggtatt tctgtttttc ctgtcagtaa cgactggcgt ccattcaggc     60
ttcggcatca gtggacggca cagtatcaca gtgaccaccg tcgcctccgc tggcaatata    120
ggtgaggatg gcatcctgtc ctgtaccttt gagccggaca tcaaactgtc tgacatagtg    180
atacaatggc tgaaggaggg ggtgctcggt ctggtacatg agtttaagga agggaaggat    240
gaactgtccg agcaggatga gatgttccgg gggaggaccg ctgtgttcgc cgatcaggta    300
atcgtcggaa atgcaagtct cagattgaaa aatgtgcaac tgactgatgc tggcacgtat    360
aaatgctaca ttatcacaag taagggcaaa ggaaatgcta accttgagta taaaacaggc    420
gcattctcaa tgcccgaggt caatgtcgac tataatgcca gcagtgaaac attgcgctgt    480
gaagctcccc gctggttccc ccagccaacc gtggtctggg cctctcaggt tgatcagggg    540
gctaactttt ccgaggtgag caacaccagc ttcgaactca actctgagaa tgtgaccatg    600
aaagttgtgt ctgtcctgta taatgtaaca atcaacaaca cttattcatg catgattgaa    660
aacgacatcg ccaaggcaac aqgtgatatt aaggtaactg aatccgagat caaacggcgg    720
tctgagccta agtcatgtga caagacccat acgtgcccac cctgtcccgc tccagaactg    780 ctgggggggac ctagcgttttc cttgttcccc ccaaagccca aggacaccct catgatctca    840
cggactcccg aagtaacatg cgtagtagtc gacgtgagcc acgaggatcc tgaagtgaag    900
tttaattggt acgtggacgg agtcgaggtg cataatgcca aaactaaacc tcgggaggag    960
cagtataaca gtacctaccg cgtggtatcc gtcttgacag tgctccacca ggactggctg   1020
aatggtaagg agtataaatg caaggtcagc aacaaagctc ttcccgcccc aattgaaaag   1080
actatcagca aggccaaggg acaaccccgc gagcccccagg tttacacccct tccaccttca   1140
```

-continued

```
cgagacgagc tgaccaagaa ccaggtgtct ctgactcgtc tggtcaaagg tttctatcct   1200
tccgacatcg cagtggagtg ggagtcaaac gggcagcctg agaataacta caagaccaca   1260
cccccagtgc ttgatagcga tgggagcttt ttcctctaca gtaagctgac tgtggacaaa   1320
tcccgctggc agcagggaaa cgttttctct tgtagcgtca tgcatgaggc cctccacaac   1380
cattatactc agaaaagcct gagtctgagt cccggcaaa,                         1419
```

(SEQ ID NO: 111)

```
atggaatgga gctgggtatt tctgttttc ctgtcagtaa cgactggcgt ccattcaggc    60
ttcggcatca gtggacggca cagtatcaca gtgaccaccg tcgcctccgc tggcaatata   120
ggtgaggatg gcatcctgtc ctgtacccttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccc tgtgttcgc cgatcaggta    300 atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
aaagttgtgt ctgtcctgta taatgtaaca atcaacaaca cttattcatg catgattgaa   660
aacgacatcg ccaaggcaac aggtgatatt aaggtaactg aatccgagat caaacggcgg   720
tctgacaaga cccatacgtg cccaccctgt cccgctccag aactgctggg gggacctagc   780
gttttcttgt tccccccaaa gcccaaggac accctcatga tctcacggac tcccgaagta   840
acatgcgtag tagtcgacgt gagccacgag gatcctgaag tgaagtttaa ttggtacgtg   900
gacggagtcg aggtgcataa tgccaaaact aaacctcggg aggagcagta taacagtacc   960
taccgcgtgg tatccgtctt gacagtgctc ccccaggact ggctgaatgg taaggagtat   1020
aaatgcaagg tcagcaacaa agctcttccc gccccaattg aaaagactat cagcaaggcc   1080
aagggacaac cccgcgagcc ccaggtttac acccttccac cttcacgaga cgagctgacc   1140
aagaaccagg tgtctctgac ttgtctggtc aaaggtttct atccttccga catcgcagtg   1200
gagtgggagt caaacgggca gcctgagaat aactacaaga ccacacccccc agtgcttgat   1260 agcgatggga gcttttttcct ctacagtaag ctgactgtgg acaaatcccg ctggcagcag   1320
ggaaacgttt tctcttgtag cgtcatgcat gaggccctcc acaaccatta tactcagaaa   1380
agcctgagtc tgagtcccgg caaa,                                         1404
```

(SEQ ID NO: 112)

```
atggaatgga gctgggtatt tctgttttc ctgtcagtaa cgactggcgt ccattcaggc    60
ttcggcatca gtggacggca cagtatcaca gtgaccaccg tcgcctccgc tggcaatata   120
ggtgaggatg gcatcctgtc ctgtacccttt gagccggaca tcaaactgtc tgacatagtg   180
atacaatggc tgaaggaggg ggtgctcggt ctggtacatg agtttaagga agggaaggat   240
gaactgtccg agcaggatga gatgttccgg gggaggaccc tgtgttcgc cgatcaggta    300 atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
```

```
aaagttgtgt ctgtcctgta taatgtaaca atcaacaaca cttattcatg catgattgaa    660
aacgacatcg ccaaggcaac aggtgatatt aaggtaactg aatccgagat cgacaagacc    720
catacgtgcc caccctgtcc cgctccagaa ctgctggggg gacctagcgt tttcttgttc    780
cccccaaagc ccaaggacac cctcatgatc tcacggactc ccgaagtaac atgcgtagta    840
gtcgacgtga gccacgagga tcctgaagtg aagtttaatt ggtacgtgga cggagtcgag    900
gtgcataatg ccaaaactaa acctcgggag gagcagtata acagtaccta ccgcgtggta    960
tccgtcttga cagtgctcca ccaggactgg ctgaatggta aggagtataa atgcaaggtc   1020
agcaacaaag ctcttcccgc cccaattgaa aagactatca gcaaggccaa gggacaaccc   1080
cgcgagcccc aggtttacac ccttccacct tcacgagacg agctgaccaa gaaccaggtg   1140
tctctgactt gtctggtcaa aggtttctat ccttccgaca tcgcagtgga gtgggagtca   1200
aacgggcagc ctgagaataa ctacaagacc acaccccag tgcttgatag cgatgggagc    1260 ttttcctct acagtaagct gactgtggac aaatcccgct ggcagcaggg aaacgttttc    1320
tcttgtagcg tcatgcatga ggccctccac aaccattata ctcagaaaag cctgagtctg   1380
agtcccggca aa,                                                      1392
or
                                                        (SEQ ID NO: 113)
atggaatgga gctgggtatt tctgtttttc ctgtcagtaa cgactggcgt ccattcaggc     60
ttcggcatca gtgacggca cagtatcaca gtgaccaccg tcgcctccgc tggcaatata    120
ggtgaggatg gcatcctgtc ctgtacccttt gagccggaca tcaaactgtc tgacatagtg   180
atacaatggc tgaaggaggg ggtgctcggt ctggtcatg agtttaagga agggaaggat    240
gaactgtccg agcaggatga gatgttccgg gggaggaccg ctgtgttcgc cgatcaggta   300
atcgtcggaa atgcaagtct cagattgaaa aatgtgcaac tgactgatgc tggcacgtat   360
aaatgctaca ttatcacaag taagggcaaa ggaaatgcta accttgagta taaaacaggc   420
gcattctcaa tgcccgaggt caatgtcgac tataatgcca gcagtgaaac attgcgctgt   480
gaagctcccc gctggttccc ccagccaacc gtggtctggg cctctcaggt tgatcagggg   540
gctaactttt ccgaggtgag caacaccagc ttcgaactca actctgagaa tgtgaccatg   600
aaagttgtgt ctgtcctgta atgtaaca atcaacaaca cttattcatg catgattgaa    660
aacgacatcg ccaaggcaac aggtgatatt aaggtaactg aatccgagat caaacggcgg   720
tctcacctgc agctgctgaa ctccaaggac aagacccata cgtgcccacc ctgtcccgct   780
ccagaactgc tggggggacc tagcgttttt c ttgttccccc caaagcccaa ggacaccctc   840
atgatctcac ggactcccga agtaacatgc gtagtagtcg acgtgagcca cgaggatcct   900
gaagtgaagt ttaattggta cgtggacgga gtcgaggtgc ataatgccaa aactaaacct   960
cgggaggagc agtataacag tacctaccgc gtggtatccg tcttgacagt gctccaccag   1020
gactggctga atggtaagga gtataaatgc aaggtcagca caaagctct cccgccccca   1080 attgaaaaga ctatcagcaa ggccaaggga caaccccgcg agccccaggt ttacaccctt   1140
ccaccttcac gagacgagct gaccaagaac caggtgtctc tgacttgtct ggtcaaaggt   1200
ttctatcctt ccgacatcgc agtggagtgg gagtcaaacg ggcagcctga gaataactac   1260
aagaccacac ccccagtgct tgatagcgat gggagctttt tcctctacag taagctgact   1320
gtggauaaat cccgctggca gcagggaaac gttttctctt gtagcgtcat gcatgaggcc   1380
ctccauaacc attatactca gaaaagcctg agtctgagtc ccggcaaa.               1428
```

In another embodiment, a representative human B7-H4 fusion protein has at least 80%, 85%, 90%, 95%, 99% or 100% sequence identity to:

(SEQ ID NO: 114)
```
MASLGQILFW SIISIIIILA GAIALIIGFG ISGRHSITVT TVASAGNIGE DGIQSCTFEP    60
DIKLSDIVIQ WLKEGVLGLV HEFKEGKDEL SEQDEMFRGR TAVFADQVIV GNASLRLKNV   120
QLTDAGTYKC YIITSKGKGN ANLEYKTGAF SMPEVNVDYN ASSETLRCEA PRWFPQPTVV   180
WASQVDQGAN FSEVSNTSFE LNSENVTMKV VSVLYNVTIN NTYSCMIEND IAKATGDIKV   240
TESEIKRRSE PKSCDKTHTC PPCPAPELLG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPFSRD ELTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
K.                                                                481
```

In another embodiment, a representative human B7-H4 fusion protein has at least 80%, 85%, 90%, 95%, 99% or 100% sequence identity to:

(SEQ ID NO: 115)
```
MASLGQILFW SIISIIIILA GAIALIIGFG ISGRHSITVT TVASAGNIGE DGIQSCTFEP    60
DIKLSDIVIQ WLKEGVLGLV HEFKEGKDEL SEQDEMFRGR TAVFADQVIV GNASLRLKNV   120
QLTDAGTYKC YIITSKGKGN ANLEYKTGAF SMPEVNVDYN ASSETLRCEA PRWFPQPTVV   180
WASQVDQGAN FSEVSNTSFE LNSENVTMKV VSVLYNVTIN NTYSCMIEND IAKATGDIKV   240
TESEIKRRSD KTHTCPPCPA PELLGGPSVF LFPPKPKDTL MISRTPEVTC VVVDVSHEDP   300
EVKFNWYVDG VEVHNAKTKP REEQYNSTYR VVSVLTVLHQ DWLNGKEYKC KVSNKALPAP   360
IEKTISKAKG QPREPQVYTL PPSRDELTKN QVSLTCLVKG FYPSDIAVEW ESNGQPENNY   420
KTTPPVLDSD GSFFLYSKLT VDKSRWQQGN VFSCSVMHEA LHNHYTQKSL SLSPGK,      476
```
(SEQ ID NO: 116)
```
MASLGQILFW SIISIIIILA GAIALIIGFG ISGRHSITVT TVASAGNIGE DGIQSCTFEP    60
DIKLSDIVIQ WLKEGVLGLV HEFKEGKDEL SEQDEMFRGR TAVFADQVIV GNASLRLKNV   120
QLTDAGTYKC YIITSKGKGN ANLEYKTGAF SMPEVNVDYN ASSETLRCEA PRWFPQPTVV   180
WASQVDQGAN FSEVSNTSFE LNSENVTMKV VSVLYNVTIN NTYSCMIEND IAKATGDIKV   240
TESEIDKTHT CPPCPAPELL GGPSVFLFPP KPKDTLMISR TPEVTCVVVD VSHEDPEVKF   300
NWYVDGVEVH NAKTKPREEQ YNSTYRVVSV LTVLHQDWLN GKEYKCKVSN KALPAPIEKT   360
ISKAKGQPRE PQVYTLPPSR DELTKNQVSL TCLVKGFYPS DIAVEWESNG QPENNYKTTP   420
PVLDSDGSFF LYSKLTVDKS RWQQGNVFSC SVMHEALHNH YTQKSLSLSP GK,          472
```
(SEQ ID NO: 117)
```
MASLGQILFW SIISIIIILA GAIALIIGFG ISGRHSITVT TVASAGNIGE DGIQSCTFEP    60
DIKLSDIVIQ WLKEGVLGLV HEFKEGKDEL SEQDEMFRGR TAVFADQVIV GNASLRLKNV   120
QLTDAGTYKC YIITSKGKGN ANLEYKTGAF SMPEVNVDYN ASSETLRCEA PRWFPQPTVV   180
WASQVDQGAN FSEVSNTSFE LNSENVTMKV VSVLYNVTIN NTYSCMIEND IAKATGDIKV   240
TESEIKRRSH LQLLNSKDKT HTCPPCPAPE LLGGPSVFLF PPKPKDTLMI SRTPEVTCVV   300
VDVSHEDPEV KFNWYVDGVE VHNAKTKPRE EQYNSTYRVV SVLTVLHQDW LNGKEYKCKV   360
SNKALPAPIE KTISKAKGQP REPQVYTLPP SRDELTKNQV SLTCLVKGFY PSDIAVEWES   420
```

-continued

```
NGQPENNYKT TPPVLDSDGS FFLYSKLTVD KSRWQQGNVF SCSVMHEALH NHYTQKSLSL    480

SPGK,                                                                484

(SEQ ID NO: 118)
MASLGQILFW SIISIIIILA GAIALIIGFG ISGRHSITVT TVASAGNIGE DGILSCTFEP     60

DIKLSDIVIQ WLKEGVLGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIKRRSE PKSCDKTHTC PPCPAPELLG GPSVFLFPPK PKDTLMISRT PEVTCVVVDV    300

SHEDPEVKFN WYVDGVEVHN AKTKPREEQY NSTYRVVSVL TVLHQDWLNG KEYKCKVSNK    360

ALPAPIEKTI SKAKGQPREP QVYTLPPSRD ELTKNQVSLT CLVKGFYPSD IAVEWESNGQ    420

PENNYKTTPP VLDSDGSFFL YSKLTVDKSR WQQGNVFSCS VMHEALHNHY TQKSLSLSPG    480

K,                                                                   481

(SEQ ID NO: 119)
MASLGQILFW SIISIIIILA GAIALIIGFG ISGRHSITVT TVASAGNIGE DGILSCTFEP     60

DIKLSDIVIQ WLKEGVLGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIKRRSD KTHTCPPCPA PELLGGPSVF LFPPKPKDTL MISRTPEVTC VVVDVSHEDP    300

EVKFNWYVDG VEVHNAKTKP REEQYNSTYR VVSVLTVLHQ DWLNGKEYKC KVSNKALPAP    360

IEKTISKAKG QPREPQVYTL PPSRDELTKN QVSLTCLVKG EYPSDIRVEW ESNGQPENNY    420

KTTPPVLDSD GSFFLYSKLT VDKSRWQQGN VFSCSVMHEA LHNHYTQKSL SLSPGK,       476

(SEQ ID NO: 120)
MASLGQILFW SIISIIIILA GAIALIIGFG ISGRHSITVT TVASAGNIGE DGILSCTFEP     60

DIKLSDIVIQ WLKEGVLGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIDKTHT CPPCPAPELL GGPSVFLFPP KPKDTLMISR TPEVTCVVVD VSHEDPEVKF    300

NWYVDGVEVH NAKTKPREEQ YNSTYRVVSV LTVLHQDWLN GKEYKCKVSN KALPAPIEKT    360

ISKAKGQPRE PQVYTLPPSR DELTKNQVSL TCLVKGFYPS DIAVEWESNG QPENNYKTTP    420

PVLDSDGSFF LYSKLTVDKS RWQQGNVFSC SVMHEALHNH YTQKSLSLSP GK,           472

(SEQ ID NO: 121)
MASLGQILFW SIISIIIILA GAIALIIGFG ISGRHSITVT TVASAGNIGE DGILSCTFEP     60

DIKLSDIVIQ WLKEGVLGLV HEFKEGKDEL SEQDEMFRGR TAVFADQVIV GNASLRLKNV    120

QLTDAGTYKC YIITSKGKGN ANLEYKTGAF SMPEVNVDYN ASSETLRCEA PRWFPQPTVV    180

WASQVDQGAN FSEVSNTSFE LNSENVTMKV VSVLYNVTIN NTYSCMIEND IAKATGDIKV    240

TESEIKRRSH LQLLNSKDKT HTCPPCPAPE LLGGPSVFLF PPKPKDTLMI SRTPEVTCVV    300

VDVSHEDPEV KFNWYVDGVE VHNAKTKPRE EQYNSTYRVV SVLTVLHQDW LNGKEYKCKV    360

SNKALPAPIE KTISKAEGQP REPQVYTLPP SRDELTKNQV SLTCLVKGEY PSDIAVEWES    420

NGQPENNYKT TPPVLDSDGS FFLYSKLTVD KSRWQQGNVF SCSVMHEALH NHYTQKSLSL    480

SPGK,                                                                484

(SEQ ID NO: 122)
MEWSWVFLFF LSVTTGVHSG FGISGRHSIT VTTVASAGNI GEDGIQSCTF EPDIKLSDIV     60

IQWLKEGVLG LVHEFKEGKD ELSEQDEMFR GRTAVFADQV IVGNASLRLK NVQLTDAGTY    120
```

-continued

```
KCYIITSKGK GNANLEYKTG AFSMPEVNVD YNASSETLRC EAPRWFPQPT VVWASQVDQG        180

ANFSEVSNTS FELNSENVTM KVVSVLYNVT INNTYSCMIE NDIAKATGDI KVTESEIKRR        240

SEPKSCDKTH TCPPCPAPEL LGGPSVFLFP PKPKDTLMIS RTPEVTCVVV DVSHEDPEVK        300

FNWYVDGVEV HNAKTKPREE QYNSTYRVVS VLTVLHQDWL NGKEYKCKVS NKALPAPIEK        360

TISKAKGQPR EPQVYTLPPS RDELTKNQVS LTCLVKGFYP SDIAVEWESN GQPENNYKTT        420

PPVLDSDGSF FLYSKLTVDK SRWQQGNVFS CSVMHEALHN HYTQKSLSLS PGK,              473
                                                                (SEQ ID NO: 123)
MEWSWVFLFF LSVTTGVHSG FGISGRHSIT VTTVASAGNI GEDGIQSCTF EPDIKLSDIV         60

IQWLKEGVLG LVHEFKEGKD ELSEQDEMFR GRTAVFADQV IVGNASLRLK NVQLTDAGTY        120

KCYIITSKGK GNANLEYKTG AFSMPEVNVD YNASSETLRC EAPRWFPQPT VVWASQVDQG        180

ANFSEVSNTS FELNSEDVTM KVVSVLYNVT INNTYSCMIE NDIAKATGDI KVTESEIKRR        240

SDKTHTCPPC PAPELLGGPS VELFETKPKD TLMISRTPEV TCVVVDVSHE DPEVKFNWYV        300

DGVEVHNAKT KPREEQYNST YRVVSVLTVL HQDWLNGKEY KCKVSNKALP APIEKTISKA        360

KGQPREPQVY TLPPSRDELT KNQVSLTCLV KGFYPSDIAV EWESNGQPEN NYKTTPPVLD        420

SDGSFFLYSK LTVDKSRWQQ GNVFSCSVMH EALHNHYTQK SLSLSPGK,                    468
                                                                (SEQ ID NO: 124)
MEWSWVFLFF LSVTTGVHSG FGISGRHSIT VTTVASAGNI GEDGIQSCTF EPDIKLSDIV         60

IQWLKEGVLG LVHEFKEGKD ELSEQDEMFR GRTAVFADQV IVGNASLRLK NVQLTDAGTY        120

KCYIITSKGK GNANLEYKTG AFSMPEVNVD YNASSETLRC EAPRWFPQPT VVWASQVDQG        180

ANFSEVSNTS FELNSENVTM KVVSVLYNVT INNTYSCMIE NDIAKATGDI KVTESEIDKT        240

HTCPPCPAPE LLGGPSVFLF PPKPKDTLMI SRTPEVTCVV VDVSHEDPEV KFNWYVDGVE        300

VHNAKTKPRE EQYNSTYRVV SVLTVLHQDW LNGKEYKCKV SNKALPAPIE KTISKAKGQP        360

REPQVYTLPP SRDELTKNQV SLTCLVKGFY PSDIAVEWES NGQPENNYKT TPPVLDSDGS        420

FFLYSKLTVD KSRWQQGNVF SCSVMHEALH NHYTQKSLSL SPGK,                        464
                                                                (SEQ ID NO: 125)
MEWSWVFLFF LSVTTGVHSG FGISGRHSIT VTTVASAGNI GEDGIQSCTF EPDIKLSDIV         60

IQWLKEGVLG LVHEFKEGKD ELSEQDEMFR GRTAVFADQV IVGNASLRLK NVQLTDAGTY        120

KCYIITSKGK GNANLEYKTG AFSMPEVNVD YNASSETLRC EAPRWFPQPT VVWASQVDQG        180

ANFSEVSNTS FELNSENVTM KVVSVLYNVT INNTYSCMIE NDIAKATGDI KVTESEIKRR        240

SHLQLLNSKD KTHTCPPCPA PELLGGPSVF LFPPKPKDTL MISRTPEVTC VVVDVSHEDP        300

EVKFNWYVDG VEVHNAKTKP REEQYNSTYR VVSVLTVLHQ DWLNGKEYKC KVSNKALPAP        360

IEKTISKAKG QPREPQVYTL PPSRDELTKN QVSLTCLVKG FYPSDIAVEW ESNGQPENNY        420

KTTPPVLDSD GSFFLYSKLT VDKSRWQQGN VESCSVMHEA LHNHYTQKSL SLSPGK,           476
                                                                (SEQ ID NO: 126)
MEWSWVFLFF LSVTTGVHSG FGISGRHSIT VTTVASAGNI GEDGILSCTF EPDIKLSDIV         60

IQWLKEGVLG LVHEFKEGKD ELSEQDEMFR GRTAVFADQV IVGNASLRLK NVQLTDAGTY        120

KCYIITSKGK GNANLEYKTG AFSMPEVNVD YNASSETLRC EAPRWFPQPT VVWASQVDQG        180

ANFSEVSNTS FELNSENVTM KVVSVLYNVT INNTYSCMIE NDIAKATGDI KVTESEIKRR        240

SEPKSCDKTH TCPPCPAPEL LGGPSVFLFP PKPKDTLMIS RTPEVTCVVV DVSHEDPEVK        300

FNWYVDGVEV HNAKTKPREE QYNSTYRVVS VLTVLHQDWL NGKEYKCKVS NKALPAPIEK        360

TISKAKGQPR EPQVYTLPPS RDELTKNQVS LTCLVKGFYP SDIAVEWESN GQPENNYKTT        420

PPVLDSDGSF FLYSKLTVDK SRWQQGNVFS CSVMHEALHN HYTQKSLSLS PGK,              473
```

-continued (SEQ ID NO: 127)
MEWSWVFLFF LSVTTGVHSG FGISGRHSIT VTTVASAGNI GEDGILSCTF EPDIKLSDIV      60

IQWLKEGVLG LVHEFKEGKD ELSEQDEMFR GRTAVFADQV IVGNASLRLK NVQLTDAGTY     120

KCYIITSKGK GNANLEYKTG AFSMPEVNVD YNASSETLRC EAPRWFPQPT VVWASQVDQG     180

ANFSEVSNTS FELNSENVTM KVVSVLYNVT INNTYSCMIE NDIAKATGDI KVTESEIKRR     240

SDKTHTCPPC PAPELLGGPS VFLFPPKPKD TLMISRTPEV TCVVVDVSHE DPEVKFNWYV     300

DGVEVHNAKT KPREEQYNST YRVVSVLTVL HQDWLNGKEY KCKVSNKALP APIEKTISKA     360

KGQPREPQVY TLPPSRDELT KNQVSLTCLV KGFYPSDIAV EWESNGQPEN NYKTTPPVLD     420

SDGSFFLYSK LTVDKSRWQQ GNVFSCSVMH EALHNHYTQK SLSLSPGK,                468

(SEQ ID NO: 128)
MEWSWVFLFF LSVTTGVHSG FGISGRHSIT VTTVASAGNI GEDGILSCTF EPDIKLSDIV      60

IQWLKEGVLG LVHEFKEGKD ELSEQDEMFR GRTAVFADQV IVGNASLRLK NVQLTDAGTY     120

KCYIITSKGK GNANLEYKTG AFSMPEVNVD YNASSETLRC EAPRWFPQPT VVWASQVDQG     180

ANFSEVSNTS FELNSENVTM KVVSVLYNVT INNTYSCMIE NDIAKATGDI KVTESEIDKT     240

HTCPPCPAPE LLGGPSVFLF PPKPKDTLMI SRTPEVTCVV VDVSHEDPEV KFNWYVDGVE     300

VHNAKTKPRE EQYNSTYRVV SVLTVLHQDW LNGKEYKCKV SNKALPAPIE KTISKAKGQP     360

REPQVYTLPP SRDELTKNQV SLTCLVKGFY PSDIAVEWES NGQPENNYKT TPPVLDSDGS     420

FFLYSKLTVD KSRWQQGNVF SCSVMHEALH NHYTQKSLSL SPGK,                    464
or (SEQ ID NO: 129)
MEWSWVFLFF LSVTTGVHSG FGISGRHSIT VTTVASAGNI GEDGILSCTF EPDIKLSDIV      60

IQWLKEGVLG LVHEFKEGKD ELSEQDEMFR GRTAVFADQV IVGNASLRLK NVQLTDAGTY     120

KCYIITSKGK GNANLEYKTG AFSMPEVNVD YNASSETLRC EAPRWFPQPT VVWASQVDQG     180

ANFSEVSNTS FELNSENVTM KVVSVLYNVT INNTYSCMIE NDIAKATGDI KVTESEIKRR     240

SHLQLLNSKD KTHTCPPCPA PELLGGPSVF LFPPKPKDTL MISRTPEVTC VVVDVSHEDP     300

EVKFNWYVDG VEVHNAKTKP REEQYNSTYR VVSVLTVLHQ DWLNGKEYKC KVSNKALPAP     360

IEKTISKAKG QPREPQVYTL PPSRDELTKN QVSLTCLVKG FYPSDIAVEW ESNGQPENNY     420

KTTPPVLDSD GSFFLYSKLT VDKSRWQQGN VFSCSVMHEA LHNHYTQKSL SLSPGK.        476

The amino acid sequence of the human B7-H4 fusion protein of SEQ ID NO:114 and SEQ ID NO:122 without the signal sequence is:

(SEQ ID NO: 130)
GFGISGRHSI TVTTVASAGN IGEDGIQSCT FEPDIKLSDI VIQWLKEGVL GLVHEFKEGK      60

DELSEQDEMF RGRTAVFADQ VIVGNASLRL KNVQLTDAGT YKCYIITSKG KGNANLEYKT     120

GAFSMPEVNV DYNASSETLR CEAPRWFPQP TVVWASQVDQ GANFSEVSNT SFELNSENVT     180

MKVVSVLYNV TINNTYSCMI ENDIAKATGD IKVTESEIKR RSEPKSCDKT HTCPPCPAPE     240

LLGGPSVFLF PPKPKDTLMI SRTPEVTCVV VDVSHEDPEV KFNWYVDGVE VHNAKTKPRE     300

EQYNSTYRVV SVLTVLHQDW LNGKEYKCKV SNKALPAPIE KTISKAKGQP REPQVYTLPP     360

SRDELTKNQV SLTCLVKGFY PSDIAVEWES NGQPENNYKT TPPVLDSDGS FFLYSKLTVD     420

KSRWQQGNVF SCSVMHEALH NHYTQKSLSL SPGK.                               454

The amino acid sequence of the human B7-H4 fusion protein of SEQ ID NO:115 and SEQ ID NO:123 without the signal sequence is:

```
                                                    (SEQ ID NO: 131)
GFGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKOYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESETKR RSDKTHTCPP CPAPELLGGP   240

SVFLFPPKPK DTLMISRTPE VTCVVVDVSH EDPEVKFNWY VDGVEVHNAK TKPREEQYDS   300

TYRVVSVLTV LHQDWLNGKE YKCKVSNKAL PAPIEKTISK AEGQPREPQV YTLPPSRDEL   360

TKNQVSLTCL VKGFYPSDIA VEWESNGQPE NNYKTTPPVL DSDGSFFLYS KLTVDXSRWQ   420

QGNVFSCSVM HEALHNHYTQ KSLSLSPGK.                                   449
```

The amino acid sequence of the human B7-H4 fusion protein of SEQ ID NO:116 and SEQ ID NO:124 without the signal sequence is:

```
                                                    (SEQ ID NO: 132)
GFGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQF TVVWASQVDQ GANFSEVSNT SFELNSENVT   180

MKVVSVLYNV TINNTYSCMI ENDIAKATGD IKVTESEIDK THTCPPCPAP ELLGGPSVFL   240

FETKPKDTLM ISRTPEVTCV VVDVSHEDPE VKFNWYVDGV EVHNAKTKPR EEQYNSTYRV   300

VSVLTVLHQD WLNGKEYKCK VSNKALPAPI EKTISKAKGQ PREPQVYTLP PSRDELTKNQ   360

VSLTCLVKGF YPSDIAVEWE SNGQPENNYK TTPPVLDSDG SFFLYSKLTV DKSRWQQGNV   420

FSCSVMHEAL HNHYTQKSLS LSPGK.                                       445
```

The amino acid sequence of the human B7-H4 fusion protein of SEQ ID NO:117 and SEQ ID NO:125 without the signal sequence is:

```
                                                    (SEQ ID NO: 133)
GFGISGRHSI TVTTVASAGN IGEDGIQSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CERPRWFPQP TVVWASQVDQ GANFSEVSNT SFELNSENVT   180

MKVVSVLYNV TINNTYSCMI ENDIRKATGD IKVTESEIKR RSHLQLLNSK DKTHTCPPCP   240

APELLGGPSV FLFPPKPKDT LMISRTPEVT CVVVDVSHED PEVKFNWYVD GVEVHNAKTK   300

PREEQYNSTY RVVSVLTVLH QDWLNGKEYK CKVSNKALPA PIEKTISKAK GQPREPQVYT   360

LPPSRDELTK NQVSLTCLVK GFYPSDIAVE WESNGQPENN YKTTPPVLDS DGSFFLYSKL   420

TVDKSRWQQG NVFSCSVMHE ALHNHYTQKS LSLSPGK.                          457
```

The amino acid sequence of the human B7-H4 fusion protein of SEQ ID NO:118 and SEQ ID NO:126 without the signal sequence is:

```
                                                    (SEQ ID NO: 134)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CERPRWFPQP TVVWASQVDQ GANFSEVSNT SFELNSENVT   180

MKVVSVLYNV TINNTYSCMI ENDIAKATGD IKVTESEIKR RSEPKSCDKT HTCPPCPAPE   240

LLGGPSVFLF PPKPKDTLMI SRTPEVTCVV VDVSHEDPEV KFNWYVDGVE VHNAKTKPRE   300
```

```
EQYNSTYRVV SVLTVLHQDW LNGKEYKCKV SNKALPAPIE KTISKAKGQP REPQVYTLPP   360

SRDELTKNQV SLTCLVKGFY PSDIAVEWES NGQPENNYKT TPPVLDSDGS FFLYSKLTVD   420

KSRWQQGNVF SCSVMHEALH NHYTQKSLSL SPGK.                              454
```

The amino acid sequence of the human B7-H4 fusion protein of SEQ ID NO:119 and SEQ ID NO:127 without the signal sequence is:

```
                                                    (SEQ ID NO: 135)
GEGISGRHSI TVTTVASAGN IGEDGILSCT FEPDIKISDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEIKR RSDKTHTCPP CPAPELLGGP   240

SVFLFPPKPK DTLMISRTPE VTCVVVDVSH EDPEVKFNWY VDGVEVHNAK TKPREEQYNS   300

TYRVVSVLTV LHQDWLNGKE YKCKVSNKAL PAPIEKTISK AKGQPREPQV YTLPPSRDEL   360

TKNQVSLTCL VKGFYPSDIA VEWESNGQPE NNYKTTPPVL DSDGSFFLYS KLTVDKSRWQ   420

QGNVFSCSVM HEALHNHYTQ KSLSLSPGK.                                    449
```

The amino acid sequence of the human B7-H4 fusion protein of SEQ ID NO:120 and SEQ ID NO:128 without the signal sequence is:

```
                                                    (SEQ ID NO: 136)
GEGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAKATGD IKVTESEIDK THTCPPCPAP ELLGGPSVFL   240

FPPKPKDTLM ISRTPEVTCV VVDVSHEDPE VKFNWYVDGV EVRNAKTKPR EEQYNSTYRV   300

VSVLTVLHQD WLNGKEYKCK VSNKALPAPI EKTISKAKGQ PREPQVYTLP PSRDELTKNQ   360

VSLTCLVXGF YPSDIAVEWE SNGQPENNYK TTPPVLDSDG SFFLYSKLTV DKSRWQQGNV   420

FSCSVMHEAL HNHYTQKSLS LSPGK.                                        445
```

The amino acid sequence of the human B7-H4 fusion protein of SEQ ID NO:121 and SEQ ID NO:129 without the signal sequence is:

```
                                                    (SEQ ID NO: 137)
GFGISGRHSI TVTTVASAGN IGEDGILSCT FEPDIKLSDI VIQWLKEGVL GLVHEFKEGK    60

DELSEQDEMF RGRTAVFADQ VIVGNASLRL KNVQLTDAGT YKCYIITSKG KGNANLEYKT   120

GAFSMPEVNV DYNASSETLR CEAPRWFPQP TVVWASQVDQ GANFSEVSNT SFELNSENVT   180

MKVVSVLYNV TINNTYSCMI ENDIAEATGD IKVTESEIKR RSHLQLLNSK DKTHTCPPCP   240

APELLGGPSV FLFPPKPKDT LMISRTPEVT CVVVDVSHED PEVKFNWYVD GVEVHNAKTK   300

PREEQYNSTY RVVSVLTVLH QDWINGKEYE CKVSNKALPA PIEKTISKAK GQPREPQVYT   360

LPPSRDELTR NQVSLTCLVK GFYPSDIAVE WESNGQPENN YKTTPPVLDS DGSFFLYSKL   420

TVDKSRWQQG NVFSCSVMHE ALHNHYTQKS LSLSPGK.                           457
```

The aforementioned exemplary fusion proteins can incorporate any combination of the variants described herein. In another exemplary embodiment the terminal lysine of the aforementioned exemplary fusion proteins is deleted.

The disclosed fusion proteins can be isolated using standard molecular biology techniques. For example, an expression vector containing a DNA sequence encoding a B7-H4-Ig fusion protein is transfected into 293 cells by calcium phosphate precipitation and cultured in serum-free DMEM. The supernatant is collected at 72 h and the fusion protein is purified by Protein G, or preferably Protein A SEPHAROSE® columns (Pharmacia, Uppsala, Sweden).

F. Fusion Protein Dimers and Multimers

B7-H4 fusion polypeptides can be dimerized or multimerized. Dimerization or multimerization can occur between or among two or more fusion proteins through dimerization or multimerization domains, including those described above. Alternatively, dimerization or multimerization of fusion proteins can occur by chemical crosslinking. Fusion protein dimers can be homodimers or heterodimers. Fusion protein multimers can be homomultimers or heteromultimers.

Fusion protein dimers as disclosed herein are of formula II:

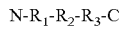

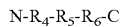

or, alternatively, are of formula III:

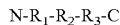

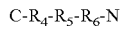

wherein the fusion proteins of the dimer provided by formula II are defined as being in a parallel orientation and the fusion proteins of the dimer provided by formula III are defined as being in an antiparallel orientation. Parallel and antiparallel dimers are also referred to as cis and trans dimers, respectively. "N" and "C" represent the N- and C-termini of the fusion protein, respectively. The fusion protein constituents "$R_1$", "$R_2$" and "$R_3$" are as defined above with respect to formula I. With respect to both formula II and formula III, "$R_4$" is a B7-H4 polypeptide or a second polypeptide, "$R_5$" is an optional peptide/polypeptide linker domain, and "$R_6$" is a B7-H4 polypeptide or a second polypeptide, wherein "$R_6$" is a B7-H4 polypeptide when "$R_4$" is a second polypeptide, and "$R_6$" is a second polypeptide when "$R_4$" is a B7-H4 polypeptide. In one embodiment, "$R_1$" is a B7-H4 polypeptide, "$R_4$" is also a B7-H4 polypeptide, and "$R_3$" and "$R_6$" are both second polypeptides.

Fusion protein dimers of formula II are defined as homodimers when "$R_1$"="$R_4$", "$R_2$"="$R_5$" and "$R_3$"="$R_6$". Similarly, fusion protein dimers of formula III are defined as homodimers when "$R_1$"="$R_6$", "$R_2$"="$R_5$" and "$R_3$"="$R_4$". Fusion protein dimers are defined as heterodimers when these conditions are not met for any reason. For example, heterodimers may contain domain orientations that meet these conditions (i.e., for a dimer according to formula II, "$R_1$" and "$R_4$" are both B7-H4 polypeptides, "$R_2$" and "$R_5$" are both peptide/polypeptide linker domains and "$R_3$" and "$R_6$" are both second polypeptides), however the species of one or more of these domains is not identical. For example, although "$R_3$" and "$R_6$" may both be B7-H4 polypeptides, one polypeptide may contain a wild-type B7-H4 amino acid sequence while the other polypeptide may be a variant B7-H4 polypeptide. An exemplary variant B7-H4 polypeptide is B7-H4 polypeptide that has been modified to have increased or decreased binding to a target cell, increased activity on immune cells, increased or decreased half life or stability.

Dimers of fusion proteins that contain either a $C_H1$ or $C_L$ region of an immunoglobulin as part of the polypeptide linker domain preferably form heterodimers wherein one fusion protein of the dimer contains a $C_H1$ region and the other fusion protein of the dimer contains a $C_L$ region.

Fusion proteins can also be used to form multimers. As with dimers, multimers may be parallel multimers, in which all fusion proteins of the multimer are aligned in the same orientation with respect to their N- and C-termini. Multimers may be antiparallel multimers, in which the fusion proteins of the multimer are alternatively aligned in opposite orientations with respect to their N- and C-termini. Multimers (parallel or antiparallel) can be either homomultimers or heteromultimers.

G. Peptide and Polypeptide Modifications

The fusion proteins may be modified by chemical moieties that may be present in polypeptides in a normal cellular environment, for example, phosphorylation, methylation, amidation, sulfation, acylation, glycosylation, sumoylation and ubiquitylation. Fusion proteins may also be modified with a label capable of providing a detectable signal, either directly or indirectly, including, but not limited to, radioisotopes and fluorescent compounds.

The fusion proteins may also be modified by chemical moieties that are not normally added to polypeptides in a cellular environment. For example, the disclosed fusion proteins may also be modified by covalent attachment of polymer chains, including, but not limited to, polyethylene glycol polymer (PEG) chains (i.e. pegylation). Conjugation of macromolecules to PEG has emerged recently as an effective strategy to alter the pharmacokinetic (PK) profiles of a variety of drugs, and thereby to improve their therapeutic potential. PEG conjugation increases retention of drugs in the circulation by protecting against enzymatic digestion, slowing filtration by the kidneys and reducing the generation of neutralizing antibodies. In addition, PEG conjugates can be used to allow multimerization of the fusion proteins.

Modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptides include lysinyl and amino terminal residues derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N=C=N—R') such as 1-cyclohexyl-3-(2-morpholinyl-(4-ethyl)carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia. Fusion proteins may also include one or more D-amino acids that are substituted for one or more L-amino acids.

H. Modified Binding Properties

Binding properties of the B7-H4 polypeptides, fragments and fusions thereof (collectively referred to as B7-H4 polypeptides) are relevant to the dose and dose regimen to be administered. In one embodiment the disclosed B7-H4 polypeptides have binding properties to at least one receptor on a T cell that demonstrate a higher term, or higher percentage, of occupancy of receptor molecules on immune cells relative to other ligands of the receptor molecules. In other embodiments, the disclosed B7-H4 polypeptides have reduced binding affinity to a receptor on T cells relative to wildtype B7-H4, allowing the protein to dissociate in a period of less than three months, two months, one month, three weeks, two weeks, one week, or a few days after administration.

In some embodiments the B7-H4 polypeptides, or fragments, or fusions thereof have a relatively high affinity for its receptor, and may therefore have a relatively slow off rate. In other embodiments, the B7-H4 polypeptides are administered intermittently over a period of days, weeks or months to dampen immune responses which are allowed to recover prior to the next administration, which may serve to reduce the immune response without completely turning the immune response off and may avoid long term side effects.

III. Isolated Nucleic Acid Molecules

Isolated nucleic acid sequences encoding B7-H4 polypeptides, fragments and fusions thereof are disclosed herein. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-B7-H4 proteins). The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids encoding B7-H4 fusion polypeptides may be optimized for expression in the expression host of choice. Codons may be substituted with alternative codons encoding the same amino acid to account for differences in codon usage between the mammal from which the B7-H4 nucleic acid sequence is derived and the expression host. In this manner, the nucleic acids may be synthesized using expression host-preferred codons.

Nucleic acids can be in sense or antisense orientation, or can be complementary to a reference sequence encoding a B7-H4 polypeptide. Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

Nucleic acids encoding polypeptides can be administered to subjects in need thereof. Nucleic delivery involves introduction of "foreign" nucleic acids into a cell and ultimately, into a live animal. Compositions and methods for delivering nucleic acids to a subject are known in the art (see Understanding Gene Therapy, Lemoine, N. R., ed., BIOS Scientific Publishers, Oxford, 2008).

IV. Vectors and Host Cells

Vectors encoding B7-H4 polypeptides, fragments and fusions thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences, are typically expressed as a fusion with the encoded polypeptide. Such tags can be inserted anywhere within the polypeptide including at either the carboxyl or amino terminus Examples of useful tags include, but are not limited to, green fluorescent protein (GFP), glutathione S-transferase (GST), polyhistidine, c-myc, hemagglutinin, Flag™ tag (Kodak, New Haven, Conn.), maltose E binding protein and protein A. In one embodiment, a nucleic acid molecule encoding a B7-H4 fusion polypeptide is present in a vector containing nucleic acids that encode one or more domains of an Ig heavy chain constant region, preferably having an amino acid sequence corresponding to the hinge, $C_H2$ and $C_H3$ regions of a human immunoglobulin Cγ1 chain.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the B7-H4 fusion polypeptides described herein.

The vectors described can be used to express B7-H4 in cells, for example, cells for transplantation such as islet cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo. For example, nucleic acids encoding polypeptides disclosed herein can be administered directly to lymphoid tissues or tumors. Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs are known in the art.

Nucleic acids may also be administered in vivo by viral means. Nucleic acid molecules encoding fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

In addition to virus- and carrier-mediated gene transfer in vivo, physical means well-known in the art can be used for direct transfer of DNA, including administration of plasmid DNA and particle-bombardment mediated gene transfer.

V. Pharmaceutical Compositions

Pharmaceutical compositions including fusion polypeptides disclosed herein are provided. Pharmaceutical compositions containing peptides or polypeptides may be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the polypeptide compositions disclosed herein and nucleic acids encoding the same, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. For polypeptide compositions, generally dosage levels of 0.001 to 20 mg/kg of body weight daily are administered to mammals. Generally, for intravenous injection or infusion, dosage may be lower.

In certain embodiments, the polypeptide compositions are administered locally, for example by injection directly into a site to be treated. Typically, the injection causes an increased localized concentration of the polypeptide compositions which is greater than that which can be achieved by systemic administration. In the case of organ transplants, the protein may be administered locally to a site near the transplanted organ. The polypeptide compositions can be combined with a matrix as described above to assist in creating a increased localized concentration of the polypeptide compositions by reducing the passive diffusion of the polypeptides out of the site to be treated.

1. Formulations for Parenteral Administration

In a preferred embodiment, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN 20, TWEEN 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Topical Administration

Fusion proteins disclosed herein can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations will require the inclusion of penetration enhancers.

3. Controlled Delivery Polymeric Matrices

Fusion proteins disclosed herein may also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release,* 5:13-22 (1987); Mathiowitz, et al., *Reactive Polymers,* 6:275-283 (1987); and Mathiowitz, et al., *J. Appl. Polymer Sci.,* 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

In another embodiment, B7-H4 polypeptides or fragments, or fusions thereof are administered with transplanted cells encapsulated within a matrix to allow release of the B7-H4 polypeptides or fragments, or fusions thereof over a period of time in the area of transplantation. The matrix can be a polymeric matrix made using any polymer suitable for cell encapsulation. Exemplary polymeric materials suitable for encapsulating cells include, but are not limited to alginate, agarose, hyaluronic acid, collagen, synthetic monomers, albumin, fibrinogen, fibronectin, vitronectin, laminin, dextran, dextran sulfate, chondroitin sulfate, dermatan sulfate, keratan sulfate, chitin, chitosan, heparan, heparan sulfate, or a combination thereof. For example, for treatment of diabetes, B7-H4 polypeptides or fragments, or fusions thereof can be encapsulated with pancreatic islet cells within a polymeric matrix. Encapsulation of pancreatic islet cells is described, for example, in Barnett, et al., *Nature Medicine,* 13(8):986-91 (2007)).

VI. Methods of Manufacture

A. Methods for Producing Fusion Proteins

Isolated fusion proteins can be obtained by, for example, chemical synthesis or by recombinant production in a host cell. To recombinantly produce a fusion protein, a nucleic acid containing a nucleotide sequence encoding the fusion protein can be used to transform, transduce, or transfect a bacterial or eukaryotic host cell (e.g., an insect, yeast, or mammalian cell). In general, nucleic acid constructs include a regulatory sequence operably linked to a nucleotide sequence encoding the fusion protein. Regulatory sequences (also referred to herein as expression control sequences) typically do not encode a gene product, but instead affect the expression of the nucleic acid sequences to which they are operably linked.

Useful prokaryotic and eukaryotic systems for expressing and producing polypeptides are well known in the art include, for example, *Escherichia coli* strains such as BL-21, and cultured mammalian cells such as CHO cells.

In eukaryotic host cells, a number of viral-based expression systems can be utilized to express fusion proteins. Viral based expression systems are well known in the art and include, but are not limited to, baculoviral, SV40, retroviral, or vaccinia based viral vectors.

Mammalian cell lines that stably express variant fusion proteins can be produced using expression vectors with appropriate control elements and a selectable marker. For example, the eukaryotic expression vectors pCR3.1 (Invitrogen Life Technologies) and p91023(B) (see Wong et al. (1985) *Science* 228:810-815) are suitable for expression of variant costimulatory polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza Group Ltd.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin or by metabolic selection using the Glutamine Synthetase-NS0 system). The transfected cells can be cultured such that the polypeptide of interest is expressed, and the polypeptide can be recovered from, for example, the cell culture supernatant or from lysed cells. Alternatively, a fusion protein can be produced by (a) ligating amplified sequences into a mammalian expression vector such as pcDNA3 (Invitrogen Life Technologies), and (b) transcribing and translating in vitro using wheat germ extract or rabbit reticulocyte lysate.

Fusion proteins can be isolated using, for example, chromatographic methods such as affinity chromatography, ion exchange chromatography, hydrophobic interaction chromatography, DEAE ion exchange, gel filtration, and hydroxylapatite chromatography. In some embodiments, fusion proteins can be engineered to contain an additional domain containing amino acid sequence that allows the polypeptides to be captured onto an affinity matrix. For example, an Fc-fusion polypeptide in a cell culture supernatant or a cytoplasmic extract can be isolated using a protein A column. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus Other fusions that can be useful include enzymes that aid in the detection of the polypeptide, such as alkaline phosphatase Immunoaffinity chromatography also can be used to purify costimulatory polypeptides. Fusion proteins can additionally be engineered to contain a secretory signal (if there is not a secretory signal already present) that causes the fusion protein to be secreted by the cells in which it is produced. The secreted fusion proteins can then conveniently be isolated from the cell media.

B. Methods for Producing Isolated Nucleic Acid Molecules

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a variant costimulatory polypeptide. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Fusion protein-encoding nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992. Examples of amino acid positions that can be modified include those described herein.

VII. Methods of Use

The B7-H4 polypeptides or fragments, or fusions thereof disclosed herein are useful as therapeutic agents. One embodiment provides a method for inhibiting or reducing transplant rejection in a host by administering to the host an effective amount of a B7-H4 polypeptide or fragment, or fusion thereof. Immune cells, preferably T cells, can be contacted in vivo or ex vivo with B7-H4 polypeptides to decrease or inhibit immune responses including, but not limited to transplant rejection. The T cells contacted with B7-H4 fusion polypeptides can be any cell which express the T cell receptor, including α/β and γ/δ T cell receptors. T-cells include all cells which express CD3, including T-cell subsets which also express CD4 and CD8. T-cells include both naive and memory cells and effector cells such as CTL. T-cells also include regulatory cells such as Th1, Tc1, Th2, Tc2, Th3, Th17, Th22, Treg, and Tr1 cells. For example the compositions can be used to modulate Th1, Th17, Th22, or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs. T-cells also include NKT-cells and similar unique classes of the T-cell lineage. The compositions can also be used to increase or promote the activity of Tregs, increase the production of cytokines such as IL-10 from Tregs, increase the differentiation of Tregs, increase the number of Tregs, or increase the survival of Tregs.

Other immune cells that can be treated with the disclosed B7-H4 polypeptides, fusion proteins, or fragments thereof include T cell precursors, antigen presenting cells, B cells, or combinations thereof. The B7-H4 compositions can be used to modulate the production of antibodies by B cells by contacting the B cells with an effective amount of the B7-H4 composition to inhibit or reduce the antibody production by the B cell relative to a control. The B7-H4 compositions can also modulate the production of cytokines by the B cells.

A. Methods of Treating Transplant Rejection

A preferred embodiment provides methods for reducing or inhibiting transplant rejection in a subject, preferably a human subject. Transplant rejection can be inhibited or reduced in a subject by administering an effective amount of B7-H4 polypeptides or fragments, or fusions thereof to inhibit or reduce the biological activity of an immune cell or to reduce the amounts of proinflammatory cytokines or other molecules associated with or that promote inflammation at a site of transplant. Exemplary proinflammatory molecules include, but are not limited to IL-1β, TNF-α, TGF-beta, IFN-γ, IL-17, IL-6, IL-23, IL-22, IL-21, and MMPs.

Th1 and Th17 are exemplary T cells that can be targeted for inhibition by B7-H4 polypeptides, fusion proteins or fragments thereof to inhibit or reduce inflammation. The B7-H4 fusion proteins are useful for treating inflammation by any or all of the following: inhibiting or reducing differentiation of Th1, Th17, Th22, and/or other cells that secrete, or cause other cells to secrete, inflammatory molecules; inhibiting or reducing activity of Th1, Th17, Th22, and/or other cells that secrete, or cause other cells to secrete, inflammatory molecules; inhibiting or reducing the Th1 and/or Th17 pathways; inhibiting or reducing cytokine production and/or secretion by Th1, Th17, Th22, and/or other cells that secrete, or cause other cells to secrete, inflammatory molecules; inhibiting or reducing proliferation of Th1, Th17, Th22, and/or other cells that secrete, or cause other cells to secrete, inflammatory molecules.

Additionally, B7-H4 polypeptides, fusion proteins or fragments thereof can cause Tregs to have an enhanced suppressive effect on the Th1, Th17, Th22 and/or other cells that secrete, or cause other cells to secrete, inflammatory molecules to reduce the level of IFN-γ and/or IL-17 produced. B7-H4 polypeptides, fusion proteins or fragments thereof can also act directly on Tregs to promote or enhance production of IL-10 to suppress the Th1 and/or Th17 pathways, or to increase the number of Tregs.

B7-H4 polypeptides, fusion proteins or fragments thereof act at multiple points in multiple pathways. For example, they can inhibit the development of naïve T cells into either Th1 or Th17 cells. Alternatively, they can interact with Th1 cells or Th17 cells, or both to inhibit or reduce the production of proinflammatory molecules. Additionally, they can target Tregs to cause an enhanced suppressive effect on the Th1 and/or Th17 pathways to reduce the level of INF-γ and/or IL-17 produced. B7-H4 compositions can also act directly on Tregs to promote or enhance production of IL-10 to suppress the Th1 and/or Th17 pathway. Additionally they can work by enhancing recruitment or expansion (or both) of Treg cells in the region of engrafted tissue or at peripheral sites.

1. Inhibition of the Th1 Pathway a. Inhibition of Th1 Development

One method for inhibiting or reducing transplant rejection includes administering an effective amount of a B7-H4 polypeptide or fragment, or fusion thereof to inhibit or block naïve T cells from developing into Th1 cells in a subject in need thereof by an amount effective to inhibit or reduce transplant rejection relative to a control. It has been discovered that transplant rejection can be inhibited or reduced by blocking naïve T cells from differentiating into Th1 cells by administering B7-H4 polypeptides or fragments, or fusions thereof or variants thereof. In one embodiment, the B7-H4 polypeptide or fragment, or fusion thereof increases the suppressive ability of Tregs on naïve T cells to inhibit or reduce naïve T cells from differentiating into Th1 cells and thereby reduce the number of Th1 cells in a subject. Alternatively, the B7-H4 polypeptide or fragment, or fusion thereof inhibits or reduces proliferation of Th1 cells. By restricting the number of Th1 cells that can develop in the subject, the amount of proinflammatory molecules being produced such as INF-γ can be reduced or contained. INF-γ stimulates the production or release of other proinflammatory molecules including IL-1β, TNF-α, and MMPs. Thus, by controlling the number of Th1 cells in a subject, the levels of these other proinflammatory molecules can be controlled, thereby reducing transplant rejection.

b. Inhibition of Proinflammatory Molecules

Another embodiment provides a method of inhibiting or reducing transplant rejection in a subject by administering to the subject an effective amount of a B7-H4 polypeptide or fragment, or fusion thereof to inhibit or reduce production of proinflammatory molecules by Th1 cells by an amount effective to inhibit or reduce transplant rejection in the subject. Exemplary proinflammatory molecules produced by Th1 cells includes IFN-γ. In this embodiment the B7-H4 polypeptide or fragment, or fusion thereof can interact directly with the Th1 cell and inhibit or reduce IFN-γ production by the Th1 cells. In this embodiment, the amount of proinflammatory molecules are regulated rather than the population of Th1 cells.

2. Inhibition of the Th17 Pathway a. Inhibition of Th17 Development

Transplant rejection can also be inhibited or reduced in a subject by administering an effective amount of a B7-H4 polypeptide or fragment, or fusion thereof to inhibit or block naïve T cells from developing into Th17 cells by an amount effective to inhibit or reduce transplant rejection in the subject relative to a control. In one embodiment, the B7-H4 polypeptide or fragment, or fusion thereof increases the suppressive activity of Tregs on the differentiation of naïve T cells into Th17 cells by an amount sufficient to reduce the number of Th17 cells in a subject. Alternatively, the B7-H4 polypeptide or fragment, or fusion thereof inhibits or reduces proliferation of Th17 cells. By reducing the population of Th17 cells in a subject, the amount of IL-17 being produced can be reduced, as well as IL-22 and IL-21. IL-17 is a proinflammatory molecule that causes increases in other proinflammatory molecules such as IL-1β, TNF-α, and MMPs. Thus, by reducing the amount of IL-17 these other proinflammatory molecules can be reduced thereby reducing or inhibiting transplant rejection.

b. Inhibition of IL-17 Production

Still another embodiment provides a method for inhibiting or reducing transplant rejection in a subject by administering an effective amount of B7-H4 polypeptide or fragment, or fusion thereof, to inhibit production of IL-17 by Th17 cells, as well as IL-22 and IL-21 by an amount effective to inhibit or reduce transplant rejection relative to a control. In this embodiment, the B7-H4 polypeptide or fusion protein can act directly on Th17 cells, for example by binding to Th17 cells resulting in inhibition of IL-17 (or IL-22 and IL-21) production by those Th17 cells. As noted above, inhibition or reduction of IL-17 (and IL-22 or IL-21) leads to the reduction of other proinflammatory molecules, thereby reducing or inhibiting transplant rejection.

3. Inhibiting Th1 and Th17 Pathways

The disclosed B7-H4 polypeptide or fragment, or fusion thereof can be used to inhibit both the Th1 and Th17 pathways simultaneously. Using one anti-inflammatory agent to inhibit two separate pathways provides more robust inhibition or reduction of the immune response thereby reducing or inhibiting transplant rejection. Inhibition of the Th1 and Th17 pathways inhibits or reduces the recruitment of neutrophils and may thereby reduce one or more symptoms of inflammation. In one embodiment, inhibition of the Th1 and Th17 pathways reduce or inhibit the proliferation of neutrophils and or macrophages.

4. Tregs

Inflammation can also be treated by administering a B7-H4 polypeptide or fragment, or fusion thereof to a subject in an amount effective to target IL-10 producing Tregs to enhance the suppressive activity on the Th1 and/or Th17 pathways. In this embodiment the disclosed B7-H4 polypeptides or fragments, or fusions thereof cause an increased suppressive effect on IL-17 production relative to Tregs alone thereby inhibiting or reducing transplant rejection relative to a control.

Another embodiment provides a method for inhibiting or reducing transplant rejection by administering an effective amount of a B7-H4 polypeptide or fragment, or fusion thereof to increase production of IL-10 by Tregs. Increased production of IL-10 results in the decreased production of IL-17 by Th17 cells and deceased production of IFN-α by Th1 cells. In this embodiment, the B7-H4 polypeptides or fragments, or fusions thereof can interact directly with Tregs to increase IL-10 production by the Tregs and thereby inhibit or reduce transplant rejection in a subject relative to a control.

Additionally the B7-H4 polypeptides or fragments, or fusions thereof can work by enhancing recruitment or expansion (or both) of Treg cells in the region of engrafted tissue. Thus, another embodiment provides a method for inhibiting or reducing transplant rejection in a subject by administering to the subject an effective amount of a B7-H4-Ig fusion protein to enhance recruitment of Treg cells in the region of the engrafted tissue. Increased infiltration of Treg cells into the engrafted tissue can increase the level of IL-10 locally and result in the decreased production of IL-17 by Th17 cells and deceased production of IFN-α by Th1 cells at the site of transplantation. This can lead to prolonged survival and decreased rejection of the transplant.

Still another embodiment provides a method for inhibiting or reducing transplant rejection in a subject by administering an effective amount of B7-H4 polypeptides or fragments, or fusions thereof to inhibit or interfere with the Th1 pathway, Th17 pathway and to enhance the suppressive effect on the Th17 pathway by Tregs by an amount effective to inhibit or reduce transplant rejection in the subject relative to a control.

The B7-H4 polypeptides, fusion proteins thereof and fragments thereof can also be administered to a subject in an amount effective to increase Treg cell populations or numbers.

IL-10 and TGF-β production by Tregs can be increased relative to a control by contacting the Tregs with an effective amount of B7-H4 polypeptides or fragments, or fusions thereof having B7-H4 activity. The increase can occur in vitro or in vivo.

5. Soluble B7-H4

Soluble B7-H4 (sH4) acts as a decoy molecule that binds to the B7-H4 receptor and may block endogenous B7-H4 from binding to its receptor. sH4 does not deliver an inhibitory signal like cell-surface B7-H4. B7-H4 inhibits cell cycle progression of T cells in the presence of antigen stimulation. B7-H4 can inhibit innate immunity by suppressing proliferation of neutrophil progenitors. It is believed that elevated levels of sH4 block the inhibitory effect of endogenous B7-H4.

Therefore, transplant rejection can be inhibited or reduced by interfering with the biological activity of sH4 in vivo, for example, by administering to an individual in need thereof an effective amount of an agent that inhibits or decreases the ability of sH4 to bind to the B7-H4 receptor, or augments the activity of the endogenous inhibitory B7-H4 molecules. Interference of sH4 biological activity can be accomplished by administering B7-H4 fusion polypeptides disclosed herein.

Administration is not limited to the treatment of existing conditions, diseases or disorders (i.e. an existing inflammatory or autoimmune disease or disorder) but can also be used to prevent or lower the risk of developing such diseases in an individual, i.e., for prophylactic use. Thus, the disclosed composition can be administered prior to transplant, during transplant, and after transplant.

6. Transplants

The transplanted material can be cells, tissues, organs, limbs, digits or a portion of the body, preferably the human body. The transplants are typically allogenic or xenogenic. The disclosed B7-H4 polypeptides, fusion proteins, or fragments thereof are administered to a subject in an effective amount to reduce or inhibit transplant rejection. B7-H4 polypeptides, fusion proteins, or fragments thereof can be administered systemically or locally by any acceptable route of administration. In some embodiments, B7-H4 polypeptides or fragments, or fusions thereof are administered to a site of transplantation prior to, at the time of, or following transplantation. In one embodiment, the B7-H4 polypeptides or fragments, or fusions thereof are administered to a site of transplantation parenterally, such as by subcutaneous injection.

In other embodiments, or B7-H4 polypeptides, fusion proteins, or fragments thereof are administered directly to cells, tissue or organ to be transplanted ex vivo. In one embodiment, the transplant material is contacted with B7-H4 polypeptides, fusion proteins thereof, and fragments thereof prior to transplantation, after transplantion, or both.

In other embodiments, B7-H4 polypeptides or fragments, or fusions thereof are administered to immune tissues or organs, such as lymph nodes or the spleen.

The transplant material can be modified prior to transplant. For example, the transplant material can be genetically modified to express a protein that aids in the inhibition or reduction of transplant rejection. In a preferred embodiment, the transplant material is genetically modified to express B7-H4 polypeptides or fragments, or fusions thereof in an amount effective to inhibit or reduce transplant rejection in a transplant recipient.

The transplant material can be treated with enzymes or other materials that remove cell surface proteins, carbohydrates, or lipids that are known or suspected in being involved with immune responses such as transplant rejection.

B7-H4 acts at multiple points in the inflammatory pathway and at a higher level whereby it acts as a master regulator to control to influence the expression and/or activity of effectory cytokines such as TNF-α. Therefore, the B7-H4 compositions described herein are particularly useful for treating patients that do not respond to TNF-α blockers such as Enbrel, Remicade, Cimzia and Humira. In addition, because of its activity as a master regulator in the inflammatory pathway, the B7-H4 compositions disclosed are particularly useful for treating chronic transplant rejection.

a. Cells

Populations of any types of cells can be transplanted into a subject. The cells can be homogenous or heterogenous. Heterogeneous means the cell population contains more than one type of cell. Exemplary cells include progenitor cells such as stem cells and pluripotent cells which can be harvested from a donor and transplanted into a subject. The cells are optionally treated prior to transplantation as mention above. Such treatment includes transfecting the cells ex vivo with a nucleic acid construct enabling the cells to express B7-H4 polypeptides or fragments, or fusions thereof in vitro and in vivo. Methods for transfecting cells are well known in the art.

Ex vivo methods of nucleic acid delivery can include, for example, the steps of harvesting cells from a subject, culturing the cells, transducing them with an expression vector, and maintaining the cells under conditions suitable for expression of the encoded polypeptides. These methods are known in the art of molecular biology. An exemplary nucleic acid vector includes but is not limited to an adenoviral vector. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. Other exemplary cells that can be transplanted include, but are not limited to, islet cells, hematopoietic cells, muscle cells, cardiac cells, neural cells, embryonic stem cells, adult stem cells, T cells, lymphocytes, dermal cells, mesoderm, endoderm, and ectoderm cells.

b. Tissues

Any tissue can be used as a transplant. Exemplary tissues include skin, adipose tissue, cardiovascular tissue such as veins, arteries, capularies, valves; neural tissue, bone marrow, pulmonary tissue, ocular tissue such as corneas and lens, cartilage, bone, and mucosal tissue. The tissue can be modified as discussed above.

c. Organs

Exemplary organs that can be used for transplant include, but are not limited to kidney, liver, heart, spleen, bladder, lung, stomach, eye, tongue, pancreas, intestine, etc. The organ to be transplanted can also be modified prior to transplantation as discussed above.

One embodiment provides a method of inhibiting or reducing chronic transplant rejection in a subject by administering an effective amount of a B7-H4 polypeptide or fragment, or fusion thereof to inhibit or reduce chronic transplant rejection relative to a control. The effects of B7-H4 polypeptides, fusion proteins thereof, and fragments thereof on Treg cell are particularly important in this context.

B. Graft-Versus-Host Disease (GVHD)

The disclosed B7-H4 polypeptides or fragments, or fusions thereof can also be used to treat graft-versus-host disease (GVHD) by administering an effective amount of B7-H4 polypeptide, fusion proteins thereof, or fragments thereof to alleviate one or more symptoms associated with GVHD. GVHD is a major complication associated with allogeneic hematopoietic stem cell transplantation in which functional immune cells in the transplanted marrow recognize the recipient as "foreign" and mount an immunologic attack. It can also take place in a blood transfusion under certain circumstances. Symptoms of GVD include skin rash or change in skin color or texture, diarrhea, nausea, abnormal liver function, yellowing of the skin, increased susceptibility to infection, dry, irritated eyes, and sensitive or dry mouth.

D. Diabetes

The B7-H4 polypeptides and fusion proteins thereof can also be used to treat diabetes. The method includes transplanting insulin producing cells in a subject and administering to the subject an effective amount of a B7-H4 polypeptide or fragment, or fusion thereof to reduce or inhibit transplant rejection. Preferably the insulin producing cells are beta cells or islet cells. In certain embodiments, the insulin producing cells are recombinant cells engineered to produce insulin. The insulin producing cells may also be genetically modified to produce B7-H4 polypeptides or fragments, or fusions thereof, as described herein.

The insulin producing cells can be encapsulated within a matrix, such as a polymeric matrix, using suitable polymers, including, but not limited to alginate, agarose, hyaluronic acid, collagen, synthetic monomers, albumin, fibrinogen, fibronectin, vitronectin, laminin, dextran, dextran sulfate, chondroitin sulfate, dermatan sulfate, keratan sulfate, chitin, chitosan, heparan, heparan sulfate, or a combination thereof E. Combination Therapy B7-H4 polypeptides or fragments, or fusions thereof can be used alone or in combination with additional therapeutic agents. The additional therapeutic agents include, but are not limited to, immunosuppressive agents (e.g., antibodies against other lymphocyte surface markers (e.g., CD40, alpha-4 integrin) or against cytokines), other fusion proteins (e.g., CTLA-4-Ig (Orencia®), TNFR-Ig (Enbrel®)), TNF-α blockers such as Enbrel, Remicade, Cimzia and Humira, cyclophosphamide (CTX) (i.e. Endoxan®, Cytoxan®, Neosar®, Procytox®, Revimmune™), methotrexate (MTX) (i.e. Rheumatrex®, Trexall®), belimumab (i.e. Benlysta®), or other immunosuppressive drugs (e.g., cyclosporin A, FK506-like compounds, rapamycin compounds, or steroids), anti-proliferatives, cytotoxic agents, or other compounds that may assist in immunosuppression.

In a preferred embodiment, the additional therapeutic agent functions to inhibit or reduce T cell activation and cytokine production through a separate pathway. In one such embodiment, the additional therapeutic agent is a CTLA-4 fusion protein, such as CTLA-4 Ig (abatacept). CTLA-4 Ig fusion proteins compete with the co-stimulatory receptor, CD28, on T cells for binding to CD80/CD86 (B7-1/B7-2) on antigen presenting cells, and thus function to inhibit T cell activation. In a preferred embodiment, the additional therapeutic agent is a CTLA-4-Ig fusion protein known as belatacept. Belatacept contains two amino acid substitutions (L104E and A29Y) that markedly increase its avidity to CD86 in vivo. In another embodiment, the additional therapeutic agent is Maxy-4.

In another embodiment, the second therapeutic agent preferentially treats chronic transplant rejection or GvHD, whereby the treatment regimen effectively targets both acute and chronic transplant rejection or GvHD. In a preferred embodiment the second therapeutic is a TNF-α blocker.

In another embodiment, the second therapeutic agent increases the amount of adenosine in the serum, see, for example, WO 08/147482. In a preferred embodiment, the second therapeutic is CD73-Ig, recombinant CD73, or another agent (e.g. a cytokine or monoclonal antibody or small molecule) that increases the expression of CD73, see for example WO 04/084933. In another embodiment the second therapeutic agent is Interferon-beta.

In a preferred embodiment, the compositions are used in combination or succession with compounds that increase Treg activity or production. Exemplary Treg enhancing agents include but are not limited to glucocorticoid fluticasone, salmeterol, antibodies to IL-12, IFN-γ, and IL-4; vitamin D3, and dexamethasone, and combinations thereof. Antibodies to other proinflammatory cytokines can also be used in combination or alternation with the disclosed B7-H4 polypeptides, fusion proteins, or fragments thereof. Preferred antibodies bind to IL-6, IL-23, IL-22 or IL-21.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art (See, e.g. WO95122972, WO 95116691, WO 95104738, U.S. Pat. No. 6,015,809; 5,989,591; U.S. Pat. Nos. 5,567,709; 5,559,112; 5,530,006; 5,484,790; 5,385,908; 5,202,332; 5,162,333; 5,780,462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds include, for example, those described in WO 00101385. Preferably, the language "rapamycin compound" as used herein does not include FK506-like compounds.

Other suitable therapeutics include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof In another embodiment, the additional therapeutic agents includes compositions that inhibit or interfere with sH4 activity, to treat inflammatory disorders in subjects. In one embodiment, B7-H4 fusion polypeptides are administered to a subject for the treatment of an inflammatory disease wherein the subject has little or non-detectable amounts of sH4. In another embodiment, B7-H4 fusion polypeptides are administered to treat one or more symptoms of an inflammatory disease in subjects having elevated levels of sH4. Elevated levels of sH4 can be determined by comparing levels of sH4 is subjects known to have an inflammatory disorder with levels of sH4 in subjects that do not have an inflammatory disorder.

F. Selection of Candidates for Transplantation

Detection of sH4 and B7-H4 can be used to evaluate candidates for transplantation. Elevated levels of sH4 may block the inhibitory effect of endogenous B7-H4, therefore it is believed that levels of sH4 in serum may be predictive of a patient's likelihood of rejecting transplanted material. As B7-H4 is a negative regulator of T cell responses, levels of B7-H4 expressed at the cell surface may also be predictive of a patient's likelihood of rejecting transplanted material. Levels of sH4 present in a biological sample from the individual can be determined prior to transplantation. The amounts of sH4 that correlate with transplantation rejection, including different levels of severity, can be predetermined by quantifying sH4 in patients who have had successful transplantations and those who have had unsuccessful transplantations. The levels of sH4 present in the biological sample of the transplantation candidate can be compared to the predetermined reference levels of sH4 present in biological samples from other individuals, and used to predict the candidate's likelihood of a successful transplantation. For example if 75% of patients having about "x" level of sH4 have experienced rejection of a transplant, than a patient having about "x" level of sH4 may have a 75% chance of rejecting a transplantation. Other factors that may influence a patient's likelihood of rejecting a transplant are known in the art and may be considered when determining a patient's chance of rejecting a transplantation. For example donor age, recipient diabetes, sex of the recipient, chronic GVHD, and T cell levels may also be considered.

The candidate's likelihood of a successful transplantation can be used to select patients for transplantation. For example, patients whose level of sH4 corresponds with a 0%, 10%, 20%, 30%, 40%, 50%, 60%, or 70% likelihood of rejection may be a good candidate for transplantation, while a patient whose level of sH4 corresponds with a 80%, 90%, or 100% likelihood of rejection may not be a good candidate for transplantation. The levels of sH4 in biological samples of the candidate for transplantation can additionally or alternatively be compared to amounts of sH4 indicative of different stages of an inflammatory response or autoimmune disease.

Alternatively, the amount of sH4 can be correlated to levels of neutrophils. Neutrophils are thought to contribute to early allograph rejection (Healy, et al., *Eur J Cardiothorac Surg*, 29:760-766 (2006)). Therefore, in certain individuals, elevated levels of neutrophils may be predictive of transplantation rejection, particularly acute rejection. Thus, sH4 levels in an individual can be correlated to neutrophil levels. Levels of sH4 that correspond to specific levels of neutrophils can be predetermined by assaying the levels of sH4 in subjects and assaying the levels of neutrophils in the subjects. Once the reference levels are determined, a biological sample from a subject can be assayed for sH4 levels. The resulting sH4 levels are then compared to the predetermined sH4 levels correlated to specific levels of neutrophils. The resulting sH4 levels are matched to the predetermined levels to determine the neutrophils levels in the subject. The number of neutrophils in a healthy individual ranges from about 15,000 to 20,000 cells/W.

The amount of sH4 in a sample can be determined using conventional techniques such as enzyme-linked immunosorbent assays, mass spectrometry, spectrophotometry, or a combination thereof Methods for detecting the presence and/or measuring a level of sH4 in a biological sample, may include use of an sH4-specific antibody or an anti-B7-H4 antibody. Preferably the antibody recognizes an epitope on any one of the polypeptides encoded by SEQ ID NOs:2-7, 9-20, 24-33, 42-80, The methods generally include:

a) contacting the sample with an antibody specific for sH4; and b) detecting binding between the antibody and molecules of the sample.

Detection of specific binding of the sH4-specific antibody, when compared to a suitable control, is an indication that sH4 is present in the sample. Suitable controls include a sample known not to contain sH4, and a sample contacted with an antibody not specific for sH4, e.g., an anti-idiotype antibody.

A variety of methods to detect specific antibody-antigen interactions are known in the art and can be used in the method, including, but not limited to, standard immunohistological methods, immunoprecipitation, an enzyme immunoassay, and a radioimmunoassay. In general, the sH4-specific antibody will be detectably labeled, either directly or indirectly. Direct labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. The antibody may be attached (coupled) to an insoluble support, such as a polystyrene plate or a bead. Indirect labels include second antibodies specific for sH4-specific antibodies, wherein the second antibody is labeled as described above; and optionally contain members of specific binding pairs, e.g., biotin-avidin. The biological sample may be brought into contact with and immobilized on a solid support or carrier, such as nitrocellulose, that is capable of immobilizing cells, cell particles, or soluble proteins. The support may then be washed with suitable buffers, followed by contacting with a detectably-labeled sH4-specific antibody.

Still other embodiments provide methods for detecting the presence and/or measuring a level of sH4 in a biological sample. The methods generally include:

a) contacting the sample with an sH4 ligand, for example a B7-H4 receptor or fragment thereof that binds sH4; and b) detecting binding between the B7-H4 receptor and molecules of the sample.

Detection of specific binding of the B7-H4 receptor is an indication that sH4 polypeptides are present in the sample.

Methods for detecting binding between a B7-H4 receptor and sH4 are known in the art and include immunoprecipitation of B7-H4 receptor-ligand complexes using an antibody specific to the B7-H4 receptor, as long as the antibody does not disrupt B7-H4 receptor sH4 binding. Alternatively, the B7-H4 receptor used may be a fusion protein which provides for specific immunoprecipitation of the fusion partner, an enzymatic detection, a fluorescent signal (e.g., a green fluorescent protein). The B7-H4 receptor can be labeled with any detectable label, as described above. The B7-H4 receptor can be attached, directly or through a linker, to an insoluble support (e.g., polystyrene beads, magnetic beads, and the like), thereby providing a means for separating sH4/receptor complexes from the biological sample, and subsequently detecting the presence of and/or measuring the amount (level) of sH4.

EXAMPLES

Example 1

Effect of B7-H4-Ig in Allogeneic Islet Graft Transplantation

Figure 2:
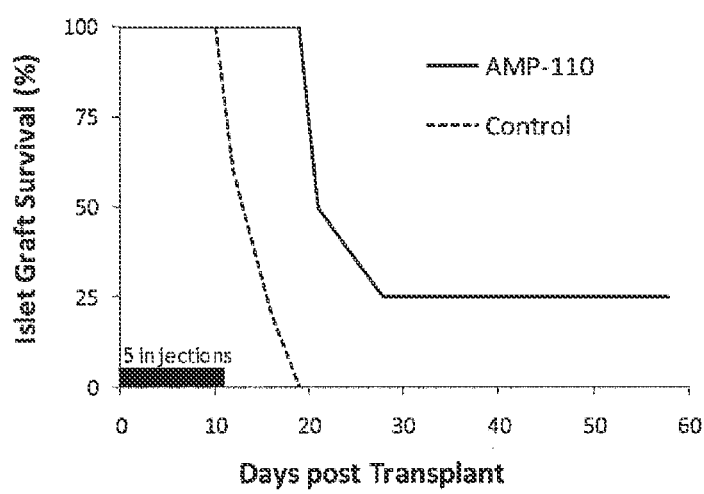
FIG. 2 is a line graph of percent islet survival versus days post transplant in mice treated with B7-H4-Ig (solid line) or a control (dashed line).

An allogeneic transplant model of C57BL/6 (B6) mice as recipients and BALB/c mice as islet donors were used to study the in vivo effects of B7-H4-Ig in prolonging islet graft survival of transplant recipients. Female B6 mouse recipients (n=4) were rendered diabetic by i.p administration of streptozotocin (STZ, 200 mg/kg), a widely used drug that is specifically toxic to islet cells and results in a permanent state of hyperglycemia. After STZ injection, the mice were tested for blood glucose level (BGL) by Glucometer Elite and signs of diabetes. Two to three days after STZ administration, B6 mice demonstrating signs of diabetes were used as transplantation recipients. Islet cells for allogeneic transplantation were isolated from pancreata of 8- to 10-week-old BALB/c donor mice by collagenase digestion (donor pancreata was perfused in bile situ through the common duct with collagenase), followed by separation on a discontinuous Ficoll gradient and purified by handpicking under a stereo microscope. Then, groups of 500 islets were transplanted under the left kidney capsule of each recipient. The transplant recipients were then treated with i.p. injections of B7-H4.Ig (250 µg) on Day 0. This was followed by injection of the same amount of reagents, respectively, on Days 2, 4, 6, and 8. BGL was measured every 2 days. Clinical recurrence of diabetes was defined as a random BGL reading of >250 mg/dl for three consecutive days, and survival of islet cells is determined by the ability of mice to maintain a BGL reading of less than 250 mg/dl. To determine the effects of B7-H4.Ig injection on islet transplantation in B6 mice with diabetes, graft-survival curves of the B7-H4-Ig treatment and no-treatment groups were compared by Kaplan-Meier analysis. FIG. 1 illustrates diabetes disease induction in the recipient B6 mice and allogeneic islet transplant together with B7-H4-Ig administration. FIG. 2 shows the results of this experiment that injection of B7-H4-Ig slowed the transplant rejection and prolonged graft survival in allogeneic islet transplant-recipient B6 mice.

Example 2

B7-H4-Ig Increase Survivability in an Allogenic Transplant Mouse Model of GvHD

Transplantation and Treatment Protocol

Recipient Balb/C mice were lethally irradiated with a dose of 8.4 Gy and were reconstituted within 4 hours with a single intravenous inoculum of either $5 \times 10^6$ allogeneic bone marrow (BM) cells from C57B/6+ spleen cells ($1.5 \times 10^7$) or $5 \times 10^6$ syngeneic bone marrow cells. To avoid bias from cage-related effects, animals in different groups were randomized between cages. Four groups of mice were given included. Group I was a syngeneic BM transplant that BM cells from Balb/C mice were transferred to Balb/C mice and served as a negative control. Group II was an allogenic bone marrow transplant in which control IgG (0.5 mg) was administered on Day 0, 1, 7 and 14. Group III was an allogenic bone marrow transplant in which B7-H4-Ig (0.5 mg) was administered on Day 0, 1, 7, and 14. Group IV was allogeneic bone marrow transplants treated with phosphate buffered saline (PBS) on Day 0, 1, 7, and 14. There were 4 mice in the negative, syngeneic BM transplantation group and 8 mice each in the other 3 groups. FIG. 3 is a schematic diagram of an experimental design for the graft versus host disease assay.

Results

Figure 5:
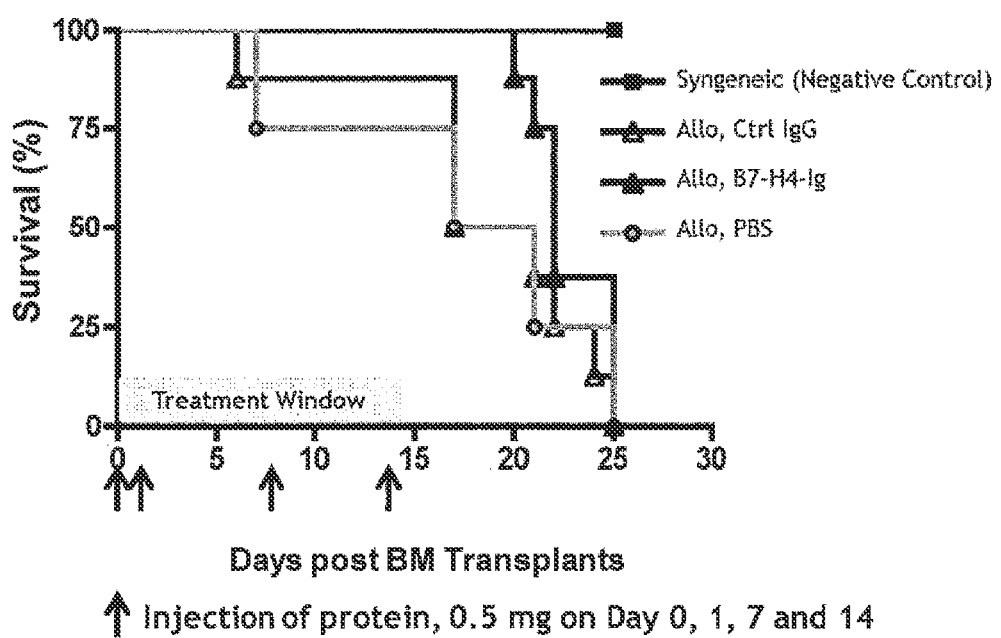
FIG. 5 is a line graph showing percent survival versus days post bone marrow transplant of mice treated in FIG. 3. Syngeneic transplant (solid square), allogenic transplant treated with control IgG (open triangle), allogenic transplant treated with B7-H4-Ig (solid triangle), allogenic transplant treated with phosphate buffered saline (open circle). The indicated protein was injected at 0.5 mg on Days 0, 1, 7, and 14 as indicated by the arrows.

FIG. 4A shows that allogenic BM transplanted mice treated with B7-H4-Ig had significantly reduced diarrhea clinic score compared to allogenic BM transplanted mice treated with control IgG on Day 7 post transplantation. FIG. 4B shows that allogenic BM transplanted mice treated with B7-H4-Ig showed reduced weight loss compared to allogenic transplanted mice treated with control IgG. FIG. 5 shows that allogenic BM transplanted mice treated with B7-H4-Ig transiently survived longer compared to controls. Taken together the results show with optimized dose regimen B7-H4-Ig potentially can be useful for allogeneic BM transplantation.

Example 3

B7-H4-Ig Blocks Pathogenic CD4$^+$ T Cell Infiltration and Promotes Accumulation of Tregs Materials and Methods Immunochemical Staining Mice were anesthetized with nembutal and perfused with phosphate-buffered saline (PBS). Brains and spinal cords from each mouse were frozen in OCT (Miles Laboratories; Elkhart, Ind.) in liquid nitrogen. Tissue from the lower lumbar region of the spinal cord was sectioned at 6 µm on a Reichert-Jung 1800 cryotome and mounted on Superfrost Plus electrostatically charged slides. Cross-sections (10 µm thick for brains and 6 µm for spinal cords) from longitudinal sections of brain and spinal cord were performed. Tissues were stained with biotin-conjugated antibody to mouse CD4, PLP and FoxP3. Positive staining of biotinylated antibodies was visualized by a Tyramide Signal Amplification (TSA) Direct kit (NEN, Boston, Mass.) according to manufacturer's instructions and fluoroscein anti-mouse IgG (Vector Laboratories). Sections were counterstained with 4,6-diamidino-2-phenylindole (DAPI; Sigma-Aldrich) and then coverslipped with Vectashieldmounting medium (Vector Laboratories). Slides were examined and images were acquired via epifluorescence using the SPOT RT camera (Diagnostic Instruments, Sterling Heights, Mich.). Sections from each group were analyzed at 40 or 100× magnification.

Results

An in vitro iTreg induction study with B7-H4-Ig provides evidence that B7-H4-Ig promotes iTreg differentiation. Using purified nTreg cells from FoxP3-GFP transgenic mice in the in vitro suppression assay, a decrease in activation and proliferation of CD4$^+$ T effector cells by B7-H4-Ig was demonstrated. The addition of B7-H4-Ig to the suppression assay in the presence of low numbers of nTreg cells has a significant effect on blocking effector T cell activation and proliferation in vitro.

Figure 6:
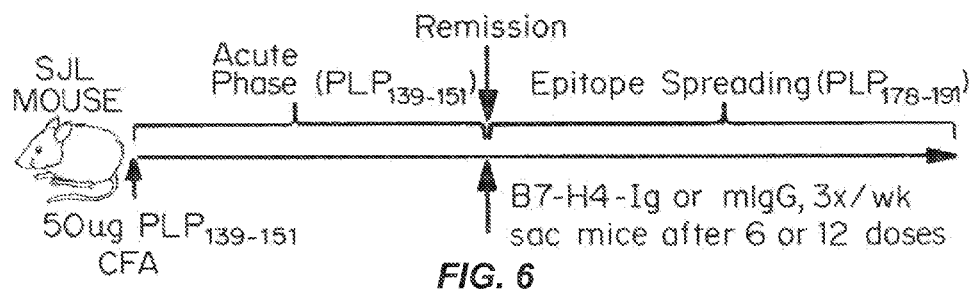
FIG. 6 is a schematic illustration of experimental autoimmune encephalomyelitis (EAE) induction and treatment regimen in an in vivo study utilizing an auto-immune R-EAE murine model for Multiple Sclerosis (MS).

The effect of B7-H4-Ig treatment on the number of Treg cells in vivo was analyzed in this study. The effect of B7-H4-Ig on the number and phenotype of CD4$^+$ T cells infiltrating into the CNS following B7-H4-Ig treatment, the relevant site for activity in vivo, was determined. As shown in FIG. 6, SLJ mice (10 mice per groups) were immunized with $PLP_{139-151}$ mice (10 mice per groups) were immunized with $PLP_{139-151}$ following the standard protocol to induce R-EAE disease. SJL mice were first immunized with $PLP_{139-151}$ peptide. B7-H4-Ig treatment started during remission (Day 23). Mice received mouse Control IgG, 100 µg, or B7-H4-Ig at either 60 or 300 gig, 3 times per week for 2 weeks or 4 weeks. Half of the animals (5 mice from each group) were euthanized on Day 35, after 6 doses of B7-H4-Ig. The rest of the animals (5 mice from each group) were euthanized on Day 50, after 12 doses of B7-H4-Ig. Mouse spleens, draining lymph nodes, spinal cords and brains were collected, tissues were made into a single cell suspension and counted via the use of a hemocytometer, and analyzed for the presence of effector/memory CD4$^+$ T cells (CD4$^+$CD44$^+$) and Treg cells (CD4$^+$CD25$^+$FoxP3$^+$). Whole cerebellar and lumbar spinal cord tissue samples were snap frozen and processed as described above to analyze the number of CD4$^+$ and FoxP3$^+$ cells present within the CNS by histology.

Figure 7A:
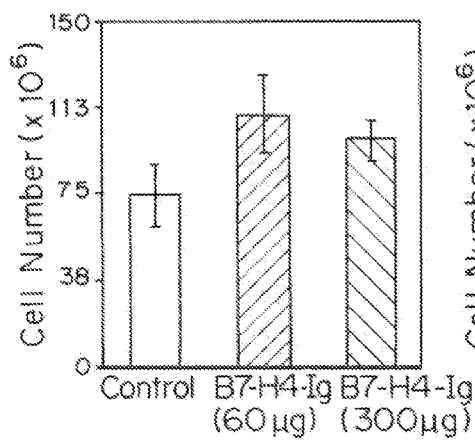
FIGS. 7A, 7B, and 7C are bar graphs showing the total lymphocyte cell number ($\times 10^6$) in the spleen (A), draining lymph nodes (B), and CNS isolated on day 50 from SJL mice immunized with 50 µg of PLP peptide emulsified in CFA. Mice were treated with Control IgG or B7-H4-Ig during remission: 60 or 300 µg per dose, 3 doses/wk, for 2 weeks (6 doses).
Figure 7B:
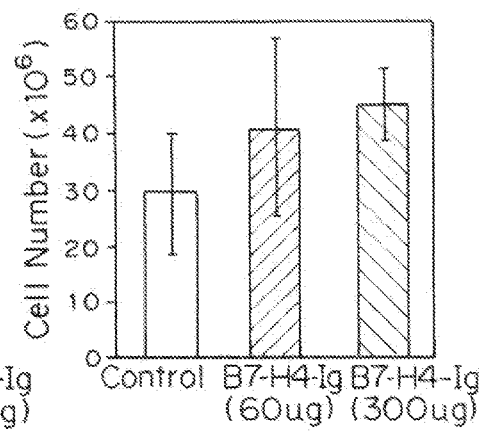
Figure 7C:
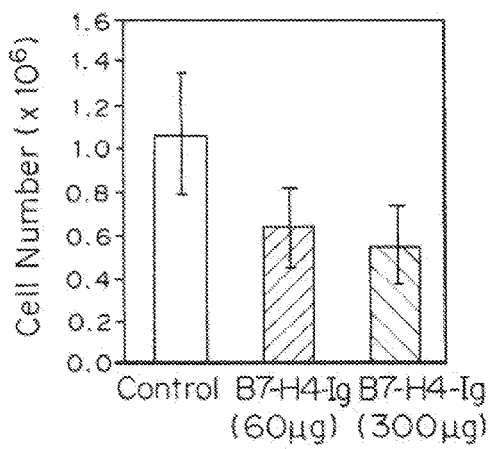

As demonstrated in FIGS. 7A, 7B, and 7C treatment with murine B7-H4-Ig showed a trend toward increasing numbers of CD4$^+$ T cells in the spleens (7A) and the draining lymph nodes (7B), and in contrast a decrease in the total numbers of infiltrating CD4$^+$ T cells within the CNS (7C) after 6 treatments.

Figure 8A:
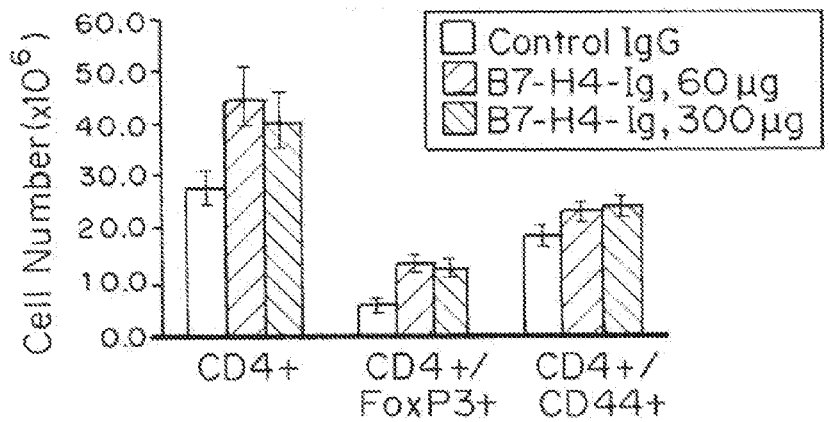
FIGS. 8A, 8B, and 8C are bar graphs showing T cell subset number ($\times 10^6$) isolated from the spleen (A), draining lymph node (B), or CNS as described in FIG. 45, which were CD4+ (T cells), CD4+/FoxP3+ (Treg), and CD4+/CD44+ (effector/memory T cells). The data is presented as the mean number of cells for each phenotype from individual mouse.
Figure 8B:
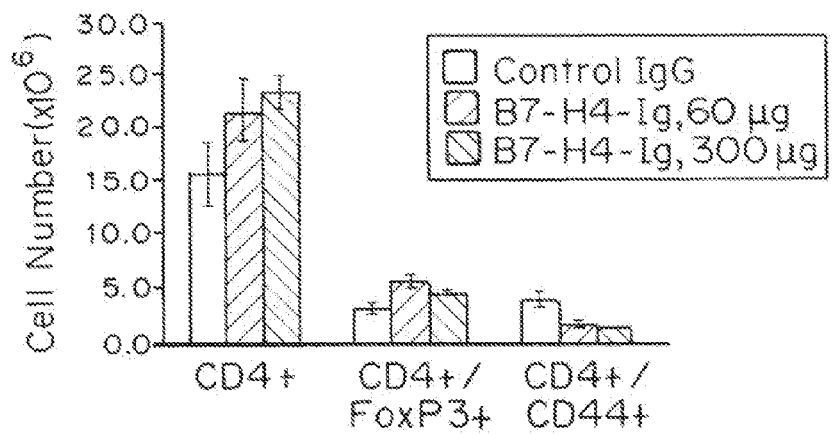
Figure 8C:
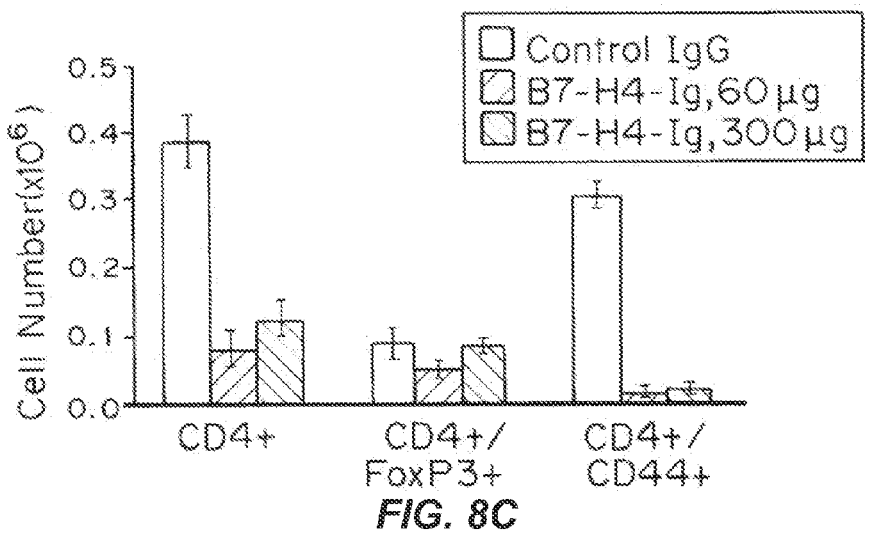
Figure 9:
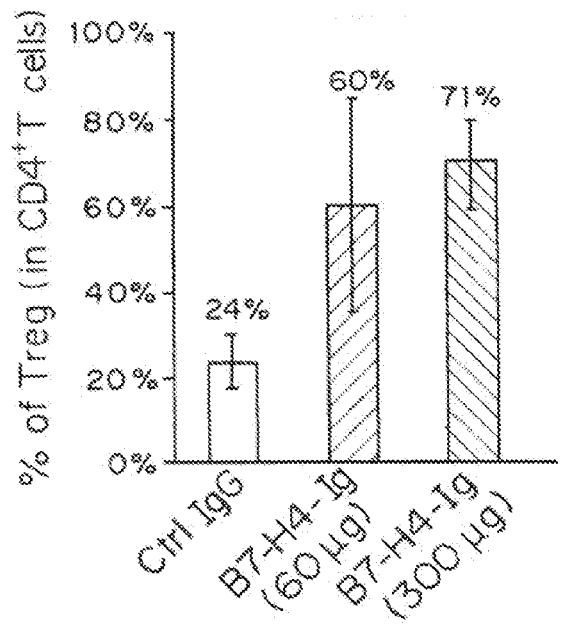
FIG. 9 is a bar graph showing the percentage of Treg in CD4+ T cells from FIG. 46, for Control IgG, 60, or 300 µg B7-H4-Ig treatments.

Cells isolated from spleen, draining lymph node and also lumbar spinal cord were stained for CD4, CD44 and FoxP3 followed by FACS analysis to obtain the number of total CD4$^+$ T cells, Treg (CD4$^+$/Foxp3$^+$) and effector/memory CD4$^+$ T cells (CD4$^+$/CD44$^+$). The data is presented in FIGS. 8A, 8B, and 8C as the mean number of cells for each phenotype from individual mouse. When the number of Treg (CD4$^+$/FoxP3$^+$) cells was calculated, B7-H4-Ig treatment remarkably increased the number of Treg cells within the spleen 8A and lymph node 8B, suggesting the increase in the CD4$^+$ T cell population was due in part to the increase of Treg cells. B7-H4-Ig treatment also decreased effector/memory T cells (CD4$^+$/CD44$^+$) within the CNS when compared to Control IgG treated mice 8C. Similar data was obtained after the full course of 12 treatments. FIGS. 8A, 8B, and 8C also reveals that while there were fewer CD4$^+$ T cells infiltrating into the CNS, the amount of Treg cells in the CNS appeared constant 8C, indicating that B7-H4-Ig altered the ratio of Treg cells to total CD4+ T cells within the CNS. Indeed, as shown in FIG. 9, the percentage of Treg cells among CD4+ T cells was significantly higher in the CNS from B7-H4-Ig treated mice compared with CNS from Control IgG injected mice.

The level of demyelination via anti-PLP staining in control IgG and B7-H4-Ig treated mice was also analyzed. The results indicate that there is not a significant, detectable difference in the level of PLP staining between groups, i.e., no significant difference in the level of demyelination. However, the T cell infiltrates into the CNS were also examined histologically, by staining and counting the total number of CD4+ T cells, and FoxP3+ cells in cross section samples taken from the lumbar spinal cord. Histological data correlates with the flow cytometric analysis with regard to the total number of CD4+ T cells and the number of FoxP3+ Treg cells present. The histology data is in line with the FACS data in demonstrating that B7-H4-Ig treatment increases the number of FoxP3+ cells within the CNS. It also shows that the FoxP3+ cells are co-localized with effector CD4+ T cells within the CNS, allowing them to exert their suppressive effect on pathogenic T cells.

Overall the data clearly demonstrate that B7-H4-Ig treatment favorably alters the ratio of Treg cells to total CD4+ T cells within the CNS, and is consistent with the proposed mechanism of action which suggests that B7-H4-Ig treatment both inhibits CD4+ T cell activation and increases Treg cell function and/or numbers. Similar findings were achieved after the full 12 doses (Day 50 post disease induction,).

Figure 10A:
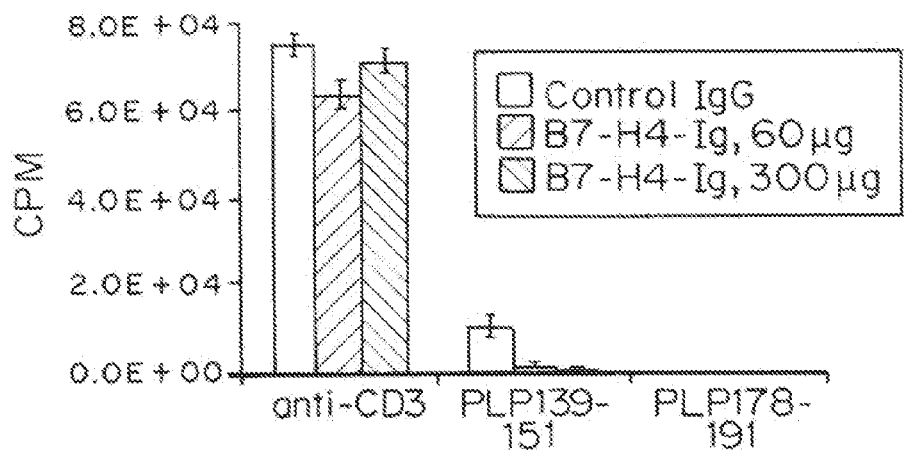
FIGS. 10A and 10B are bar graphs showing the proliferation (CPU (counts per minute)) of total splenocytes (A) and lymph node cells (B) isolated on day 35 from SJL mice immunized with 50 ng of PLP peptide emulsified in CFA, and activated in vitro in the presence of anti-CD3 (1 ug/ml), $PLP_{139-151}$ or $PLP_{178-191}$ (20 µg/mL). Mice were treated with Control IgG or B7-H4-Ig during remission: 60 or 300 µg per dose, 3 doses/wk, for 2 weeks (6 doses).
Figure 10B:
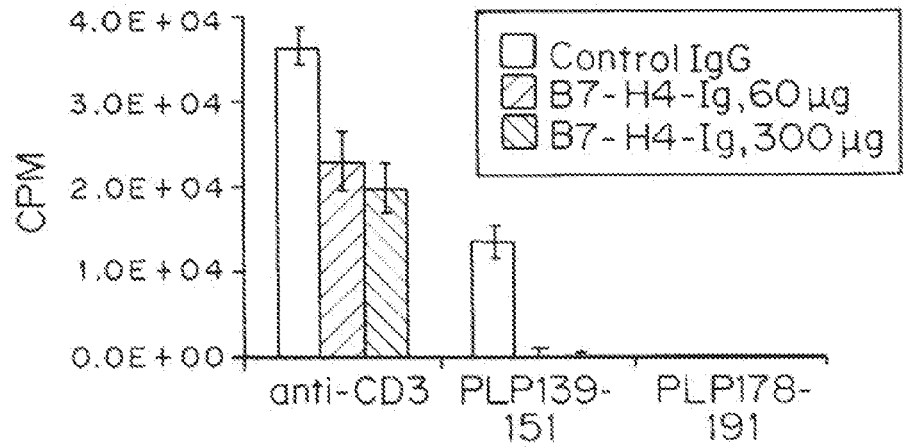
Figure 11:
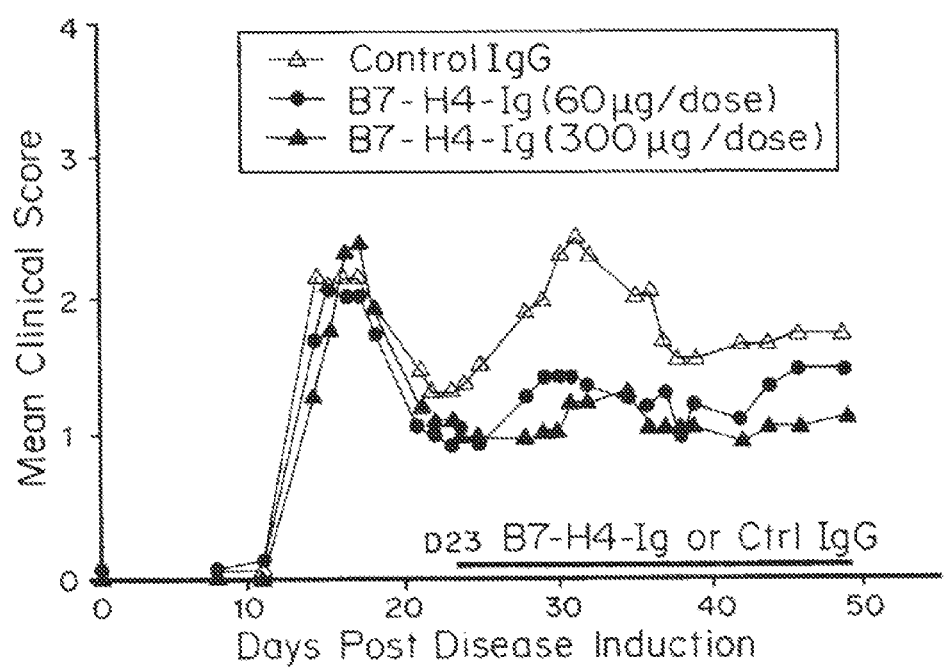
FIG. 11 is a line graph showing the mean clinical score of SJL mice over the 50 day time course (days) following disease induction. Mice were treated with 60 µg B7-H4-Ig (—●—), 300 µg B7-H4-Ig (—▲—), or Control IgG (—Δ—) three time a week beginning on day 23 post disease induction.

The impact of B7-H4-Ig treatment on epitope spreading was also examined To do so, spleens and draining lymph nodes were collected from the same mice that were analyzed for the number and phenotype of CD4+ T cells. SJL mouse were immunized with 50 µg of $PLP_{139-151}$ peptide emulsified in CFA. Mice were treated B7-H4-Ig during remission: 60 or 100 ug per dose, 3 doses/wk, for 2 weeks (6 doses). On Day 35 total splenocytes and lymph node cells ($5 \times 10^5$ cells per 200 ul culture) were activated in separate wells per mouse in the presence of anti-CD3 (1 ug/ml), $PLP_{139-151}$ or $PLP_{178-191}$ (20 µg/mL). At 24 hours following the initiation of culture, 1 µCi of $^3$[H] tritiate thymidine was added to each well and wells were analyzed at 72 hours post the initiation of culture. This presented as the mean CPM. As shown in FIGS. 10A and 10B, treatment of mice with B7-H4-Ig decreased the proliferative response to both $PLP_{139-151}$ and $PLP_{178-191}$. Therefore, B7-H4-Ig treatment during remission of ongoing R-EAE in SJL mice appears to decrease epitope spreading via an increase in the number of Treg cells. The mean clinical score of this study presented in FIG. 11 show that B7-H4-Ig at both 3 mg/kg (60 µg/dose) and 15 mg/kg (300 µg/dose) doses significantly prevented the primary relapsing. The higher dose appears more efficacious to lower the disease score at later time points (beyond Day 42 post disease initiation).

Unless defined otherwise, all technical and scientific terms used herein have the same meanings as commonly understood by one of skill in the art to which the disclosed invention belongs.

Those skilled in the art will recognize, or be able to ascertain using no more than routine experimentation, many equivalents to the specific embodiments of the invention described herein. Such equivalents are intended to be encompassed by the following claims.

We claim:

1. A method for inhibiting or reducing rejection of a tissue or organ transplant in a human subject,
comprising administering to the subject two or more pharmaceutical dosage units, each dosage unit comprising
a dose of 3 mg/kg to 25 mg/kg of a fusion protein comprising a B7-H4 polypeptide comprising the IgV domain of SEQ ID NO:63 or SEQ ID NO:64 fused to a second polypeptide or fused to a linker peptide fused to a second polypeptide,
wherein at least two of the dosage units are administered at least two days apart and within two weeks,
to increase the ratio of regulatory T cells (Tregs) relative to total CD4+ cells in the subject and reduce rejection of the tissue or organ transplant in the subject for at least a week post administration.

2. A method for inhibiting or reducing rejection of a tissue or organ transplant in a human subject,
comprising administering to the subject two or more pharmaceutical dosage units, each dosage unit comprising
a dose of 3 mg/kg to 25 mg/kg of a fusion protein comprising a B7-H4 polypeptide comprising the IgV domain of SEQ ID NO:63 or SEQ ID NO:64 fused to a second polypeptide or fused to a linker peptide fused to a second polypeptide comprising
the hinge, $C_H2$ and $C_H3$ regions of an immunoglobulin,
wherein at least two of the dosage units are administered at least two days apart and within two weeks,
to increase the ratio of regulatory T cells (Tregs) relative to total CD4+ cells in the subject and reduce rejection of the tissue or organ transplant in the subject for at least a week post administration.

3. The method of claim 1, wherein the pharmaceutical dosage unit further comprises a second therapeutic agent.

4. The method of claim 3 wherein the second therapeutic agent is selected from the group consisting of glucocorticoid fluticasone, salmeterol; antibodies to IL-12, IL-6, IFN-γ, IL-23, IL-22, IL-21 and IL-4; vitamin D3, CTLA-4-Ig, belatacept, dexamethasone, and combinations thereof.

5. The method of claim 1 wherein the transplant is an allogeneic transplant.

6. The method of claim 1, wherein the transplant is a skin graft, a tissue transplant, an organ transplant, or a bone marrow transplant.

7. A method for treating one or more symptoms of graft versus host disease (GVHD) in a human subject,
comprising administering to the subject two or more pharmaceutical dosage units, each dosage unit comprising
a dose of 3 mg/kg to 25 mg/kg of a fusion protein comprising a B7-H4 polypeptide comprising the IgV domain of SEQ ID NO:63 or SEQ ID NO:64 fused to a second polypeptide or fused to a linker peptide fused to a second polypeptide,
wherein at least two of the dosage units are administered at least two days apart and within two weeks,
to increase the ratio of regulatory T cells (Tregs) relative to total CD4+ cells in the subject and reduce one or more symptoms of GVHD in the subject for at least a week post administration.

8. A method for treating one or more symptoms of graft versus host disease (GVHD) in a human subject,
comprising administering to the subject two or more pharmaceutical dosage units, each dosage unit comprising
a dose of 3 mg/kg to 25 mg/kg of a fusion protein comprising a B7-H4 polypeptide comprising the IgV domain of SEQ ID NO:63 or SEQ ID NO:64 fused to a second polypeptide or fused to a linker peptide fused to a second polypeptide,
wherein the second polypeptide comprises the hinge, $C_H2$ and $C_H3$ regions of an immunoglobulin,
wherein at least two of the dosage units are administered at least two days apart and within two weeks,
to increase the ratio of regulatory T cells (Tregs) relative to total CD4+ cells in the subject and reduce one or more symptoms of GVHD in the subject for at least a week post administration.

9. A method for inhibiting or reducing rejection of a tissue or organ transplant in a human subject comprising administering to the subject two or more pharmaceutical dosage units, each dosage unit comprising a dose of 3 mg/kg to 25 mg/kg of a fusion protein comprising a B7-H4 polypeptide comprising the IgV domain of B7-H4 fused to a second polypeptide or fused to a linker peptide fused to a second polypeptide,
wherein at least two of the dosage units are administered at least two days apart and within two weeks,
to increase the ratio of regulatory T cells (Tregs) relative to total CD4+ cells in the subject and reduce rejection of tissue or organ transplant in the subject for at least a week post administration.

10. The method of claim 2, wherein the immunoglobulin is a human IgG1.

11. A method for inhibiting or reducing rejection of a tissue or organ transplant in a human subject,
comprising administering to the subject two or more pharmaceutical dosage units, each dosage unit comprising
a dose of 3 mg/kg to 25 mg/kg of a fusion protein comprising the amino acid sequence of SEQ ID NO:130 wherein at least two of the dosage units are administered at least two days apart and within two weeks,
to increase the ratio of regulatory T cells (Tregs) relative to total CD4+ cells in the subject and reduce rejection of tissue or organ transplant in the subject for at least a week post administration.

12. The method of claim 8, wherein the immunoglobulin is a human IgG1.

13. The method of claim 8, wherein the second polypeptide comprises the hinge, $C_H2$ and $C_H3$ regions of an immunoglobulin.

14. The method of claim 13, wherein the immunoglobulin is a human IgG1.

15. A method for treating one or more symptoms of graft versus host disease (GVHD) in a human subject,
comprising administering to the subject two or more pharmaceutical dosage units, each dosage unit comprising 3 mg/kg to 25 mg/kg of a fusion protein comprising the amino acid sequence of SEQ ID NO:130
wherein at least two of the dosage units are administered at least two days apart and within two weeks,
to increase the ratio of regulatory T cells (Tregs) relative to total CD4+ cells in the subject and reduce one or more symptoms of GVHD in the subject for at least a week post administration.

16. A method for treating one or more symptoms of graft versus host disease (GVHD) in a human subject comprising administering to the subject two or more pharmaceutical dosage units, each dosage unit comprising a dose of 3 mg/kg to 25 mg/kg of a fusion protein comprising a B7-H4 polypeptide comprising the IgV domain of B7-H4 fused to a second polypeptide or fused to a linker peptide fused to a second polypeptide,
wherein at least two of the dosage units are administered at least two days apart and within two weeks,
to increase the ratio of regulatory T cells (Tregs) relative to total CD4+ cells in the subject and reduce one or more symptoms of graft versus host disease (GVHD) in the subject for at least a week post administration.

17. The method of claim 1, wherein at least three of the dosage units are administered at least two days apart and within two weeks.

18. The method of claim 1, wherein at least two of the dosage units are administered at least two days apart and within one week.

19. The method of claim 1, wherein at least three of the dosage units are administered at least two days apart and within one week.

20. The method of claim 9, wherein at least three of the dosage units are administered at least two days apart and within two weeks.

21. The method of claim 9, wherein at least two of the dosage units are administered at least two days apart and within one week.

22. The method of claim 9, wherein at least three of the dosage units are administered at least two days apart and within one week.

23. The method of claim 11, wherein at least three of the dosage units are administered at least two days apart and within two weeks.

24. The method of claim 11, wherein at least two of the dosage units are administered at least two days apart and within one week.

25. The method of claim 11, wherein at least three of the dosage units are administered at least two days apart and within one week.

26. The method of claim 15, wherein at least three of the dosage units are administered at least two days apart and within two weeks.

27. The method of claim 15, wherein at least two of the dosage units are administered at least two days apart and within one week.

28. The method of claim 15, wherein at least three of the dosage units are administered at least two days apart and within one week.

29. The method of claim 1, wherein the administration is effective to reduce rejection of the tissue or organ transplant in the subject for at least 10 days post administration.

30. The method of claim 1, wherein the administration is effective to reduce rejection of the tissue or organ transplant in the subject for at least two weeks post administration.

31. The method of claim 1, wherein the administration is effective to reduce rejection of the tissue or organ transplant in the subject for at least three weeks post administration.

32. The method of claim 7, wherein the administration is effective to reduce one or more symptoms of GVHD in the subject for at least 10 days post administration.

33. The method of claim 7, wherein the administration is effective to reduce one or more symptoms of GVHD in the subject for at least two weeks post administration.

34. The method of claim 7, wherein the administration is effective to reduce one or more symptoms of GVHD in the subject for at least three weeks post administration.

35. The method of claim 11, wherein the administration is effective to reduce rejection of the tissue or organ transplant in the subject for at least 10 days post administration.

36. The method of claim 11, wherein the administration is effective to reduce rejection of the tissue or organ transplant in the subject for at least two weeks post administration.

37. The method of claim 11, wherein the administration is effective to reduce rejection of the tissue or organ transplant in the subject for at least three weeks post administration.

38. The method of claim 15, wherein the administration is effective to reduce one or more symptoms of GVHD in the subject for at least 10 days post administration.

39. The method of claim 15, wherein the administration is effective to reduce one or more symptoms of GVHD in the subject for at least two weeks post administration.

40. The method of claim 15, wherein the administration is effective to reduce one or more symptoms of GVHD in the subject for at least three weeks post administration.

* * * * *

UNITED STATES PATENT AND TRADEMARK OFFICE
CERTIFICATE OF CORRECTION

PATENT NO. : 9,005,616 B2
APPLICATION NO. : 13/392399
DATED : April 14, 2015
INVENTOR(S) : Solomon Langermann and Linda Liu It is certified that error appears in the above-identified patent and that said Letters Patent is hereby corrected as shown below:

In the Claims

Column 327, claim 13, line 9, replace "claim 8" with --claim 9--.

Signed and Sealed this
Twenty-ninth Day of September, 2015

Michelle K. Lee
*Director of the United States Patent and Trademark Office*